(12) United States Patent
Eberle et al.

(10) Patent No.: US 10,258,240 B1
(45) Date of Patent: Apr. 16, 2019

(54) OPTICAL FIBER PRESSURE SENSOR

(71) Applicant: Vascular Imaging Corporation, Rancho Cordova, CA (US)

(72) Inventors: Michael J. Eberle, Fair Oaks, CA (US); Diana Margaret Tasker, Sacramento, CA (US); Howard Neil Rourke, Sacramento, CA (US); David J. Spamer, Granite Bay, CA (US)

(73) Assignee: Vascular Imaging Corporation, Rancho Cordova, CA (US)

( * ) Notice: Subject to any disclaimer, the term of this patent is extended or adjusted under 35 U.S.C. 154(b) by 401 days.

(21) Appl. No.: 14/949,605

(22) Filed: Nov. 23, 2015

Related U.S. Application Data

(60) Provisional application No. 62/083,799, filed on Nov. 24, 2014.

(51) Int. Cl.
*A61B 5/00* (2006.01)
*A61B 5/0215* (2006.01)
(Continued)

(52) U.S. Cl.
CPC ........ *A61B 5/0084* (2013.01); *A61B 5/02154* (2013.01); *A61B 5/6851* (2013.01);
(Continued)

(58) Field of Classification Search
CPC ..... A61B 5/0215; A61B 5/03; A61B 5/02154; A61B 5/036; A61B 5/6851; A61M 25/09
(Continued)

(56) References Cited

U.S. PATENT DOCUMENTS 3,789,841 A   2/1974   Antoshkiw
3,906,938 A   9/1975   Fleischhacker
(Continued)

FOREIGN PATENT DOCUMENTS

WO   WO-2002/019903 A1   3/2002
WO   WO-2007/041542 A2   4/2007
(Continued)

OTHER PUBLICATIONS

"Fiber optic miniature pressure sensor", .25 & .40mm Specifications, (Feb. 27, 2012), 2 pgs.
(Continued)

*Primary Examiner* — Christopher D Koharski
*Assistant Examiner* — Roland Dinga
(74) *Attorney, Agent, or Firm* — Schwegman Lundberg & Woessner, P.A.

(57) ABSTRACT

In an example, an apparatus includes an elongated assembly, at least a portion of which is sized, shaped, or otherwise configured to be inserted into a human body to measure a physiological parameter at an internal location within the body. The elongated assembly can include an elongated member. The elongated assembly can include an optical fiber pressure sensor, located at a distal portion of the elongated member. The elongated assembly can include a housing disposed about the optical fiber pressure sensor. The elongated assembly can include a guidewire tube, coupled to the housing, the guidewire tube defining a receptacle sized and shaped to accept a guidewire to permit the distal portion of the elongated member to slide along the guidewire during insertion of the elongated assembly into the human body.

7 Claims, 69 Drawing Sheets

(51) Int. Cl.
*A61B 19/00* (2006.01)
*A61M 25/01* (2006.01)

(52) U.S. Cl.
CPC .............. *A61B 2019/5206* (2013.01); *A61B 2019/5261* (2013.01); *A61B 2562/0247* (2013.01); *A61M 2025/0177* (2013.01)

(58) Field of Classification Search
USPC ........................................................ 600/478
See application file for complete search history.

(56) References Cited

U.S. PATENT DOCUMENTS

| | | | |
|---|---|---|---|
| 3,995,623 | A | 12/1976 | Blake et al. |
| 4,554,929 | A | 11/1985 | Samson et al. |
| 4,712,566 | A | 12/1987 | Hok |
| 4,907,332 | A | 3/1990 | Christian et al. |
| 4,917,097 | A | 4/1990 | Proudian et al. |
| 4,917,102 | A | 4/1990 | Miller et al. |
| 4,932,959 | A | 6/1990 | Horzewski et al. |
| 4,936,310 | A | 6/1990 | Engstrom et al. |
| 4,941,473 | A | 7/1990 | Tenerz et al. |
| 4,955,384 | A | 9/1990 | Taylor et al. |
| 4,958,642 | A | 9/1990 | Christian et al. |
| 4,961,433 | A | 10/1990 | Christian |
| 4,966,163 | A | 10/1990 | Kraus et al. |
| 4,967,753 | A | 11/1990 | Haase et al. |
| 5,007,434 | A | 4/1991 | Doyle et al. |
| 5,018,529 | A | 5/1991 | Tenerz |
| 5,050,606 | A | 9/1991 | Tremulis |
| 5,059,851 | A | 10/1991 | Corl et al. |
| 5,085,223 | A | 2/1992 | Lars et al. |
| 5,125,058 | A | 6/1992 | Tenerz et al. |
| 5,125,137 | A | 6/1992 | Corl et al. |
| 5,135,503 | A | 8/1992 | Abrams |
| 5,163,445 | A | 11/1992 | Christian et al. |
| 5,167,233 | A | 12/1992 | Eberle et al. |
| 5,195,375 | A | 3/1993 | Tenerz |
| 5,226,421 | A | 7/1993 | Frisbie et al. |
| 5,226,423 | A | 7/1993 | Tenerz et al. |
| 5,240,437 | A | 8/1993 | Christian |
| 5,246,007 | A | 9/1993 | Frisbie et al. |
| 5,271,404 | A | 12/1993 | Corl et al. |
| 5,325,860 | A | 7/1994 | Seward et al. |
| 5,341,818 | A | 8/1994 | Abrams et al. |
| 5,348,481 | A | 9/1994 | Ortiz |
| 5,358,409 | A | 10/1994 | Obara |
| 5,411,476 | A | 5/1995 | Abrams et al. |
| 5,413,508 | A | 5/1995 | Obara |
| 5,423,331 | A | 6/1995 | Wysham |
| 5,427,118 | A | 6/1995 | Nita et al. |
| 5,514,128 | A | 5/1996 | Hillsman et al. |
| 5,517,989 | A | 5/1996 | Frisbie et al. |
| 5,520,194 | A | 5/1996 | Miyata et al. |
| 5,551,301 | A | 9/1996 | Cowan |
| 5,558,101 | A | 9/1996 | Brooks et al. |
| 5,571,094 | A | 11/1996 | Sirhan |
| 5,581,144 | A | 12/1996 | Corl et al. |
| 5,668,320 | A | 1/1997 | Cowan |
| 5,603,327 | A | 2/1997 | Eberle et al. |
| 5,637,089 | A | 6/1997 | Abrams et al. |
| RE35,648 | E | 11/1997 | Tenerz et al. |
| 5,688,234 | A | 11/1997 | Frisbie |
| 5,694,946 | A | 12/1997 | Tenerz et al. |
| 5,695,111 | A | 12/1997 | Nanis et al. |
| 5,715,827 | A | 2/1998 | Corl et al. |
| 5,740,596 | A | 4/1998 | Corl et al. |
| 5,797,856 | A | 8/1998 | Frisbie et al. |
| 5,873,835 | A | 2/1999 | Hastings et al. |
| 5,897,819 | A | 4/1999 | Miyata et al. |
| 5,908,385 | A | 6/1999 | Chechelski et al. |
| 5,910,364 | A | 6/1999 | Miyata et al. |
| 5,938,624 | A | 8/1999 | Akerfeldt et al. |
| 5,984,853 | A | 11/1999 | Smith |
| 6,025,670 | A | 2/2000 | Corl et al. |
| 6,049,958 | A | 4/2000 | Eberle et al. |
| 6,089,103 | A | 7/2000 | Smith |
| 6,090,052 | A | 7/2000 | Akerfeldt et al. |
| 6,106,476 | A | 8/2000 | Corl et al. |
| 6,106,486 | A | 8/2000 | Tenerz et al. |
| 6,112,598 | A | 9/2000 | Tenerz et al. |
| 6,142,958 | A | 11/2000 | Hammarstrom et al. |
| 6,165,292 | A | 12/2000 | Abrams et al. |
| 6,167,763 | B1 | 1/2001 | Tenerz et al. |
| 6,175,669 | B1 | 1/2001 | Colston et al. |
| 6,182,513 | B1 | 2/2001 | Stemme et al. |
| 6,191,862 | B1 | 2/2001 | Swanson et al. |
| 6,196,980 | B1 | 3/2001 | Akerfeldt et al. |
| 6,210,339 | B1 | 4/2001 | Kiepen et al. |
| 6,241,651 | B1 | 6/2001 | Smith et al. |
| 6,248,083 | B1 | 6/2001 | Smith et al. |
| 6,265,792 | B1 | 7/2001 | Granchukoff |
| 6,280,539 | B1 | 8/2001 | Abrams et al. |
| 6,312,380 | B1 | 11/2001 | Hoek et al. |
| 6,336,906 | B1 | 1/2002 | Hammarstrom et al. |
| 6,343,514 | B1 | 2/2002 | Smith |
| 6,379,369 | B1 | 4/2002 | Abrams et al. |
| 6,390,993 | B1 | 5/2002 | Cornish et al. |
| 6,409,677 | B1 | 6/2002 | Tulkki |
| 6,419,745 | B1 | 7/2002 | Burkett et al. |
| 6,423,012 | B1 | 7/2002 | Kato et al. |
| 6,428,336 | B1 | 8/2002 | Akerfeldt |
| 6,445,939 | B1 | 9/2002 | Swanson et al. |
| 6,461,301 | B2 | 10/2002 | Smith |
| 6,461,453 | B1 | 10/2002 | Abrams et al. |
| 6,491,648 | B1 | 12/2002 | Cornish et al. |
| 6,517,481 | B2 | 2/2003 | Hoek et al. |
| 6,546,804 | B2 | 4/2003 | Stemme et al. |
| 6,552,796 | B2 | 4/2003 | Magnin et al. |
| 6,565,514 | B2 | 5/2003 | Svanerudh et al. |
| 6,570,659 | B2 | 5/2003 | Schmitt |
| 6,585,660 | B2 | 7/2003 | Dorando et al. |
| 6,592,570 | B2 | 7/2003 | Abrams et al. |
| 6,602,228 | B2 | 8/2003 | Nanis et al. |
| 6,615,067 | B2 | 9/2003 | Hoek et al. |
| 6,615,667 | B2 | 9/2003 | Smith |
| 6,659,957 | B1 | 12/2003 | Vardi et al. |
| 6,666,829 | B2 | 12/2003 | Cornish et al. |
| 6,672,172 | B2 | 1/2004 | Tulkki et al. |
| 6,673,025 | B1 | 1/2004 | Richardson et al. |
| 6,682,608 | B2 | 1/2004 | Abrams et al. |
| 6,692,446 | B2 | 2/2004 | Hoek |
| 6,695,915 | B2 | 2/2004 | Burkett et al. |
| 6,733,819 | B2 | 5/2004 | Burkett et al. |
| 6,754,608 | B2 | 6/2004 | Svanerudh et al. |
| 6,767,327 | B1 | 7/2004 | Corl et al. |
| 6,779,257 | B2 | 8/2004 | Kiepen et al. |
| 6,852,109 | B2 | 2/2005 | Winston |
| 6,884,225 | B2 | 4/2005 | Kato et al. |
| 6,891,984 | B2 | 5/2005 | Petersen et al. |
| 6,908,442 | B2 | 6/2005 | von Malmborg et al. |
| 6,926,674 | B2 | 8/2005 | Tenerz et al. |
| 6,938,474 | B2 | 9/2005 | Melvås |
| 6,976,965 | B2 | 12/2005 | Corl et al. |
| 6,993,974 | B2 | 2/2006 | Tenerz et al. |
| 7,011,636 | B2 | 3/2006 | Tenerz |
| 7,021,152 | B2 | 4/2006 | Tenerz |
| 7,097,620 | B2 | 8/2006 | Corl et al. |
| 7,117,703 | B2 | 10/2006 | Kato et al. |
| 7,150,723 | B2 | 12/2006 | Meguro et al. |
| 7,182,757 | B2 | 2/2007 | Miyata et al. |
| 7,187,453 | B2 | 3/2007 | Belleville |
| 7,222,539 | B2 | 5/2007 | Tulkki |
| 7,241,286 | B2 | 7/2007 | Atlas |
| 7,244,319 | B2 | 7/2007 | Abrams et al. |
| 7,245,789 | B2 | 7/2007 | Bates et al. |
| 7,254,946 | B1 | 8/2007 | Quinn |
| 7,259,862 | B2 | 8/2007 | Duplain |
| 7,263,894 | B2 | 9/2007 | Tenerz |
| 7,274,956 | B2 | 9/2007 | Mott et al. |
| RE39,863 | E | 10/2007 | Smith |
| 7,326,088 | B2 | 2/2008 | Tulkki |
| 7,331,236 | B2 | 2/2008 | Smith et al. |
| 7,343,811 | B2 | 3/2008 | Tenerz et al. |

(56) References Cited

U.S. PATENT DOCUMENTS

| | | |
|---|---|---|
| 7,399,283 B2 | 7/2008 | Kato |
| 7,447,388 B2 | 11/2008 | Bates et al. |
| 7,450,989 B2 | 11/2008 | Svanerudh |
| 7,472,601 B1 | 1/2009 | Tenerz et al. |
| 7,532,920 B1 | 5/2009 | Ainsworth et al. |
| 7,553,444 B2 | 6/2009 | Kato |
| 7,645,233 B2 | 1/2010 | Tulkki et al. |
| 7,660,492 B2 | 2/2010 | Bates et al. |
| 7,676,910 B2 | 3/2010 | Kiepen et al. |
| 7,680,363 B2 | 3/2010 | Wakahara et al. |
| 7,689,071 B2 | 3/2010 | Belleville et al. |
| 7,724,148 B2 | 5/2010 | Samuelsson et al. |
| 7,753,852 B2 | 7/2010 | Maschke |
| 7,762,954 B2 | 7/2010 | Nix et al. |
| 7,775,988 B2 | 8/2010 | Pijls |
| 7,775,992 B2 | 8/2010 | von Malmborg et al. |
| 7,914,458 B2 | 3/2011 | Hossack et al. |
| 7,918,947 B2 | 4/2011 | Kato |
| 7,931,603 B2 | 4/2011 | Von Malmborg et al. |
| 7,946,997 B2 | 5/2011 | Hubinette |
| 7,967,761 B2 | 6/2011 | Smith |
| 7,967,762 B2 | 6/2011 | Corl et al. |
| 7,998,089 B2 | 8/2011 | Smith |
| 8,038,628 B2 | 10/2011 | von Malmborg et al. |
| 8,059,923 B2 | 11/2011 | Bates et al. |
| 8,298,156 B2 | 10/2012 | Manstrom et al. |
| 8,317,715 B2 | 11/2012 | Belleville et al. |
| 8,412,312 B2 | 4/2013 | Judell et al. |
| 8,478,384 B2 | 7/2013 | Schmitt et al. |
| 8,485,985 B2 | 7/2013 | Manstrom |
| 8,583,218 B2 | 11/2013 | Eberle |
| 8,641,639 B2 | 2/2014 | Manstrom et al. |
| 8,676,299 B2 | 3/2014 | Schmitt et al. |
| 8,677,299 B1 | 3/2014 | Alpert et al. |
| 2002/0059827 A1 | 5/2002 | Smith |
| 2003/0220588 A1 | 11/2003 | Tenerz et al. |
| 2004/0180581 A1 | 9/2004 | von Malmborg et al. |
| 2004/0225232 A1 | 11/2004 | Malmborg et al. |
| 2005/0121734 A1 | 6/2005 | Degertekin et al. |
| 2006/0241503 A1 | 10/2006 | Schmitt et al. |
| 2006/0241505 A1 | 10/2006 | Ahmed et al. |
| 2007/0255144 A1 | 11/2007 | Tulkki et al. |
| 2008/0161696 A1 | 7/2008 | Schmitt et al. |
| 2008/0165366 A1 | 7/2008 | Schmitt |
| 2008/0200769 A1* | 8/2008 | Sharma .............. A61B 5/0071 600/300 |
| 2009/0036754 A1 | 2/2009 | Pons et al. |
| 2009/0180730 A1 | 7/2009 | Foster et al. |
| 2010/0087732 A1 | 4/2010 | Eberle et al. |
| 2010/0199773 A1 | 8/2010 | Zhou |
| 2010/0228112 A1 | 9/2010 | Von Malmborg |
| 2010/0234698 A1 | 9/2010 | Manstrom et al. |
| 2010/0241008 A1 | 9/2010 | Belleville et al. |
| 2011/0071405 A1 | 3/2011 | Judell et al. |
| 2011/0144502 A1 | 6/2011 | Zhou et al. |
| 2011/0178413 A1* | 7/2011 | Schmitt .............. A61B 5/0066 600/478 |
| 2012/0108943 A1 | 5/2012 | Bates et al. |
| 2012/0136244 A1 | 5/2012 | Manstrom |
| 2012/0220883 A1 | 8/2012 | Manstrom et al. |
| 2012/0227505 A1 | 9/2012 | Belleville |
| 2012/0238869 A1 | 9/2012 | Schmitt et al. |
| 2012/0310081 A1 | 12/2012 | Adler et al. |
| 2013/0051731 A1 | 2/2013 | Belleville |
| 2013/0096409 A1 | 4/2013 | Hiltner |
| 2013/0131523 A1 | 5/2013 | Suchecki et al. |
| 2013/0218032 A1 | 8/2013 | Belleville |
| 2013/0303914 A1 | 11/2013 | Hiltner et al. |
| 2013/0310698 A1 | 11/2013 | Judell et al. |
| 2013/0317359 A1 | 11/2013 | Wilson et al. |
| 2013/0317372 A1 | 11/2013 | Eberle et al. |
| 2013/0324864 A1 | 12/2013 | Manstrom |
| 2013/0331714 A1 | 12/2013 | Manstrom et al. |
| 2014/0005558 A1 | 1/2014 | Gregorich |
| 2014/0024950 A1 | 1/2014 | Hiltner et al. |
| 2014/0039325 A1 | 2/2014 | Belleville |
| 2014/0058275 A1 | 2/2014 | Gregorich et al. |
| 2014/0081244 A1 | 3/2014 | Voeller et al. |
| 2014/0094697 A1 | 4/2014 | Petroff et al. |
| 2014/0100462 A1 | 4/2014 | Rourke et al. |
| 2014/0107624 A1 | 4/2014 | Belleville |
| 2014/0180031 A1 | 6/2014 | Anderson |
| 2014/0180034 A1 | 6/2014 | Hoseit et al. |
| 2014/0200438 A1 | 7/2014 | Millett et al. |
| 2015/0141843 A1 | 5/2015 | Eberle et al. |
| 2015/0141854 A1 | 5/2015 | Eberle et al. |
| 2015/0196210 A1* | 7/2015 | McCaffrey .......... A61B 5/02158 600/488 |
| 2016/0018593 A1 | 1/2016 | Tasker et al. |
| 2016/0066794 A1* | 3/2016 | Klinder ................ A61B 5/026 600/424 |

FOREIGN PATENT DOCUMENTS

| | | |
|---|---|---|
| WO | WO-2012/061935 A1 | 5/2012 |
| WO | WO-2013/177577 A2 | 11/2013 |
| WO | WO-2013/177577 A3 | 11/2013 |

OTHER PUBLICATIONS

"IFU, GW, HI-TORQUE Guide Wires, Global, CE", Abbott Vascular, (Feb. 8, 2010), 1-6.

"OPP-M Fiber optic miniature physiological* pressure sensor", [online]. [retrieved on Feb. 27, 2012]. Retrieved from the Internet: <http://opsens.com/en/industries/products/pressure/opp-m/>, (2012), 1 pg.

"Opsens Signs First Major Agreement in the Medical Field Granting Distribution Rights of its FFR Products for Japan, Korea and Taiwan in US$5 Million Transaction", Press Release, Quebec City, Quebec, (Nov. 19, 2012), 3 pgs.

"Optical Pressure & Temperature Sensing", Opsens, (Feb. 27, 2012), 29 pgs.

"Route / PROWATERfiex and Rinato / PROWATER Guidewire Specifications", [online] [retrieved on May 24, 2012]. Retrieved from the Internet: <http://www.asahi-intecc.com/medical/international/product/ptca_gw.php>, (2012), 1 pg.

Haga, Yoichi, et al., "Multi-functional Active Catheter", vol. 8, Issue 1, (Nov. 2000), 147-186.

Mineta, T, et al., "Batch fabricated flat meandering shape memory alloy actuator for active catheter", Sensors and Actuators A 88, (2001), 112-120.

Mineta, Takashi, "An active guide wire with shape memory alloy bending actuator fabricated by room temperature process", Sensors and Actuators A 97-98, (2002), 632-637.

Siebes, M., et al., "Single-Wire Pressure and Flow Velocity Measurement to Quantify Coronary Stenosis Hemodynamics and Effects of Percutaneous Interventions"; Circulation, 109, (2004), 756-762.

* cited by examiner

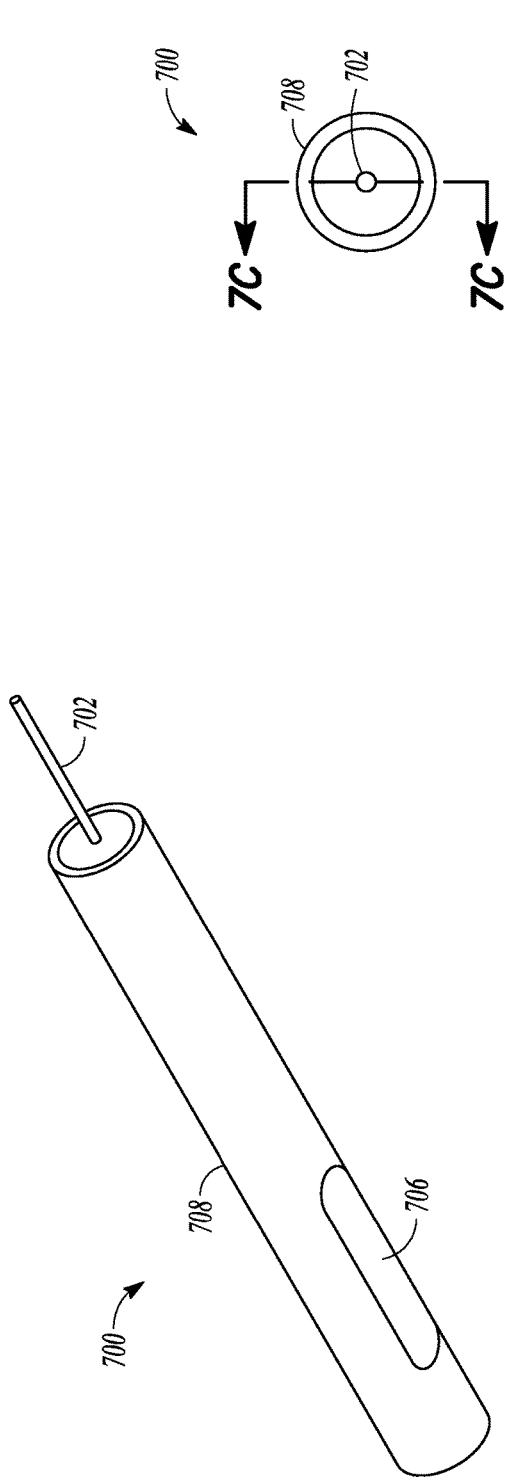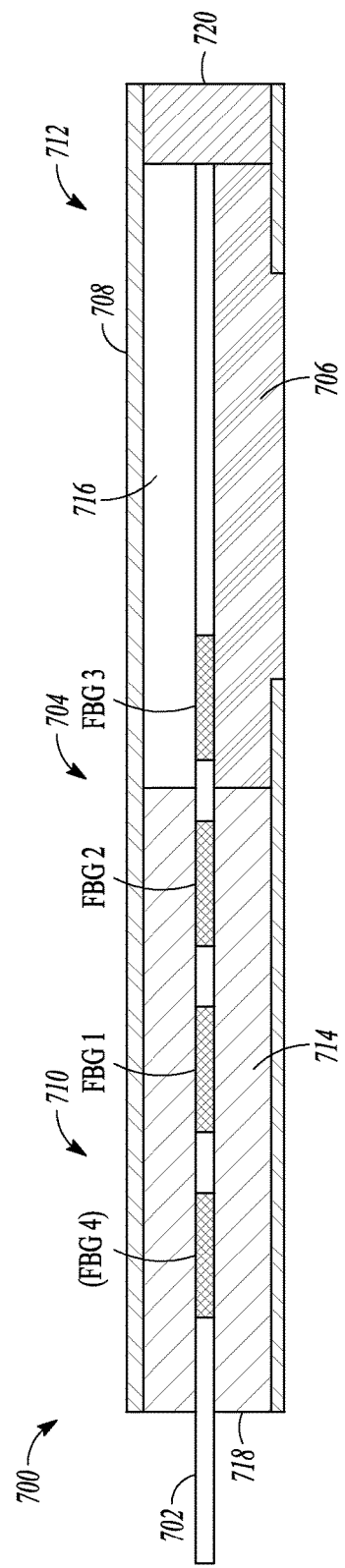

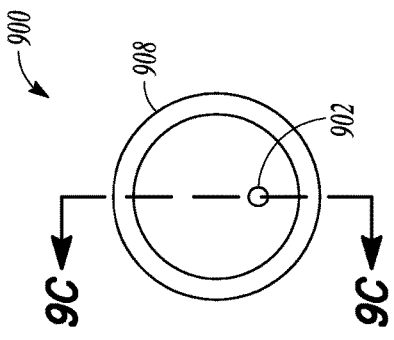
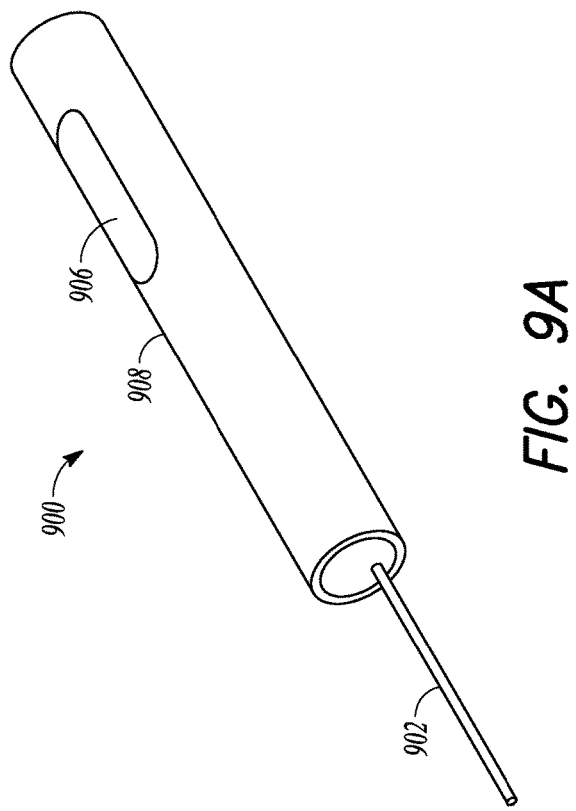
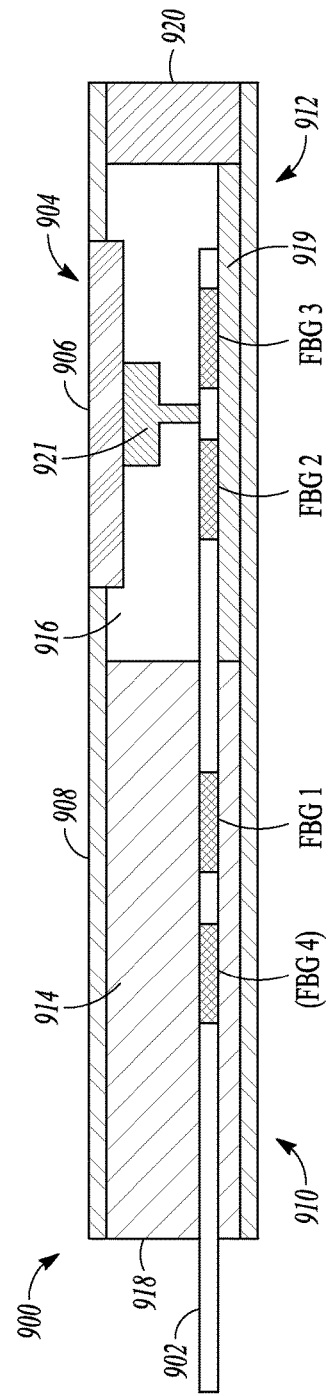
FIG. 9A
FIG. 9B
FIG. 9C

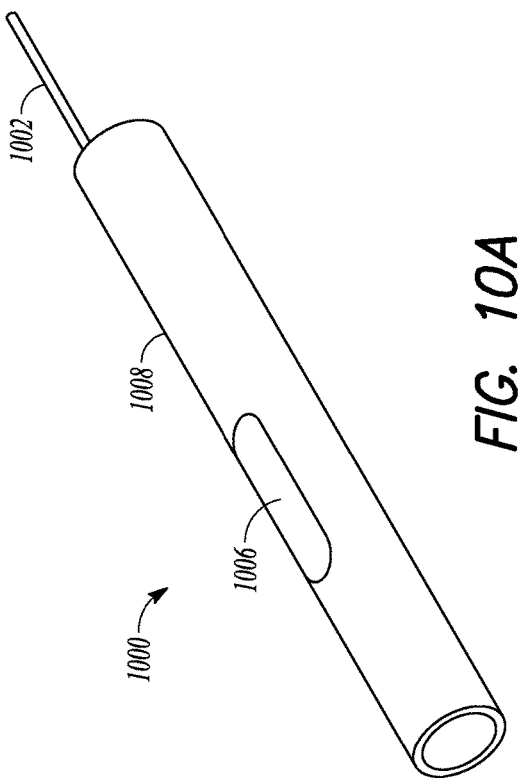
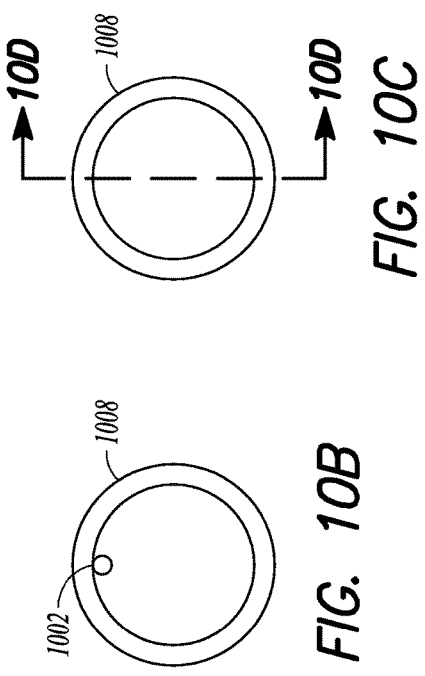
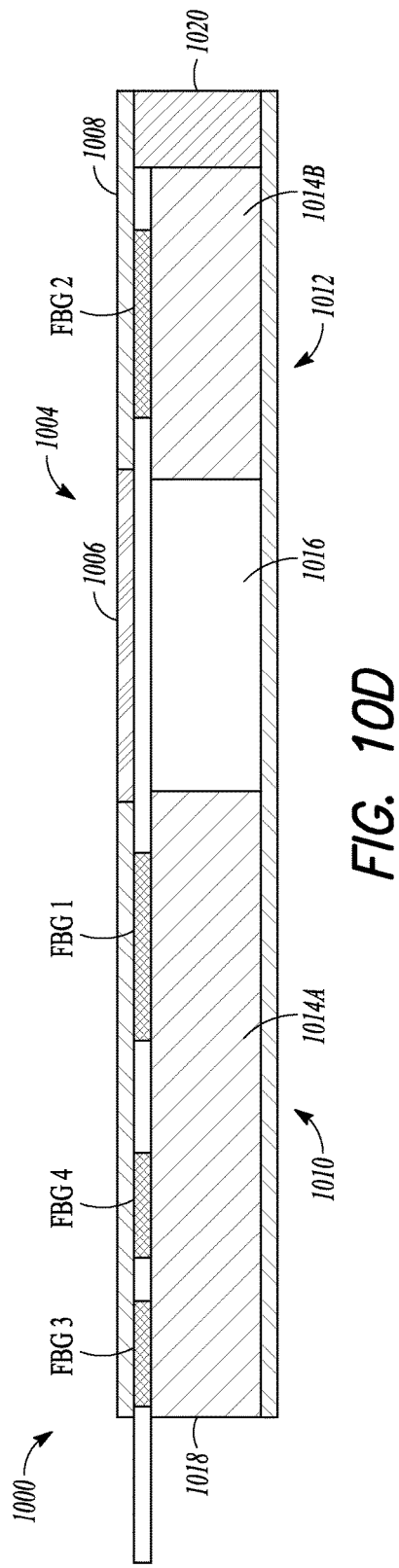

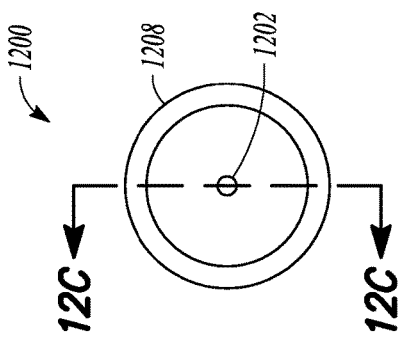
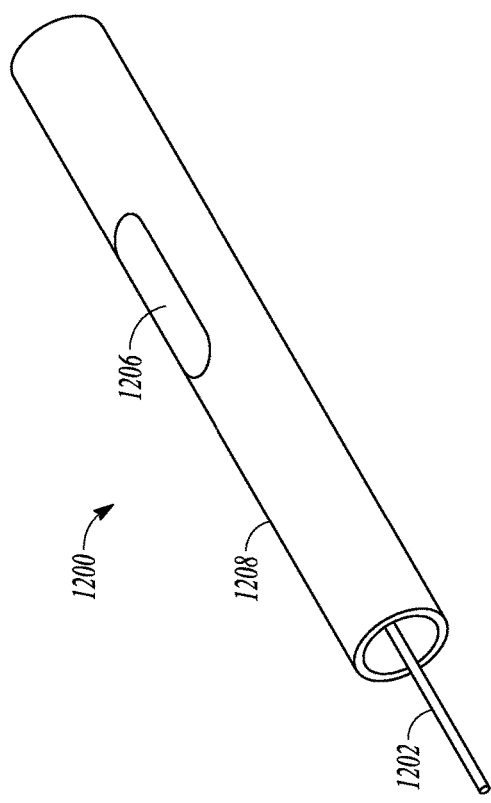
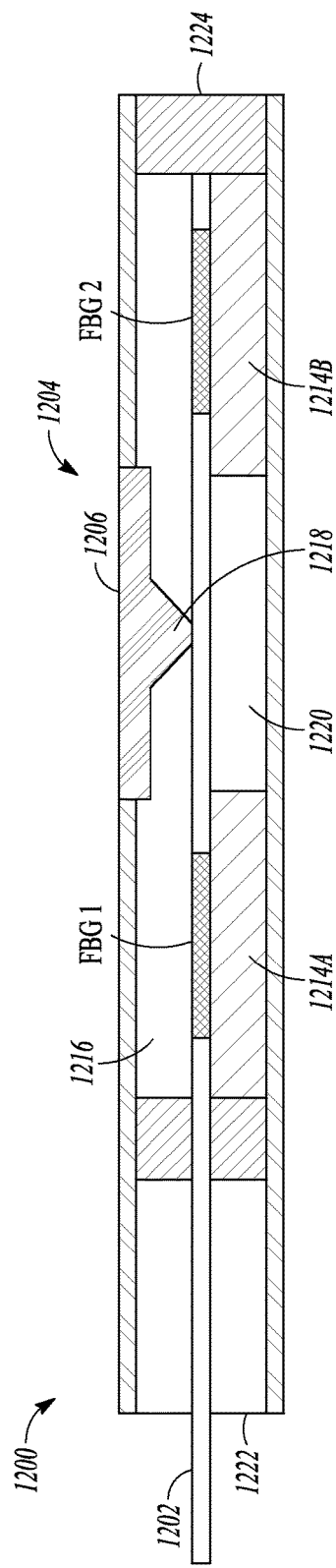
FIG. 12A
FIG. 12B
FIG. 12C

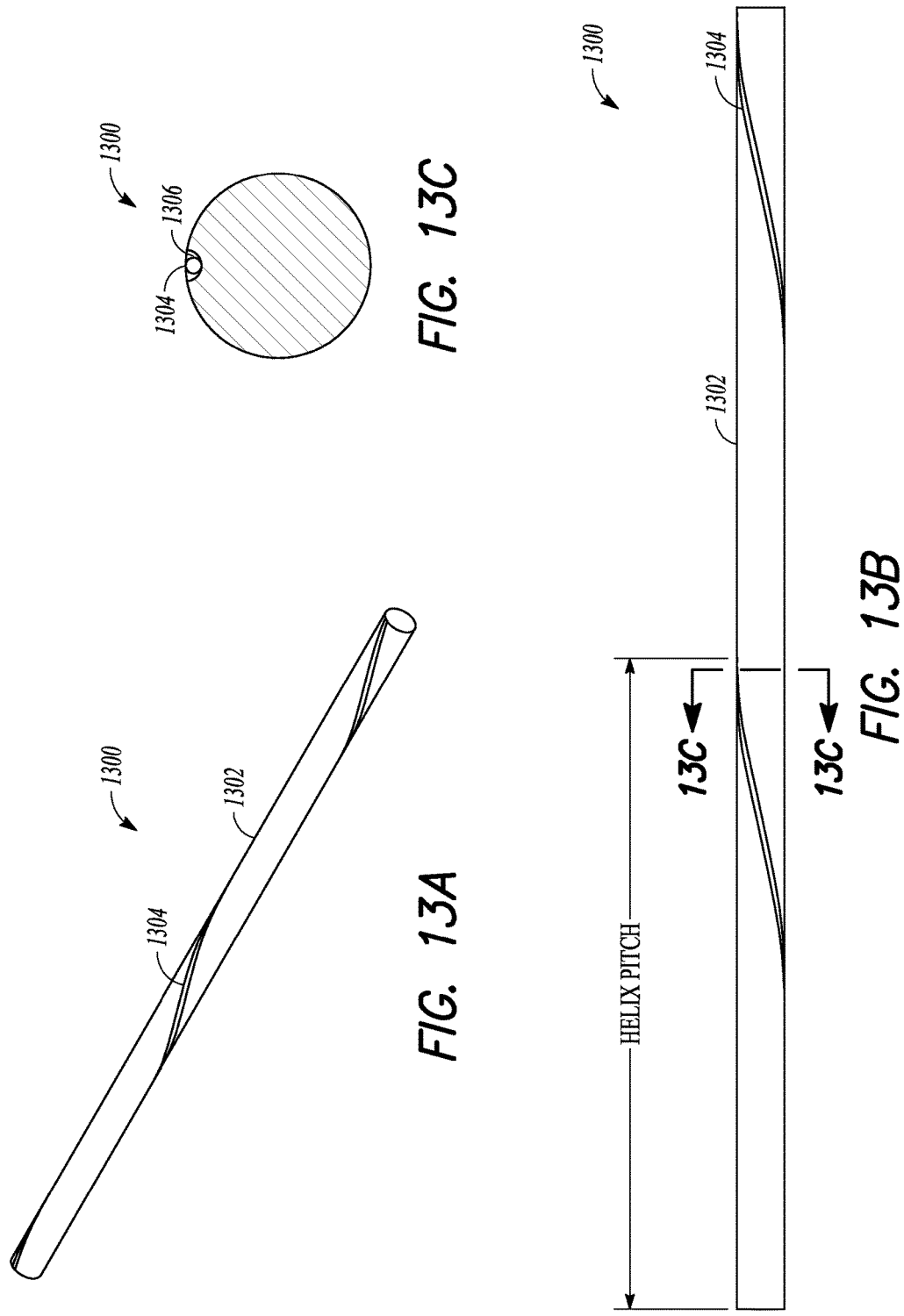

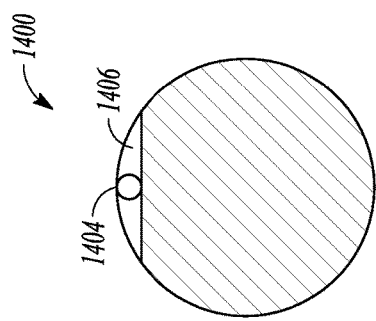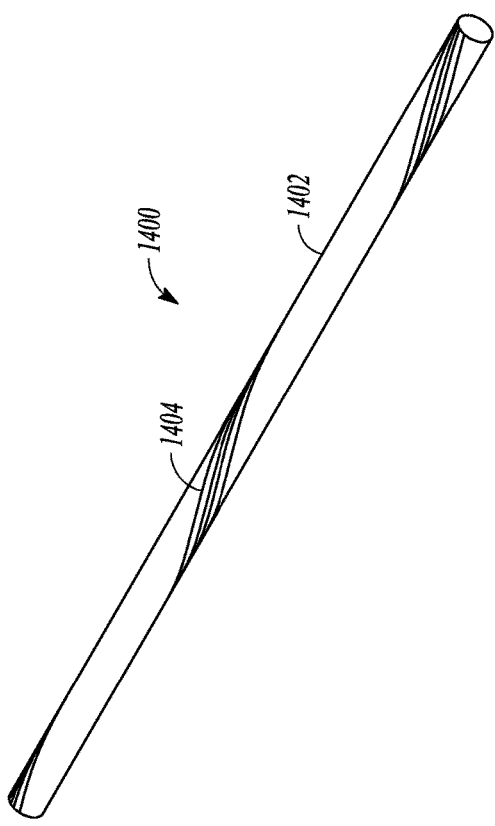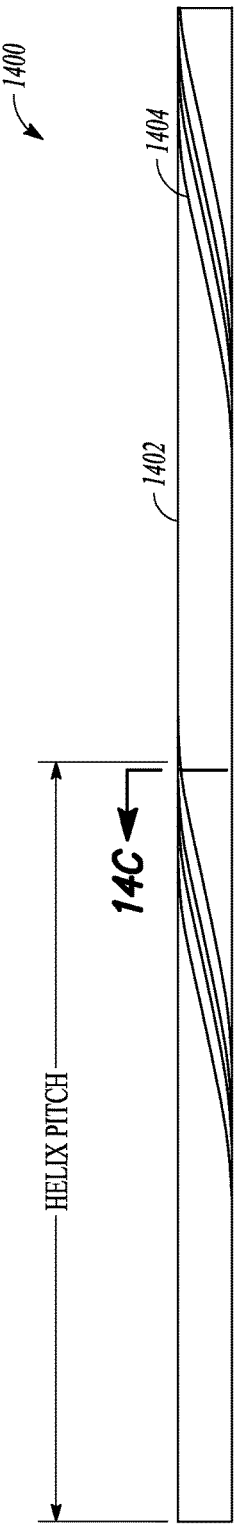

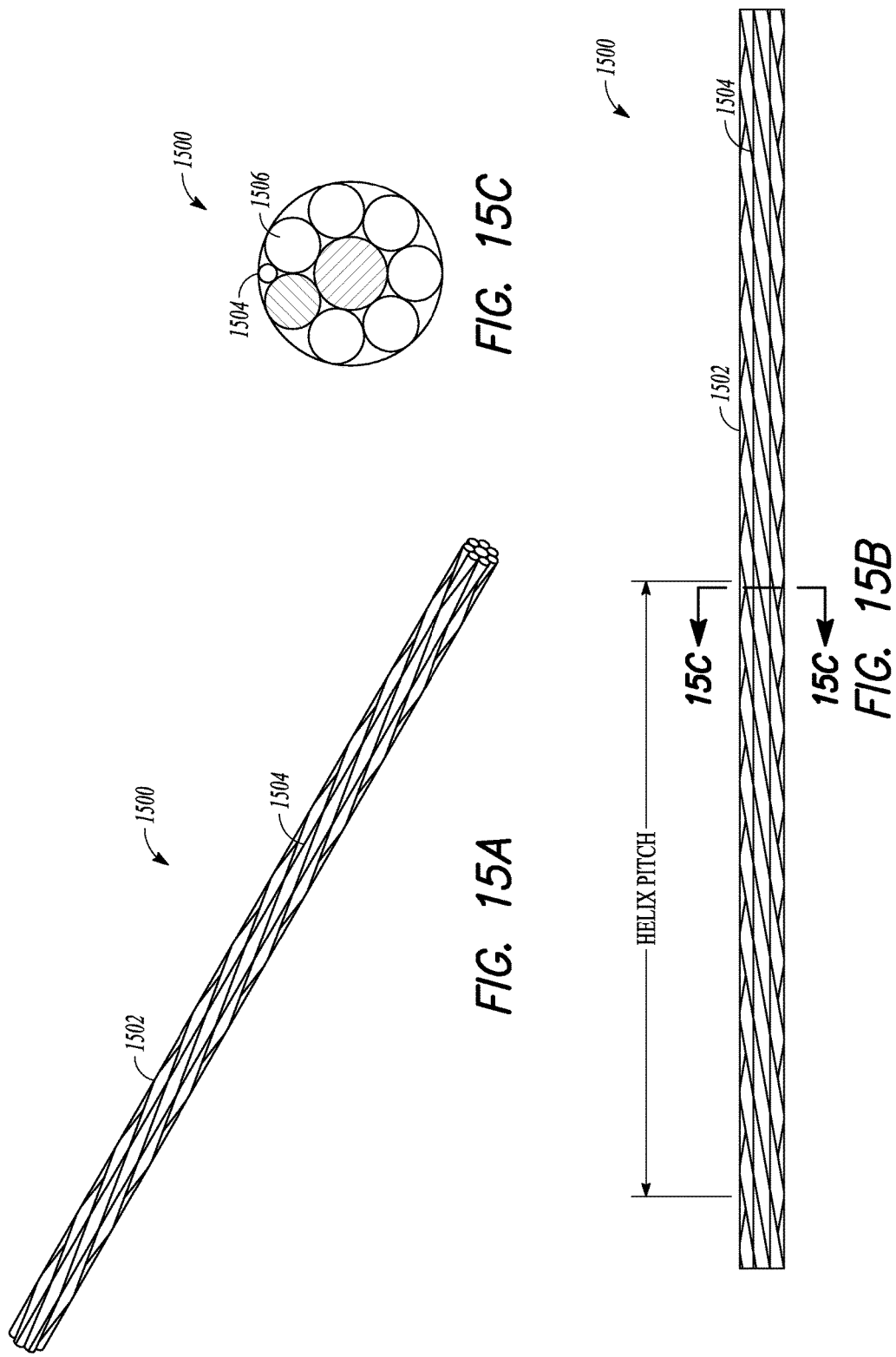

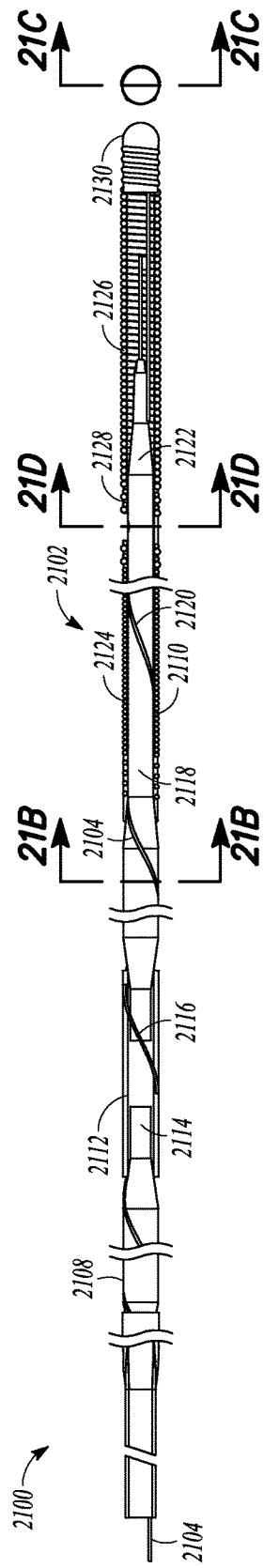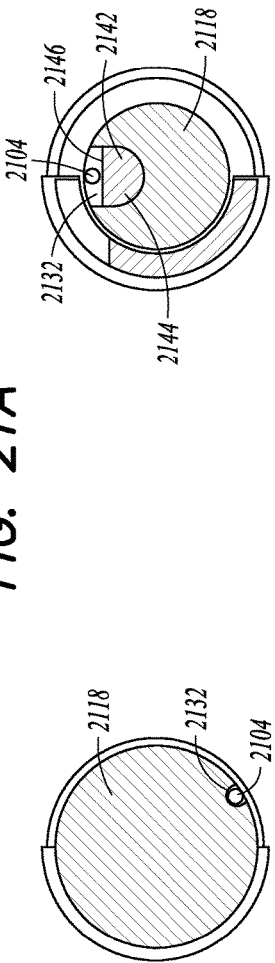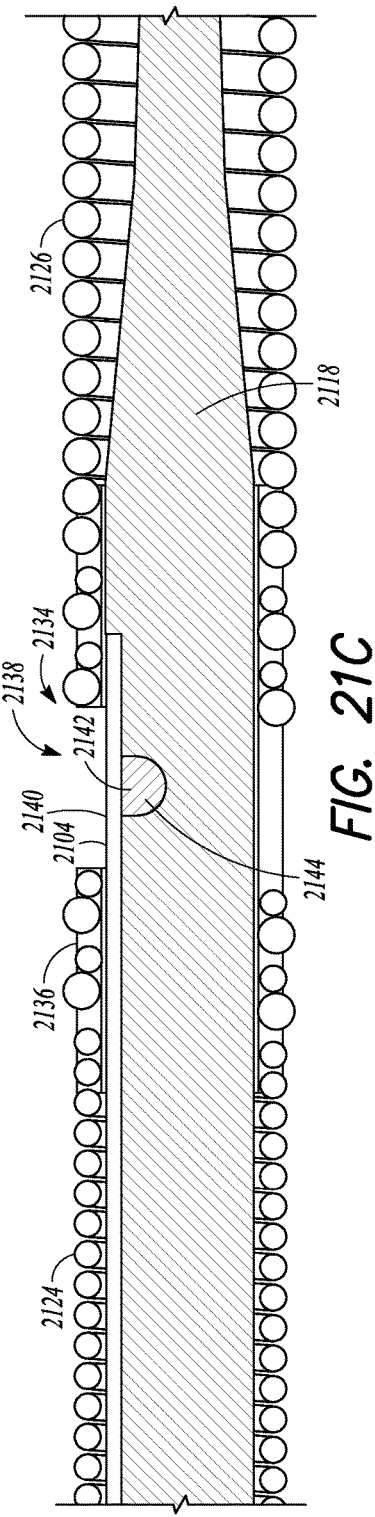
FIG. 21A
FIG. 21B
FIG. 21D
FIG. 21C

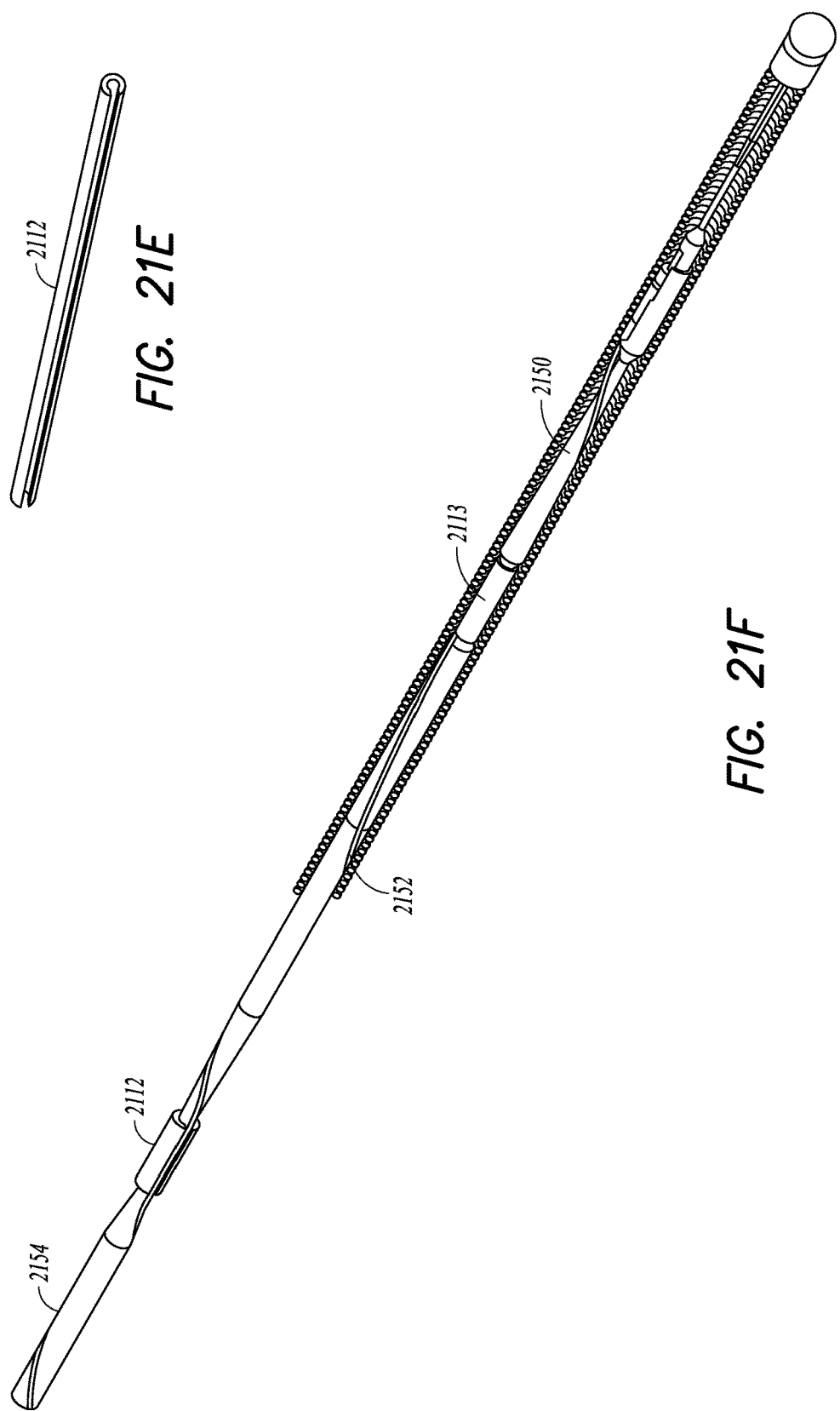

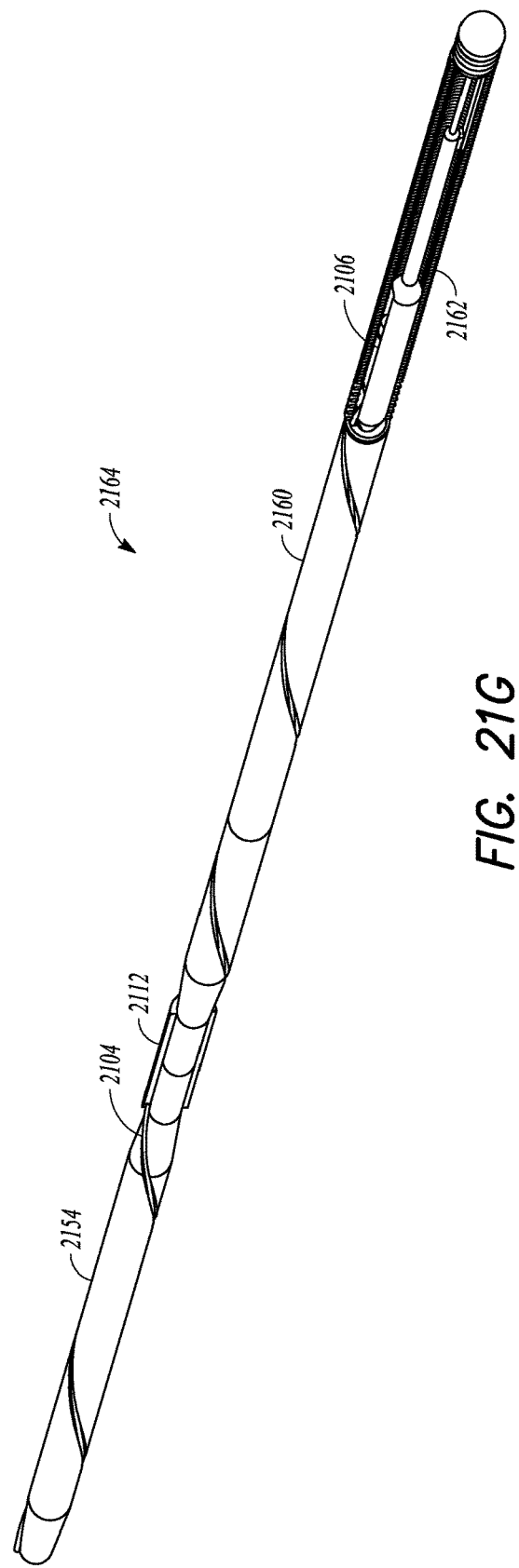

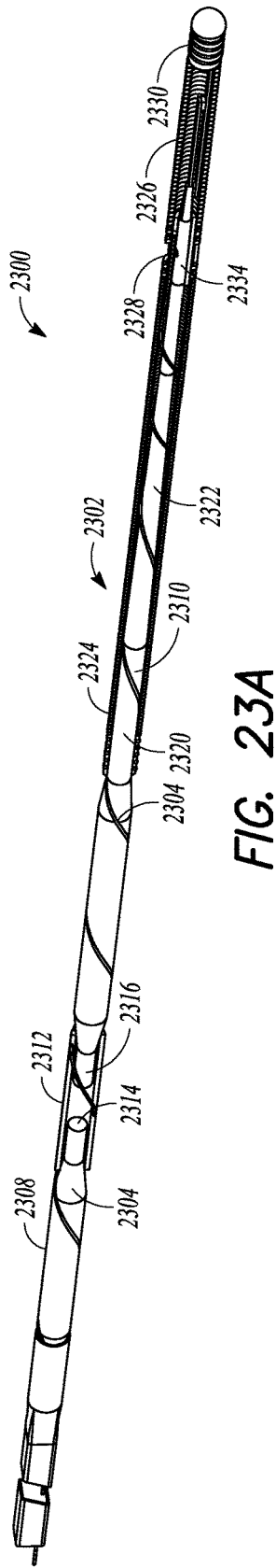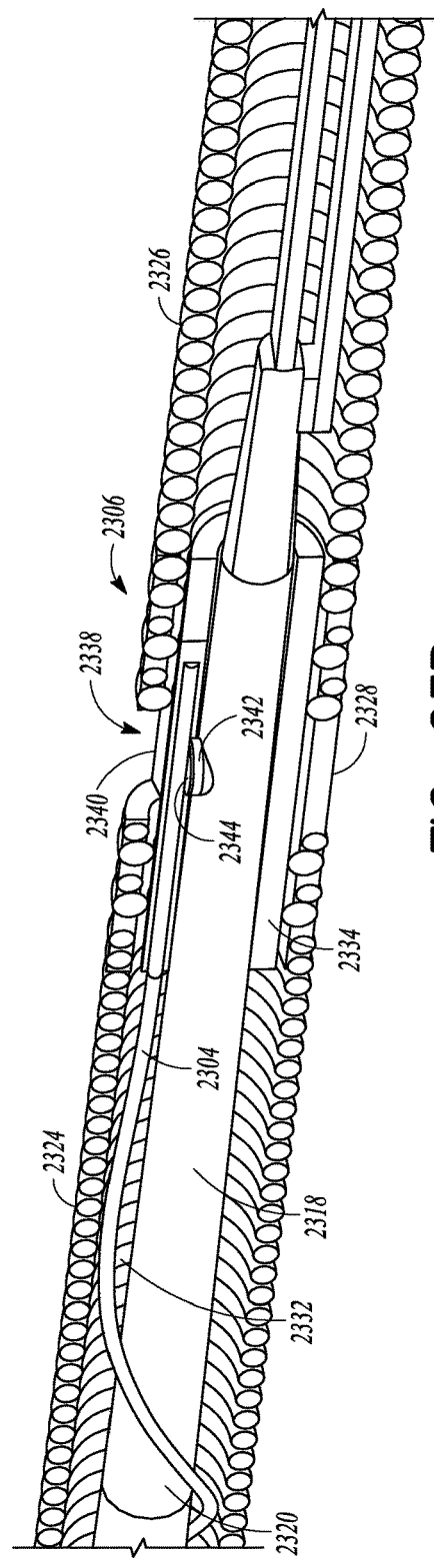
FIG. 23A
FIG. 23B

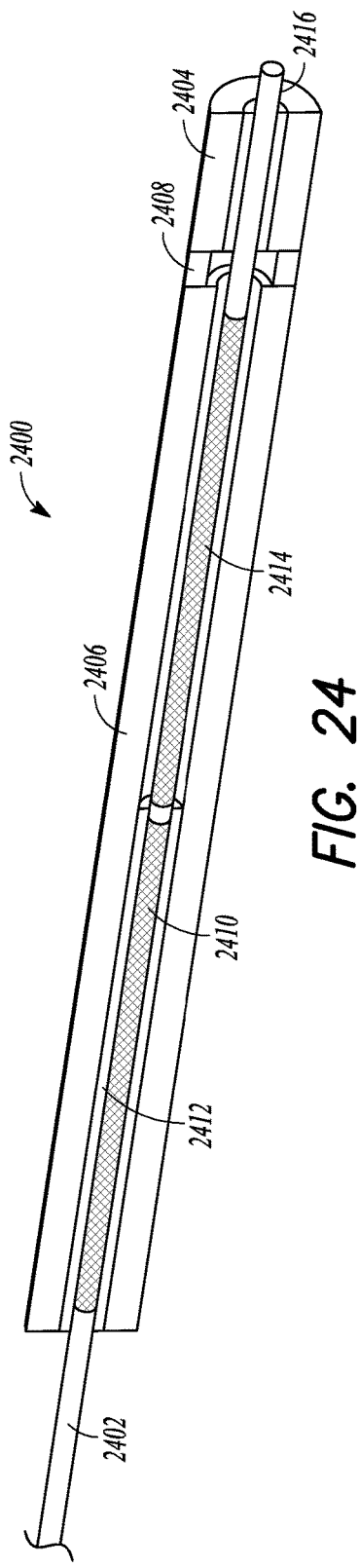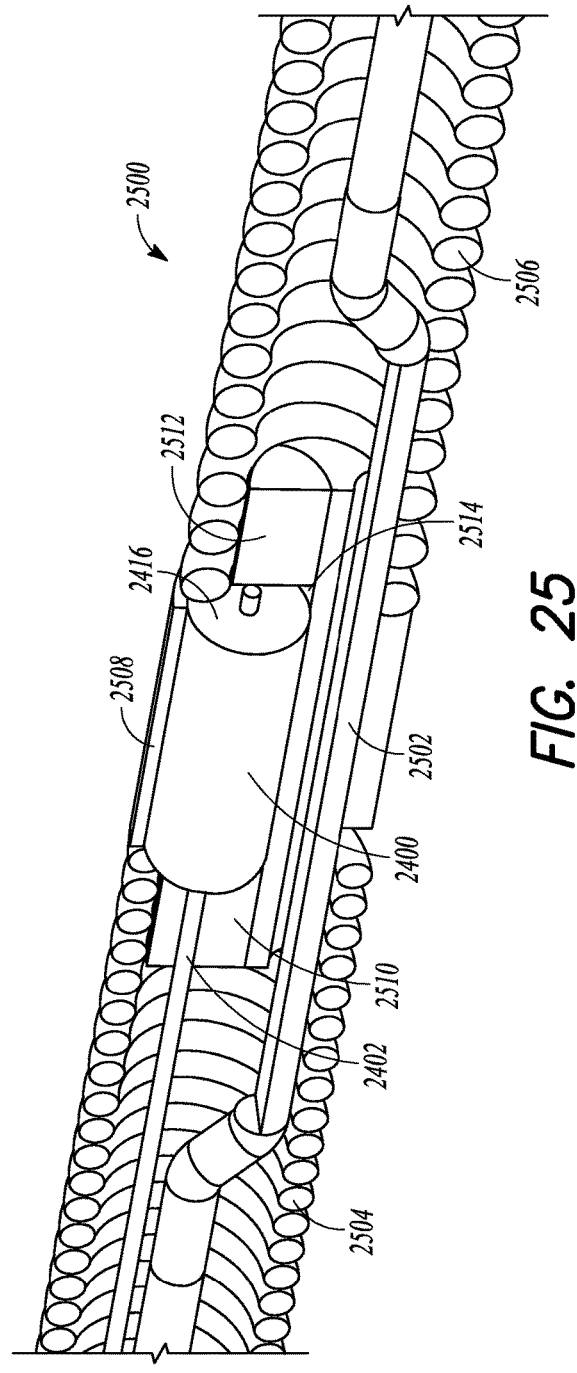

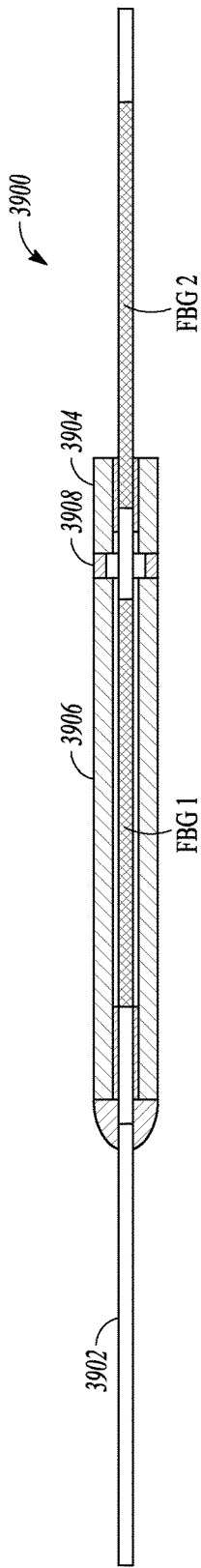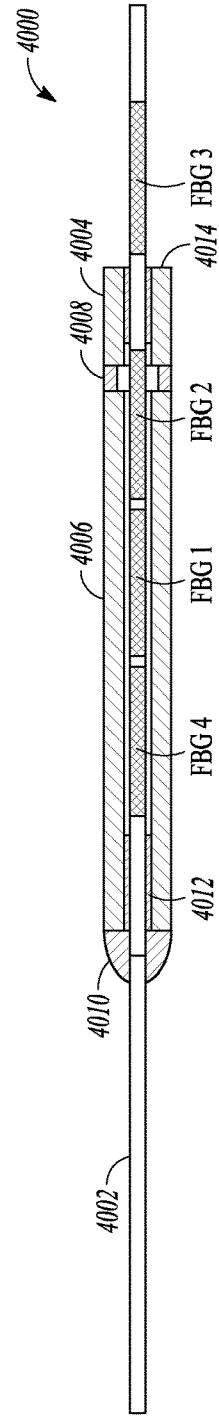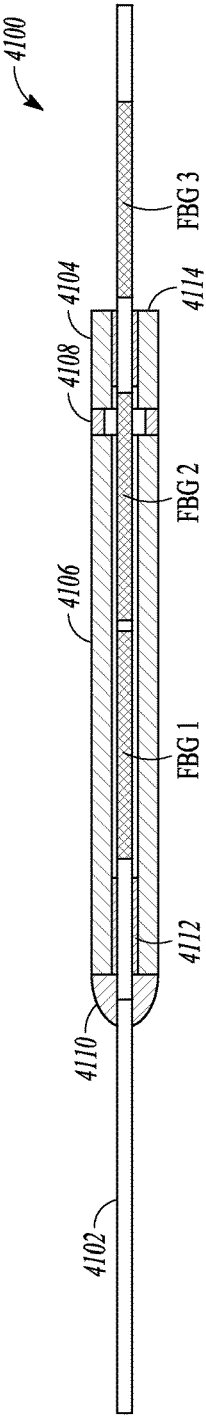

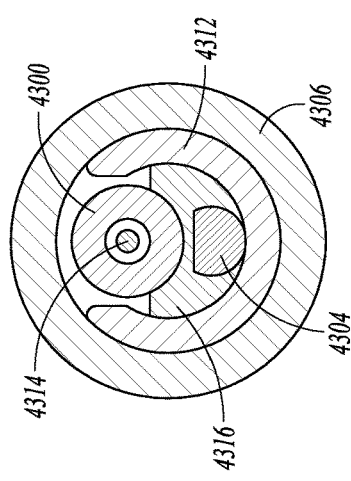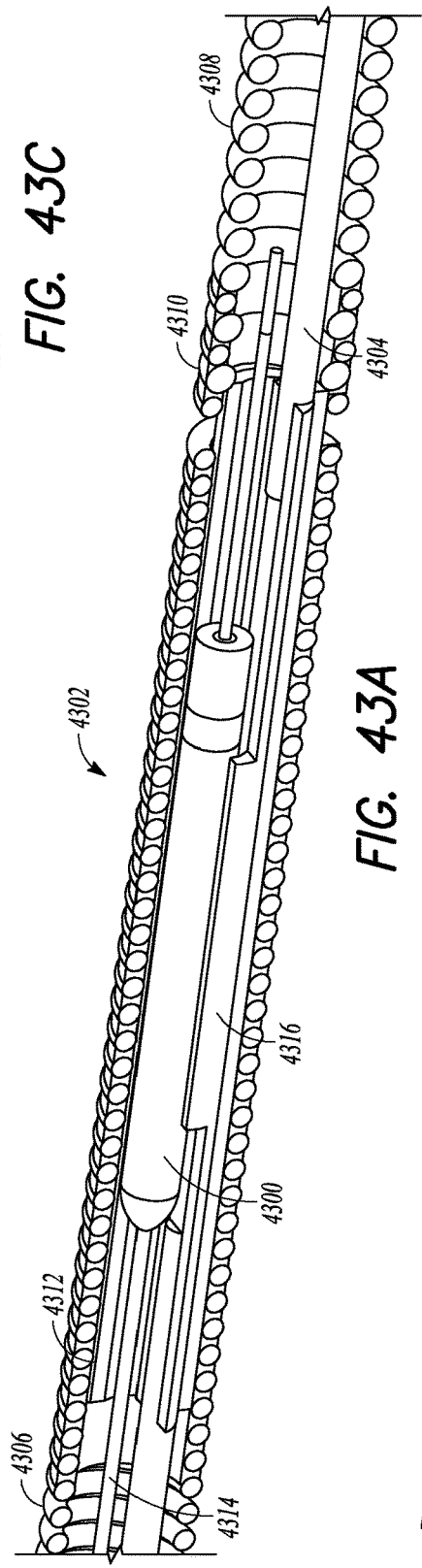
FIG. 43C
FIG. 43A
FIG. 43B

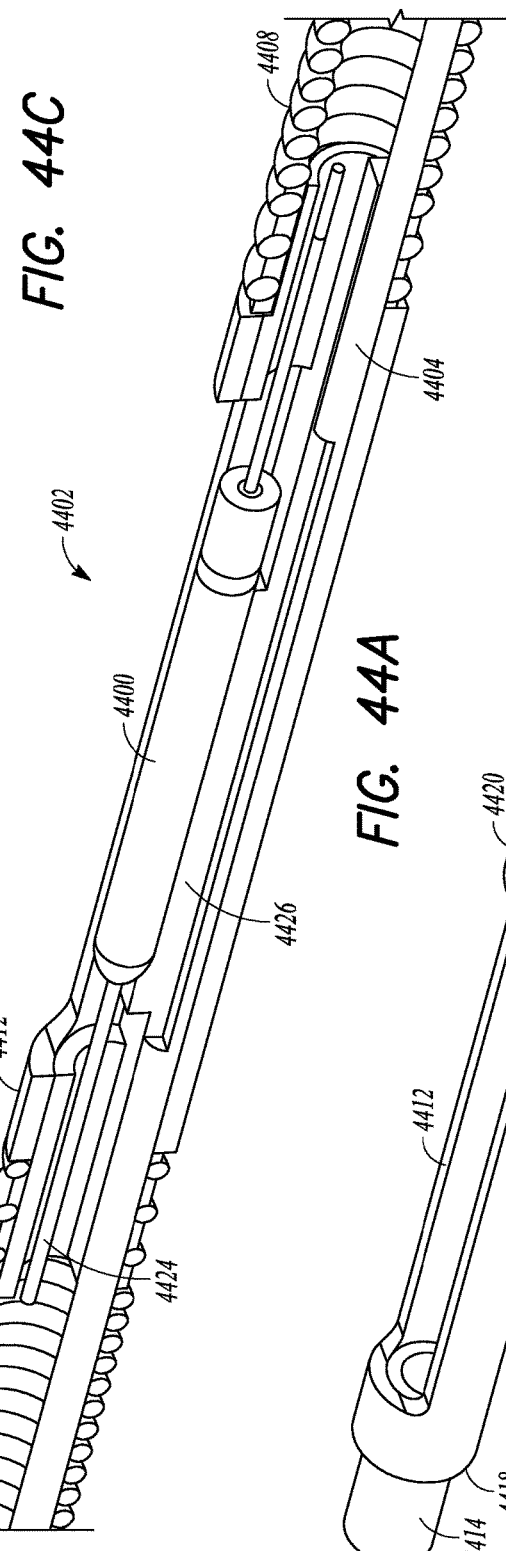
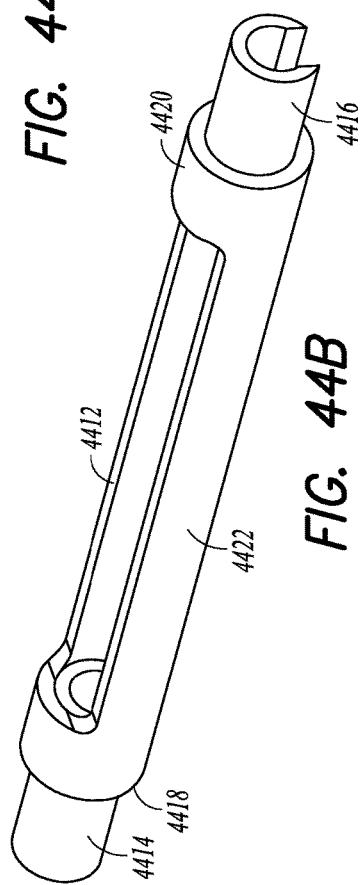
FIG. 44A
FIG. 44B
FIG. 44C

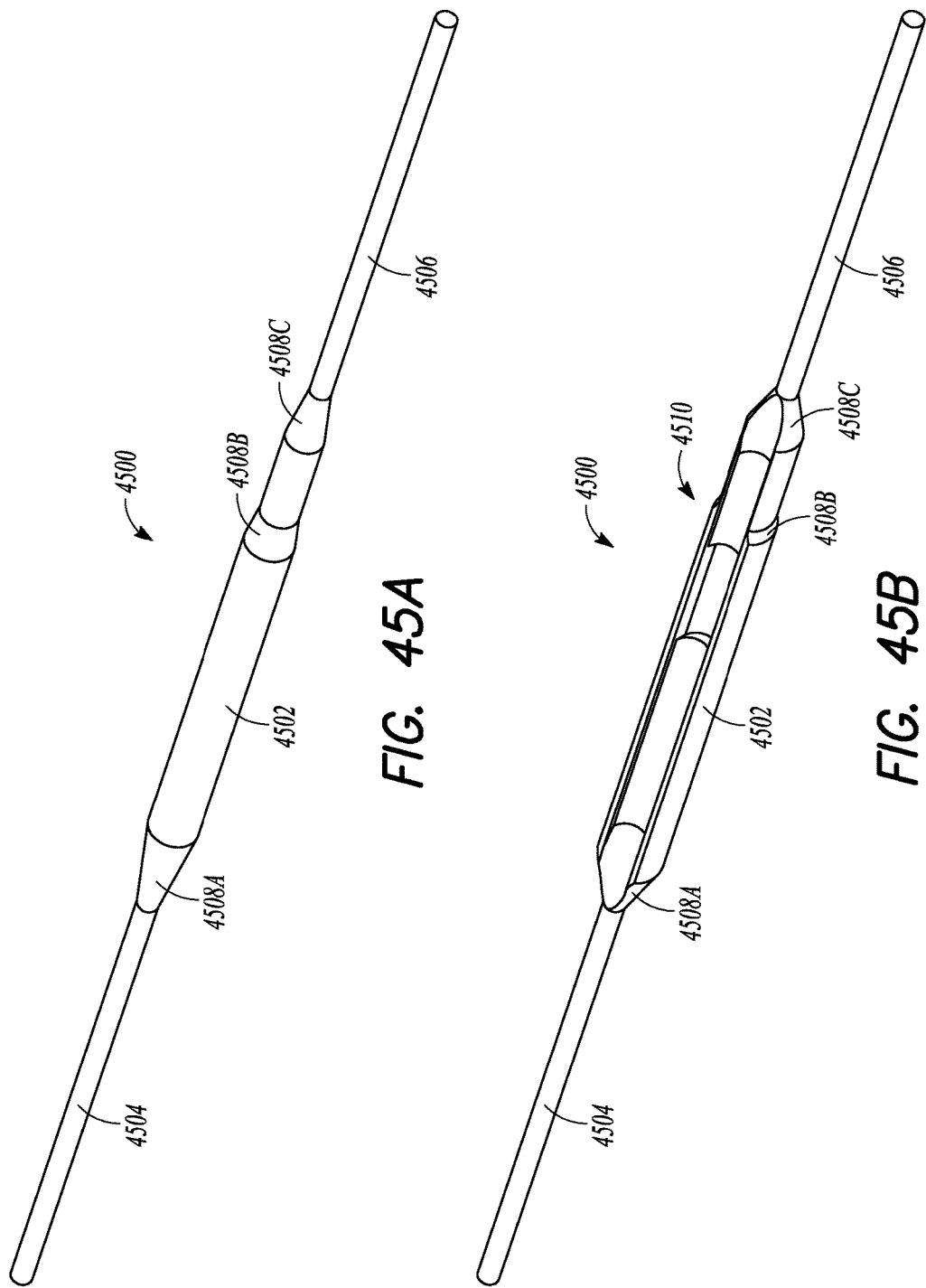

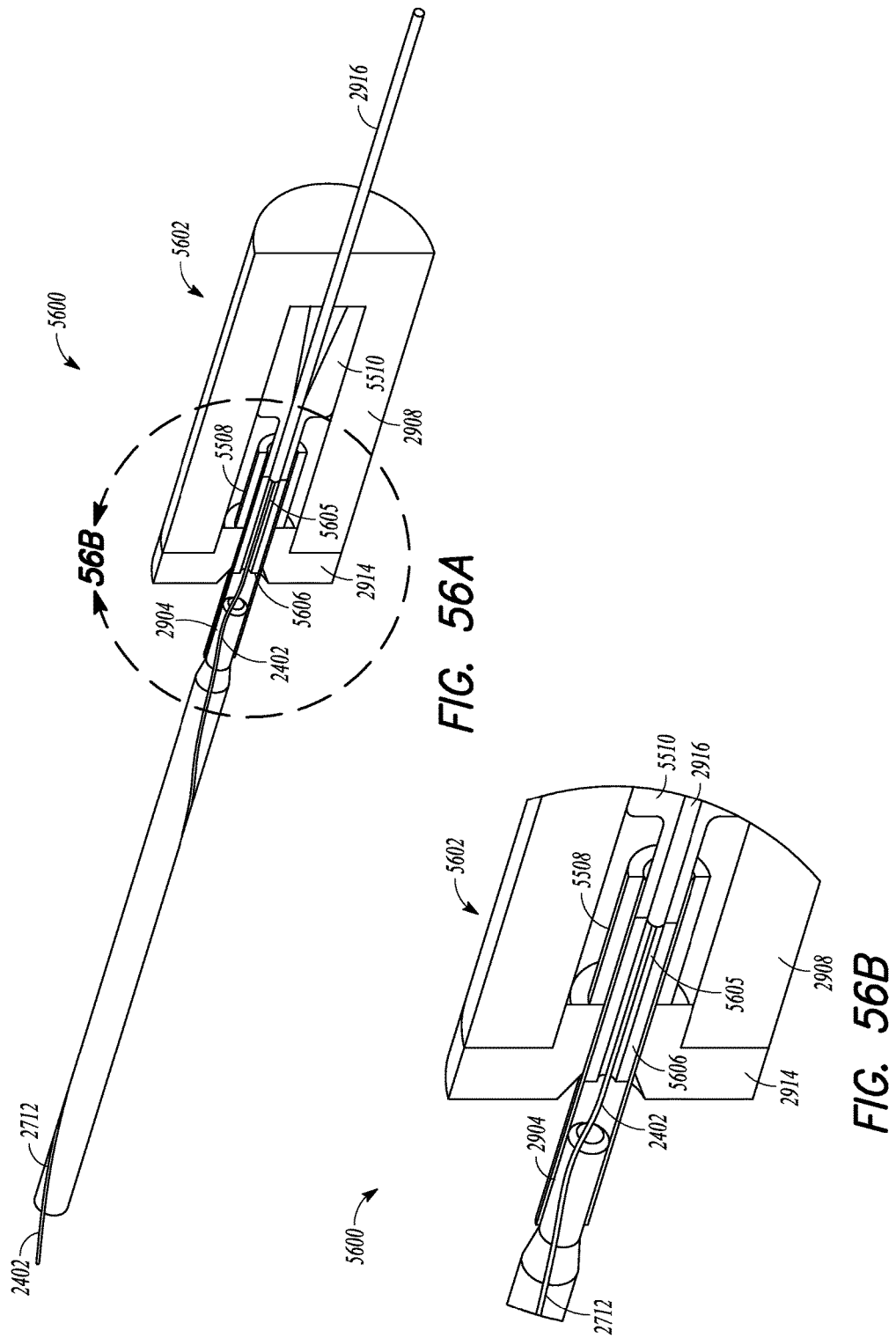

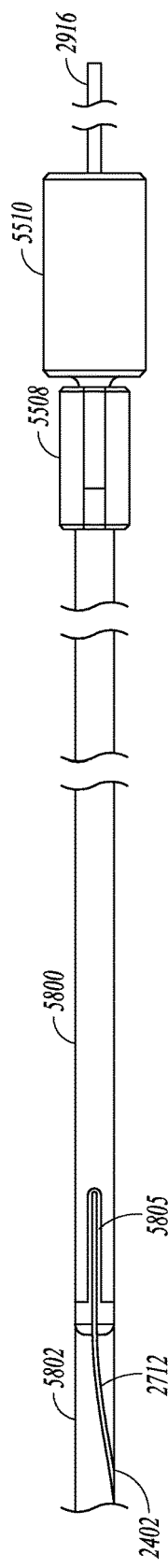
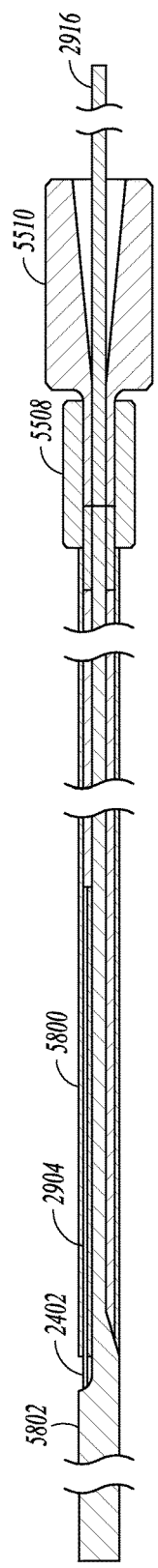
FIG. 58A
FIG. 58B

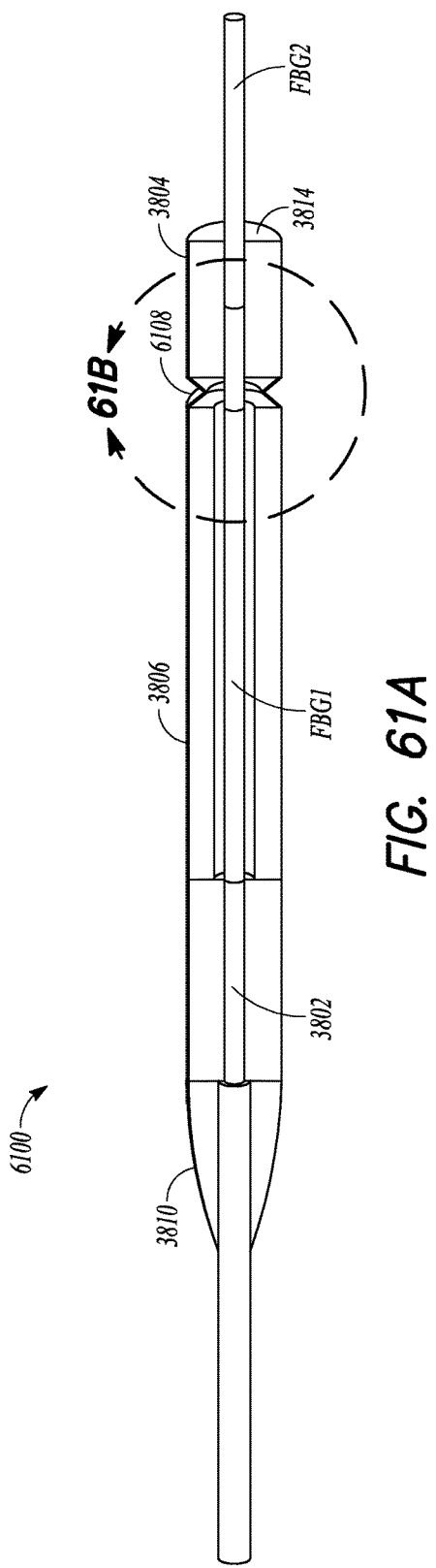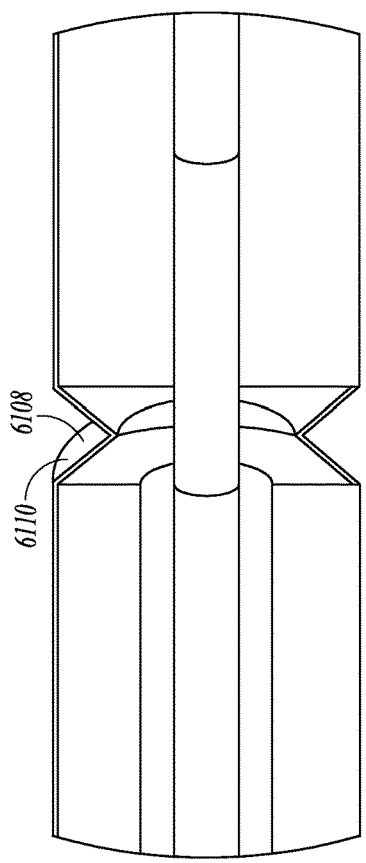
FIG. 61A
FIG. 61B

OPTICAL FIBER PRESSURE SENSOR

CLAIM OF PRIORITY

This application claims the benefit of priority of U.S. Provisional Patent Application Ser. No. 62/083,799, which was filed on Nov. 24, 2014, which is incorporated by reference herein in its entirety.

TECHNICAL FIELD

This document pertains generally to pressure sensing devices, imaging devices and methods and, in particular, to pressure sensing devices, imaging devices and methods using optical elements and techniques.

BACKGROUND

U.S. Patent Application Publication No. 2009/0180730 to Foster et al. is directed toward a device for sensing an acoustic signal. The device includes a flexible portion including a laser active region having an emitted wavelength that varies according to a mechanical force acting on the flexible portion, and including a flexible support member operable to flex or bend according to the acoustic signal. The flexible portion is coupled with the support member so as to cause the flexible portion to flex or bend in accordance with the support member, thereby changing the emitted wavelength of the laser active region of the flexible portion.

U.S. Pat. No. 7,680,363 to Wakahara et al. ("Wakahara") is directed toward an optical fiber pressure sensor capable of detecting a more minute pressure change. A base film is formed with a through hole passing through first and second surfaces. An optical fiber is fixed to the base film at a region other than the Fiber Bragg Grating (FBG) portion, such that the FBG portion is positioned on the through hole in plan view. The optical fiber pressure sensor is attached to an object body such that the second surface of the base film is closely attached to a surface of the object body directly or indirectly.

OVERVIEW

The present applicant has recognized, among other things, that other approaches to pressure sensing guidewires exhibit mechanical performance suitable for diagnostic assessment of coronary obstructions, but typically are not suitable for delivery of therapeutic devices. The present applicant has recognized that the other pressure sensing technology, namely piezoresistive or piezocapacitive silicon pressure sensors, and associated electrical cables, are relatively large compared to the size of the components of a typical therapy delivering guidewire. The present applicant has recognized that the incorporation of such other pressure sensing technology into a coronary guidewire substantially restricts the design of the mechanical components of the guidewire and results in significant compromises to the mechanical performance. The present applicant has recognized that a smaller pressure sensing technology, when incorporated into a contemporary coronary guidewire, would be advantageous in restoring the required mechanical performance requirements.

Optical fiber technology can be used in pressure sensors for oil discovery and production, as well as in larger diagnostic catheters for patients. The present applicant has recognized that telecommunication industry standard optical fiber would be too large to incorporate into high performance coronary guidewires. Accordingly, the present applicant has recognized, among other things, that miniaturization of the optical fiber and optical fiber based pressure sensor presents both a major challenge and a major advantage for incorporation into a coronary guidewire while minimizing the impact on the mechanical performance of the guidewire.

The present applicant has recognized, among other things, that the intrinsic sensitivity of an optical fiber sized for insertion into a body lumen may not be sufficient to generate an easily detectable signal within the range of pressures associated with a patient. The present applicant has recognized that miniaturization of the optical fiber can impart more flexibility into the fiber. This can be used to mechanically enhance the sensitivity of the fiber to pressure, such as with an extrinsic arrangement. The present applicant has recognized that using Fiber Bragg Gratings in the miniaturized optical fiber can provide a highly cost effective and readily manufacturable design. In addition, the present applicant has recognized that one or more other factors—such as the temperature coefficient of one or more Fiber Bragg Gratings (FBGs)—can be significantly higher than the intrinsic pressure sensitivity of the optical fiber. As such, a small drift in temperature within a patient can appear as a large pressure change artifact, which, in the context of pressure sensing, is unwanted and likely not acceptable due to the need for accurate pressure measurements. Accordingly, the present applicant has recognized that, among other things, it can be advantageous to provide an optical fiber pressure sensor guidewire that can include temperature calibration, compensation, or correction for an optical fiber pressure sensor, such as a Fiber Bragg Grating (FBG) arrangement for sensing pressure within a body lumen.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

FIGS. 7A-7C depict an example of a pressure sensor that can be used to implement various techniques of this disclosure.

FIGS. 9A-9C depict another example of a pressure sensor that can be used to implement various techniques of this disclosure.

FIGS. 10A-10D depict another example of a pressure sensor that can be used to implement various techniques of this disclosure.

FIGS. 12A-12C depict another example of a pressure sensor that can be used to implement various techniques of this disclosure.

FIGS. 13A-13G depict an example of a guidewire in combination with an optical fiber pressure sensor, in accordance with this disclosure.

FIGS. 14A-14C depict another example of a guidewire in combination with an optical fiber pressure sensor, in accordance with this disclosure.

FIGS. 15A-15C depict another example of a guidewire in combination with an optical fiber pressure sensor, in accordance with this disclosure.

FIGS. 21A-21G depict various examples of a guidewire in combination with an optical fiber pressure sensor, in accordance with this disclosure.

FIGS. 23A-23B depict another example of a guidewire in combination with an optical fiber pressure sensor, in accordance with this disclosure.

FIG. 24 shows an example of a portion of a concentric pressure sensor assembly.

FIG. 25 shows an example of the pressure sensor assembly as it can be prefinished and included or otherwise incorporated into a percutaneous intravascular guidewire assembly.

FIGS. 39-41 depict examples of portions of various pressure sensor assemblies.

FIG. 43A-43C depict another example of a guidewire in combination with an optical fiber pressure sensor.

FIG. 44A-44C depict another example of a guidewire in combination with an optical fiber pressure sensor.

FIGS. 45A-45B depict an example of a core wire that can be used in combination with an optical fiber pressure sensor.

FIGS. 56A and 56B show another example of a proximal region of a guidewire assembly, such as one of the various guidewire assemblies described herein, terminating at a proximal end connector.

FIGS. 58A-58B depict another example of a proximal region of a guidewire assembly, terminating at a proximal end connector.

FIGS. 61A and 61B depict another example of a portion of a pressure sensor assembly.

DETAILED DESCRIPTION

Figure 1:
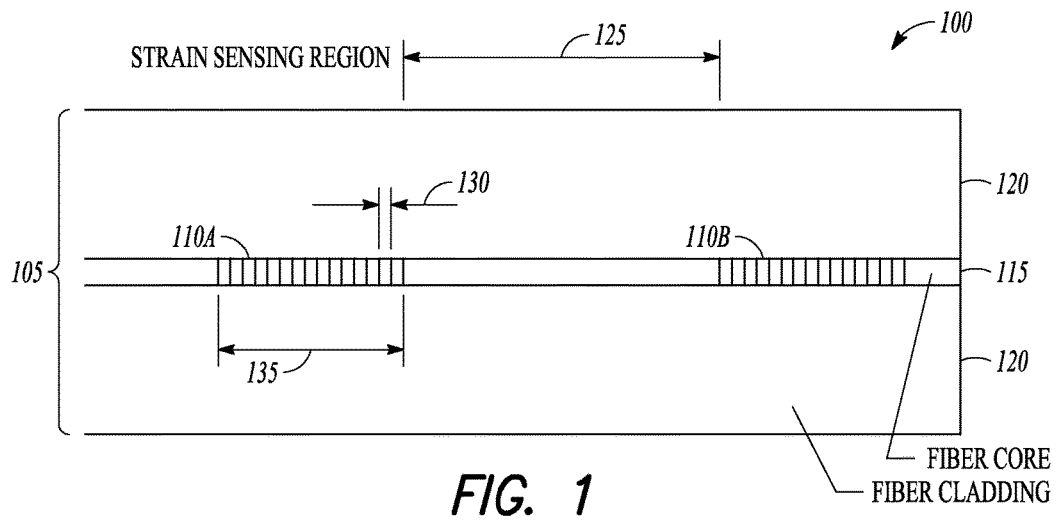
FIG. 1 is a cross-sectional side view illustrating generally, by way of example, but not by way of limitation, an example of an FBG pressure sensor in an optical fiber.

Before or during an invasive medical procedure, it can be desirable for a clinician, e.g., a physician, to take one or more pressure measurements from within a body lumen of a patient, e.g., a blood vessel, such as an artery or vein. For example, before implanting a stent at the site of an occlusion in a blood vessel, it can be desirable to determine the physiologic effect of the occlusion on the patient before making a decision whether to implant the stent. Furthermore, it can also be advantageous to measure the physiologic result of the stent implantation to ensure that the occlusion has been relieved. One way to determine the effect of the occlusion on the patient is to measure the drop in blood pressure across the occlusion, such as using a Fractional Flow Reserve (FFR) technique, an Instantaneous Wave-Free Ratio (iFR) technique, a Post-Interventional Peripheral FFR (pFFR) technique and others. Generally speaking, according to data generated by long term studies using the FFR technique, if there is more than a 20-25% drop in pressure across the occlusion during maximum blood flow, the patient can be considered a candidate for coronary stent implantation. Otherwise, it can be preferable to treat the patient with a pharmaceutical regimen rather than implant a stent. Occlusions that look visibly similar, using an intravascular or other imaging modality, can be vastly different in terms of pressure drop across the occlusion. Therefore, an accurate measurement of pressure drop across an occlusion may help to tease out those occlusions that should be treated using a stent from those occlusions that are adequately treated by a pharmaceutical regimen.

Measurement of pressure in a blood vessel has been achieved by incorporating miniaturized pressure sensors into guidewires that are small enough to be steered through the lumen of the vessel without also causing an obstruction, which would significantly alter the blood flow and create false pressure readings. These guidewires are typically of the same size as the guidewires which are used to treat coronary lesions, for example 0.014" diameter. However, incorporating pressure sensing capability into a small guidewire typically requires significant volume of the guidewire being used to accommodate the miniaturized sensing technology. Often, for example, the solid guidewire core wire is replaced by a more fragile hollow tube. These changes lead to compromises in the mechanical performance of the guidewire which can make it less suitable for delivering therapy, such as a stent in a coronary artery, which leads to time consuming and potentially risky exchanges of the guidewire as well as increased use of x-rays and contrast media. Therefore, the present applicant has recognized that there is a need to further miniaturize the pressure sensing technology such that the incorporation into a steerable guidewire has no significant effect on the mechanical performance of the guidewire. A high performance steerable guidewire with on-board highly miniaturized pressure sensing capability could, therefore, be used throughout a procedure to both measure the pressure and deliver therapy without the need to exchange guidewires.

The present applicant has recognized that it is desirable to incorporate highly miniaturized pressure measurement capability into high performance guidewires. Additionally, the present applicant has recognized that miniaturized pressure sensing capability can be combined with other highly miniaturized sensing or imaging technologies to achieve a high performance guidewire that can be used to guide and to fully optimize the treatment of a lesion. By way of example, the pressure sensing capability can be combined with highly miniaturized intravascular ultrasound (IVUS) imaging sensors to achieve a high performance guidewire for functional pressure measurement as well as real-time imaging of vessel structures, previously placed stents, obstructions, blood flow and other uses by itself or in combination with other devices. IVUS imaging is used to create an accurate visual record of the structure of the blood vessel, enabling accurate on-screen measurements of structural dimensions, storage of images, blood flow detection and visualization, as well as tissue characterization and other techniques.

The present applicant has recognized that a high performance guidewire incorporating highly miniaturized pressure sensing capability as well as, for example, IVUS imaging, could be used for functional pressure assessment of a lesion prior to treatment, imaging and on-screen measurement of the vasculature and lesions, accurate lesion sizing for optimal stent selection, real-time visually guided optimized stent deployment, and post-procedural functional measurement to confirm optimal treatment and other highly valuable uses. Highly miniaturized IVUS sensors can also be used for flow visualization using Doppler techniques, correlation techniques and other methods, and also tissue characterization, blood velocity measurements and other uses. Multiple arrays of IVUS sensors can be incorporated to create different viewing planes, such as a forward looking direction, and also 3-dimensional imaging. The present applicant has recognized that optical sensor technologies using optical fibers and optical sensors could be miniaturized to achieve the highly miniaturized sensing capabilities mentioned above and other sensing capabilities. Furthermore, multiple sensors or combinations of sensor types can be achieved and incorporated into a single guidewire. In addition, multiple measurements from the various combined sensors can be converted to data for presentation to the user through separate or combined consoles or modules on one or more screens or communication devices, or all on a single screen or communication device either serially or at once. The data may be displayed in real time and may also be recorded for subsequent playback during the procedure. The data can also be stored in a data system which can allow for entry into the patient record as well as further subsequent review.

The present applicant has recognized, among other things, the advantages and desirability of miniaturization of an optical fiber and optical fiber based pressure sensor or sensors, and other sensors, for incorporation into a coronary guidewire, which, in turn, can optionally be used for lesion assessment, guiding a balloon catheter or other device for positioning and securing the stent at the desired location, or for guiding other treatment techniques such as atherectomy, balloon angioplasty, thrombus aspiration, treatment of aneurysms and other uses.

The present applicant has recognized that multiple highly miniaturized pressure sensors, for example, can be incorporated into a high performance guidewire. The multiple highly miniaturized pressure sensors can be in optical communication with a single optical fiber or multiple optical fibers. Furthermore, the present applicant has recognized that the highly miniaturized pressure sensors, and other sensors, can be incorporated into guidewires of multiple different designs, and into other devices such as catheters or other devices for imaging, such as IVUS and optical coherence tomography, aspiration, treatment and the like.

The present applicant has recognized that the highly miniaturized sensors can be incorporated into very low profile catheters which can track over the present guidewires described herein as well as over conventional guidewires without sensors on-board. The present applicant has recognized that the miniaturized sensors can be adapted to various needs, for example the number of sensors that can fit into a larger device can be more than the number of sensors that can be incorporated into a 0.014" guidewire, for example. Increasing the number of sensors can allow, for example, the optimization of IVUS imaging in larger vessels. Furthermore, the size of the sensors can also be adapted for optimal functionality when incorporated in other devices. For example, the IVUS sensors can be adapted to operate at other ultrasonic wavelengths by variation of their size. In addition to the above mentioned uses in blood vessels, the guidewire or other devices incorporating the highly miniaturized sensors could be used in other places within the body for example in the brain, the ovaries, the heart, lungs and other suitable places.

An optical fiber pressure sensor based on FBG technology can have an intrinsic pressure sensitivity of about 0.00038 picometers (pm)/mmHg (about 0.02 pm/psi). Such an optical fiber pressure sensor based on FBG technology can have an intrinsic temperature sensitivity of about 10 pm/degree Celsius (° C.). The temperature sensitivity can increase if the optical fiber pressure sensor includes or is integrated or packaged with one or more materials having a higher coefficient of thermal expansion. The range of blood pressures in a patient is relatively low, e.g., about 0 millimeters of mercury (mmHg) to about 300 mmHg, and there is a need for high resolution within that range, e.g., 1-2 mmHg, where 51.7 mmHg equals 1 pound per square inch (psi), such as to adequately characterize the blood pressure drop across a blood vessel occlusion.

Based on these numbers, an uncompensated or uncorrected change in temperature of 0.1° C. can result in an equivalent intrinsic pressure drift of about 2632 mmHg or more than 1000 times the desired blood pressure measurement resolution. As mentioned above, when using an optical fiber pressure sensor capable of insertion into a body lumen of a patient, e.g., an animal such as a human, a small, uncompensated or uncorrected drift in temperature within the patient, e.g., as a result of an injected imaging contrast medium, can appear as an artifact that incorrectly indicates a large change in pressure. This can be due in part to the relatively low intrinsic sensitivity of the optical fiber pressure sensor to pressure and the relatively high intrinsic sensitivity to temperature of the optical fiber associated with the optical fiber pressure sensor. As such, a small, uncompensated drift in temperature can be unacceptable due to the need for accurate pressure measurements.

Using one or more techniques of this disclosure, a Fiber Bragg Grating (FBG) interferometer or other optical fiber pressure sensor guidewire can be temperature compensated, such as for permitting accurate pressure sensing within a body lumen. In addition, this disclosure describes techniques for increasing the overall sensitivity of an optical fiber pressure sensor guidewire, such as to generate an easily detectable blood pressure indicating output signal providing the desired resolution and accommodating the range of pressures associated with the patient.

It should be noted that the optical fiber described in this disclosure can have a diameter of between about 20 microns and about 80 microns (where a micron is a unit of length equal to one millionth of a meter). By way of comparison, a standard telecommunication optical fiber has a diameter of about 125 microns. This marked reduction in size can cause numerous challenges arising from the differences in the optics properties and mechanical behavior of such a drastically reduced size optical fiber.

FIG. 1 is a cross-sectional side view illustrating generally, by way of example, but not by way of limitation, an example of a strain-detecting or pressure-detecting optical FBG sensor 100 in an optical fiber 105. The FBG sensor 100 can sense pressure received from a nearby area, and can transduce the received pressure into an optical signal within the optical fiber 105. The FBG sensor 100 can include Fiber Bragg gratings 110A-B in an optical fiber core 115, such as surrounded by an optical fiber cladding 120. The gratings 110A-B can be separated by a strain or pressure sensing region 125, which, in an example, can be about a millimeter in length. In an example, strain or pressure can be sensed, such as by detecting a variation in length of the optical path between these gratings 110A-B.

A Fiber Bragg Grating can be implemented as a periodic change in the optical refractive index of a selected axial portion of the optical fiber core 115. Light of specific wavelengths traveling down such a portion of the core 115 will be reflected. The period (distance or spacing) 130 of the periodic change in the optical index can determine the particular wavelengths of light that will be reflected. The degree of optical refractive index change and the axial length 135 of the grating 110A-B can determine the ratio of light reflected to that transmitted through the grating 110A-B.

Figure 2:
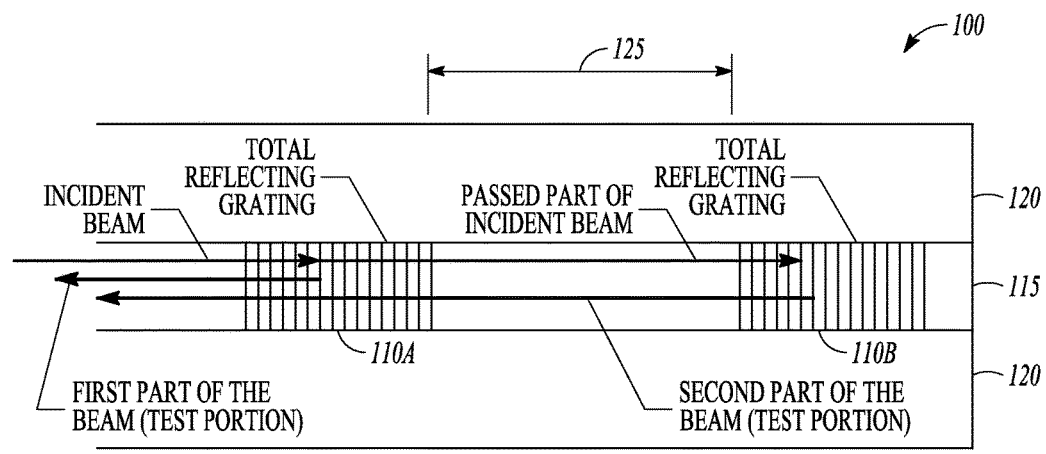
FIG. 2 is a cross-sectional side view illustrating generally, by way of example, but not by way of limitation, an example of an FBG grating interferometer sensor.

FIG. 2 is a cross-sectional side view illustrating generally, by way of example, but not by way of limitation, an operative example of an interferometric FBG sensor 100. The example of FIG. 2 can include two gratings 110A-B, which can act as mirrors that can both be partially reflective such as for a specific range of wavelengths of light passing through the fiber core 115. Generally, the reflectivity of each grating of a particular pair of gratings 110A-B will be substantially similar to the other grating in that particular pair of gratings 110A-B, but can differ between gratings of a particular pair of gratings 110A-B for particular implementations, or between different pairs of gratings 110A-B, or both. This interferometric arrangement of FBGs 110A-B can be capable of discerning the "optical distance or optical pathlength" between FBGs 110A-B with extreme sensitivity. The "optical distance or pathlength" can be a function of the effective refractive index of the material of fiber core 115 as well as the physical distance 125 between FBGs 110A-B. Thus, a change in the refractive index can induce a change in optical path length, even though the physical distance 125 between FBGs 110A-B has not substantially changed.

An interferometer, such as can be provided by the FBG sensor 100, can be understood as a device that can measure the interference between light reflected from each of the partially reflective FBGs 110A-B. When the optical path length between the FBG gratings 110A-B is an exact integer multiple of the wavelength of the optical signal in the optical fiber core 115, then the light that passes through the FBG sensor 100 will be a maximum and the light reflected will be a minimum, such that the optical signal can be substantially fully transmitted through the FBG sensor 100. This addition or subtraction of grating-reflected light, with light being transmitted through the optical fiber core 115, can be conceptualized as interference. The occurrence of full transmission or minimum reflection can be called a "null" and can occur at a precise wavelength of light for a given optical path length. Measuring the wavelength at which this null occurs can yield an indication of the length of the optical path between the two partially reflective FBGs 110A-B. In such a manner, an interferometer, such as can be provided by the FBG optical fiber pressure sensor 100, can sense a small change in distance, such as a change in the optical distance 125 between FBGs 110A-B resulting from a received change in pressure. In this manner, one or more FBG sensors can be used to sense one or more pressures within a body lumen of a patient. This arrangement is an example of an FBG Fabry-Perot interferometer, which can be more particularly described as an Etalon, because the physical distance 125 between the FBGs 110A-B is substantially fixed.

The sensitivity of an interferometer, such as can be included in the FBG sensor 100, can depend in part on the steepness of the "skirt" of the null in the frequency response. The steepness of the skirt can be increased by increasing the reflectivity of the FBGs 110A-B, which also increases the "finesse" of the interferometer. Finesse can refer to a ratio of the spacing of the features of an interferometer to the width of those features. To provide more sensitivity, the finesse can be increased. The higher the finesse, the more resonant the cavity, e.g., two FBGs and the spacing therebetween. The present applicant has recognized, among other things, that increasing the finesse or steepness of the skirt of FBG sensor 100 can increase the sensitivity of the FBG sensor 100 to pressure within a particular wavelength range but can decrease the dynamic range of the FBG sensor 100. As such, keeping the wavelength of the optical sensing signal within the wavelength dynamic range of the FBG sensor 100 can be advantageous, such as to provide increased sensitivity to pressure. In an example, a closed-loop system can monitor a representative wavelength (e.g., the center wavelength of the skirt of the filtering FBG sensor 100). In response to such information, the closed-loop system can adjust the wavelength of an optical output laser to remain substantially close to the center of the skirt of the filter characteristic of the FBG sensor 100, even as forces external to the optical fiber 105, such as bending and stress, can cause shifting of the center wavelength of the skirt of the filter characteristic of the FBG sensor 100.

In an example, such as illustrated in FIG. 2, the interferometric FBG sensor 100 can cause interference between that portion of the optical beam that is reflected off the first partially reflective FBG 110A with that reflected from the second partially reflective FBG 110B. The wavelength of light where an interferometric null will occur can be very sensitive to the "optical distance" between the two FBGs 110A-B. The interferometric FBG sensor 100 of FIG. 2 can provide another very practical advantage. In the example illustrated in FIG. 2, the two optical paths along the fiber core 115 are the same, except for the sensing region between FBGs 110A-B. This shared optical path can ensure that any optical changes in the shared portion of optical fiber 105 will have substantially no effect upon the interferometric signal; only the change in the sensing region 125 between FBGs 110A-110B is sensed. Additional information regarding FBG strain sensors can be found in U.S. Patent Application Publication No. 2010/0087732 to Eberle et al., which is incorporated herein by reference in its entirety, including its disclosure of FBGs and their applications.

Figure 3:
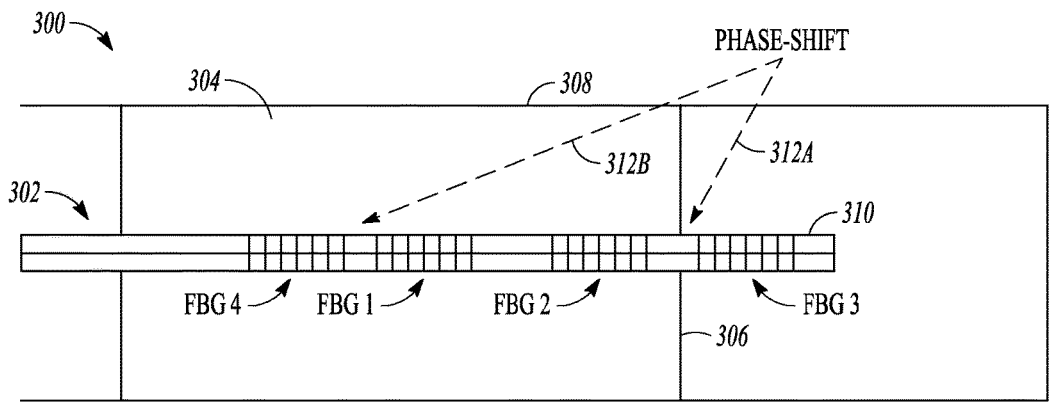
FIG. 3 is a conceptual diagram illustrating various example configurations FBG of an optical fiber pressure sensor, in accordance with this disclosure.

FIG. 3 is a conceptual diagram illustrating various examples of FBG configurations of an FBG optical fiber pressure sensor 300, in accordance with this disclosure. The FBG optical fiber pressure sensor 300 can include an optical fiber 302 that can extend longitudinally through a stiff, rigid, or solid mounting 304. As seen in FIG. 3, a portion of the optical fiber 302 extends beyond a distal end 306 of the mounting 304. The optical fiber 302 and the mounting 304 can be disposed within a housing 308. Using one or more techniques of this disclosure, such as shown and described in detail in this disclosure with respect to FIGS. 13-15, an optical fiber pressure sensor can include an optical fiber that can be combined with a guidewire, such as for diagnostic assessment of a coronary obstruction, for example.

As described in more detail below, two or more FBGs, e.g., FBGs 1-4, can be included in the FBG pressure sensor 300, such as for pressure sensing. One or more additional gratings can be included, and such additional one or more gratings can be insulated or isolated from influence caused by (1) bending (of the fiber) and/or (2) pressure. These insulated or isolated additional gratings can be arranged for providing one or more of temperature calibration, compensation, or correction. In an example, the additional grating(s) can provide an independent (of pressure and fiber bending) measure of temperature, such as for feedback to a temperature compensation scheme or method of an optical fiber pressure sensor 300. The optical fiber pressure sensor 300 can optionally include a sealed or other cavity (not depicted in FIG. 3), such as below a portion of the optical fiber 302, e.g., below FBG 3, which can amplify changes in pressure, or otherwise provide increased optical response to changes in pressure. Some example configurations that can include a sealed cavity are described in more detail below.

Figure 4A:
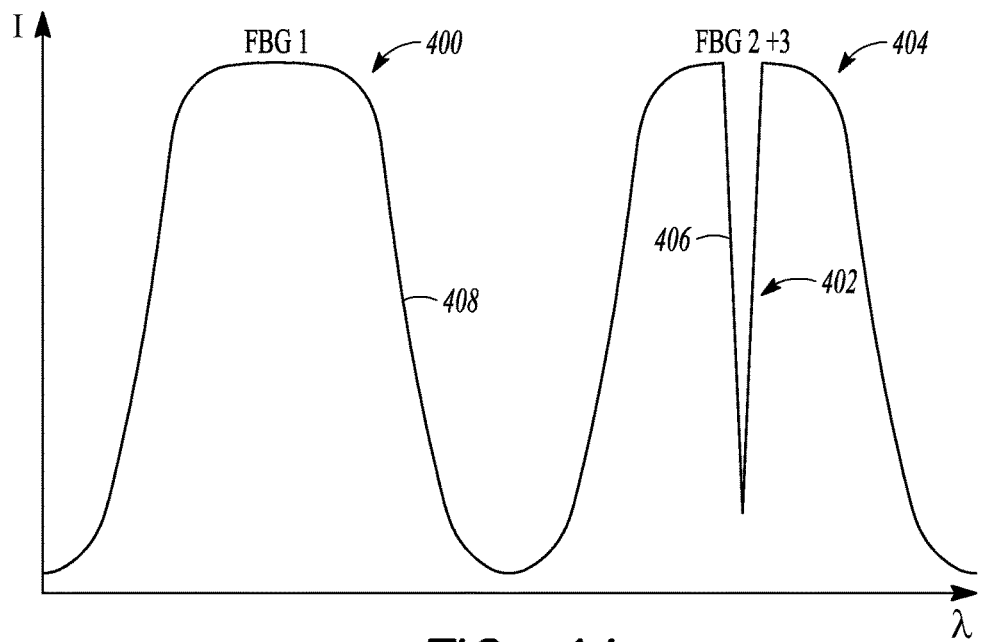
FIGS. 4A-4C depict various conceptual response diagrams related to the conceptual diagram of FIG. 3.

In FIG. 3, FBG 1 can be a FBG that produces a broad reflection band at the center of the spectrum of FBG 1, such as shown generally at 400 in the response diagram depicted in FIG. 4A, in which the x-axis represents wavelength and the y-axis represents the intensity of the reflected light. FBG 2 and FBG 3, although depicted and referred to as separate gratings, can represent a single FBG that can be split into two identical, smaller FBGs and separated by a small phase difference (or phase-shifted) of 180 degrees, for example.

For example, the phase shift could be built into a phase mask that is used to write the gratings onto the fiber, e.g., an electron beam generated phase mask. Illumination of the phase mask can result in a phase shift. In another example, a first grating can be written onto the fiber via a phase mask. Then, the phase mask can be moved by a distance equivalent to a 180 degree phase shift, for example, and a second grating can be written onto the fiber.

The reflections from FBG 2 interfere with the reflections from FBG 3 because of the phase shift between FBG 2 and FBG 3, shown as a phase shift region 312A in FIG. 3. As a result, a narrow transmission notch 402 is created within the reflection band shown generally at 404 in the wavelength response diagram depicted in FIG. 4A.

In an example, pressure changes can be detected by the optical fiber pressure sensor 300, e.g., within a patient's body, such as by detecting or amplifying the phase-shift between two FBGs, e.g., FBG 2 and FBG 3. This technique is in contrast to optical pressure sensing techniques that measure the shift in wavelength of the FBG itself. Using various techniques of this disclosure, the phase-shift between FBGs can be modified rather than a wavelength shift of the FBG itself.

As seen in FIG. 3, FBG 3 can extend distally outward beyond the distal end 306 of the mounting 304. A change in pressure can cause the distal portion 310 of the optical fiber 302 to bend slightly against the distal end 306 of the mounting 304, which, in turn, can cause the distal end 306 to mechanically act upon the phase-shift region 312A between FBG 2 and FBG 3. The mechanical forces acting upon the phase-shift region 312A between FBG 2 and FBG 3 can concentrate a stress in the phase-shift region 312A of the optical fiber 302. The concentrated stress in the phase-shift region 312A changes the refractive index of the optical fiber 302 in the stressed region, which, in turn, can alter, or amplify, the phase relationship between FBG 2 and FBG 3. The change in phase-shift between FBG 2 and FBG 3 can be quantified and the change in pressure can be determined from the quantified phase-shift.

For example, as described in more detail below, a wavelength of a narrow band laser (in relation to the wavelength response of FBGs 2 and 3) can be locked on a point on a slope 406 of the narrow transmission notch 402 in FIG. 4A, e.g., at about 50% of the depth of the notch 402. As the pressure changes, the notch 402 shifts and, consequently, the point on the slope 406 shifts. A tracking circuit can then track the point on the slope 406, and a phase-shift can be determined from its change in position. The intensity of reflected light will be modified when the notch 402 moves. In the example in the diagram, if the notch 402 moves downward in wavelength, then the intensity of the signal reflected will increase. If the notch 402 moves upward in wavelength, then the intensity of the signal reflected will decrease. If it is chosen that the laser wavelength would be on the opposite side of the notch 402, then the effect would be reversed.

As indicated above, one or more external factors such as the temperature coefficient of one or more Fiber Bragg Gratings (FBGs) can be significantly higher than the intrinsic pressure sensitivity of the optical fiber pressure sensor that can include such FBGs. As such, a small drift in temperature within a patient can spuriously appear as a large change in pressure. Such a temperature-induced artifact in the pressure response signal may be unacceptable due to the need for accurate pressure measurements. The present applicant has recognized, among other things, that it can be advantageous to provide the optical fiber pressure sensor guidewire of this disclosure with a temperature compensated Fiber Bragg Grating (FBG) arrangement, such as for accurately sensing pressure within a body lumen, for example.

The conceptual diagram of FIG. 3 can be used to describe several different configurations for a temperature compensated FBG optical fiber pressure sensor 300. Examples of more detailed configurations are shown and described below with respect to FIGS. 7-10 and FIG. 12.

In a first example of a configuration, a FBG optical fiber pressure sensor 300 can include FBGs 1-3 (FBG 4 need not be included). FBGs 2 and 3, which can be configured to operate at the same wavelength (e.g., a first wavelength between about 1000 nanometers (nm) and about 1700 nm), can form a phase-shift structure that can be used to sense pressure, such as described in detail above. To recap, a concentration in stress in the phase-shift region between the two gratings (e.g., FBG 2 and FBG 3), as a result of the bending of the optical fiber 302 changes the refractive index of the optical fiber 302 in the phase-shift region. The change in the refractive index of the optical fiber 302 in the phase-shift region can alter the phase relationship between FBG 2 and FBG 3, which can be quantified, and the change in pressure can be determined from the quantified phase-shift. The phase-shift, however, is not compensated for temperature, which may not acceptable, as explained above.

FBG 1 can be configured to be substantially independent of pressure, such as by locating it within the stiff, rigid, or solid mounting 308. Therefore, FBG 1 can be used to measure ambient temperature, such as to provide a temperature compensated optical fiber pressure sensor. FBG 1 can be configured to operate at a substantially different wavelength than that of FBGs 2 and 3 (e.g., a second wavelength between 1000 nanometers (nm) and 1700 nm). In this manner, FBG 1 has no interaction with FBGs 2 and 3. As such, FBG 1 can provide a measure of ambient temperature that is independent of pressure variations. In a manner similar to that described above with respect to tracking the change in position of the notch 402 of FIG. 4A, a wavelength of a narrow band laser (in relation to the response of the FBG 1) can be locked on a point on a slope 408 of the response of FBG 1 in FIG. 4A, e.g., at about 50% of the depth of the response. The wavelength of the locked point on the slope 408 shifts as the temperature changes. A tracking circuit can then track the locked point on the slope 408 and a change in ambient temperature can be determined from its change in position.

In order to generate a pressure signal that is ambient temperature compensated, the signal generated by FBG 1 can be used as a reference to null a shift in temperature. A controller circuit can be configured to control subtraction of the temperature reference signal (from FBG 1) from the temperature and pressure signal (from FBGs 2 and 3), such as to generate a temperature compensated pressure signal. An example of a temperature compensation technique is described in more detail in this disclosure, such as with respect to FIG. 5.

In a second example of a configuration, the FBG sensor 300 can include an optical fiber, a stiff, rigid, or solid mounting, a housing, and FBGs 1-3 (FBG 4 need not be included). FBGs 1-3 can be positioned very close to each other and can thus form a very compact structure. FBGs 2 and 3, which can be configured to operate at the same wavelength (e.g., a first wavelength between 1000 nm and 1700 nm), can form a phase-shift structure that can be used to sense pressure. The phase shift between FBGs 2 and 3 can result in a signal that changes with pressure and temperature.

FBG 1 can be configured to operate at a similar, but slightly different, wavelength than that of FBGs 2 and 3 (e.g., a second wavelength near the first wavelength of FBGs 2 and 3 and between 1000 nm and 1700 nm). In this manner, FBG 1 can form a resonant feature with FBGs 2 and 3 at a slightly different wavelength. FBG 1 can result in a signal that changes with respect to temperature changes.

Figure 4B:
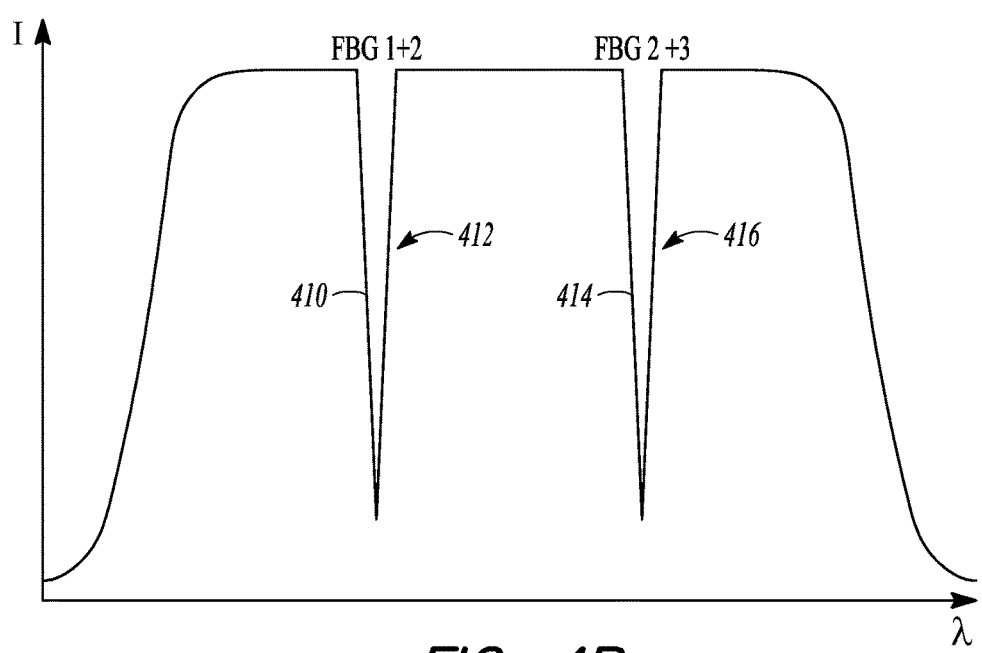

A conceptual illustration of the response of FBGs 1-3 is depicted in FIG. 4B, where the x-axis represents wavelength and the y-axis represents the intensity of the reflected light. Again, the techniques of this disclosure need not sense a shift in the wavelength of the gratings, but can instead sense a change in the phase between the gratings. The temperature compensating element, e.g., FBG 1, is in resonance with part of the pressure sensing structure, e.g., FBGs 2 and 3. As such, FBG 1 can be linked to the pressure sensing structure rather than being an independent element. Such a configuration can provide a compact structure.

Similar to the first example of a configuration, such as to generate a pressure signal that is temperature compensated, the signal generated by FBG 1 can be used as a reference, such as to null a shift in temperature. A slope 410 of the notch 412 and a slope 414 of the notch 416 can each be tracked and used to determine changes in temperature and pressure, such as based on their respective changes in position. A controller circuit can be configured to control the subtraction of the temperature reference signal (e.g., from FBG 1) from the temperature and pressure signal (e.g., from FBGs 2 and 3) such as to generate a temperature compensated pressure signal.

In a third example of a configuration, the FBG sensor 300 can include an optical fiber, a stiff, rigid, or solid mounting, a housing, and FBGs 1-4. FBGs 2 and 3, which can be configured to operate at the same wavelength, can form a first phase-shift structure that can be used to sense pressure. The phase shift between FBGs 2 and 3 can result in a signal that changes with pressure or temperature, or both.

FBGs 1 and 4, which can be configured to operate at the same wavelength, can form a second phase-shift structure that can be used to sense temperature. The reflections from FBG 4 interfere with the reflections from FBG 1 because of the phase shift between FBG 4 and FBG 1, shown as a phase shift region 312B in FIG. 3. The phase shift between FBGs 1 and 4 can result in a signal that changes with temperature and that is independent of pressure.

Figure 4C:
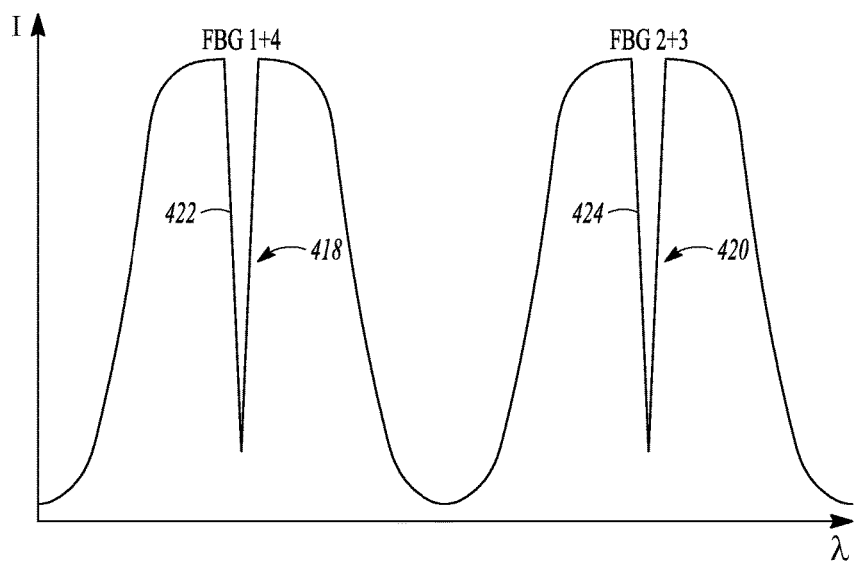

A conceptual illustration of the response of FBGs 1-4 of the third example of a configuration is depicted in FIG. 4C, where the x-axis represents wavelength and the y-axis represents the intensity of the reflected light. As seen in FIG. 4C, the response includes two notches 418, 420. The third example of a configuration can provide more accurate measurements than the first example of a configuration because the notches 418, 420 are generally more sensitive to any changes than responses without notches, e.g., the response 400 in FIG. 4A.

Similar to the first and second examples of configurations, in order to generate a pressure signal that is temperature compensated, the signal generated by FBGs 1 and 4 can be used as a reference, such as to null a shift in temperature. A slope 422 of the notch 418 and a slope 424 of the notch 420 can each be tracked and used to determine changes in temperature and pressure based on their respective changes in position. A controller circuit can be configured to control subtraction of the temperature reference signal (e.g., from FBG 1) from the temperature and pressure signal (e.g., from FBGs 2 and 3), such as to generate a temperature compensated pressure signal.

Using any one of the three examples of configurations described above, an optical fiber pressure sensor can be provided that can be suitable for delivery within a body lumen, e.g., for diagnostic assessment of coronary obstructions. In addition, any one of the three examples of configurations can compensate for temperature drift and can be fitted to a guidewire, such as for insertion into a body lumen of a patient. In any of the three examples the wavelength of the FBGs used for temperature calibration, compensation, or correction can be above or below the wavelength of the FBGs used for the pressure sensing.

Again, FIG. 3 is for conceptual purposes only and this disclosure is not limited to the three example configurations described above with respect to FIG. 3. Other FBG configurations to sense pressure and compensate for temperature drift are possible, examples of which are described in more detail below.

In addition, as described in more detail below, various techniques are disclosed for increasing the intrinsic sensitivity of an optical fiber pressure sensor, such as to generate an accurate output signal within the range of pressures associated with a patient. Generally speaking, these techniques can include focusing a response of a pressure sensor membrane into a smaller area, such as to increase the optical response to the received pressure, e.g., from pressure waves.

FIGS. 4A-4C depict various wavelength response diagrams related to the conceptual diagram and examples of configurations described above with respect to FIG. 3. In FIGS. 4A-4C, the x-axis represents wavelength and the y-axis represents the intensity of the reflected light. The response diagrams were described above in connection with the examples of configurations of FIG. 3.

Figure 5:
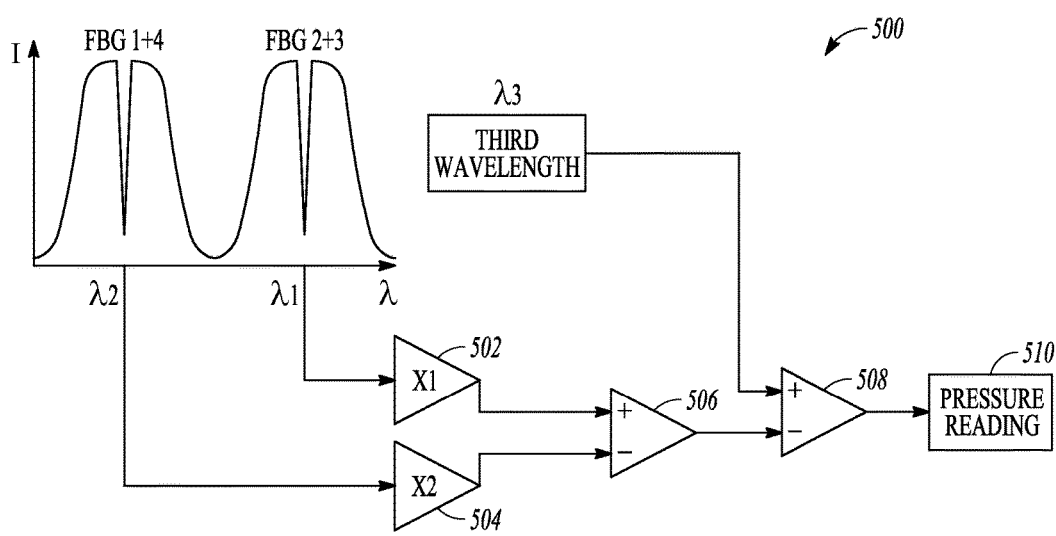
FIG. 5 is a block diagram of an example of an ambient temperature compensation technique in accordance with this disclosure.

FIG. 5 is a block diagram of an example of an ambient temperature compensation technique that can be used to implement one or more techniques of this disclosure. Although the example of a configuration of FIG. 5, shown generally at 500, will be particularly described with specific reference to the third example of a configuration described above, it is applicable to each of the example configurations described in this disclosure.

Initially, the optical fiber pressure sensor 300 of FIG. 3 can be calibrated, such as to ascertain the relative coefficients of temperature and pressure for the sensor. The magnitudes of these coefficients can be stored in a memory device. A controller circuit can be configured such that, during operation, it can read the coefficients from the memory device and apply the pressure coefficient as a first coefficient X1 and the temperature coefficient as a second coefficient X2.

As described above, a first wavelength of a narrow band laser (in relation to the response of FBGs 1 and 4) can be locked on a point on the slope 422 of the narrow transmission notch 418 in FIG. 4C, e.g., at about 50% of the length of the notch 418. A second wavelength of a narrow band laser (in relation to the response of FBGs 2 and 3) can be locked on a point on the slope 424 of the narrow transmission notch 420 in FIG. 4C, e.g., at about 50% of the depth of the notch 420.

As the pressure changes, the notch 420 shifts and, consequently, the point on the slope 424 shifts. The tracking circuit can be configured to then track the point on the slope 424. The magnitude of the change in wavelength, shown as X1 in FIG. 5, can be input into a first multiplier 502 and multiplied by the pressure coefficient X1. Similarly, as the ambient temperature of the pressure sensor changes, the notch 418 shifts and, consequently, the point on the slope 422 shifts. A tracking circuit can then track the point on the slope 422. The magnitude of the change in wavelength, shown as X2 in FIG. 5, can be input into a second multiplier 504 and multiplied by the ambient temperature coefficient X2. Similarly, The outputs of the multipliers 502, 504 can be input into a first comparator 506, which can subtract any ambient temperature drift from the pressure measurement. In this manner, ambient temperature nulling techniques can be used to provide accurate pressure measurements.

Also in accordance with this disclosure, a third wavelength that can be close in magnitude to λ1 or λ2 but not in resonance with the phase shift feature can be used to monitor a total insertion loss of the system, e.g., from any bending, insertion of the optical fiber into a connector, etc. The insertion loss is generally a static number. During operation, the controller circuit can transmit the third wavelength λ3, which can be input into a second comparator 508 along with the pressure measurement output from a first comparator 506, and the second comparator 508 can compensate the pressure measurement for any changes in insertion loss to produce a final pressure reading 510 for the optical fiber pressure sensor.

Pressure sensors constructed using optical fibers can suffer from significant pressure drift, due at least in part to the low intrinsic sensitivity of optical fibers (e.g., optical refractive index, mechanical size, etc.) to pressure. This is especially true for optical fiber pressure sensors that are designed for low pressure applications, such as sensing the pressure within the human body.

As mentioned above, when using an optical fiber pressure sensor capable of insertion into a body lumen of a patient, e.g., an animal such as a human, a small, uncompensated or uncorrected drift in temperature within the patient, e.g., as a result of an injected imaging contrast medium, can appear as an artifact that incorrectly indicates a large change in pressure. This can be due in part to the relatively low intrinsic sensitivity of the optical fiber pressure sensor to pressure and the relatively high intrinsic sensitivity to temperature of the optical fiber associated with the optical fiber pressure sensor. As such, a small, uncompensated drift in temperature can be unacceptable due to the need for accurate pressure measurements.

As described in more detail below with respect to FIGS. 6A-6B, one or more techniques of this disclosure are described that can remove and/or compensate for the effects of temperature drifts and other deleterious effects that might compromise the accuracy of the pressure reading. For example, polarization scrambling techniques, ambient temperature nulling techniques, laser tracking techniques, and laser temperature monitoring techniques can be used in combination to correct for temperature drifts that can affect the accuracy of the pressure readings.

Figure 6A:
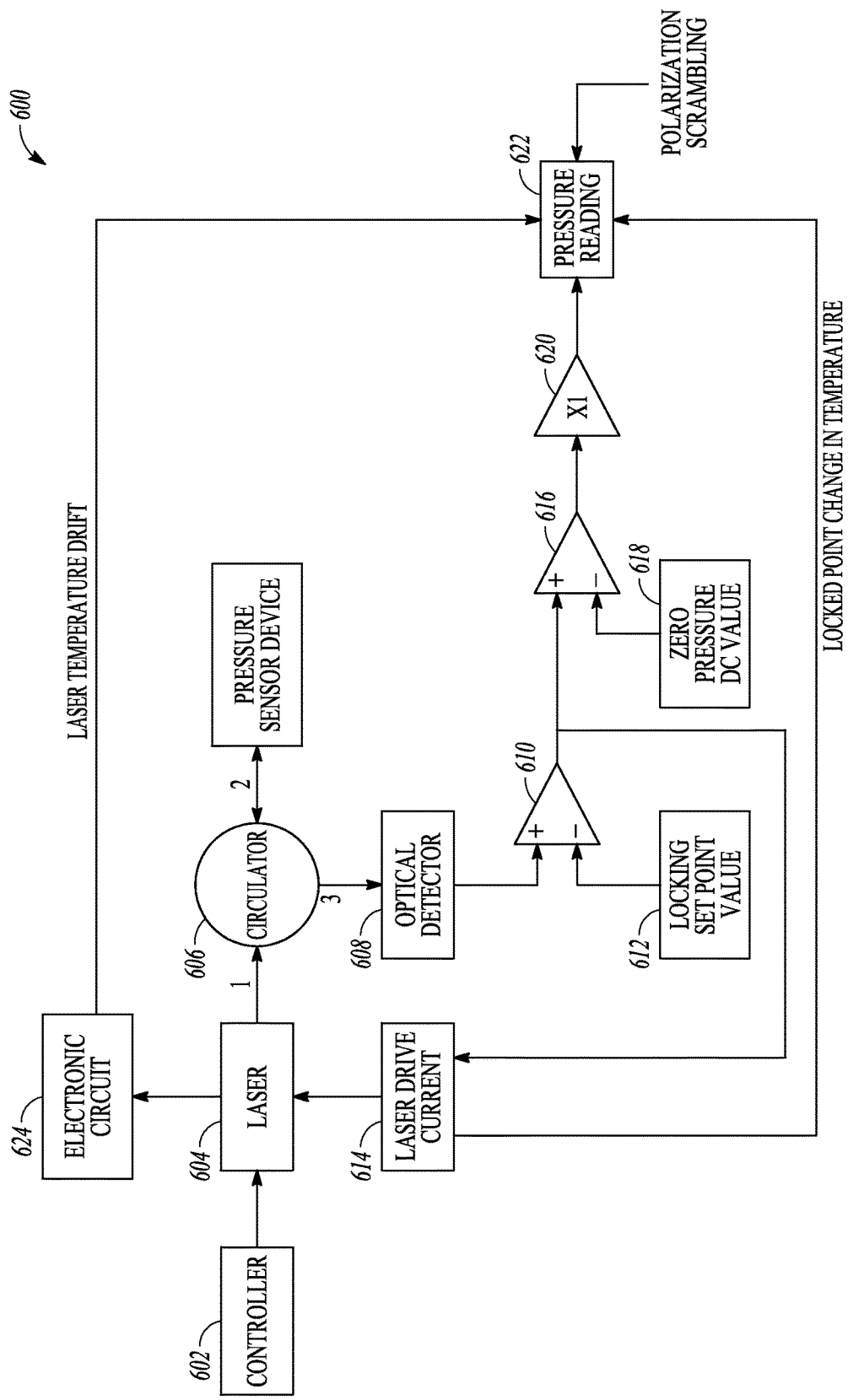
FIG. 6A is a block diagram of an example of a laser tracking system, in accordance with this disclosure.

FIG. 6A is a block diagram of an example of a laser tracking system, shown generally at 600, in accordance with this disclosure. A controller circuit 602 can be configured to control a laser 604 to generate and transmit the light from a narrow band laser into a first port (e.g., port 1) of a circulator 606. The circulator 606 can route the light out a second port (e.g., port 2) toward the optical fiber pressure sensor. The controller circuit 602 can be configured to set the wavelength of the laser on a point on a slope of a notch in the wavelength response of an FBG, such as described above. Any light reflected back from the optical fiber pressure sensor can enter the second port (e.g., port 2) of the circulator 606 and can be routed out a third port (e.g., port 3) and received by an optical detector 608.

As indicated above, laser tracking techniques can be used to correct for temperature drift. In accordance with this disclosure, the laser 604 can be actively locked at a position on a slope of a transmission notch, e.g., slope 406 of the notch 402 of FIG. 4A. Then, the system 600 can measure the change in wavelength and, in response, alter the laser's operating characteristics, e.g., drive current.

In the system 600 of FIG. 6A, a first comparator 610 can be used to provide laser tracking. The optical power of the reflected signal, which is output by the optical detector 608, can be a first input to a first comparator 610. A locking set point value 612 can be a second input to the first comparator 610. The first comparator 610 can compare the two inputs and then output a value that can be applied as an input to a laser drive current control 614 that can modulate the drive current of the laser 604. In this manner, the configuration of FIG. 6A can provide a locking loop to maintain a set point on the slope of a notch, for example.

In one example implementation, during initial setup a user can adjust the conditions of the laser 604 so that the wavelength of the laser 604 is slightly greater than the wavelength of the transmission notch. The user can adjust the wavelength of the laser 604 by adjusting the drive current of a thermoelectric cooler (TEC) of the laser 604 (large shifts in wavelength), which can alter the temperature of a submount of the laser 604, or adjust the drive current of the laser 604 itself (small shifts in wavelength).

Once the initial setup of the laser 604 is complete, the user can initiate the tracking techniques of this disclosure. The tracking techniques begin to reduce the drive current to the laser 604, which, in turn, decrease the wavelength of the laser. More particularly, as the wavelength of the laser 604 decreases toward the wavelength of the transmission notch, the comparator 610 compares the signal from the optical detector 608 and the locking set point value 612. If the signal from the optical detector 608 is higher than the locking set point value 612, the drive current of the laser 604 can be reduced via feedback from the comparator 610 to the laser drive current control 614. In some examples, reducing the laser drive current by 0.25 milliamps (mA) can shift the wavelength by 1 pm, where the coefficient of the laser 604 is about 4 pm per 1 mA of drive current.

During operation, the wavelength of the locked point on the slope can shift as the ambient temperature changes. If the wavelength of the transmission notch increases or decreases, the system 600 increases or decreases, respectively, the drive current of the laser 604 in order to track the transmission notch. As indicated above, the laser 604 can, for example, be locked on a point on a slope of the narrow transmission notch at about 50% of the depth of the notch 402. These tracking techniques can track the position of the locked point on the slope and a change in temperature can be determined from the change in position. The determined change in temperature can be an input into an algorithm executed by a pressure reading module 622, which can use the determined change in temperature to calculate an accurate pressure reading. The pressure reading module 622 can be, for example, machine or computer-implemented at least in part. For example, the controller 602 can execute instructions encoded on a computer-readable medium or machine-readable medium that implement the techniques and algorithms ascribed to the pressure reading module 622.

One advantage of tracking the shift in wavelength of the FBG sensor by modulating the drive current of the laser is that it can linearize the response of the circuit and can be more forgiving of different power levels. That is, regardless of the built in or fixed insertion loss of the pressure sensor, which can vary by construction variables or variations in connecting in-line optical connectors, the amount by which the drive current will change for a given wavelength shift will be constant. Optical fiber pressure sensors that utilize a change in power to demodulate the signal are sensitive to changes in insertion loss. By knowing the shift in laser wavelength for a given drive current change, the current reading can be converted to a wavelength and hence to a pressure reading.

Optical sensing schemes exist that directly measure the change in wavelength of the sensor response. In one example, the sensor can be illuminated with broadband light and the spectral response can be measured with an Optical Spectrum Analyzer (OSA). This is not feasible for this application as the update times can be too slow and the required wavelength precision is beyond this type of instrument. Alternatively, techniques exist that measure the change in intensity of the optical power as the laser tracks up and down the slope of the FBG sensor. One disadvantage of this technique, however, is that the power response will be non-linear for large excursions as the laser approaches the top of the filter (lower slope) and the bottom of the filter (higher slope). Without compensation this technique can yield inaccurate results.

Continuing with the description of FIG. 6A, the output of the first comparator 610 can be applied as a first input to a second comparator 616. A zero pressure DC value 618 can be applied as a second input to the second comparator 616, which can subtract the initial DC value and output a zero pressure reading. The outputted zero pressure reading from the second comparator 616 can be multiplied at a multiplier 620 by a coefficient of wavelength shift with the drive current that results in an output of an actual wavelength shift. The outputted actual wavelength shift can then be converted to a pressure reading at 622.

As indicated above, laser temperature monitoring techniques can be used to correct for temperature drifts that can affect the accuracy of the pressure readings. The lasers used to implement the various techniques described in this application have a wavelength dependency on the temperature at which they operate. A typical laser will have a wavelength dependency on operating temperature of 100 pm per degree Celsius (° C.). A well-controlled laser may have temperature stability of 0.01° C. giving a wavelength drift of 1 pm. As indicated above, however, a shift of 1 pm is equivalent to a very large pressure difference and, as such, should be accounted for in the final pressure reading.

Rather than stabilize the laser temperature to the degree required, which can increase the complexity and expense of the system 600, this disclosure describes techniques that can accurately monitor the temperature through a thermistor that is built-in to the submount of the laser 604 and that can apply this temperature information to a correction algorithm for the final pressure reading 622. To accurately monitor the temperature through the thermistor, the system 600 of FIG. 6A can include an electronic circuit 624, e.g., outside the optical system, that is configured to measure the voltage across the thermistor of the submount of the laser 604. The electronic circuit 624 can include an amplifier that can amplify the voltage signal with high enough gain that to resolve temperature changes on the order of $\frac{1}{1000}^{th}$ of a degree Celsius. These changes are on the order of hundreds of microvolts (µV). As such, it can be desirable to use high quality circuits composed of instrumentation amplifiers, for example.

In one example implementation, rather than amplifying the voltage across the thermistor, the electronic circuit 624 can subtract an offset voltage from the voltage across the thermistor, e.g., the operating voltage of the laser, before amplification. Then, the electronic circuit 624 can amplify the resulting voltage value, which is close to zero. In this manner, the electronic circuit 624 allows small changes in the temperature of the laser to be determined. The temperature change can be converted to wavelength and then to the equivalent pressure, which can then be used to determine the true pressure reading at 622.

The output from the laser, e.g., laser 604, can have a strong degree of linear polarization at the exit from the laser package. It is technically possible to preserve this linear polarization by using polarization maintaining fiber and components along the entire optical path to the FBGs. If the polarization is preserved such that the light incident upon the FBGs is aligned preferentially with a particular birefringent axis, then the response of the light to the FBGs would not be affected by the birefringence. Unfortunately, preserving the polarization in this manner is both complex and expensive.

In the absence of polarization maintaining measures, the light from the laser can arrive at the FBGs with any state of polarization depending on the nature of the optical path through which the light has traveled. Significant bending or twisting of the fiber and the birefringent nature of any components through which the light has traveled can alter the state of polarization (SOP). Although the SOP that arrives at the FBGs is not controlled, it nevertheless can have a high degree of polarization (DOP) as this characteristic is very difficult to fully randomize. A high DOP means the exact interaction of the light and the birefringent axes of the FBGs can change if there are perturbations to the system, such as bending of the guidewire during a procedure. For this reason, the system 600 of FIG. 6A can utilize polarization scrambling techniques to overcome the effects of birefringence and determine a true pressure reading. The polarization scrambling techniques scramble or average a range of polarization states so the final result is not biased to any given combination of birefringent axis of the FBG and incident polarization state.

Optical fiber pressure sensors such as the FBGs of this disclosure are subject to the effects of birefringence in the optical fiber, due to the physical imperfections of the fiber. With birefringence, different polarizations of light can have slightly different effective optical refractive indices. An effective index of the fiber that is different for different polarizations can result in a slightly different Bragg wavelength. A different Bragg wavelength can result in the appearance of movement of the point on the slope of the transmission notch at which the laser is locked. In reality, however, the point may not have moved at all.

A typical optical fiber can have birefringence on the order of $2.5 \times 10^{-6}$, which translates to a wavelength shift between the most different polarizations of 4 pm. A 4 pm wavelength shift would be equivalent to a relatively massive pressure change and, as such, should be accounted for in the final pressure reading.

The exact wavelength of the FBG can be determined by a combination of the refractive index of the medium and the physical spacing of the planes or fringes that make up the FBG, as in the following equation:

$l_B = 2n_e L$, where $l_B$=Bragg wavelength, $n_e$=effective refractive index, and L=spacing of fringes.

The polarization scrambling techniques of this disclosure can be implemented by sweeping a series of "optical waveplates" through a pseudo-random pattern with sufficient frequency that the desired signal will be averaged satisfactorily. Optical waveplates are devices that can alter the state of polarization. In order to measure a typical cardiovascular pressure profile with a heart rate of 0 beats per minute to 200 beats per minute, scrambling techniques can average at a rate that is sufficient to capture the dynamic profile, e.g., an effective frequency of several hundred hertz.

In the system 600 of FIG. 6A, the optical waveplates can be physically located between where the laser beam exits laser 604 and the FBGs of the optical fiber pressure sensor. In one example, an optical waveplate can be formed by wrapping a portion of the optical fiber around a piezoelectric material and by stretching the fiber upon application of a voltage to the piezoelectric material. In another example, an optical waveguide can be used to form an optical waveplate. The application of a voltage across electrodes built into the optical waveguide can result in the change of the refractive index.

Using the polarization scrambling techniques of this disclosure, it is not necessary to know the levels or patterns of birefringence in the system because the polarization controlling techniques do not rely upon feedback. Instead, the polarization scrambling techniques rely on an averaged polarization that is achieved by sweeping through as many available polarization states to get an average polarization value so the final result is not biased to any given combination of birefringent axis of the FBG and incident polarization state. Additional information regarding how the polarization scrambling techniques are used to determine a true pressure reading are disclosed in U.S. Provisional Application No. 61/709,700, titled "POLARIZATION SCRAMBLING FOR INTRA-BODY FIBER OPTIC SENSOR", by Howard Rourke, et al. and filed on Oct. 4, 2012, the entire content of which being incorporated herein by reference.

Figure 6B:
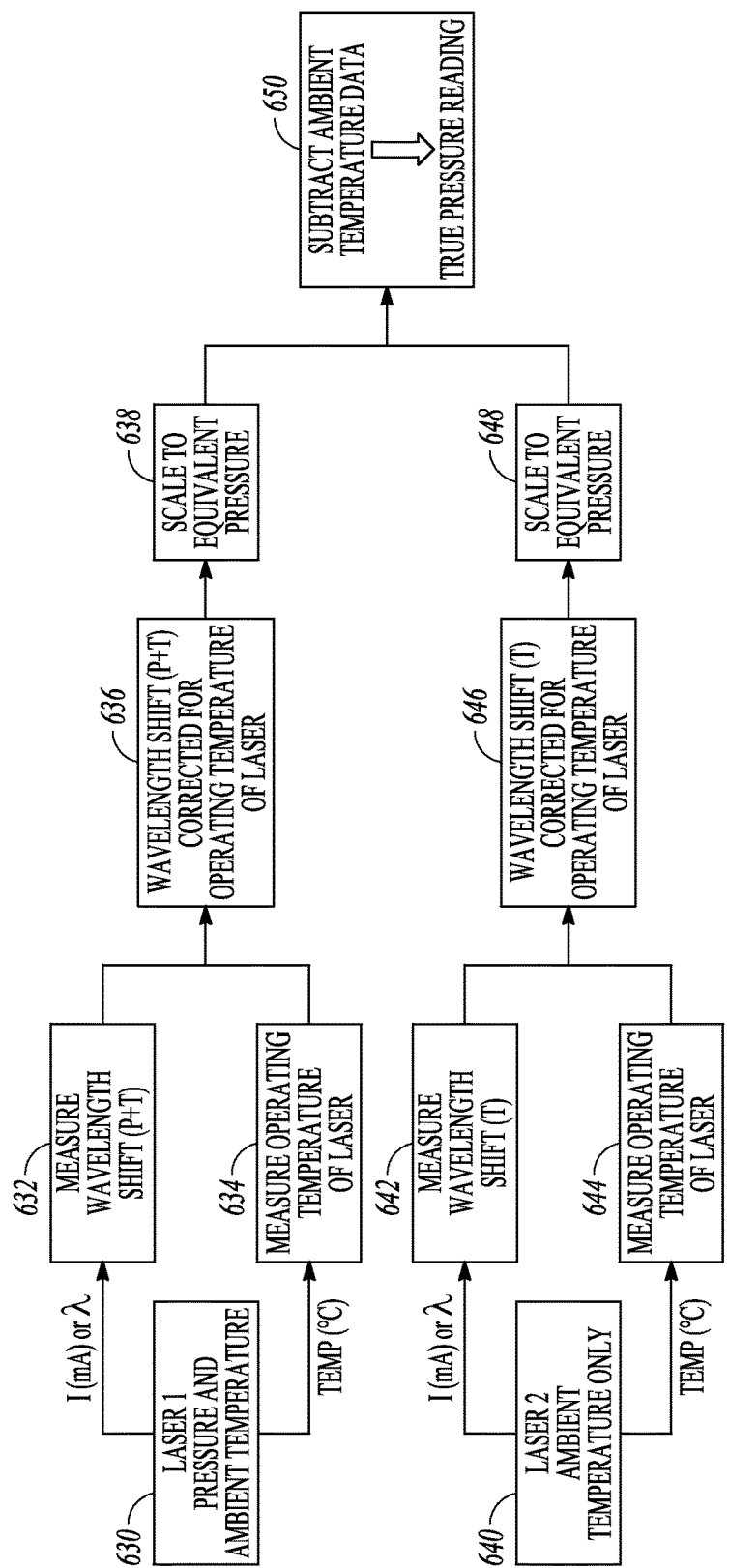
FIG. 6B is a block diagram of an example of a temperature compensation technique in accordance with this disclosure.

FIG. 6B is a block diagram of an example of a temperature compensation technique in accordance with this disclosure. As described above, in order to determine an accurate pressure reading, both the ambient temperature of the optical fiber pressure sensor and the temperature drift of the laser should be accounted for in the final pressure reading at 622 of FIG. 6A. In FIG. 6B, a first laser 630 can be locked onto a phase-shift region, e.g., phase-shift region 312A between FBG 2 and FBG 3 of FIG. 3. This phase-shift region, however, is not compensated for the ambient temperature of the pressure sensor and, as such, reacts to both pressure and temperature. Using either a measurement of the change in drive current of the laser, e.g., in milliamps, or a measurement of the change in wavelength, the controller 602 of FIG. 6A can determine the shift in wavelength at 632. Further, using the techniques described above, the controller 602 can determine the operating temperature of the first laser 630 at 634 by measuring the voltage across the submount thermistor via the electronic circuit 624 of FIG. 6A. The controller 602 can correct the determined shift in wavelength for the operating temperature of the first laser 630 by subtracting the determined operating temperature of the first laser 630 from the shift in wavelength determined at 636. Next, the corrected wavelength shift can be scaled to an equivalent pressure at 638, e.g., converted from a voltage value to a pressure value. The corrected wavelength shift at 636 and its scaled value at 638, however, have not been corrected for the ambient temperature of the pressure sensor.

In order to correct for the ambient temperature of the pressure sensor, a second laser 640 can be locked onto another phase-shift region, e.g., phase-shift region 312B between FBG 1 and FBG 4 of FIG. 3. This phase-shift region is insensitive to pressure and responds only to the ambient temperature of the pressure sensor. Using either a measurement of the change in drive current of the laser, e.g., in milliamps, or a change in wavelength, the controller 602 of FIG. 6A can determine the shift in wavelength at 642. The controller 602 can also determine the temperature of the second laser 640 at 644 by measuring the voltage across the submount thermistor via the electronic circuit 624 of FIG. 6A. The controller 602 can correct the determined shift in wavelength for the operating temperature of the second laser 640 by subtracting the determined operating temperature of the second laser 640 from the shift in wavelength determined at 646. Next, the corrected wavelength shift can be scaled to an equivalent pressure at 648, e.g., converted from a voltage value to a pressure value. Finally, at 650, the pressure determined at 648 can be subtracted from the pressure determined at 638 in order to determine a true pressure reading.

FIGS. 7A-7C depict an example of a pressure sensor that can be used to implement one or more techniques of this disclosure. The example of the pressure sensor depicted in FIGS. 7A-7C is an example of a standalone pressure sensor that can use one or more phase shift gratings. The type of grating written into the fiber can be, for example, a "phase shift" grating or a "Fabry Perot" grating. A "standalone" sensor can be capable of sensing pressure independently of the fiber being attached to a guide wire core subassembly. In contrast, an "integrated" pressure sensor can involve placing the fiber with the appropriate gratings written in it on a guide wire core and then completing the sensor once the fiber is positioned on the wire.

FIG. 7A is an example of a perspective view of an example of a optical fiber pressure sensor 700 that can include an optical fiber 702, which can be configured to transmit one or more optical sensing signals, and a temperature compensated Fiber Bragg Grating (FBG) interferometer (shown generally at 704 in FIG. 7C) that can be included in, or in optical communication with, the optical fiber 702. The FBG interferometer 704 can be configured to receive pressure (e.g., from pressure waves), and to modulate, in response to the received pressure, an optical sensing signal being delivered via the optical fiber 702 to the FBG interferometer 704. The pressure sensor 700 can include a sensor membrane 706, which can be in physical communication with the FBG interferometer 704. The sensor membrane 706 can be configured to help transmit the pressure to the FBG interferometer 704. The pressure sensor 700 can further include a sheath 708 that can, for example, help contain components of the pressure sensor 700 and/or help ease the pressure sensor through the vascular system. In some examples, the sensor membrane 706, or any of the sensor membranes referenced in this disclosure, can be considered a spring in that its material exhibits linear elasticity.

FIG. 7B is an example of a cross-sectional end view of the pressure sensor 700 of FIG. 7A. As seen in FIG. 7B, the optical fiber 702 can extend through the pressure sensor 700, such as at substantially an axial center of the pressure sensor 700.

FIG. 7C is an example of a cross-sectional side view of the pressure sensor 700 of FIG. 7A, such as can be taken along section A-A of FIG. 7B. FIG. 7C depicts the optical fiber 702 extending through a proximal portion 710 and a distal portion 712 of the pressure sensor 700. A proximal portion of the phase shift grating of FBG interferometer 704 can be captured by a stiff, rigid, or solid supporting member 714, e.g., via bonding. The supporting member 714 can be a capillary tube, for example.

In the distal portion 712, the pressure sensor 700 can define a cavity 716, e.g., filled with air, such as laterally below the distal portion of the phase shift grating of FBG interferometer 704 and laterally below the remaining distal length of the fiber 702 extending distally axially beyond the phase shift grating. In the example shown in FIG. 7C, the flexible sensor membrane 706 can be thick enough such that it contacts the fiber 702 and the fiber 702 can be attached to the flexible sensor membrane 706, e.g., via bonding. The flexible sensor membrane 706 can include, for example, a thin polymer film, a heat seal film, or a thin metal foil. The flexible sensor membrane 706 can be attached to the pressure sensor 700, such as via bonding or solder. In an example, the membrane 706 can be made by casting a silicone layer.

The pressure sensor 700 can be sealed on both the proximal end 718 and the distal end 720. In addition, the sensor membrane 706 can be sealed creating the sealed cavity 706.

The example pressure sensor 700 of FIG. 7C depicts three FBGs, namely FBGs 1-3, along with an optional FBG, namely FBG 4. FBG 1 is independent of pressure and can be used for temperature measurements to provide a temperature compensated optical fiber pressure sensor, as described above with respect to FIG. 3 and FIG. 4A.

FBGs 2 and 3 can form a phase-shift FBG structure. The surface area of the membrane 706 can concentrate a change in pressure and can focus a mechanical response to the change in pressure at the phase-shift region between FBG 2 and FBG 3. This can enhance the sensitivity of the pressure sensor 700. The mechanical forces acting upon the phase-shift region between FBG 2 and FBG 3 can concentrate a stress in the phase-shift region. The concentrated stress in the phase-shift region can change the refractive index of the optical fiber 702, which, in turn, alters the phase relationship between FBG 2 and FBG 3. The change in phase-shift between FBG 2 and FBG 3 can be detected and quantified, and the change in pressure can be determined from the quantified phase-shift.

In an example, the pressure sensor 700 can optionally further include FBG 4, e.g., located axially more proximal than FBG 1. As described above with respect to FIG. 3 and FIG. 4C, FBGs 1 and 4 can form a phase-shifted FBG structure that can be used to detect and quantify a change in temperature in the pressure sensor 700, which can be substantially independent of any pressure variations, due to the location of FBGs 1 and 4 within the stiff, rigid, or solid supporting member 714. In the configuration shown in FIG. 7C, the supporting member 714 can be disposed about FBGs 1, 2, and 4.

Figure 8B:
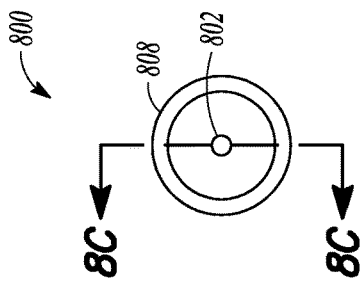
FIGS. 8A-8C depict another example of a pressure sensor that can be used to implement various techniques of this disclosure.
Figure 8A:
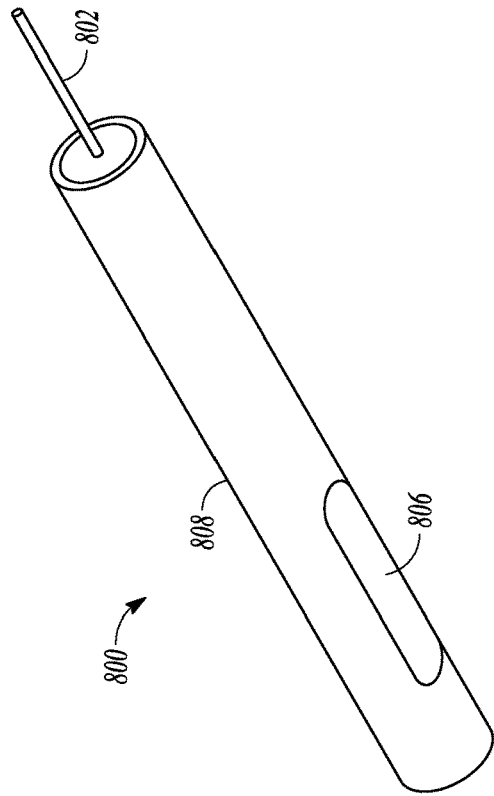
Figure 8C:
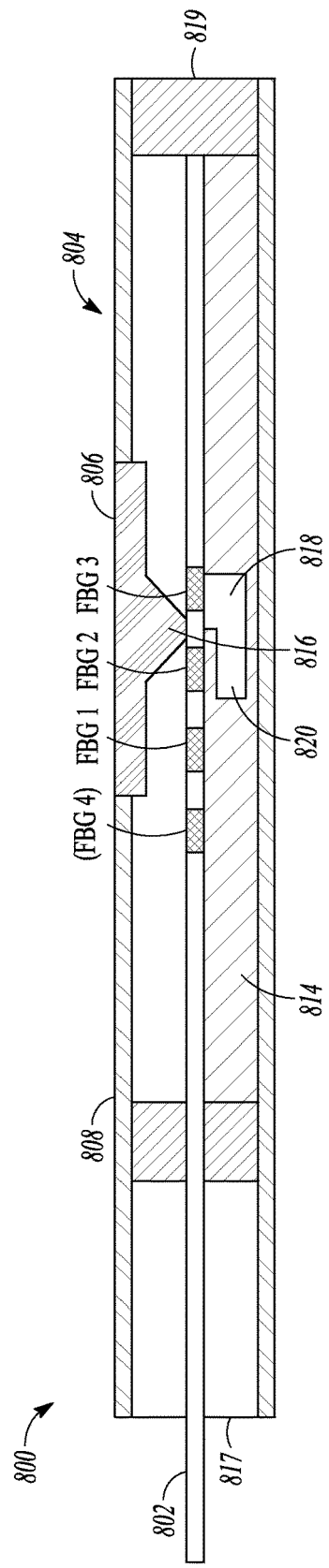

FIGS. 8A-8C depict another example of a pressure sensor that can be used to implement one or more techniques of this disclosure, such as can use a standalone pressure sensor that can use one or more phase shift gratings.

FIG. 8A is a perspective view of an example of an optical fiber pressure sensor 800 that can include an optical fiber 802, which can be configured to transmit one or more optical sensing signals, and a temperature compensated Fiber Bragg Grating (FBG) interferometer (shown generally at 804 in FIG. 8C) in optical communication with the optical fiber 802. The FBG interferometer 804 can be configured to receive pressure (e.g., from pressure waves), and to modulate, in response to the received pressure, the optical sensing signal. The pressure sensor 800 can include a sensor membrane 806 that can be in physical communication with the FBG interferometer 804. The sensor membrane 806 can be configured to transmit the pressure to the FBG interferometer 804. The pressure sensor 800 can further include a sheath 808 that can, for example, help contain components of the pressure sensor 800 and/or help ease the pressure sensor through the vascular system.

FIG. 8B is an example of a cross-sectional end view of the pressure sensor 800 of FIG. 8A. As seen in FIG. 8B, the optical fiber 802 can extend through the pressure sensor 800, such as at substantially an axial center of the pressure sensor 800.

FIG. 8C is an example of a cross-sectional side view of the pressure sensor 800 of FIG. 8A, such as can be taken along section A-A of FIG. 8B. The optical fiber 802 can be supported in part by a stiff, rigid, or solid supporting member 814. The pressure sensor 800 can defines a cavity 816, e.g., filled with air.

As seen in FIG. 8C, the sensor membrane 806 can include a tapered portion 818 that can extend inwardly toward an axial center of the pressure sensor 804. The tapered portion 818 can help focus the response of the membrane 806 against the phase-shift region between FBG 2 and FBG 3, thereby further concentrating a stress in the phase-shift region, which can enhance the sensitivity of the pressure sensor 800.

In an example, a portion of the supporting member 814 can define a reservoir 820 that can be adjacent to the fiber 802. The reservoir 820 can be filled with a gas, e.g., air. In one example, the reservoir can be filled with a gas, e.g., nitrogen, that can provide greater temperature stability than air. In one example, the reservoir 820 can be a vacuum that can provide temperature stability. The reservoir 820 can provide a configuration that can be adjacent a limited cavity 816 immediately laterally below the fiber 802 between FBG 2 and FBG 3 such that it can be acted upon by the portion 818 yet the reservoir 820 still includes a large compressible volume.

In an example, such as shown in FIG. 8C, the flexible sensor membrane 806 can include, for example, a thin polymer film, a heat seal film, or a thin metal foil. The flexible sensor membrane 806 can be attached to the pressure sensor 800, such as via bonding or solder. In an example, the membrane 806 can be made by casting a silicone layer.

The pressure sensor 800 can be sealed on both the proximal end 817 and the distal end 819. The sensor membrane 806 can be sealed, such as for creating the sealed cavity 816.

The example of a pressure sensor 800 of FIG. 8C can include three FBGs (e.g., FBGs 1-3) along with an optional FBG (e.g., FBG 4). FBG 1 can be configured to be independent of pressure and can be used for temperature measurement, such as to provide a temperature compensated optical fiber pressure sensor, such as described above with respect to FIG. 3 and FIG. 4A.

FBGs 2 and 3 can form a phase-shifted FBG structure. The surface area of the membrane 806 can be configured to concentrate a change in pressure onto the portion 818, which can focus a mechanical response to the pressure at the phase-shift region between FBG 2 and FBG 3. The mechanical force acting upon the phase-shift region between FBG 2 and FBG 3 can concentrate a stress in the phase-shift region. The concentrated stress in the phase-shift region can change the refractive index of the optical fiber 802, such as to alter the phase relationship between FBG 2 and FBG 3. The change in phase-shift between FBG 2 and FBG 3 can be detected and quantified, and the change in pressure can be determined from the quantified phase-shift.

The pressure sensor 800 can optionally further include FBG 4, e.g., located axially more proximal than FBG 1. As described above with respect to FIG. 3 and FIG. 4C, FBGs 1 and 4 can form a phase-shifted FBG structure that can be used to detect and quantify a change in temperature in the pressure sensor 800. In the configuration shown in FIG. 8C, the supporting member 814 is not disposed about FBGs 1, 2, and 4, in contrast to the configuration example of FIG. 7C.

FIGS. 9A-9C depict another example of a pressure sensor that can be used to implement one or more techniques of this disclosure. The example of the pressure sensor depicted in FIGS. 9A-9C can provide a standalone pressure sensor that can use one or more phase shift gratings.

FIG. 9A is a perspective view of an optical fiber pressure sensor 900 that can include an optical fiber 902, which can be configured to transmit one or more optical sensing signals, and a temperature compensated Fiber Bragg Grating (FBG) interferometer (shown generally at 904 in FIG. 9C), such as in optical communication with the optical fiber 902. The FBG interferometer 904 can be configured to receive pressure (e.g., from pressure waves), and to modulate, in response to the received pressure, the optical sensing signal. The pressure sensor 900 can include a sensor membrane 906 that can be in physical communication with the FBG interferometer 904. The sensor membrane 906 can be configured to transmit the pressure to the FBG interferometer 904. The pressure sensor 900 can further include a sheath 908 that can, for example, help contain components of the pressure sensor 900 and/or help ease the pressure sensor through the vascular system.

FIG. 9B is an example of a cross-sectional end view of the pressure sensor 900 of FIG. 9A. As seen in FIG. 9B, the optical fiber 902 can extend through the pressure sensor 900 at a position that is offset from an axial center of the pressure sensor 900.

FIG. 9C is an example of a cross-sectional side view of the pressure sensor 900 of FIG. 9A, such as can be taken along section A-A of FIG. 9B. FIG. 9C depicts the optical fiber 902 extending through a proximal portion 910 and a distal portion 912 of the pressure sensor 904. A proximal portion of the FBG interferometer 904 can be captured by a supporting member 914, e.g., via bonding. The supporting member 914 can include a capillary tube, for example. In the distal portion 912, the pressure sensor 900 can define a cavity 916, e.g., filled with air.

As seen in the example shown in FIG. 9C, the sensor membrane 906 can be in mechanical communication with a portion 921 that can extend laterally inwardly into the pressure sensor 904. The portion 921 can focus the response of the membrane 906 against the phase-shift region between FBG 2 and FBG 3, which can thereby further concentrate a stress in the phase-shift region, which can enhance the sensitivity of the pressure sensor 900.

In the example shown in FIG. 9C, the flexible sensor membrane 906 can include, for example, a thin polymer film, a heat seal film, or a thin metal foil. The flexible sensor membrane 806 can be attached to the pressure sensor 900, such as via bonding or solder. In an example, the membrane 906 can be made by casting a silicone layer.

The pressure sensor 900 can be sealed on both the proximal end 918 and the distal end 920. In addition, the sensor membrane 906 can be sealed creating the sealed cavity 916.

The example of a pressure sensor 900 of FIG. 9C can include three FBGs (e.g., FBGs 1-3), along with an optional FBG (e.g., FBG 4). FBG 1 can be configured to be independent of pressure, such as explained above, and can be used for temperature measurement, such as to provide a temperature compensated optical fiber pressure sensor, such as described above with respect to FIG. 3 and FIG. 4A.

FBGs 2 and 3 can form a phase-shifted FBG structure. The surface area of the membrane 906 can concentrate any change in pressure into the portion 921, which can focus a mechanical response to the pressure at the phase-shift region between FBG 2 and FBG 3. The mechanical forces acting upon the phase-shift region between FBG 2 and FBG 3 can concentrate a stress in the phase-shift region. The concentrated stress in the phase-shift region can change the refractive index of the optical fiber 902, such as to alter the phase relationship between FBG 2 and FBG 3. The change in phase-shift between FBG 2 and FBG 3 can be detected and quantified, and the change in pressure can be determined from the quantified phase-shift. The pressure sensor 900 can include a compliant layer 919 laterally underneath the optical fiber 902, such as to allow the portion 921 to act on the optical fiber 902 without damaging the optical fiber 902.

The pressure sensor 900 can optionally further include FBG 4, e.g., located more proximal than FBG 1. As described above with respect to FIG. 3 and FIG. 4C, FBGs 1 and 4 can form a phase-shifted FBG structure that can be used to quantify a change in temperature in the pressure sensor 800. In the configuration shown in FIG. 9C, the supporting member 914 can be disposed about FBGs 1 and 4.

FIGS. 10A-10D depict an example of a pressure sensor that can be used to implement one or more techniques of this disclosure. The example of a pressure sensor depicted in FIGS. 10A-10D can provide an example standalone pressure sensor that can use one or more "Fabry Perot" grating arrangements.

FIG. 10A is an example of a perspective view of an optical fiber pressure sensor 1000 that can include an optical fiber 1002, which can be configured to transmit one or more optical sensing signals, and a temperature compensated Fiber Bragg Grating (FBG) interferometer (shown generally at 1004 in FIG. 10D) that can be in optical communication with the optical fiber 1002. The FBG interferometer 1004 can be configured to receive pressure (e.g., from pressure waves), and to modulate, in response to the received pressure, the optical sensing signal. The pressure sensor 1000 can include a sensor membrane 1006 that can be in physical communication with the FBG interferometer 1004. The sensor membrane 1006 can be configured to transmit the pressure to the FBG interferometer 1004. The pressure sensor 1000 can further include a sheath 1008 that can, for example, help contain components of the pressure sensor 1000 and/or help ease the pressure sensor through the vascular system.

FIG. 10B is an example of a cross-sectional end view of the pressure sensor 1000 of FIG. 10A, depicting an example of a location of the optical fiber 1002. As seen in the example of FIG. 10B, the optical fiber 1002 can extend axially through the pressure sensor 1000, such as at a position that is axially offset from an axial center of the pressure sensor 1000. FIG. 10C is an example of a cross-sectional end view of the pressure sensor without the optical fiber 1002.

FIG. 10D is an example of a cross-sectional side view of the pressure sensor 1000 of FIG. 10A, such as can be taken along section A-A of FIG. 10C. FIG. 10D depicts an example of the optical fiber 1002 extending through a proximal portion 1010 and a distal portion 1012 of the pressure sensor 1004. A proximal portion of the optical fiber 1002 can be captured by a first supporting member 1014A and a distal portion 1012 of the optical fiber 1002 can be captured by a second supporting member 1014B, e.g., via bonding.

The pressure sensor 1000 can include a sensor member 1006. The pressure sensor 1000 can define a cavity 1016, e.g., filled with air, laterally below the sensor membrane 1006. The sensor membrane 1006 and the cavity 1016 can concentrate a stress in the area between the Fabry-Perot gratings FBG 1 and FBG 2, which can enhance the sensitivity of the pressure sensor 1000.

The flexible sensor membrane 1006 can include, for example, a thin polymer film, a heat seal film, or a thin metal foil. The flexible sensor membrane 1006 can be attached to the pressure sensor 1000, such as via bonding or solder. In an example, the membrane 1006 can be made by casting a silicone layer.

The pressure sensor 1000 can be sealed on both the proximal end 1018 and the distal end 1020. The sensor membrane 1006 can be sealed, such as for creating the sealed cavity 1016.

The example of a pressure sensor 1000 of FIG. 10D can include four FBGs (e.g., FBGs 1-4). FBGs 3 and 4 can form a phase-shifted FBG structure, such as for sensing temperature. The change in phase-shift between FBG 3 and FBG 4 can be detected and quantified, and the change in temperature can be determined from the quantified phase-shift, such as described above.

The pressure sensor 1000 can further include Fabry-Perot gratings FBG 1 and FBG 2, which can be used to sense changes in pressure. Similar to the phase-shift grating structures described above with respect to FIGS. 7-9, the Fabry-Perot gratings FBG 1 and FBG 2 can create a phase shift that can be tracked in a manner similar to that described above. That is, a notch can be created in the wavelength response to the Fabry-Perot gratings FBG 1 and FBG 2, as shown and described in more detail with respect to FIG. 11. A point on a slope of the notch can be set and tracked, a phase shift can be detected and quantified, and the change in pressure can be determined from the quantified phase-shift, such as described in detail above.

Figure 11:
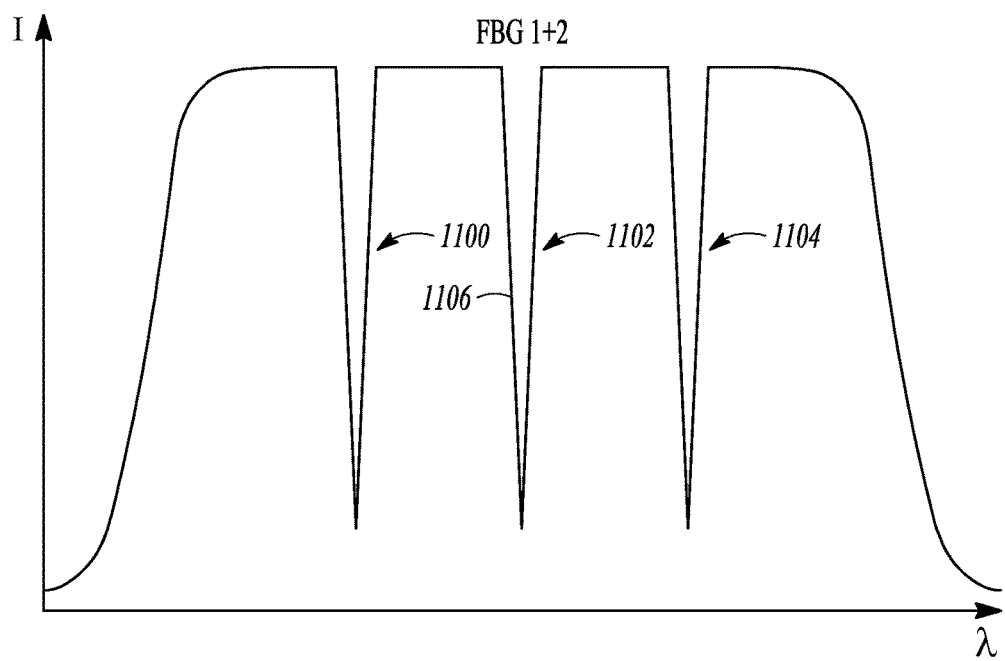
FIG. 11 depicts a conceptual response diagram related to the example of a pressure sensor shown in FIG. 10D.

FIG. 11 depicts an example of a conceptual response diagram related to the example of a pressure sensor shown in FIG. 10D. In particular, FIG. 11 depicts a conceptual wavelength response of the Fabry-Perot gratings FBG 1 and FBG 2 of FIG. 10D. As seen in the example shown in FIG. 11, the wavelength response of the Fabry-Perot gratings FBG 1 and FBG 2 can include three notches, 1100, 1102, 1104. This is in contrast to the wavelength responses of the phase-shift structures shown in FIGS. 4A-4C, which can include a single notch for a pair of FBGs. The additional notches in FIG. 11 can be a result of the increased distance between the Fabry-Perot gratings FBG 1 and FBG 2. As the distance between the Fabry-Perot gratings FBG 1 and FBG 2 increases, additional notches can occur. As the distance between the Fabry-Perot gratings FBG 1 and FBG 2 decreases, notches can disappear until the response resembles that of the phase-shift structures described above.

In a manner similar to that described above, a wavelength of a narrow band laser (in relation to the response of FBGs 1 and 2) can be locked on a point on a slope 1106 of a narrow transmission notch, e.g., notch 1102, in FIG. 11, e.g., at about 50% of the length of the notch 1102. As the pressure changes, the notch 1102 and, consequently, the point on the slope 1106 shifts. A tracking circuit can then track the point on the slope 1106 and a phase-shift can be determined from its change in position. The intensity of reflected light will be modified when the notch 1106 moves. A phase shift can be quantified, and the change in pressure can be determined from the quantified phase-shift, such as described in detail above.

FIGS. 12A-12C depict another example of a pressure sensor that can be used to implement one or more techniques of this disclosure. The example of a pressure sensor depicted in FIGS. 12A-12C can provide another example standalone pressure sensor that can use one or more Fabry-Perot grating arrangements.

FIG. 12A is an example of a perspective view of an optical fiber pressure sensor 1200 that can include an optical fiber 1202 that can be configured to transmit one or more optical sensing signals and a temperature compensated Fiber Bragg Grating (FBG) interferometer (shown generally at 1204 in FIG. 12C) in optical communication with the optical fiber 1202. The FBG interferometer 1204 can be configured to receive pressure, e.g., from pressure waves, and to modulate, in response to the received pressure, the optical sensing signal. The pressure sensor 1200 can include a sensor membrane 1206 that can be in physical communication with the FBG interferometer 1204. The sensor membrane 1206 can be configured to transmit the pressure to the FBG interferometer 1204. The pressure sensor 1200 can further include a sheath 1208 that can, for example, help contain components of the pressure sensor 1200 and/or help ease the pressure sensor through the vascular system.

FIG. 12B is an example of a cross-sectional end view of the pressure sensor 1200 of FIG. 12A. As seen in FIG. 12B, the optical fiber 1202 can extend axially through the pressure sensor 1200 such as at substantially an axial center of the pressure sensor 1200.

FIG. 12C is an example of a cross-sectional side view of the pressure sensor 1200 of FIG. 12A, such as can be taken along section A-A of FIG. 12B. The optical fiber 1202 can be supported in part by supporting members 1214A, 1214B. The pressure sensor 1200 can define a cavity 1216, e.g., filled with air.

As seen in the example of FIG. 12C, the sensor membrane 1206 can include a portion 1218 that can extend inwardly toward a center of the pressure sensor 1204 and that can taper, such as to a point. The portion 1218 can focus the response of the membrane 1206 against the area between FBG 1 and FBG 2, such as for thereby further concentrating a stress in the phase-shift region, which can enhance the sensitivity of the pressure sensor 1200.

A portion of the supporting member 1214 can define a reservoir 1220, such as laterally below the area extending axially between FBG 1 and FBG 2. The reservoir 1220 can further enhance the sensitivity of the pressure sensor 1200, such as by allowing the area between FBG 1 and FBG 2 to deflect into the reservoir 1220.

In the example shown in FIG. 12C, the flexible sensor membrane 1206 can include, for example, a thin polymer film, a heat seal film, or a thin metal foil. The flexible sensor membrane 1206 can be attached to the pressure sensor 1200, such as via bonding or solder. In an example, the membrane 1206 can be made by casting a silicone layer.

The pressure sensor 1200 can be sealed, such as on both the proximal end 1222 and the distal end 1224. The sensor membrane 1206 can be sealed, such as for creating the sealed cavity 1216.

The example of a pressure sensor 1200 of FIG. 12C can include two FBGs (e.g., Fabry-Perot gratings FBG 1 and FBG 2), which can be used to sense changes in pressure, such as described above with respect to FIG. 10D. The pressure sensor 1200 can optionally further include one or more temperature compensating FBGs. For example, the pressure sensor 1200 can include two additional FBGs (e.g., FBGs 3 and 4 of FIG. 10D), which can form a phase-shifted FBG structure, such as for sensing temperature. The change in phase-shift between FBG 3 and FBG 4 can be quantified and the change in temperature can be determined from the quantified phase-shift, such as described above.

Figure 13D:
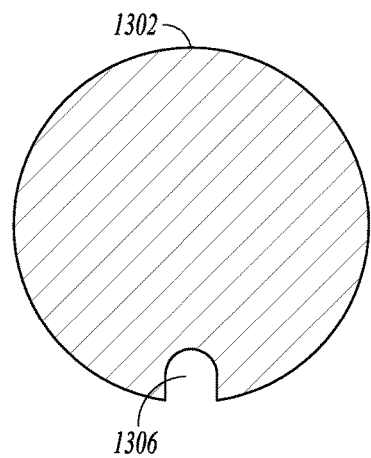

FIGS. 13A-13G depict an example of a guidewire in combination with an optical pressure sensor. FIG. 13A is an example of a perspective view illustrating a combination 1300 of a guidewire 1302 and an optical fiber 1304 attached to an optical fiber pressure sensor. An optical fiber pressure sensor can be attached at a distal end of the guidewire 1302. The optical fiber 1304 can be disposed in a smooth, rounded groove (groove 1306 of FIG. 13C) extending axially along an outer diameter of the guidewire 1302 and optionally helically wound about the guidewire 1302, such as within a helically axially extending groove. FIG. 13B is an example of a cross-sectional side view of the combination 1300 of FIG. 13A, illustrating the optional helical pitch of the combination.

FIG. 13C is an example of a cross-sectional end view of the combination 1300 of FIG. 13A, such as can be taken along section A-A of FIG. 13B. The guidewire 1302 can include a solid guidewire with a smooth, rounded groove 1306 etched out, for example, of the guidewire material (or etched out of a coating thereupon), thereby preserving most of the guidewire material, which can help preserve its mechanical properties. In this manner, the guidewire can be substantially solid, which can avoid the kinking issues that can be associated with hollow guidewires. Using a substantially solid guidewire can improve the guidewire's torque capabilities. In an example, a coating can be applied over the guidewire 1302 and over the fiber 1304, such as to help protect the fiber 1304 or to help secure the fiber 1304 to the guidewire 1302.

In some examples, the guidewires shown and described in this disclosure can have a maximum diameter (or maximum width if the guidewire does not have a circular cross-section) of less than about 0.018 inches (18 mil). In one specific example, a guidewire can have a maximum diameter (or maximum width if the guidewire does not have a circular cross-section) of about 0.014 inches (14 mil).

The grooves in the guidewires shown and described in this disclosure account for a small fraction of the overall cross-sectional area of the guidewire. In one specific example, the groove accounts for less than one percent of the cross-sectional area of the guidewire.

The smooth, shallow, rounded groove in the wire can be placed in the wire before the wire is drawn down to size or it can be etched into the final diameter wire using various techniques including lasing, electrodischarge machining, dicing, micromilling, and other micromachining techniques. In some example implementations, the groove can be sized to fit the optical fiber outer diameter, which may incorporate an optical fiber coating, and the thin layer of adhesive that will hold the optical fiber in the groove with no sharp edges or protrusions, no material extending beyond the wire diameter at the groove edges, and a groove surface finish suitable for good adhesive attachment without being so rough that the optical fiber would be subjected to microstresses when in contact with the groove surface (for example, a 12 to 16 microinch average surface roughness surface). The groove 1306 can be electropolished to achieve the desired surface quality. A thin hot melt adhesive coating may be coated onto the wire and/or the fiber and then heat-activated when the fiber is laid into the wire groove. Alternatively or additionally, the adhesive (such as a UV or heat curable material) may be applied as the fiber is laid into the groove or the fiber capture material may be coated over the fiber after it has been laid in the groove. The guidewire coating materials (such as PTFE, other hydrophobic coatings, or hydrophilic coating materials as well as heat shrink coverings) may be used to capture the fiber in the groove, or may be applied around the wire and not to the groove.

FIG. 13D is another example of a cross-sectional end view of the combination 1300 of FIG. 13A. As seen in FIG. 13D, the groove 1306 can be a smooth U-shaped groove.

Figure 13E:
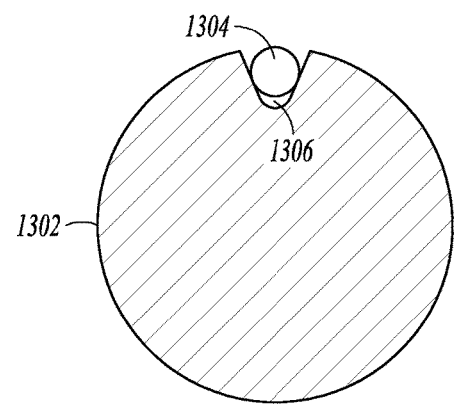

FIG. 13E is another example of a cross-sectional end view of the combination 1300 of FIG. 13A. As seen in FIG. 13E, the groove 1306 can be a smooth V-shaped groove.

Figure 13F:
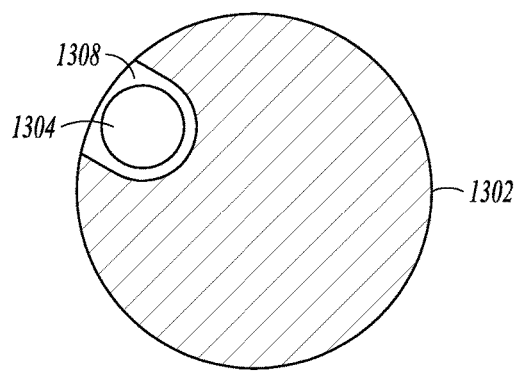

FIG. 13F is another example of a cross-sectional end view of the combination 1300 of FIG. 13A. An adhesive 1308 can be either applied to the groove 1306 or to the optical fiber 1304 or to both in order to affix the optical fiber 1304 to the groove 1306.

Figure 13G:
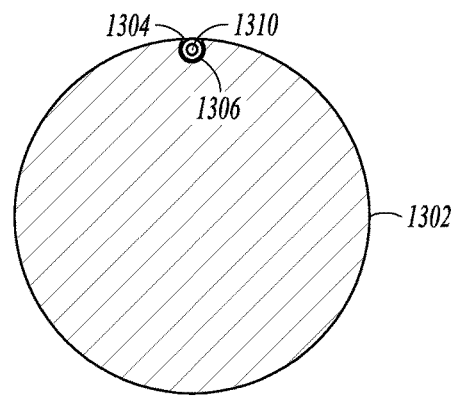

FIG. 13G is another example of a cross-sectional end view of the combination 1300 of FIG. 13A. FIG. 13G shows an alternative configuration for one or more sections of the groove 1306 that can be shaped to accommodate and retain an optical fiber 1304 having a coating 1310. The groove 1306 can have an opening that is slightly smaller than the outer diameter of the combination of the optical fiber 1304 and the coating 1310 to be accommodated. The coating 1310 can be elastically compliant or deformable and of sufficient thickness that it may be mechanically pressed into the groove 1306 and retained in place by the narrower opening of the groove 1306. This mechanical retention can be useful for temporarily or permanently holding the optical fiber 1306 in place during or after assembly. This arrangement may be used in conjunction with adhesives or coatings to optimize the placement and accommodation of the optical fiber along its length.

FIGS. 14A-14C depict an example of a guidewire in combination with an optical fiber pressure sensor. FIG. 14A is an example of a perspective view illustrating a combination 1400 of a guidewire 1402 and an optical fiber 1404 that can be attached to an optical fiber pressure sensor. An optical fiber pressure sensor can be attached at a distal end of the guidewire 1402. The optical fiber 1402 can be disposed in a flat groove (flat groove 1406 of FIG. 14C) extending axially along an outer diameter of the guidewire 1402 (or along a coating thereupon) and optionally helically wound about the guidewire 1402. FIG. 14B is a cross-sectional side view of the combination 1400 of FIG. 14A, illustrating the helical pitch of the combination. The helical design can allow any stresses, e.g., from compression and tension, to be more evenly distributed along the length of the guidewire.

FIG. 14C is a cross-sectional end view of the combination 1400 of FIG. 14A, such as can be taken along section A-A of FIG. 14B. The guidewire 1402 can include a solid guidewire with a flat groove 1406 etched out, for example, of the guidewire material, or a coating thereupon, thereby preserving most of the guidewire material and the mechanical properties associated therewith. In this manner, the guidewire can be substantially solid, which can help avoid the kinking issues that can be associated with hollow guidewires. Using a substantially solid guidewire can provide better torque capability of the guidewire. In an example, a coating can be applied over the guidewire 1402 and the fiber 1404, such as to help protect the fiber 1404 or to help secure the fiber 1404 to the guidewire 1402.

FIGS. 15A-15C depict an example of a guidewire in combination with an optical fiber pressure sensor. FIG. 15A is an example of a perspective view illustrating a combination 1500 of a multifilar guidewire 1502 and an optical fiber 1504 that can be attached to an optical fiber pressure sensor. An optical fiber pressure sensor can be attached at a distal end of the guidewire 1502. The optical fiber 1504 can be disposed in an interstice between filaments of the multifilar guidewire 1502 and optionally axially helically wound about the guidewire 1502. FIG. 15B is an example of a cross-sectional side view of the combination 1500 of FIG. 15A, illustrating an example of the helix pitch of the combination.

FIG. 15C is an example of a cross-sectional end view of the combination 1500 of FIG. 15A, such as can be taken along section A-A of FIG. 15B. The multifilar guidewire 1502 can include multiple filaments 1506. The optical fiber 1504 can be disposed in an interstice between two filaments 1506, for example, toward an outer diameter of the guidewire 1502. In this manner, the guidewire can be substantially rigid, like a solid guidewire, which can help avoid the kinking issues that can be associated with hollow guidewires. Using a substantially solid guidewire can help provide desired torque capability of the guidewire. In an example, a coating can be applied over the guidewire 1502 and the fiber 1504, such as to help protect the fiber 1504 or to help secure the fiber 1504 to the guidewire 1502.

Figure 16:
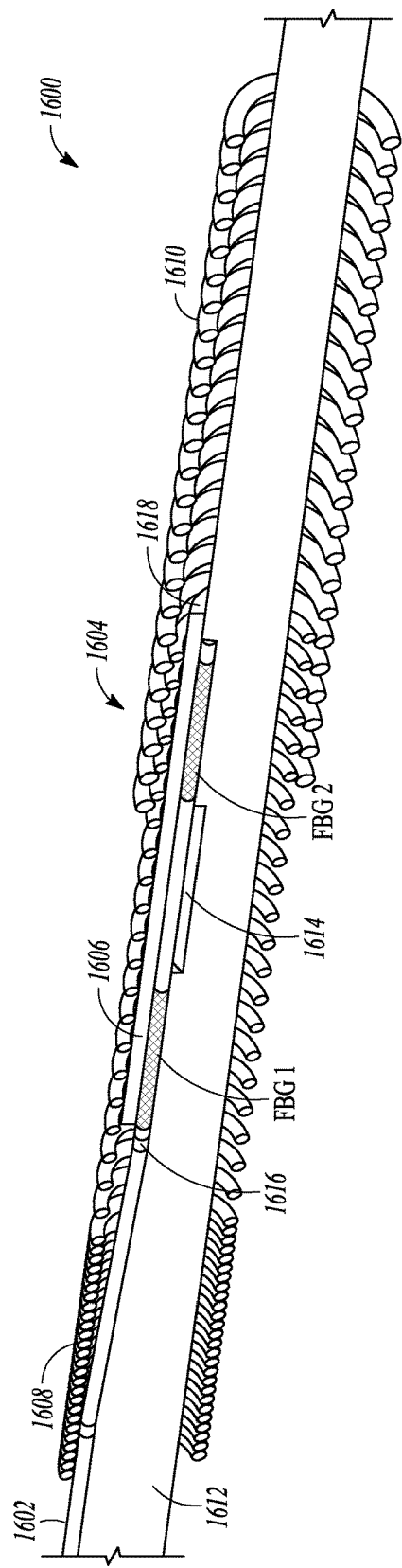
FIG. 16 depicts another example of a pressure sensor that can be used to implement various techniques of this disclosure.

FIG. 16 depicts another example of a pressure sensor that can be used to implement various techniques of this disclosure. The example of a pressure sensor depicted in FIG. 16 can provide an example of an integrated pressure sensor that can use one or more Fabry-Perot grating arrangements. Again, an "integrated" pressure sensor can involve placing the fiber with the appropriate gratings written in the fiber on a guidewire and then completing the sensor once the fiber is positioned on the wire.

FIG. 16 is an example of a perspective cross-sectional view of an optical fiber pressure sensor 1600 that can include an optical fiber 1602 that can be configured to transmit one or more optical sensing signals and a temperature compensated Fiber Bragg Grating (FBG) interferometer 1604 in optical communication with the optical fiber 1602. The FBG interferometer 1604 can be configured to receive pressure, e.g., from pressure waves, and to modulate, in response to the received pressure, the optical sensing signal. The pressure sensor 1600 can include a sensor membrane 1606 that can be in physical communication with the FBG interferometer 1604. The sensor membrane 1606 can be configured to transmit the pressure to the FBG interferometer 1604.

The example of a pressure sensor 1600 of FIG. 16 can further include Fabry-Perot gratings FBG 1 and FBG 2, which can be used to sense changes in pressure. The Fabry-Perot gratings FBG 1 and FBG 2 can create a phase shift that can be tracked in a manner similar to that described above.

The pressure sensor 1600 of FIG. 16 can further include a proximal coil 1608 and a distal coil 1610. The proximal and distal coils 1608, 1610 can provide flexibility to aid advancement of the pressure sensor 1600 through tortuous pathways. In one example, the proximal and distal coils 1608, 1610 can be affixed together via a mechanical joint (not depicted), e.g., via solder or adhesive. The proximal end of the proximal coil may be affixed to the core wire by welding, brazing, soldering or via an adhesive. The joint between the proximal and distal coils may or may not include an attachment between the coils and the core wire inside the two coils. The FBG interferometer 1604 can, in some examples, be positioned underneath the mechanical joint to provide additional protection to the FBG interferometer 1604.

In another example, the proximal and distal coils 1608 and 1610 can be coiled after the two wires that are be used to form the proximal and distal coils have been joined together to form a coil subassembly, thereby reducing or eliminating any need for another material to affix the two coils to each other. Low power fiber lasers with typical power levels of about 100 W to 200 W average and high beam quality can provide the very small spot sizes needed for this type of precision metal welding.

The pressure sensor 1600 of FIG. 16 can further include a guidewire 1612 to which the optical fiber 1602 can be attached. In the example depicted in FIG. 16, a portion of the guidewire 1612 can define a machined gap (not depicted) underneath the proximal coil 1608. The machined gap can allow the optical fiber 1602 to extend longitudinally or helically along the outer surface of the guidewire 1612 and then transition underneath the proximal coil gradually into the machined gap.

The guidewire 1612 can also define cavity 1614, e.g., filled with air, laterally below the sensor membrane 1606. The sensor membrane 1606 and the cavity 1614 can concentrate a stress in the area between the Fabry-Perot gratings FBG 1 and FBG 2, which can enhance the sensitivity of the pressure sensor 1600. The optical fiber 1602 can be securely attached to the guidewire 1612 on each side of the cavity 1614. In addition, the sensor membrane 1606 can be sealed 360 degrees around the guidewire 1612 at an optical fiber entry end 1616 of the sensor membrane 1606 and at a distal end 1618 of the optical fiber 1602 and along the edges of the membrane 1606.

Figure 17:
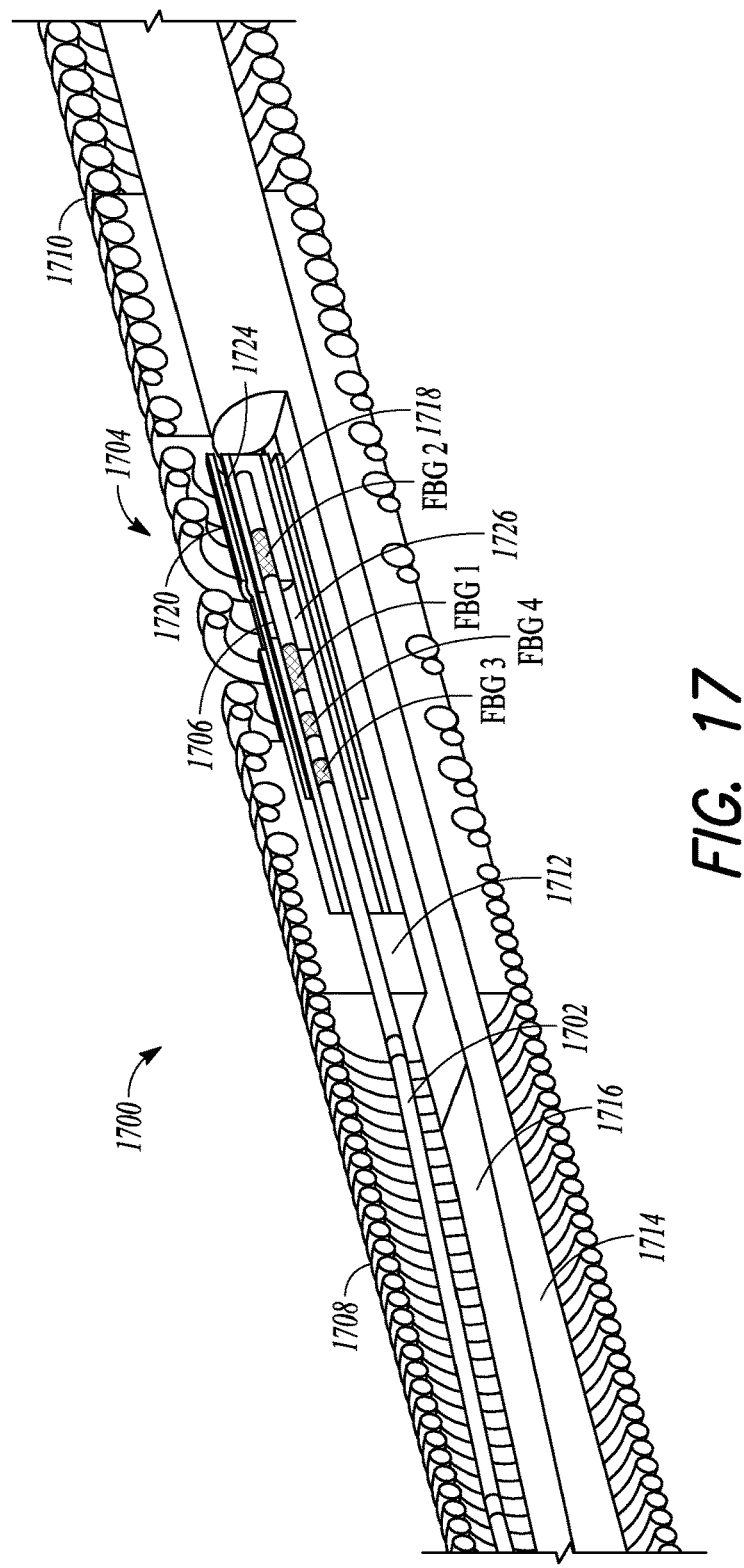
FIG. 17 depicts another example of a pressure sensor that can be used to implement various techniques of this disclosure.

FIG. 17 depicts another example of a pressure sensor that can be used to implement various techniques of this disclosure. FIG. 17 depicts another example of a pressure sensor that can be used to implement various techniques of this disclosure. The example of a pressure sensor 1700 depicted in FIG. 17 can provide an example standalone pressure sensor that can use one or more Fabry-Perot grating arrangements.

FIG. 17 is an example of a perspective cross-sectional view of an optical fiber pressure sensor 1700 that can include an optical fiber 1702 that can be configured to transmit one or more optical sensing signals and a temperature compensated Fiber Bragg Grating (FBG) interferometer 1704 in optical communication with the optical fiber 1702. The FBG interferometer 1704 can be configured to receive pressure, e.g., from pressure waves, and to modulate, in response to the received pressure, the optical sensing signal. The pressure sensor 1700 can include a sensor membrane 1706 that can be in physical communication with the FBG interferometer 1704. The sensor membrane 1706 can be configured to transmit the pressure to the FBG interferometer 1704.

The example of a pressure sensor 1700 of FIG. 17 can include four FBGs (e.g., FBGs 1-4.) FBGs 3 and 4 can form a phase-shifted FBG structure, such as for sensing temperature. The change in phase-shift between FBG 3 and FBG 4 can be detected and quantified, and the change in temperature can be determined from the quantified phase-shift, such as described above.

The pressure sensor 1700 can further include Fabry-Perot gratings FBG 1 and FBG 2, which can be used to sense changes in pressure. Similar to the phase-shift grating structures described above with respect to FIG. 10D, the Fabry-Perot gratings FBG 1 and FBG 2 can create a phase shift that can be tracked in a manner similar to that described above. That is, a notch can be created in the wavelength response to the Fabry-Perot gratings FBG 1 and FBG 2, as shown and described in detail above. A point on a slope of the notch can be set and tracked, a phase shift can be detected and quantified, and the change in pressure can be determined from the quantified phase-shift, such as described in detail above.

The pressure sensor 1700 of FIG. 17 can further include a proximal coil 1708 and a distal coil 1710. The proximal and distal coils 1708, 1710 can provide additional flexibility to aid advancement of the pressure sensor 1700 through tortuous pathways. In one example, the proximal and distal coils 1708, 1710 can be affixed together via a mechanical joint 1712, e.g., via solder or adhesive. The FBG interferometer 1704 can, in some examples, be positioned underneath the mechanical joint 1712 to provide additional protection to the FBG interferometer 1704.

The pressure sensor 1700 of FIG. 17 can further include a guidewire 1714 to which the FBG interferometer 1704 can be attached. In the example depicted in FIG. 17, a portion of the guidewire can define a machined gap 1716 underneath a portion of the proximal coil 1708 and the distal coil 1710. The machined gap 1716 can allow the optical fiber 1702 to extend longitudinally or helically along the outer surface of the guidewire 1714 and then transition underneath the proximal coil 1708 gradually into the machined gap 1716.

The example of a pressure sensor 1700 in FIG. 17 can include a cantilevered design, which can be applied to any of the examples of standalone pressure sensors described in this disclosure. More particularly, the pressure sensor 1700 can include a cantilever tube 1718 that is disposed about a distal portion of the optical fiber 1702 within the machined gap 1716. In addition, the pressure sensor 1700 can include a sensor tube 1720 disposed within the cantilever tube 1718 and about the distal portion of the optical fiber 1702. To provide support to a portion of the optical fiber 1702, the pressure sensor 1700 can also include a fiber support 1722 that is positioned between the sensor tube 1720 and a portion of the optical fiber 1702.

Between a portion of an inner surface of the cantilever tube 1718 and an outer surface of the sensor tube 1720, the pressure sensor 1700 can define a space 1724, thereby providing a double-walled housing construction. The double-walled housing construction and the space 1724 can allow the outer surface of the sensor tube 1720 to be mounted to the guidewire 1714 while isolating the FBG interferometer 1704 from motion of the guidewire 1714 and contact with the proximal coil 1708.

The FBG interferometer 1704 can also define cavity 1726, e.g., filled with air, laterally below the sensor membrane 1706 and a portion of the optical fiber 1702 and within the region defined by the sensor tube 1720. The sensor membrane 1706 and the cavity 1726 can concentrate a stress in the area between the Fabry-Perot gratings FBG 1 and FBG 2, which can enhance the sensitivity of the pressure sensor 1700.

Figure 18:
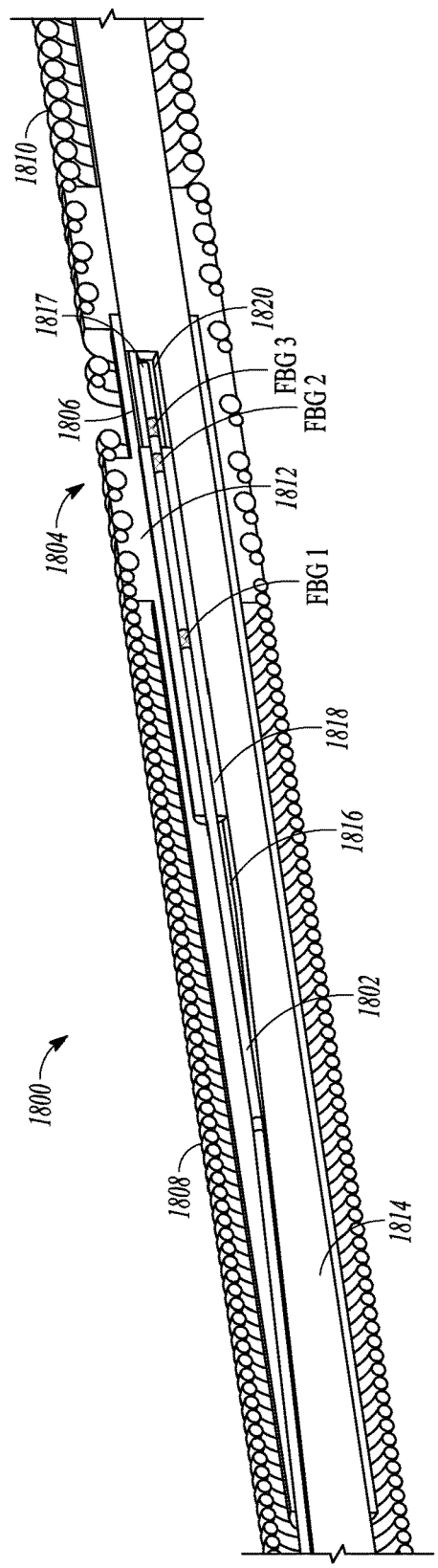
FIG. 18 depicts another example of a pressure sensor that can be used to implement various techniques of this disclosure.

FIG. 18 depicts another example of a pressure sensor that can be used to implement various techniques of this disclosure. The example of a pressure sensor depicted in FIG. 18 can provide an example of an integrated pressure sensor that can use one or more Fabry-Perot grating arrangements.

FIG. 18 is an example of a perspective cross-sectional view of an optical fiber pressure sensor 1800 that can include an optical fiber 1802 that can be configured to transmit one or more optical sensing signals and a temperature compensated Fiber Bragg Grating (FBG) interferometer 1804 in optical communication with the optical fiber 1802. The FBG interferometer 1804 can be configured to receive pressure, e.g., from pressure waves, and to modulate, in response to the received pressure, the optical sensing signal. The pressure sensor 1800 can include a sensor membrane 1806 that can be in physical communication with the FBG interferometer 1804. The sensor membrane 1806 can be configured to transmit the pressure to the FBG interferometer 1804.

The pressure sensor 1800 of FIG. 18 can further include a proximal coil 1808 and a distal coil 1810. The proximal and distal coils 1808, 1810 can provide additional flexibility to aid advancement of the pressure sensor 1800 through tortuous pathways. In one example, the proximal and distal coils 1808, 1810 can be affixed together via a mechanical joint 1812, e.g., via solder or adhesive. The FBG interferometer 1804 can, in some examples, be positioned underneath the mechanical joint 1812 to provide additional protection to the FBG interferometer 1804.

The pressure sensor 1800 of FIG. 18 can further include a guidewire 1814 to which the FBG interferometer 1804 can be attached. In the example depicted in FIG. 18, a portion of the guidewire 1814 can define a machined gap 1816 underneath a portion of the proximal coil 1808 and the distal coil 1810. The machined gap 1816 can allow the optical fiber 1802 to extend longitudinally or helically along the outer surface of the guidewire 1814 and then transition underneath the proximal coil 1808 gradually into the machined gap 1816.

The example of a pressure sensor 1800 in FIG. 18 can include a capillary tube design. More particularly, the pressure sensor 1800 can include a capillary tube 1818 to support a portion of the optical fiber 1802. The capillary tube 1818 can be disposed about a distal portion of the optical fiber 1802 within the machined gap 1816.

As seen in FIG. 18, a portion 1817 of the optical fiber 1802 can extend beyond a distal end of the capillary tube 1818 and over a cavity 1820, e.g., filled with air, that is laterally below the portion of the optical fiber 1802 that extends beyond the distal end of the capillary tube 1818. The example of a pressure sensor 1800 of FIG. 18 can include at least three FBGs (e.g., FBGs 1-3.) FBG 1 can be configured to be independent of pressure and can be used for temperature measurement, such as to provide a temperature compensated optical fiber pressure sensor, such as described above with respect to FIG. 3 and FIG. 4A.

FBGs 2 and 3 can form a phase-shift FBG structure. The surface area of the membrane 1806 can concentrate a change in pressure and can focus a mechanical response to the change in pressure at the phase-shift region between FBG 2 and FBG 3. This focused mechanical response can enhance the sensitivity of the pressure sensor 1800. The mechanical forces acting upon the phase-shift region between FBG 2 and FBG 3 can concentrate a stress in the phase-shift region. The concentrated stress in the phase-shift region can change the refractive index of the optical fiber 1802, which, in turn, alters the phase relationship between FBG 2 and FBG 3. The change in phase-shift between FBG 2 and FBG 3 can be detected and quantified, and the change in pressure can be determined from the quantified phase-shift.

As seen in FIG. 18, the sensor membrane 1806 can be disposed about the guidewire 1814, the capillary tube 1818, and the portion of the optical fiber that extends beyond the distal end of the capillary tube 1818.

Figure 19:
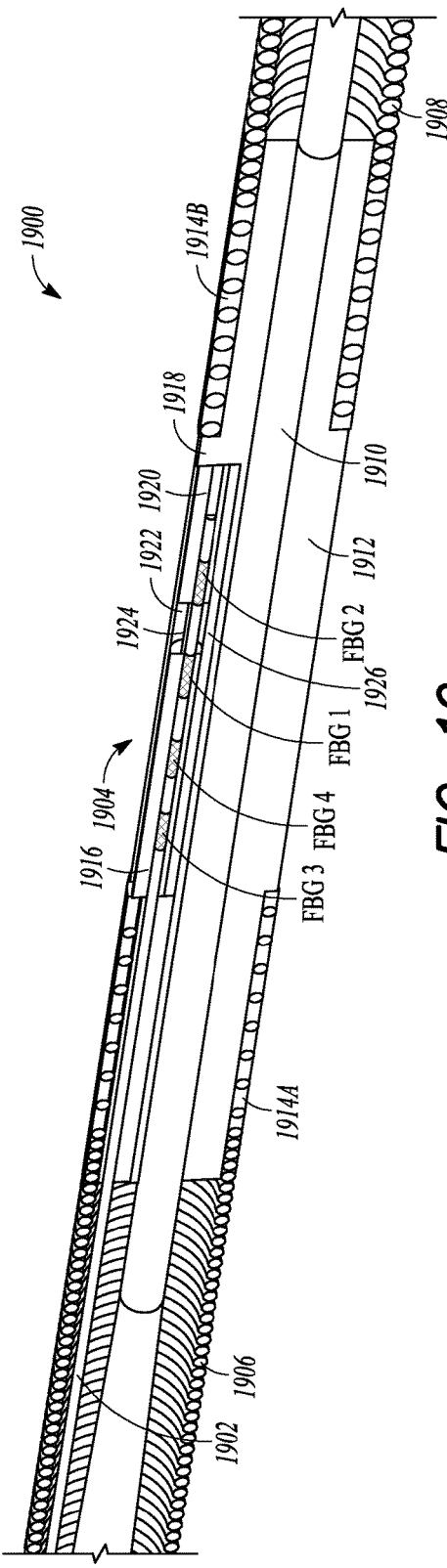
FIG. 19 depicts another example of a pressure sensor that can be used to implement various techniques of this disclosure.

FIG. 19 depicts another example of a pressure sensor that can be used to implement various techniques of this disclosure. FIG. 19 depicts another example of a pressure sensor that can be used to implement various techniques of this disclosure. The example of a pressure sensor 1900 depicted in FIG. 19 can provide an example standalone pressure sensor that can use one or more Fabry-Perot grating arrangements.

FIG. 19 is an example of a perspective cross-sectional view of an optical fiber pressure sensor 1900 that can include an optical fiber 1902 that can be configured to transmit one or more optical sensing signals and a temperature compensated Fiber Bragg Grating (FBG) interferometer 1904 in optical communication with the optical fiber 1902. The FBG interferometer 1904 can be configured to receive pressure, e.g., from pressure waves, and to modulate, in response to the received pressure, the optical sensing signal.

The example of a pressure sensor 1900 of FIG. 19 can include four FBGs (e.g., FBGs 1-4.) FBGs 3 and 4 can form a phase-shifted FBG structure, such as for sensing temperature. The change in phase-shift between FBG 3 and FBG 4 can be detected and quantified, and the change in temperature can be determined from the quantified phase-shift, such as described above.

The pressure sensor 1900 can further include Fabry-Perot gratings FBG 1 and FBG 2, which can be used to sense changes in pressure. Similar to the phase-shift grating structures described above with respect to FIG. 10D, the Fabry-Perot gratings FBG 1 and FBG 2 can create a phase shift that can be tracked in a manner similar to that described above. That is, a notch can be created in the wavelength response to the Fabry-Perot gratings FBG 1 and FBG 2, as shown and described in detail above. A point on a slope of the notch can be set and tracked, a phase shift can be detected and quantified, and the change in pressure can be determined from the quantified phase-shift, such as described in detail above.

The pressure sensor 1900 of FIG. 19 can further include a proximal coil 1906, a distal coil 1908, and a guidewire 1910. The proximal and distal coils 1906, 1908 can provide additional flexibility to aid advancement of the pressure sensor 1900 through tortuous pathways.

The pressure sensor 1900 of FIG. 19 can further include a tubular housing 1912 that can be disposed about the guidewire 1912 between the proximal and distal coils 1906, 1908. In one example, the proximal and distal coils 1906, 1908 can be affixed to the housing 1912 via mechanical joints 1914A, 1914B, e.g., via solder or adhesive. The housing 1912 can be affixed to the guidewire 1910 via a mechanical joint 1915.

In addition, the pressure sensor 1900 can include a sensor tube 1916 disposed within the housing 1912 and disposed about a distal portion of the optical fiber 1902. More particularly, the sensor tube 1916 can be positioned within an area machined out of a portion of the outer wall 1918 of the housing 1912. To provide support to the optical fiber 1902, a fiber support 1920 can be disposed about the optical fiber 1902 between the sensor tube 1916 and the optical fiber 1902.

To allow the received pressure to reach the optical fiber 1902, a portion of the sensor tube 1916 can be removed in order to define a sensor window 1922. The sensor window 1922 can be covered with the sensor membrane 1924.

The example of a pressure sensor 1900 of FIG. 19 can include four FBGs (e.g., FBGs 1-4). FBGs 3 and 4 can form a phase-shifted FBG structure, such as for sensing temperature. The change in phase-shift between FBG 3 and FBG 4 can be detected and quantified, and the change in temperature can be determined from the quantified phase-shift, such as described above.

The pressure sensor 1900 can further include Fabry-Perot gratings FBG 1 and FBG 2, which can be used to sense changes in pressure. The Fabry-Perot gratings FBG 1 and FBG 2 can create a phase shift that can be tracked in a manner similar to that described above. That is, a notch can be created in the wavelength response to the Fabry-Perot gratings FBG 1 and FBG 2, as shown and described in detail above. A point on a slope of the notch can be set and tracked, a phase shift can be detected and quantified, and the change in pressure can be determined from the quantified phase-shift, such as described in detail above.

The pressure sensor 1900 can define a cavity 1926, e.g., filled with air, laterally below the sensor membrane 1924 and the optical fiber 1902. The sensor membrane 1924 and the cavity 1926 can concentrate a stress in the area between the Fabry-Perot gratings FBG 1 and FBG 2, which can enhance the sensitivity of the pressure sensor 1900.

Figure 20:
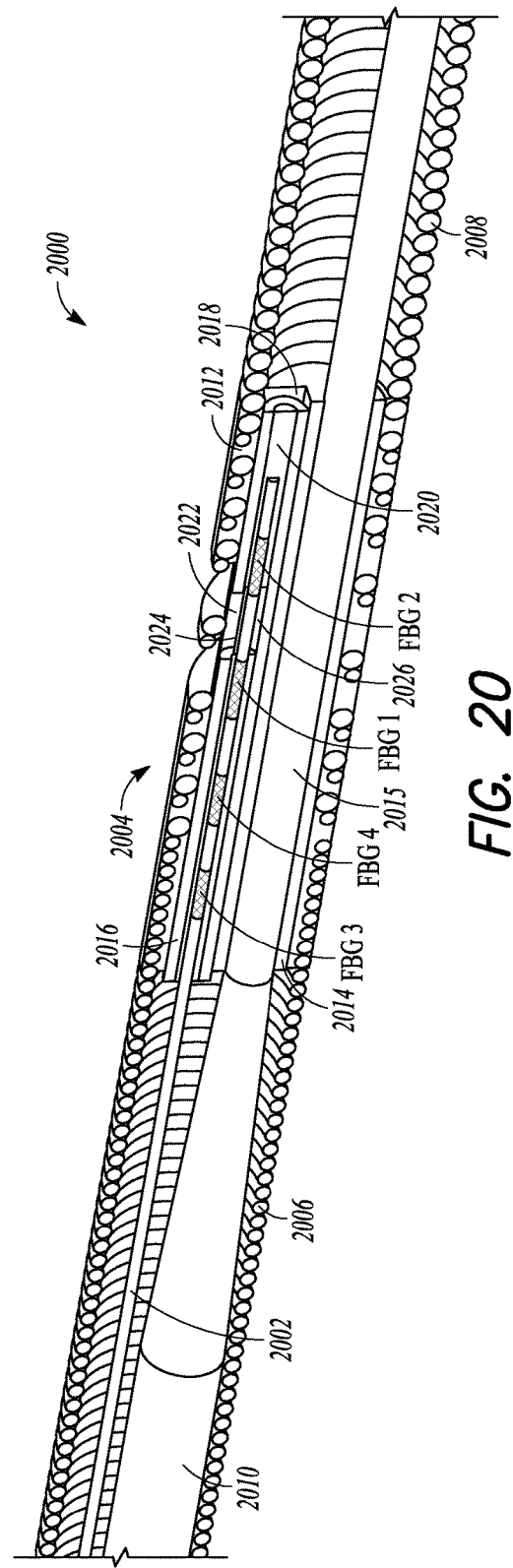
FIG. 20 depicts another example of a pressure sensor that can be used to implement various techniques of this disclosure.

FIG. 20 depicts another example of a pressure sensor that can be used to implement various techniques of this disclosure. FIG. 20 depicts another example of a pressure sensor that can be used to implement various techniques of this disclosure. The example of a pressure sensor 2000 depicted in FIG. 20 can provide an example standalone pressure sensor that can use one or more Fabry-Perot grating arrangements.

FIG. 20 is an example of a perspective cross-sectional view of an optical fiber pressure sensor 2000 that can include an optical fiber 2002 that can be configured to transmit one or more optical sensing signals and a temperature compensated Fiber Bragg Grating (FBG) interferometer 2004 in optical communication with the optical fiber 2002. The FBG interferometer 2004 can be configured to receive pressure, e.g., from pressure waves, and to modulate, in response to the received pressure, the optical sensing signal.

The example of a pressure sensor 2000 of FIG. 20 can include four FBGs (e.g., FBGs 1-4.) FBGs 3 and 4 can form a phase-shifted FBG structure, such as for sensing temperature. The change in phase-shift between FBG 3 and FBG 4 can be detected and quantified, and the change in temperature can be determined from the quantified phase-shift, such as described above.

The pressure sensor 2000 can further include Fabry-Perot gratings FBG 1 and FBG 2, which can be used to sense changes in pressure. Similar to the phase-shift grating structures described above with respect to FIG. 10D, the Fabry-Perot gratings FBG 1 and FBG 2 can create a phase shift that can be tracked in a manner similar to that described above. That is, a notch can be created in the wavelength response to the Fabry-Perot gratings FBG 1 and FBG 2, as shown and described in detail above. A point on a slope of the notch can be set and tracked, a phase shift can be detected and quantified, and the change in pressure can be determined from the quantified phase-shift, such as described in detail above.

The pressure sensor 2000 of FIG. 20 can further include a proximal coil 2006, a distal coil 2008, and a guidewire 2010. The proximal and distal coils 2006, 2008 can provide additional flexibility to aid advancement of the pressure sensor 2000 through tortuous pathways. In one example, the proximal and distal coils 2006, 2008 can be affixed together via a mechanical joint 2012, e.g., via solder or adhesive. The FBG interferometer 2004 can, in some examples, be positioned underneath the mechanical joint 2012 to provide additional protection to the FBG interferometer 2004.

The pressure sensor 2000 of FIG. 20 can further include a tubular housing 2014 that can be disposed about the guidewire 2010 and underneath the mechanical joint 2012. The housing 2014 can be affixed to the guidewire 2010 via a mechanical joint 2015. In addition, the pressure sensor 2000 can include a sensor tube 2016 disposed within the housing 2014 and disposed about a distal portion of the optical fiber 2002. In contrast to the tubular housing of FIG. 19, the tubular housing 2014 of FIG. 20 can define a lumen 2018 that extends longitudinally through the housing 2014. The sensor tube 2016 of FIG. 20 can be positioned within the lumen 2018. To provide support to the optical fiber 2002, a fiber support 2020 can be disposed about the optical fiber 2002 between the sensor tube 2016 and the optical fiber 2002.

To allow the received pressure to reach the optical fiber 2002, a portion of the sensor tube 2016 can be removed in order to define a sensor window 2022. The sensor window 2022 can be covered with a sensor membrane 2024.

The example of a pressure sensor 2000 of FIG. 20 can include four FBGs (e.g., FBGs 1-4). FBGs 3 and 4 can form a phase-shifted FBG structure, such as for sensing temperature. The change in phase-shift between FBG 3 and FBG 4 can be detected and quantified, and the change in temperature can be determined from the quantified phase-shift, such as described above.

The pressure sensor 2000 can further include Fabry-Perot gratings FBG 1 and FBG 2, which can be used to sense changes in pressure. The Fabry-Perot gratings FBG 1 and FBG 2 can create a phase shift that can be tracked in a manner similar to that described above. That is, a notch can be created in the wavelength response to the Fabry-Perot gratings FBG 1 and FBG 2, as shown and described in detail above. A point on a slope of the notch can be set and tracked, a phase shift can be detected and quantified, and the change in pressure can be determined from the quantified phase-shift, such as described in detail above.

The pressure sensor 2000 can define a cavity 2026, e.g., filled with air, laterally below the sensor membrane 2024 and the optical fiber 2002. The sensor membrane 2024 and the cavity 2026 can concentrate a stress in the area between the Fabry-Perot gratings FBG 1 and FBG 2, which can enhance the sensitivity of the pressure sensor 2000.

FIGS. 21A-21G depict various examples of a guidewire in combination with an optical fiber pressure sensor. FIG. 21A is an example of a partial cutaway view illustrating a combination 2100 of a guidewire 2102 and an optical fiber 2104 attached to an optical fiber pressure sensor 2106 (FIG. 21C).

In one example, the guidewire 2102 can be substantially similar to the guidewire shown and described in U.S. Pat. No. 5,341,818 to Abrams et al. and assigned to Abbott Cardiovascular Systems, Inc. of Santa Clara, Calif., the entire contents of which being incorporated herein by reference. The guidewire 2102 can include a proximal portion 2108 and a distal portion 2110. The distal portion 2110 can be formed at least partially of superelastic materials. The guidewire 2102 can further include a tubular connector 2112 that can connect a distal end 2114 of the proximal portion 2108 and a proximal end 2116 of the distal portion 2110.

The tubular connector 2112 joining the proximal portion 2108 and the distal portion 2110 of the wire may be stainless steel (such as 304 series stainless steel) or nitinol material and may be grooved or slotted to accommodate the fiber. The groove or slot in the tubular connector 2112 may be aligned to the centerline of the tubular connector 2112 or it may be angled across the tubular connector 2112 to match the helix angle of the fiber groove path along the proximal or distal portions of the wire. The wire ends and the tubular connector 2112 may be adhesively joined, braze or solder attached to each other, the coupler may be welded to the wire end, or the tubular connector 2112 may be swaged or crimped onto the wire end.

In the case of a nitinol connector 2112, the connector 2112 can be expanded mechanically or by cooling it to martensite phase and deforming it. Once the nitinol connector 2112 has been expanded it can be installed over the wire and allowed to return to austenite phase, causing it to clamp down on the wire end. FIG. 21E depicts a perspective view of an example of a connector 2112.

The guidewire core material can affect the flexibility, support, steering and trackability of the guidewire while the guidewire core diameter can influence the flexibility, support, and torque of the guidewire. Suitable guidewire core materials can include the 18-8 stainless steels such as 304V, 304LV, and other 300 series alloys, nickel-based super alloys (such as, for example, MP35N), cobalt chromium molybdenum based super alloys, and nitinol.

Some examples of suitable metals and metal alloys that can be used to construct a guidewire include 304L and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material. Stainless steel and superalloy materials provide excellent support, transmission of push force and torque characteristics but can be less flexible and more susceptible to kinking than nitinol. Nitinol can provide excellent flexibility and steering but can be less torqueable than stainless steel.

The guidewire core metal alloy materials can be subjected to thermomechanical processing to achieve the desired mechanical properties. To achieve the spring temper and ultimate tensile strength (for example, of greater than 300 ksi) desirable for the guidewire proximal shaft, the austenitic stainless steel 304V can be significantly cold worked (e.g. between 93 and 95% cold worked for UTS of 316 to 334 ksi). In wire form, 304V can gain tensile strength when stress relieved under a reducing atmosphere between 350 and 427 degrees Celsius. Nitinol wire can be cold worked (typically between 10 and 75%) during drawing and the amount of cold work in the wire prior to its final heat treatment (or shape set anneal) can dictate the ultimate tensile strength of the nitinol wire. The final heat treatment (or shape set anneal) for guidewires can be a straightening process performed under controlled time, temperature, and pressure conditions. The wire can be heat treated well above the austenite to martensite transformation temperature (450 to 600 C) while being subjected to longitudinal stresses to impart a straight memory to the wire. The shape set anneal process can define the final mechanical properties of the wire such as an ultimate yield strength of greater than 155 ksi.

Coupling different materials together to provide the best properties for each guidewire region can be a significant reason for choosing to join different wire sections together. The present inventors have also recognized that coupling different diameter wires together, whether those wires are the same material or different materials, can be advantageous. When the fiber groove is formed during the fiber draw processing or by other means into a constant diameter wire, coupling together two dissimilar diameter grooved wires can maintain the fiber groove sized appropriately for the fiber as the wire diameter is increased or decreased. An example is shown in FIG. 21F where a proximal connector 2113 joins a larger diameter stainless steel proximal shaft 2150 to a smaller diameter nitinol intermediate portion 2152 and a distal connector 2112 joins a small diameter stainless steel distal portion 2154 to the nitinol intermediate wire 2152.

In another example, when there is only a single joint between the proximal stainless steel shaft and a distal superelastic nitinol section that extends all the way to the distal tip, it can be desirable to either leave the region of the shapeable tip in the cold-worked or as-drawn condition so that shaping or permanent deformation of that region is possible when the physician intends to form the tip or to eliminate the superelasticity in the shapeable tip region by reversing the final strain anneal.

The coupled wire joints can be welded together rather than joined together using a tubular connector. This is relatively straightforward if the two wires are the same material but if they are dissimilar materials it is significantly more challenging. A laser based joining process can be used to directly melt the two wires to be joined or to melt a filler material at the joint. It can be desirable to optimize joints of stainless steel to nitinol to avoid the intermetallic phase rich in iron and titanium because Fe2Ti is a brittle intermetallic. A nickel or tantalum interlayer between the stainless steel and nitinol can be used to facilitate a laser weld join between these two materials.

Another laser joining process designed to form joints that are significantly smaller than the laser beam spot size can take advantage of heat accumulation at the joint interface. Laser irradiating one of the base materials (for example, the nitinol wire) and scanning toward the nitinol stainless steel interface with a laser power and speed such that the equilibrium temperature of the irradiated piece does not exceed its melt temperature (controlling the Gaussian laser spot to be the same diameter as the wires to be joined). Heat accumulation due to the thermal resistance of the interface can cause the temperature to rise above the melt temp of the nitinol as the laser beam approaches the interface, forming a molten layer. The laser beam can be turned off as it reaches the interface and the melt layer is quenched when it comes in contact with the adjacent cold work piece to form a seamless braze-like joint.

Combining a PTFE coated stainless steel proximal shaft with a superelastic nitinol distal portion via a tube coupler as described by FIGS. 21A, 21E, and 21F and their associated descriptions (or by directly joining the stainless steel shaft to the superelastic nitinol distal end) and employing the polymer sleeve or jacket as described above over the distal nitinol portion proximal of a cavity 2162 containing the sensor 2106 results in the optical fiber pressure sensor guidewire shown in FIG. 21G. The polymer sleeve or jacket 2160 can be coated with a durable hydrophilic coating, an intermediate coil can be deployed over the 2162 with an uncoated radiopaque coil over the corewire distal of the cavity 2162 and sensor 2106. This guidewire sensor assembly 2164 can have the mechanical performance of a second generation high torque frontline guidewire with pressure sensing capability.

In some example configurations, the fiber pressure sensor assembly can include a flexible polymer jacket or sleeve over the tapered distal end of the guidewire core. As used in this disclosure, the term polymer, as used with regard to polymer coatings, is intended to be interpreted broadly and can include all polymers, prepolymers and the like that are suitable for use as a coating of a fiber pressure sensor assembly. A non-limiting list of suitable materials can include polyurethanes, including polyurethane thermoplastic elastomers; polyamides (nylons); polyethers; polyesters; polyacetals; acrylics; methacrylics; cellulosics; fluoropolastics; epoxies; keton-based resins and polymers; polyimide based resins and polymers; bismaleimides; nitriles; polyarylates; polycarbonates; liquid crystal polymers; terephthalate resins and polymers including polybutylene terephthalate and polyethylene terephthalate; polyetherimides; polyolefins including polyethylenes, polypropylenes, polybutylenes, polybutadienes; polyvinyls including polystyrenes and polyvinyl chlorides; elastomers especially thermoplastic elastomers; silicones; rubbers; ionomers; ceramers; dendritic polymers; and derivatives, copolymers, multipolymers, blends and/or mixtures of any of the previous listed resins and polymers within each group and between each group, the latter including polyether block amide elastomers such as COPA and PEBAX.

The polymer sleeve or jacket covering the guidewire core between the proximal shaft the distal coil can provide a smoother surface and therefore greater lubricity than would a proximal coil disposed over that section, thereby allowing for smoother tracking through tortuous vasculature. The polymer sleeve or jacket may also be coated with, for example, a hydrophilic coating. The polymer sleeve or jacket may also cover coils, leaving the distal coil exposed provides better tactile feedback. The optical fiber may be positioned under (or within the wall thickness) the polymer sleeve or jacket as was described for routing the optical fiber along the pressure sensor assembly length covered by a proximal coil or a slotted flexible tube. Alternatively, a groove may be created (for example by lasing, by various mechanical means including scribing, a hot wire, etc. or depending on the polymer by thermally softening the sleeve or jacket as the fiber is wrapped into place) in the polymer sleeve or jacket to accommodate the fiber. The guidewire 2102 can further include a core wire 2118 having an elongated portion 2120 and a tapered portion 2122 extending distally beyond the elongated portion 2120. In addition, the guidewire 2102 can include a proximal coil 2124 disposed about the elongated portion 2120 and a distal coil 2126 disposed about a portion of each of the elongated portion 2120 and the tapered portion 2122 and extending distally beyond the tapered portion 2122. The proximal coil 2124 and the distal coil 2126 can be joined together via a mechanical joint 2128, e.g., solder or adhesive. The guidewire 2102 can further include a distal plug 2130, about which a portion of the distal coil 2126 can be wound, or a conventional solder tip. Additional information regarding the components and construction of the guidewire 2102 can be found in U.S. Pat. No. 5,341,818.

Regarding construction of the combination 2100 of the guidewire 2102 and the optical fiber 2104 attached to an optical fiber pressure sensor 2106 (FIG. 21C), in one example, a narrow, shallow channel or groove 2132 (FIG. 21B) can be cut into the outer wall of the components that form the guidewire 2102, e.g., the core wire 2118 and the tubular connector 2112. The optical fiber 2104 can be positioned within the groove 2132. Due to the relatively small dimensions of optical fiber 2104, the dimensions of the groove 2132 can have minimal impact on the performance of the guidewire 2102.

The groove 2132 can extend along the length of the guidewire 2102 substantially parallel to a longitudinal axis of the guidewire 2102. In another example, the groove 2132 can spiral about the guidewire 2102, e.g., a helically axially extending groove. In other examples, the groove 2132 can extend along a portion of the length of the guidewire 2102 substantially parallel to a longitudinal axis of the guidewire 2102 and then the groove 2132 can spiral about another portion of the length of the guidewire 2102, e.g., a helically axially extending groove. The pitch of the spiral can be varied along the length of the guidewire.

The groove 2132 can be fabricated using various techniques that include, but are not limited to, etching, machining, and laser ablation. In addition, the groove 2132 can be fabricated at various stages during the construction of the guidewire 2102, e.g., before or after applying a coating to the guidewire 2102.

The optical fiber 2104 can be bonded to the groove 2132 using various techniques. For example, the optical fiber 2104 can be bonded to the groove 2132 by applying a hot melt adhesive to the optical fiber 2104 prior to positioning the optical fiber 2104 in the groove 2132 and then subsequently applying heat.

In other examples, rather than a groove 2132 that is cut into the outer wall of the components that form the guidewire 2102, the guidewire 2102 can define a lumen (not depicted) that extends along a portion of the length of the guidewire 2102 substantially parallel to a longitudinal axis of the guidewire 2102. The lumen can be coaxial with the longitudinal axis of the guidewire 2102, or the lumen can be radially offset from the longitudinal axis of the guidewire 2102. The optical fiber 2104 can extend along the length of the guidewire 2102 through the lumen. The dimensions of the lumen can have minimal impact on the performance of the guidewire 2102.

In another example, the guidewire 2102 can be constructed to include an annular gap (not depicted) between the proximal coil 2124 and the elongated portion 2120. The optical fiber 2104 can then extend along the length of the elongated portion 2120 between an outer surface of the elongated portion 2120 and an inner surface of the proximal coil 2124. The optical fiber 2104 can be wound about the elongated portion 2120. In some examples, the optical fiber 2104 can be secured to the elongated portion 2120, e.g., via an adhesive.

FIG. 21B is an example of a cross-sectional view of the combination 2100 of FIG. 21A, such as taken along section B-B of FIG. 21A. The guidewire 2102, e.g., a solid guidewire, can include the fabricated groove 2132. FIG. 21B illustrates the optical fiber 2104 positioned within the groove 2132 of the core wire 2118 of the guidewire 2102.

FIG. 21C is an example of a cross-sectional view of the combination 2100 of FIG. 21A, such as taken along section E-E of FIG. 21A. More particularly, FIG. 21C depicts another example of a pressure sensor 2106 that can be used to implement various techniques of this disclosure.

The optical fiber pressure sensor 2106 can include the optical fiber 2104 that can be configured to transmit one or more optical sensing signals and a temperature compensated Fiber Bragg Grating (FBG) interferometer 2134 in optical communication with the optical fiber 2104. The FBG interferometer 2134 can be configured to receive pressure, e.g., from pressure waves, and to modulate, in response to the received pressure, the optical sensing signal.

The example of a pressure sensor 2106 of FIG. 21C can further include FBGs (not depicted) similar to those described in detail above with respect to various examples of pressure sensors, e.g., FIG. 10D, which can be used to sense changes in pressure. The FBGs can create a phase shift that can be tracked in a manner similar to that described above.

The pressure sensor 2106 of FIG. 21C can further include the proximal coil 2124 and the distal coil 2126. The proximal and distal coils 2124, 2126 can provide flexibility to aid advancement of the pressure sensor 2106 through tortuous pathways. In one example, the proximal and distal coils 2124, 2126 can be affixed together via a mechanical joint 2136. The FBG interferometer 2134 can, in some examples, be positioned underneath the mechanical joint 2136 to provide additional protection to the FBG interferometer 2134.

As indicated above, the guidewire 2102 can be fabricated with a groove 2132 (FIG. 21B) to which the optical fiber 2104 can be attached. A portion of the optical fiber 2104 can extend underneath the mechanical joint 2136. To allow the received pressure to reach the optical fiber 2104, a portion of the mechanical joint 2136 can be removed in order to define a sensor window, shown generally at 2138. The sensor window 2138 can be covered with the sensor membrane 2140.

In the example depicted in FIG. 21C, the pressure sensor 2106 can be constructed by fabricating a small cavity 2142 in the core wire 2118 that is in communication with the groove 2132 at the distal end of the optical fiber 2104. The cavity 2142 can, for example, be 100 microns in diameter by 100 microns in depth. The guidewire 2102 can be constructed of the superelastic material, or a different super stiff material may be substituted at this location (not depicted), for example, aluminum oxide ($Al_2O_3$) or Alumina ceramic which can be precision molded to define the cavity 2142 and the groove 2132.

The pressure sensor 2106 can further include a microballoon 2144 placed into the cavity 2142. In some examples, an adhesive (not depicted) can be placed in the cavity 2142 to secure the microballoon 2144 in place. The microballoon 2144 can be filled with a gas, sealed, and heat expanded such that, when expanded, the microballoon 2144 can fill the cavity 2142 and maintain a sealed reference chamber. If an upper surface of the microballoon 2144 is constricted during its expansion, a flat diaphragm can be achieved. The optical fiber 2104 with FBGs can be positioned in the groove 2132 and across the flat diaphragm of the microballoon 2144.

The remaining space of the cavity 2142 and the groove 2132 can be filled with an adhesive (not depicted) such as silicone to capture the optical fiber 2104, to attach the optical fiber 2104 to the guidewire 2102, to attach the optical fiber 2104 to the microballoon 2144, and to define a relatively thin silicone diaphragm in mechanical communication with the chamber defined by the microballoon 2144 where the optical fiber 2104 is embedded. As a pressure is applied, each of the silicone, the optical fiber 2104, and the microballoon 2144 can flex due to compression of the sealed chamber. The flexing can transmit the received pressure to the FBG interferometer 2134, which can create a responsive phase shift between FBGs (not depicted) that can be tracked in a manner similar to that described above.

FIG. 21D is an example of a cross-sectional view of the combination 2100 of FIG. 21A, such as taken along section A-A of FIG. 21A. More particularly, FIG. 21D depicts a cross-sectional view of the pressure sensor 2106 of FIG. 21C. As seen in FIG. 21D and as described above with respect to FIG. 21C, the pressure sensor 2106 of FIG. 21C can include the microballoon 2144 positioned within the cavity 2142. The optical fiber 2104 with FBGs can be positioned in the groove 2132 and across the flat diaphragm 2146 of the microballoon 2144.

Any of optical fiber pressure sensors described in this disclosure can be combined with the guidewire 2102 shown and described above with respect to FIG. 21A and in U.S. Pat. No. 5,341,818. Further, the techniques of this disclosure are not limited to the use of a single sensor in combination with a guidewire, e.g., guidewire 2102. Rather, two or more sensors, e.g., pressure sensors, can be combined with a guidewire by defining sensor regions in which each of the two or more sensors can function at a respective, unique wavelength and can be addressed accordingly by a laser matching the wavelength of the respective sensor. Each laser can be multiplexed onto the optical fiber using standard techniques, e.g., wavelength-division multiplexing (WDM), found in telecommunications systems.

By way of example, two pressure sensors can be positioned along the length of the core wire 2118. One pressure sensor can be located as shown in FIG. 21A. A second sensor can be positioned proximally such that it can record the pressure proximal to an obstruction in the blood vessel. With this example configuration, the guidewire can measure the aortic pressure (Pa) and the distal pressure (Pd), thereby allowing the computation of FFR as Pa/Pd without relying on external pressure sensors. This can simplify the configuration of console equipment interconnection as the pressure sensor console would not need to be connected to an external pressure monitoring system.

By way of a further example, the two (or more) pressure sensors can be configured using a single fiber with each pressure sensor operating at a unique and separable wavelength. In the case of two sensors, taking the examples of pressure sensor embodiments detailed herein, such as those in FIGS. 60 and 61, the proximal sensor can be configured such that the distal temperature sensing portion can accommodate sufficient slack in the fiber placement so that the pressure sensor operation would not be impeded.

In yet another configuration, the incorporation of multiple pressure sensors can be achieved through integration of multiple optical fibers and sensors, each operational at the same wavelength of light or alternatively at more than one wavelength. Multiple optical fibers can be accommodated in various exemplary ways. The optical fibers can be placed in close proximity to each other along the length of the guidewire, or the optical fibers can be evenly or unevenly spaced around the circumference of the guidewire, such as in double or multiple helical formation or other winding patterns, or straight along the length of the guidewire. To accommodate the multiple optical fibers, the groove along the length of the guidewire can be widened, or separate grooves can be furnished around the circumference of the guidewire. Alternatively, a larger luminal bore can be made through the guidewire core.

In another example, the guidewire 2102 of FIG. 21A can be combined with other sensor techniques. For example, the same guidewire can be used for both intravascular ultrasound (IVUS) imaging and pressure sensing by using the imaging sensor configurations described in U.S. Pat. No. 7,245,789 to Bates et al., and assigned to Vascular Imaging Corp, the entire contents of which being incorporate herein by reference. By way of specific example, one of the optical fibers in a 32 fiber arrangement can extend distally beyond an imaging sensor region, where an optical fiber pressure sensor, such as any of the optical fiber pressure sensors described in this disclosure, can be included that utilizes a different wavelength than that used by the imaging arrangement.

Figure 22:
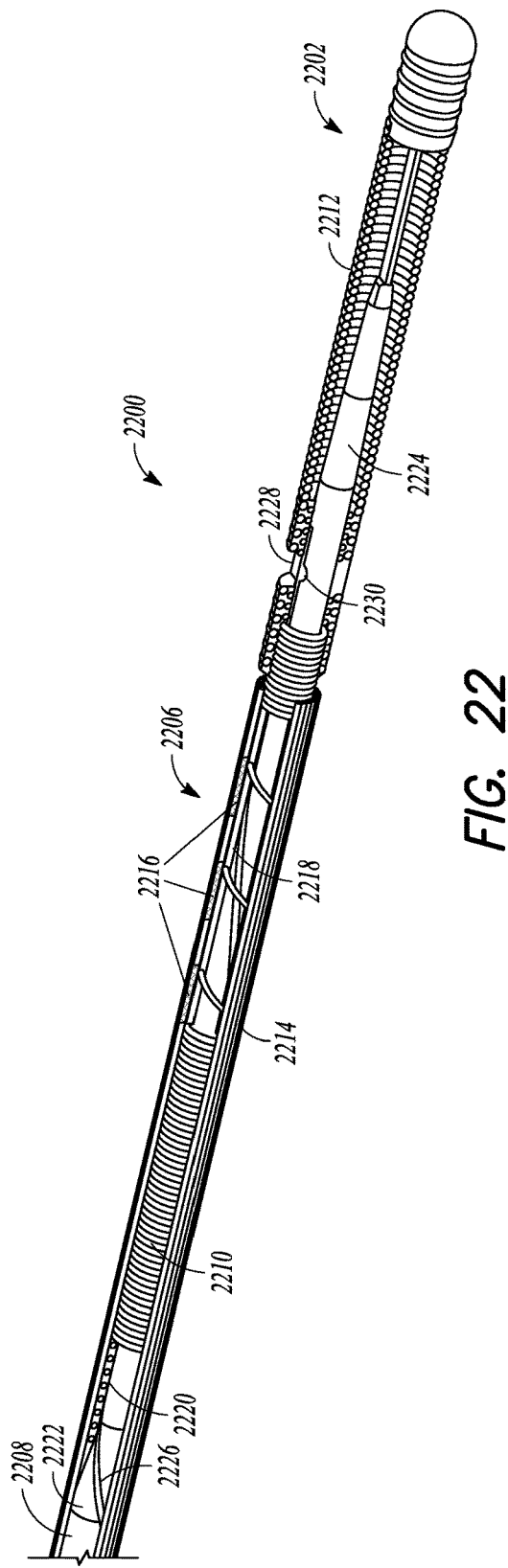
FIG. 22 depicts an example of a combination of a guidewire with an optical fiber pressure sensor and an imaging sensor, in accordance with this disclosure.

FIG. 22 depicts an example of a combination 2200 of a guidewire 2202 with an optical fiber pressure sensor 2204 and an imaging sensor 2206, e.g., using the imaging sensor configurations described in U.S. Pat. No. 7,245,789. In particular, FIG. 22 is an example of a perspective partial cutaway view of the combination 2200.

The guidewire 2202 is similar in construction to the guidewire 2102 described above with respect to FIG. 21A, and as shown and described in U.S. Pat. No. 5,341,818. The guidewire 2202 can include a core wire 2208, a proximal coil 2210, and a distal coil 2212.

The imaging sensor 2206 can include an optical fiber ribbon 2214 having a plurality of optical fibers, e.g., 32 optical fibers, disposed about the core wire 2208 of the guidewire 2202, and a plurality of imaging gratings 2216 to couple light into and/or out of one or more respective optical fibers of the ribbon 2214.

The guidewire 2202 can further include a backing 2218 disposed about the core wire 2208 and positioned between the core wire 2208 and the optical fiber ribbon 2214. In addition, the guidewire 2202 can include a mechanical joint 2220 for joining a proximal portion 2222 of the guidewire 2202 to a distal portion 2224 of the guidewire 2202.

In one example, the pressure sensor 2204 can be similar to the pressure sensor 2106 of FIG. 21C. For purposes of conciseness, the pressure sensor 2204 will not be described in detail again. The pressure sensor 2204 can include a single optical fiber 2226 that extends longitudinally along the length of the guidewire 2202, e.g., within a groove in the outer surface of the core wire 2208 and underneath the optical fiber ribbon 2214. The pressure sensor 2204 can further include a pressure sensing window 2228 and pressure sensor membrane 2230, as described in detail above. The pressure sensor 2204 of FIG. 22 is not limited to the design of the pressure sensor 2106 of FIG. 21C. Rather, any of the pressure sensor configurations described in this disclosure can be applied to the combination 2200.

In one example, an outer diameter of the guidewire 2202 can be reduced along the length of the guidewire 2202 up to the distal coil 2212 to allow the optical fiber ribbon 2214 to be disposed about the outer surface of the guidewire 2202. By way of specific example, the outer diameter of the proximal coil 2210 can be reduced from 0.014" to 0.011" and the pressure sensor 2204 can be incorporated with the guidewire 2202 either in a surface groove or a coaxial hole of the core wire 2208. The optical fiber ribbon 2214, e.g., a 32 optical fiber arrangement, of the imaging sensor 2206 can then be positioned over the 0.011" outer diameter of the guidewire 2202 so that the assembly contains 33 optical fibers, for example. This configuration can separate the multiplexing requirements of the imaging sensor 2206 and the pressure sensor 2204, and can allow the pressure sensor 2204 to operate at any wavelength, including that of the imaging sensor 2206.

In another example, the guidewire 2202 of FIG. 22 can be attached to one or more consoles by way of a connector. The connector can contain the 32 or more optical fibers according to the construction of the guidewire 2202. For the example where the one or more pressure sensors are formed in the same optical fibers of the imaging sensor(s), the 32 or more imaging fibers can be attached to a console using, for example, the connection techniques described in U.S. Pat. No. 8,583,218 to Michael J. Eberle and WIPO Patent Application No. WO 2014/159702 to Tasker et al., the entire content of each incorporated herein by reference.

The console or connecting apparatus can contain circuitry and/or modules adapted to split or separate the optical signals for pressure sensing and imaging. The signals for imaging can be directed to a control and signal detection apparatus for subsequent processing into images. The signals for pressure sensing can be directed to a control and signal detection apparatus for processing and conversion into pressure signals.

The functionality of imaging and pressure sensing can be contained in a single console for display on a single screen or separate screens or other indicators. Alternatively, the imaging and pressure functionality can be contained in separate consoles or modules within one or more consoles for display on one or more screens. For the example where the one or more pressure sensors are formed on optical fibers separate to the 32 or more image sensing optical fibers, the separation means may be unnecessary. As illustrated by these and other examples, the combination guidewire of FIG. 22 can enable simultaneous or serial imaging and pressure sensing capabilities when attached to one or more consoles or modules. Although the example of a 32 optical imaging fiber coronary guidewire has been described, the techniques of the current disclosure can be applied to guidewires containing more or less than 32 optical fibers, larger guidewires, catheters, smaller or larger optical fibers, various IVUS imaging configurations including various ultrasonic frequencies and more.

FIGS. 23A-23B depict another example of a guidewire in combination with an optical fiber pressure sensor. FIG. 23A is an example of a partial cutaway view illustrating a combination 2300 of a guidewire 2302 and an optical fiber 2304 attached to an optical fiber pressure sensor 2306 (FIG. 23B).

The guidewire 2302 can include a proximal portion 2308 and a distal portion 2310. The distal portion 2310 can be formed at least partially of superelastic materials. The guidewire 2302 can further include a tubular connector 2312 that can connect a distal end 2314 of the proximal portion 2308 and a proximal end 2316 of the distal portion 2310.

The guidewire 2302 can further include a core wire 2318 having an elongated portion 2320 and a tapered portion 2322 extending distally beyond the elongated portion 2320. In addition, the guidewire 2302 can include a proximal coil 2324 disposed about the elongated portion 2320 and the tapered portion 2322. The guidewire 202 can also include a distal coil 2326 disposed about a portion of the tapered portion 2322 and extending distally beyond the tapered portion 2322. The proximal coil 2324 and the distal coil 2326 can be joined together via a mechanical joint 2328, e.g., solder or adhesive. The guidewire 2302 can further include a distal plug 2330, about which a portion of the distal coil 2326 can be wound, or a conventional solder tip.

Regarding construction of the combination 2300 of the guidewire 2302 and the optical fiber 2304 attached to an optical fiber pressure sensor 2306, in one example, a narrow, shallow channel or groove (not depicted) can be cut into the outer wall of the components that form the guidewire 2302, e.g., the core wire 2318 and the tubular connector 2312. The optical fiber 2304 can be positioned within the groove. Due to the relatively small dimensions of optical fiber 2304, the dimensions of the groove can have minimal impact on the performance of the guidewire 2302.

The groove can extend along the length of the guidewire 2302 substantially parallel to a longitudinal axis of the guidewire 2302. In another example, the groove can spiral about the guidewire 2302, e.g., a helically axially extending groove. In other examples, the groove can extend along a portion of the length of the guidewire 2302 substantially parallel to a longitudinal axis of the guidewire 2302 and then the groove can spiral about another portion of the length of the guidewire 2302, e.g., a helically axially extending groove. The pitch of the spiral can be varied along the length of the guidewire.

The groove can be fabricated using various techniques that include, but are not limited to, etching, machining, and laser ablation. In addition, the groove can be fabricated at various stages during the construction of the guidewire 2302, e.g., before or after applying a coating to the guidewire 2302.

The optical fiber 2304 can be bonded to the groove using various techniques. For example, the optical fiber 2304 can be bonded to the groove by applying a hot melt adhesive to the optical fiber 2304 prior to positioning the optical fiber 2304 in the groove and then subsequently applying heat.

The guidewire 2302 can be constructed to include an annular gap, shown in FIG. 23B at 2332, between the proximal coil 2324 and the portions 2320, 2322. The optical fiber 2304 can then extend along the length of the portions 2320, 2322 of the distal portion 2310 between an outer surface of the portions and an inner surface of the proximal coil 2324. The optical fiber 2304 can be wound about the elongated portion 2320. In some examples, the optical fiber 2304 can be secured to the elongated portion 2320, e.g., via an adhesive.

The combination 2300 can further include a sleeve 2334 disposed about the core wire 2318 and underneath the mechanical joint 2328, to receive a distal portion of the optical fiber 2304. In one example, sleeve 2334 can be constructed of aluminum oxide ($Al_2O_3$), or other stiff material. The core wire 2318 can taper as it extends underneath the mechanical joint.

FIG. 23B is an example of a partial cutaway view of a portion of the combination 2300 of FIG. 23A. More particularly, FIG. 23B depicts another example of a pressure sensor 2306 that can be used to implement various techniques of this disclosure.

The optical fiber pressure sensor 2306 can include the optical fiber 2304 that can be configured to transmit one or more optical sensing signals and a temperature compensated Fiber Bragg Grating (FBG) interferometer 2334 in optical communication with the optical fiber 2304. The FBG interferometer 2334 can be configured to receive pressure, e.g., from pressure waves, and to modulate, in response to the received pressure, the optical sensing signal.

The example of a pressure sensor 2306 of FIG. 23B can further include FBGs (not depicted) similar to those described in detail above with respect to various examples of pressure sensors, e.g., FIG. 10D, which can be used to sense changes in pressure. The FBGs can create a phase shift that can be tracked in a manner similar to that described above.

The pressure sensor 2306 of FIG. 23B can further include the proximal coil 2324 and the distal coil 2326. The proximal and distal coils 2324, 2326 can provide flexibility to aid advancement of the pressure sensor 2306 through tortuous pathways. In one example, the proximal and distal coils 2324, 2326 can be affixed together via a mechanical joint 2328. The FBG interferometer 2334 can, in some examples, be positioned underneath the mechanical joint 2328 to provide additional protection to the FBG interferometer 2334.

As indicated above, the guidewire 2302 can be constructed to include an annular gap 2332 between the proximal coil 2324 and the portion 2320 to allow the optical fiber 2304 to extend along the length of the portion 2320. The sleeve 2334 can include a lumen, groove, or pocket to receive the distal end of the optical fiber 2304. To allow the received pressure to reach the optical fiber 2304, a portion of the mechanical joint 2328 and the sleeve 2334 can be removed in order to define a sensor window, shown generally at 2338. The sensor window 2338 can be covered with the sensor membrane 2340.

In the example depicted in FIG. 23B, the pressure sensor 2306 can be constructed by fabricating a small cavity 2342 in the core wire 2318. The cavity 2342 can, for example, be 100 microns in diameter by 100 microns in depth. The guidewire 2302 can be constructed of the superelastic material, or a different super stiff material may be substituted at this location (not depicted), for example, $Al_2O_3$, or Alumina ceramic which can be precision molded to define the cavity 2342.

The pressure sensor 2306 can further include a microballoon 2344 placed into the cavity 2342. In some examples, an adhesive (not depicted) can be placed in the cavity 2342 to secure the microballoon 2344 in place. The microballoon 2344 can be filled with a gas, sealed, and heat expanded such that, when expanded, the microballoon 2344 can fill the cavity 2342 and maintain a sealed reference chamber. If an upper surface of the microballoon 2344 is constricted during its expansion, a flat diaphragm can be achieved. The optical fiber 2304 with FBGs can be positioned in the sleeve 2334 and across the flat diaphragm of the microballoon 2344.

As a pressure is applied, the optical fiber 2304 and the microballoon 2344 can flex due to compression of the sealed chamber. The flexing can transmit the received pressure to the FBG interferometer 2334, which can create a responsive phase shift between FBGs (not depicted) that can be tracked in a manner similar to that described above.

FIG. 24 shows an example of a portion of a concentric pressure sensor assembly 2400. The concentric pressure sensor assembly 2400 can include or be coupled to an optical fiber 2402, such as a reduced-diameter longitudinally extending central optical fiber 2402. The concentric pressure sensor assembly 2400 can be located at or near a distal region of the optical fiber 2402. In an example, the pressure sensor assembly 2400 can include at least one Fabry-Perot interferometer, such as in the optical fiber 2402. The Fabry-Perot interferometer can modulate the wavelength of light in the optical fiber 2402, such as in response to environmental pressure variations that can stretch or compress the optical fiber 2402, e.g., longitudinally and linearly. The modulated light in the optical fiber 2402 can be used to communicate information about the environmental pressure variations at or near the distal end of the optical fiber 2402 to a proximal end of the optical fiber 2402, such as for coupling the resulting optical signal to an optoelectronic or other optical detector, which, in turn, can be coupled to electronic or optical signal processing circuitry, such as for extracting or processing the information about the sensed environmental pressure variations.

A distal portion of the optical fiber 2402 (e.g., more distal than the one or more Fabry-Perot interferometers) can be securely captured, anchored, or affixed, such as at a hard, solid, or inelastic distal disk assembly, distal endcap, or other distal anchor 2404, such as can be located at a distal end portion of the concentric pressure sensor assembly 2400. The hard, solid, or inelastic material (e.g., fused silica or other suitable material) of the distal anchor 2404 can be relatively inflexible, e.g., relative to the dimensional variation of the optical fiber 2402 in response to the targeted environmental pressure variations to be measured. In an illustrative example, any dimensional variation of the distal anchor 2404 can be less than or equal to $\frac{1}{20}$, $\frac{1}{100}$, or $\frac{1}{1000}$ of any dimensional variation of a pressure-sensing portion of the optical fiber 2402 measured in response to the targeted environmental pressure variations, such as the pressure variations that can be present in a percutaneous in vivo intravascular human blood pressure sensing application.

The tubular or other distal anchor 2404 can be attached to a hard, solid, or inelastic (e.g., fused silica) tubular or other housing 2406, such as by a soft, flexible, elastic, or compliant gasket 2408 that can be located therebetween. A first sensing region 2410 of the optical fiber 2402 can be securely captured, anchored, or affixed, to the housing 2406, such as via a tubular or other attachment (e.g., hardened epoxy or other adhesive) region 2412. A second sensing region 2414 of the optical fiber 2402 can be located within the housing 2406, such as suspended (e.g., freely or within a compliant material) between the encapsulator or attachment region 2412 and the hard distal anchor 2404. The suspended portion of the optical fiber 2402 can be installed or securely held longitudinally under tension. This can permit both positive and negative direction longitudinal displacement variations in the suspended portion of the optical fiber 2402, which, in turn, can permit sensing of both positive and negative environmental pressure variations, as explained herein.

The gasket 2408 material (e.g., medical grade silicone) can be relatively more flexible, soft, elastic, or compliant than the housing 2406 and than the distal anchor 2404, such as to allow longitudinal dimensional variation of gasket 2408 and the suspended second sensing region 2414 of the optical fiber 2402 in response to the targeted environmental pressure variations to be measured, such as the pressure variations that can be present in a percutaneous in vivo intravascular human blood pressure sensing application. The first sensing region 2410 can be securely fixed to the hard housing 2406 by the encapsulator or attachment region 2412, while the second sensing region 2414 can be suspended within the hard housing 2406 and subject to longitudinal dimensional variation (along with longitudinal dimensional variation of the compliant gasket 2408). Therefore, the first sensing region 2410 can be shielded from or made insensitive to environmental pressure variations, but sensitive to environmental temperature variations, while the second sensing region 2414 can be sensitive to both environmental pressure and temperature variations. In this way, light modulation in the first sensing region 2410 due to temperature variations can be measured and used to compensate for or null-out the light modulation effect of similar temperature variations experienced by the second sensing region 2414 that is being used to measure environmental pressure variations. In an illustrative example, the first sensing region 2410 can include a first Fabry-Perot interferometer, and the second sensing region 2414 can include a second Fabry-Perot interferometer. These respective interferometers can be written with different wavelengths. This can permit each interferometer to be individually separately addressed by selecting a corresponding wavelength of light to provide to the proximal end of the optical fiber 2402 to perform the selective individual addressing of the interferometers.

FIG. 24 can be conceptualized as an arrangement in which at least one optical fiber sensing region can be suspended from or between two anchors (e.g., hard tubes 2404, 2406) that can be separated from each other by a compliant region (e.g., gasket 2408) that can allow the anchoring tubes 2404, 2406 (and hence the suspended portion of the optical fiber 2402) to experience longitudinal displacement in response to environmental pressure variations. Based on finite element modeling (FEM) simulation analysis and experimental laboratory data obtained from prototypes, corresponding to the arrangement illustrated in FIG. 24, a pressure sensitivity can be obtained that can be at least 100 to 150 times the pressure sensitivity of an optical fiber without such arrangement of hard tubes 2404, 2406 separated from each other by the compliant gasket 2408.

In an illustrative example, the entire pressure sensor assembly 2400 can be less than or equal to 1.5 millimeters in length, such as less than or equal to 1.0 millimeter in length. The pressure sensor assembly 2400 can have an outer diameter that can be less than or equal to 125 micrometers. For comparison, 125 micrometers is the outer diameter of a typical single standard optical fiber as used in telecommunications. The tubular housing 2406 can have an inner lumen diameter of about 50 micrometers. In an example, the entire pressure sensor assembly 2400 can be conveniently incorporated within a percutaneous or other guidewire, such as can be used for guiding an intravascular device (e.g., a stent, such as a coronary stent) to a desired location within a blood vessel. For example, the entire pressure sensor assembly 2400 can be included within a solder or other joint of such a guidewire, such as between spring coils forming a body of the guidewire. Using fused silica or other glass components for all or portions of the tubular housing 2406 or the fused silica distal anchor 2404 can provide components that can provide a good matching of the temperature coefficient of expansion of these materials to the temperature coefficient of expansion of the material of the optical fiber 2402.

The arrangement shown in the illustrative example of FIG. 24 can advantageously be durable, can be easy to make, can perform well such as in detecting and amplifying an environmental pressure variation, or can consistently be made in a small form factor.

FIG. 25 shows an example of the pressure sensor assembly 2400 as it can be prefinished and included or otherwise incorporated into a percutaneous intravascular guidewire assembly 2500. The guidewire assembly 2500 can include a core guidewire 2502, a flexible proximal spring coil region 2504 and a flexible distal spring coil region 2506 that can terminate at a rounded and atraumatic distal tip. A generally cylindrical or other connector block 2508 can be included between and interconnecting the proximal spring coil region 2504 and the distal spring coil region 2506. The connector block 2508 can include a reduced diameter proximal end seat region 2510 and a reduced diameter distal end seat region 2512, about which windings of the flexible proximal spring coil region 2504 and a flexible distal spring coil region 2506 can respectively be wound, such as with their outer circumferences flush with an outer circumference of a midportion of the connector block 2508 between the proximal end seat region 2510 and the reduced diameter distal end seat region 2512. The connector block 2508 can provide a housing for the pressure sensor assembly 2400. The optical fiber 2402 can extend proximally from the pressure sensor assembly 2400 in the connector block 2508 through the proximal spring coil region 2504, such as to an optical connector at a proximal end of the guidewire assembly 2500, where it can be optically coupled to optical, electronic, or optoelectronic signal generation or processing circuitry. The core guidewire 2502 of the guidewire assembly 2500 can bend or jog off of the concentric longitudinal axis of the guidewire assembly 2500, such as at or near the connector block 2508, if needed to allow enough room for the pressure sensor assembly 2500 to be housed within the connector block 2508 while also allowing passage of the core guidewire 2502 through the connector block 2508 in such a lateral offset arrangement.

The connector block 2508 can provide a lateral axis portal 2514 that can be located beyond a distal end region 2516 of the pressure sensor assembly 2400 such as to leave a distal end region 2516 of the pressure sensor assembly 2400 exposed to nearby environmental pressures to be measured, while providing a ceramic or other hard protective circumferential housing region that can protect the pressure sensor assembly 2400 from lateral pressure or lateral torque that may otherwise influence the pressure sensor measurement to be obtained by longitudinal spatial variations of the pressure sensor assembly 2400.

Figure 26:
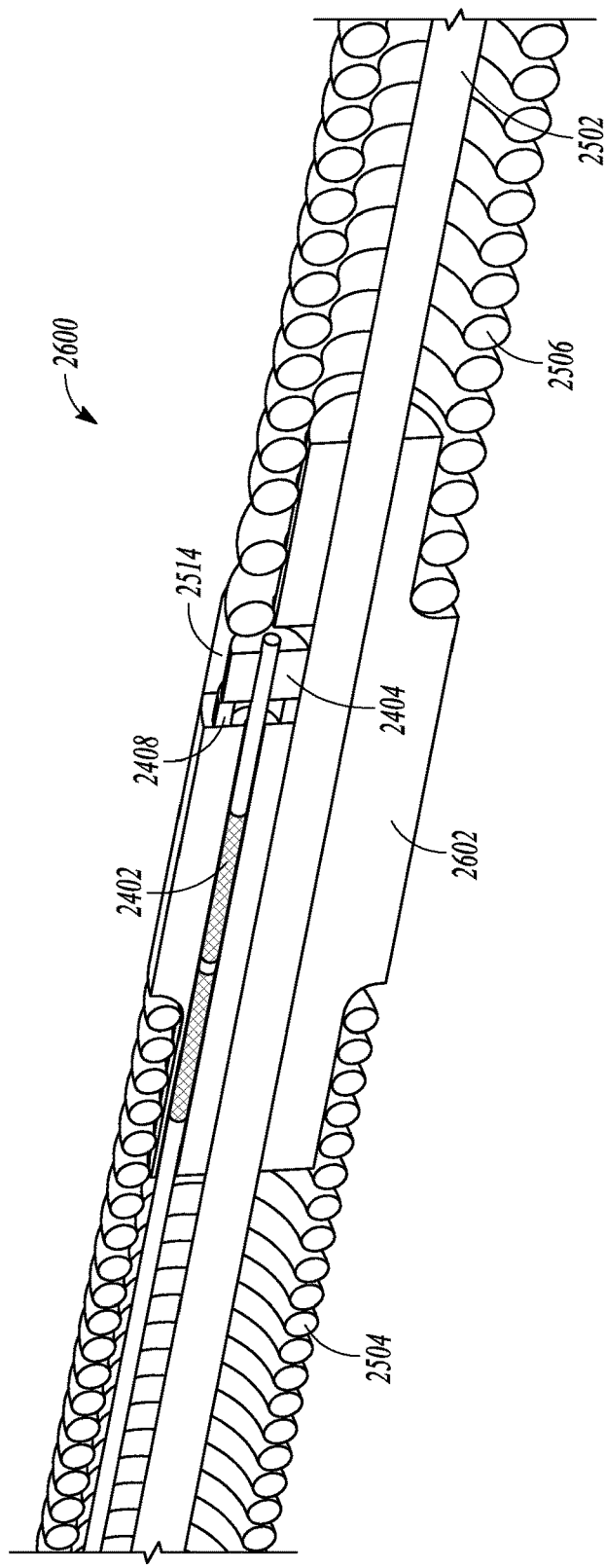
FIG. 26 shows an example illustrating how components of the pressure sensor assembly can be integrated into or otherwise incorporated into a percutaneous intravascular guidewire assembly.

FIG. 26 shows an example illustrating how components of the pressure sensor assembly 2400 can be integrated into or otherwise incorporated into a percutaneous intravascular guidewire assembly 2600. FIG. 26 is similar to FIG. 25 in some respects, but in FIG. 26 the connector block 2602 can provide a concentric axially aligned longitudinal passage for the core guidewire 2502, such that it need not bend or jog as shown in FIG. 25. This can help preserve or utilize the mechanical properties or characteristics of the core guidewire 2502 or those of the guidewire assembly 2600. One or more components of the pressure sensor assembly 2400 can be laterally offset from the concentric axially aligned core guidewire 2502, such as within the connector block 2602. The connector block 2602 can include a lateral axis portal 2514. The distal anchor 2404 and the gasket 2408 can be located in or near the lateral axis portal 2514, and can optionally be laterally recessed or otherwise shielded from lateral pressure or torque that may otherwise influence the pressure sensor measurement to be obtained by longitudinal spatial variations of the integrated components of the pressure sensor assembly 2400, such as explained above with respect to FIG. 25. The connector block 2602 can be constructed with a passage for the optical fiber 2402 sized, shaped, or otherwise configured such as to provide a first sensing region 2410 of the optical fiber 2402 that can be affixed to a housing provided by the connector block 2602, such as explained herein. A second sensing region 2414 of the optical fiber 2402 can be suspended within a housing provided by the connector block 2602, such as explained herein. The optical fiber 2402 can extend outward from the connector block 2602 proximally, such as through the proximal spring coil region 2504, such as with the optical fiber 2402 extending so as to be laterally offset from a longitudinal central axis of the guidewire assembly 2600.

Figure 27:
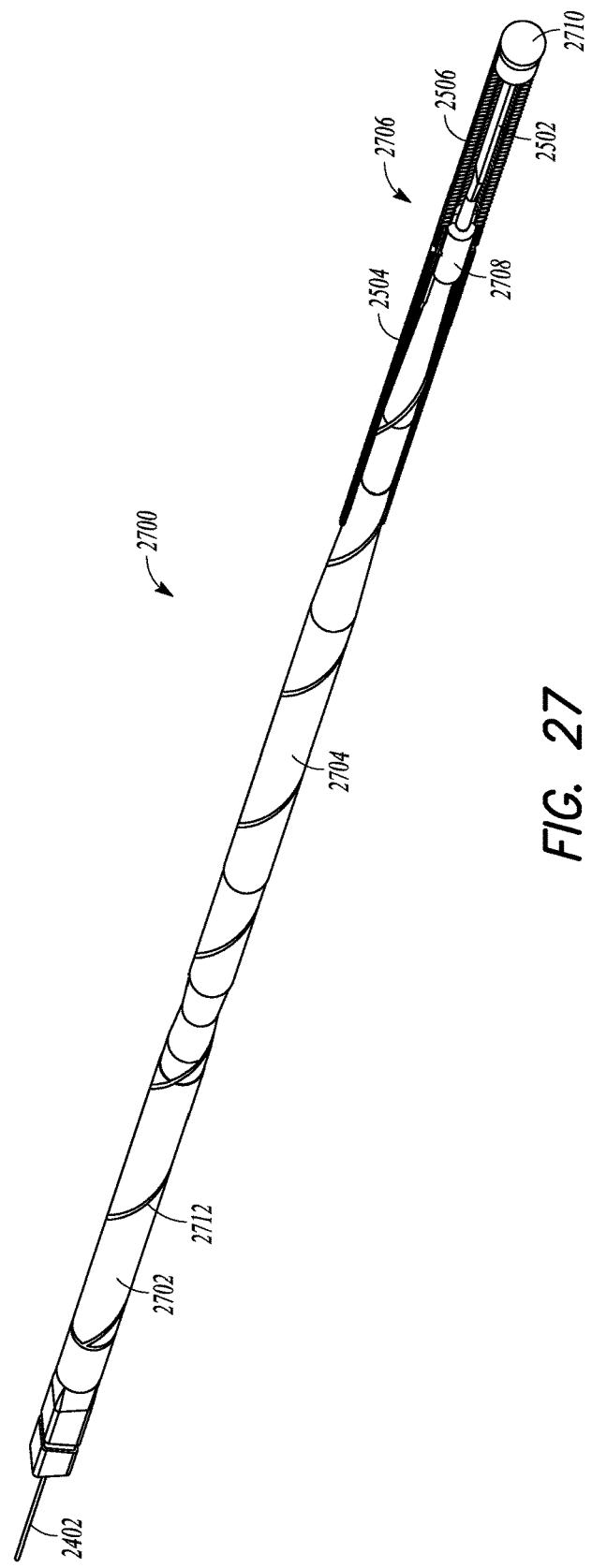
FIG. 27 shows an example in which components of the pressure sensing assembly can be retrofitted to or otherwise integrated into an existing guidewire assembly.

FIG. 27 shows an example in which components of the pressure sensing assembly 2400 can be retrofitted to or otherwise integrated into an existing guidewire assembly 2700, such as a RUNTHROUGH® guidewire, available from Terumo Kabushiki Kaisha, also known as Terumo Corp. The guidewire assembly 2700 can include a proximal region 2702, that can be constructed from a first material, such as stainless steel, and a distal region 2706 that can be constructed from a second material, such as nitinol. Either of both of the proximal region 2702 and the distal region 2704 can taper inward in a direction toward the distal end of the guidewire assembly 2700, such as in one or more tapering regions, which can be contiguous or separated by respective non-tapering regions. A distal region 2706 of the guidewire assembly 2700 can include a proximal spring coil region 2504, a distal spring coil region 2506, a connector block 2708 (e.g., containing components of the pressure sensor assembly 2400, such as described herein) therebetween from which a flattened or other core guidewire can extend distally toward and connecting to an atraumatic rounded distal tip 2710.

At least one groove 2712 can be formed on an outward circumferential surface of the guidewire assembly 2700. The groove 2712 can extend from a proximal end or region of the guidewire assembly 2700 toward and to a distal portion of the guidewire assembly 2700 and can terminate at a proximal side of the connector block 2708. The groove 2712 can extend along all or a portion of the length of the guidewire assembly 2700, such as in a spiral helix or otherwise. The pitch of the helix can be fixed or multi-valued (e.g., a looser pitch (e.g., between 30 mm and 50 mm) at a proximal portion of the guidewire assembly 2700 and a tighter pitch (e.g., between 5 mm and 10 mm pitch) at the distal (e.g., over a length of about 30 centimeters) portion of the guidewire assembly 2700). The helical arrangement can help accommodate flexing curvature in the guidewire assembly 2700 as it is introduced along tortuous vascular or other non-linear paths. A tighter pitch can be more accommodating to curvature in the guidewire assembly 2700. The groove 2712 can carry the optical fiber 2402 therein, such as can be secured therein by an adhesive underlayer (e.g., UV-cured adhesive, hot-melt adhesive, epoxy or other two-part adhesive) or overlayer (e.g., such as any suitable overcoating used for an existing guidewire). In an example, the groove 2712 can be about 40 micrometers across and about 40 micrometers deep, and can be constructed so as to only occupy about 1/100 or less of the surface area of the guidewire assembly 2700, thereby leaving the mechanical properties of the guidewire assembly 2700 substantially intact as though the groove 2712 were not present. For retrofitting an existing guidewire, the groove 2712 can be formed by laser-etching or other suitable process. The guidewire can additionally or alternatively formed together with the groove 2712, such as during drawing of the guidewire body during its manufacture, such as by mechanically scoring the guidewire body or otherwise. If a portion of the guidewire body is tapered down (e.g., toward a distal end, such as using centerless or other grinding), then any grooves that were formed during the guidewire drawing, but removed by the grinding, can be replaced by a respective connecting groove that can be formed after grinding, such as by laser-etching the ground portion of the guidewire body.

Figure 28:
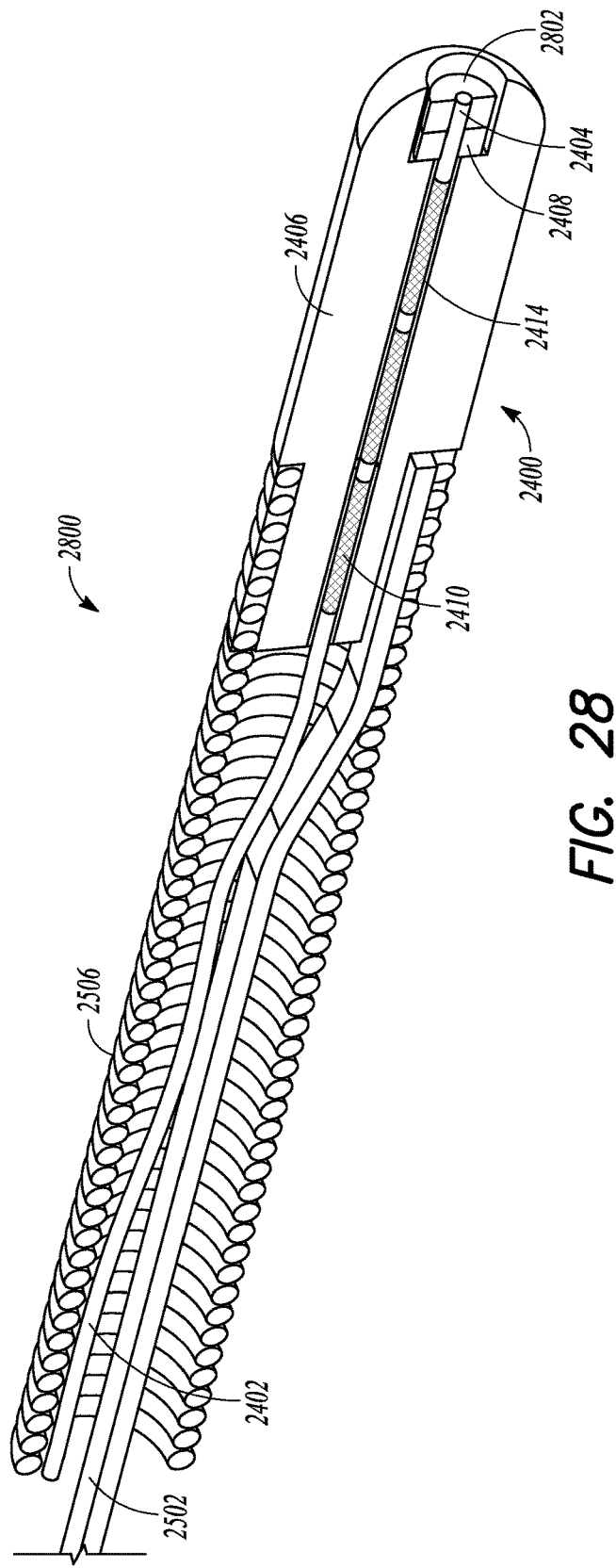
FIG. 28 shows an example in which the pressure sensor assembly (e.g., as explained herein) can be located at a distal end of a guidewire assembly.

FIG. 28 shows an example in which the pressure sensor assembly 2400 (e.g., as explained herein) can be located at a distal end of a guidewire assembly 2800, e.g., more distal than the distal spring coil region 2506, such as within or providing a rounded atraumatic distal tip. A flattened or other distal end of the core guidewire 2502 can connect to a proximal end of the housing 2406 of the pressure sensor assembly 2400. More proximal regions of the guidewire assembly 2800 can include a proximal spring coil region 2504, a connector block (such as a connector block 2508, which can optionally include a second, more proximal pressure sensor as described with respect to FIG. 25), and other elements such as shown in FIG. 25.

The distal end pressure sensor assembly 2400 can include an anchored first sensing region 2410 and a suspended second sensing region 2414, such as explained herein. The gasket 2408 and the distal anchor 2404 can be located within a cylindrical or other recess 2802 that can be exposed to the ambient environment about the distal end of the guidewire assembly 2800. In an example such as shown in FIG. 28, the recess 2802 can be cylindrical and can extend longitudinally along the central axis of the guidewire assembly 2800, such as to face longitudinally outward from the distal end of the guidewire assembly 2800. In an example, the distal end of the optical fiber 2402 can be attached to the anchor 2404, and both the anchor 2404 and the gasket 2408 can be suspended within the recess 2802, such as by tension in the optical fiber 2402 to which the anchor 2404 can be attached with the gasket 2408 captured proximal to the anchor 2404. This can help provide pressure sensing due to longitudinal optical fiber tension variations near the distal end of the guidewire assembly 2800, and can help isolate the effect of lateral pressure variations or torque upon the pressure sensor assembly 2400.

Having a pressure sensor located at a guidewire distal tip can provide advantages in certain applications, such as where information about pressure distal to an occlusion may be desirable. For example, when pushing a guidewire across a chronic total vascular occlusion, it may be difficult to determine whether the distal tip is within a lumen of the blood vessel or within a subintimal layer of the blood vessel. A distal-tip pressure sensor can permit providing distal-tip pressure information that can be useful in determining the nature of such location of the distal tip of the guidewire assembly 2800. In an example in which a distal tip pressure sensor is provided together with a more proximal pressure sensor (e.g., located between the proximal spring coil region 2504 and the distal spring coil region 2506), a pressure differential across an occlusion can be sensed and provided to a user, such as for diagnostic or interventional (e.g., stent-placement) purposes.

Guidewires that are used to measure pressure in body lumens, e.g., coronary arteries, and the derived index of Fractional Flow Reserve (FFR), need to perform their measurement accurately in a challenging environment. The proximal end of a steerable guidewire is typically handled by the coronary interventionalist, for example, and is exposed to various contaminants such as blood, contrast fluid and saline. The interventionalist is accustomed to keeping the guidewire relatively clean, by wiping with saline wetted gauze cloths, in order to ensure that any catheters which are inserted over the wire do not get stuck or do not introduce emboli into the coronary arteries.

Over the last 15 years, electrical based pressure guidewires have come into practice. For these devices, the physician is accustomed to extra care in the region of the disconnectable proximal electrical connections. Typically a saline wipe as well as a drying step is performed before the proximal end is inserted into the mating electrical connector. Contamination or fluids in the electrical connector can lead to unreliable pressure readings.

The present inventors have determined that it can be desirable to improve the reliability of the proximal optical connection of the current invention and to facilitate the connection process. The present inventors have determined that it is desirable that the alignment between the cores of the standard fiber and the reduced cladding fiber in the electrical connection be accurate to the order of 1 micrometer to minimize optical losses. This level of accuracy is typically achieved in optical connectors utilized in the telecommunications industry, however the connectors used would be too expensive to implement and would also be too large.

Figure 29A:
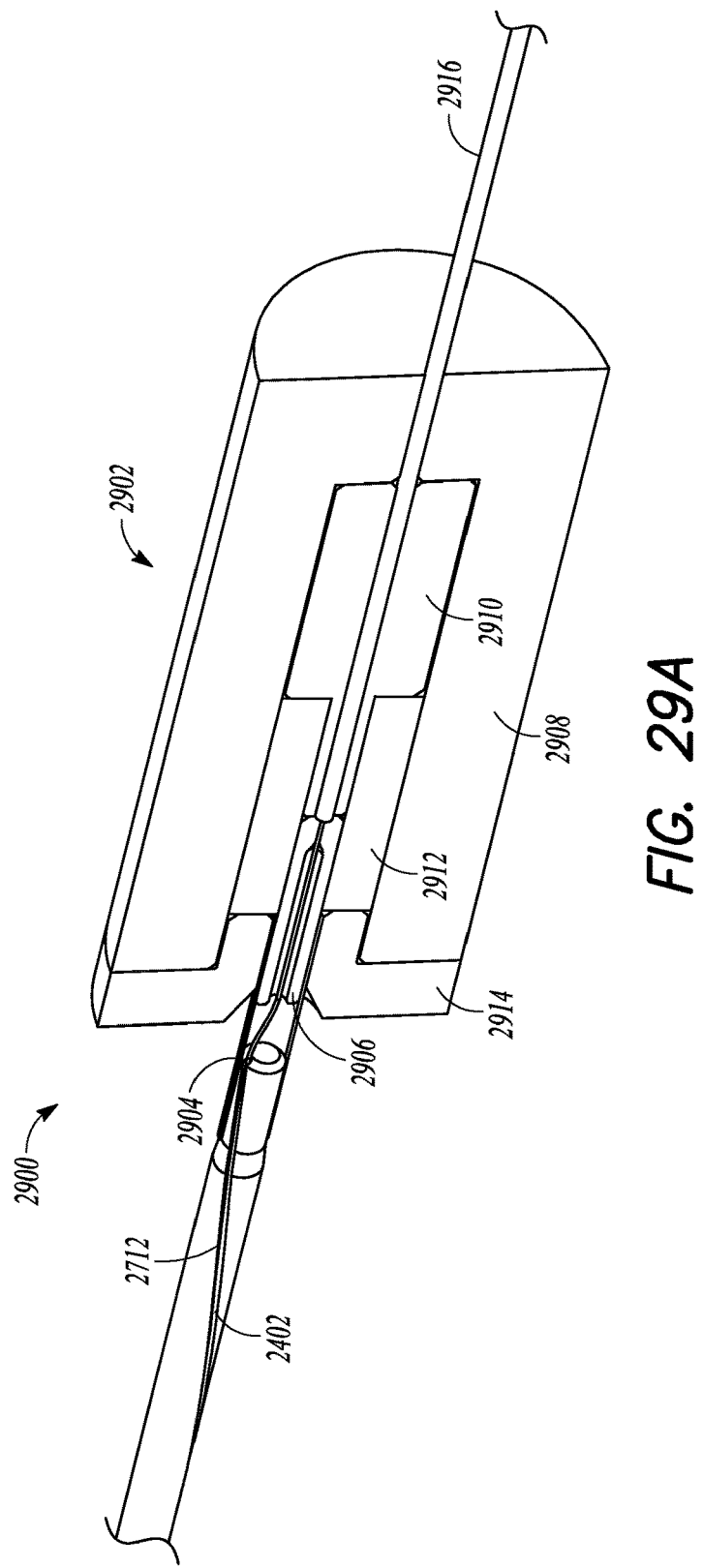
FIG. 29A shows an example of a proximal region of a guidewire assembly, such as one of the various guidewire assemblies described herein, terminating at a proximal end connector.

FIG. 29A shows an example of a proximal region of a guidewire assembly 2900, such as one of the various guidewire assemblies described herein, terminating at a proximal end connector 2902. The guidewire assembly 2900 can include a helically wound optical fiber 2402 that can be located in a helical groove 2712 along the guidewire body. The proximal end connector 2902 can include separable portions: (1) a distal portion that can include a metal or other tube 2904 (also referred to as a tubular coupler) having an interior lumen diameter that can be attached to both the outer diameter of the body of the proximal region of the guidewire assembly 2900 and the outer diameter of a ceramic or other distal ferrule 2906 such that the optical fiber can extend from a periphery of the guidewire body to and through a center axis lumen of the distal ferrule 2906; and (2) a proximal portion that can include a connector housing 2908 carrying a ceramic or other proximal ferrule 2910, a split sleeve ferrule guide 2912, and a distal receptacle guide 2914 that can provide a tapered portion into which a portion of the distal ferrule 2906 and the metal tube 2904 can be received.

The split sleeve ferrule guide 2912 can be made from ceramic (for example, zirconia) or metal (for example, nickel, beryllium copper, or phosphor bronze). The fit of the split sleeve ferrule guide 2912 to the ferrule 2906 should be sized such that the split opens slightly as the ferrule 2906 is inserted into the split sleeve ferrule guide 2912 in order to hold and locate the ferrule 2906 as accurately as possible. The split sleeve ferrule guide fit to the ferrule is typically based on the force needed to insert the ferrule 2906 into the split sleeve ferrule guide 2912 and the force needed to withdraw the ferrule 2906 from the split sleeve ferrule guide 2912. For these miniaturized connector components, the ferrule withdrawal force from the split sleeve ferrule guide would ideally be less than 100 grams force and preferably less than 70 grams force.

The optical fiber 2402 can terminate at a flat or dome polished (e.g., ultrapolished physical connector, "UPC") proximal end of the distal ferrule 2906, where it can butt against and optically couple with a flat or dome polished (e.g., UPC) distal end of the proximal ferrule 2910, which can provide a center axis lumen through which an optical fiber 2402 can extend in a proximal direction, such as to an optical, electronic, or optoelectronic signal generation or processing apparatus. While the optical fibers 2402 and 2916 can be the same diameter, in an example, the optical fiber 2402 can be a small diameter optical fiber (e.g., 25 micrometers outer diameter) and the optical fiber 2916 can be a standard sized telecommunications optical fiber (e.g., 125 micrometers outer diameter), such as with the mode field diameter (MFD) of the optical fiber 2402 being less than or equal to the MFD of the optical fiber 2916. When the proximal end of the guidewire terminating in connector portion 2902 is detached, other components can be easily slipped over the guidewire. The present inventors have determined that the desired alignment accuracy of the proximal connection, namely 1 micrometer, can be relieved by employing optical pathway devices that utilize beam spreading techniques such that the optical beam at the connection interface is significantly larger than the core size utilized in the standard and reduced cladding fibers, as shown and described below with respect to FIG. 29B.

Figure 29B:
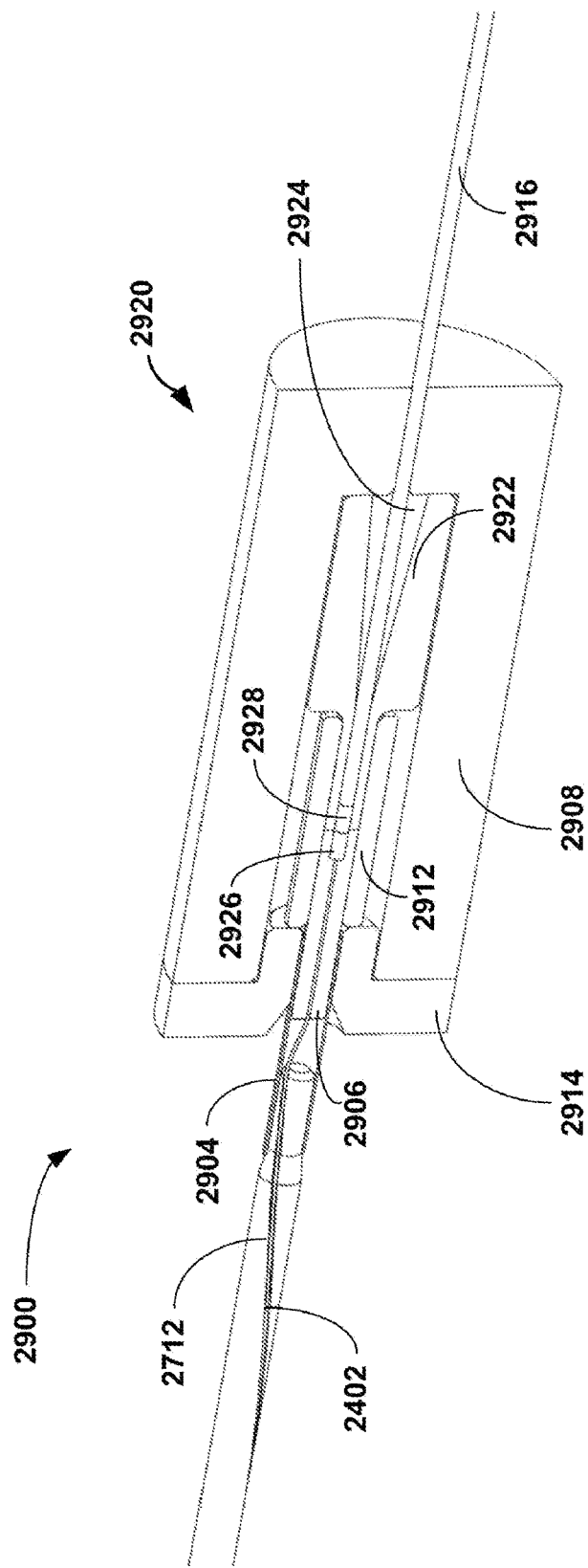
FIG. 29B shows another example of a proximal region of a guidewire assembly, such as one of the various guidewire assemblies described herein, terminating at a proximal end connector.

FIG. 29B shows another example of a proximal region of a guidewire assembly 2900, such as one of the various guidewire assemblies described herein, terminating at a proximal end connector 2920. Many of the components of FIG. 29B are similar to those shown and described above with respect to FIG. 29A and, for purposes of conciseness, will not be described again. It should be noted that the proximal ferrule 2922 of FIG. 29B defines a conical region, shown at 2924, in contrast to the proximal ferrule 2910 of FIG. 29A.

As indicated above, the guidewire assembly 2900 of FIG. 29B can utilize beam spreading techniques. Typical beam spreading devices include, but are not limited to lenses, gradient-index (GRIN) lenses, ball lenses and the like. These devices may be utilized as illustrated in FIG. 29B. For example, a first fiber lens 2926, e.g., a GRIN lens, can be attached to the reduced cladding fiber 2402 in the proximal end of the guidewire assembly 2900, and a second fiber lens 2928, e.g., a GRIN lens, may be attached to the distal end of the standard fiber 2916. The utilization of these types of lenses can greatly reduce the alignment accuracy of the interface, can minimize any optical losses and can also reduce the optical loss effects of micro contaminants that the physician does not remove from the proximal end of the guidewire. In addition, the relief of the preferred alignment accuracy requirement allows for the use of lower cost components to hold the fibers and lenses.

Figure 29C:
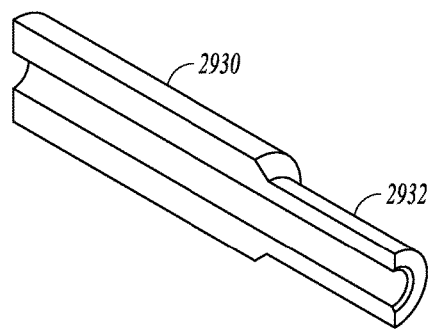
FIG. 29C shows another example of a ferrule that can be used in combination with the various guidewire assemblies described herein.

FIG. 29C shows another example of a ferrule that can be used in combination with the various guidewire assemblies described herein. The present inventors have recognized that it can be advantageous for one or both ends of the distal ferrule and the proximal ferrule to be stepped. FIG. 29C depicts an example of a ferrule 2930, which can include a smaller diameter 2932 (or step) at the end of the ferrule 2930, e.g., the distal end of the distal ferrule 2906 of FIG. 29A. The step 2932 can act as a mechanical stop at its interface into the coupling tube, which can protect the fiber as it transitions from the guidewire into the ferrule. A very short step at the proximal end of the distal ferrule 2906 (FIG. 29A) or the distal end of the proximal ferrule 2910 (FIG. 29A) can provide for a relief as the two ferrule faces mate together where any particles remaining after the connector cleaning could reside without interfering with the contact of the optical surfaces.

Figure 29D:
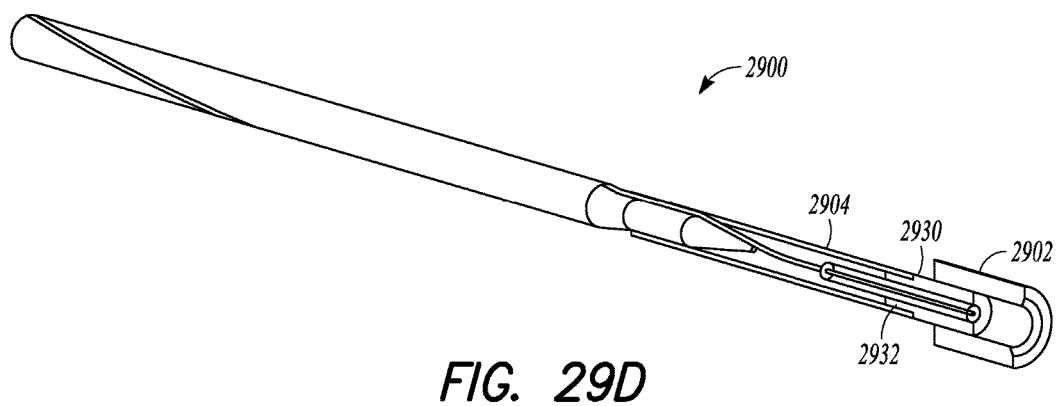
FIG. 29D shows another example of a proximal region of a guidewire assembly terminating at a proximal end connector and using the ferrule of FIG. 29C.

FIG. 29D shows another example of a proximal region of a guidewire assembly 2900 terminating at a proximal end connector 2902 and using the ferrule 2930 of FIG. 29C. The step 2932 can act as a mechanical stop for the ferrule 2930 at its interface into the coupling tube 2904.

Using various techniques described above, changes in ambient pressure can be detected by measuring the wavelength change, e.g., quantified change in phase-shift, by an FBG sensor within a housing, e.g., housing 308 of FIG. 3. As described above with respect to FIGS. 4A-4C and FIG. 6A, the change in phase-shift can be quantified by locking a laser at a position on a slope of the transmission notch of the resonant feature, tracking a particular optical power level in the resonant feature, and adjusting the bias current of the laser which, in turn, subtly changes the wavelength to maintain this "locked" relationship.

These techniques can produce satisfactory results when the optical insertion loss is constant. In some example implementations, however, the overall insertion loss of the pressure sensor and/or system can change during the measurement, e.g., kinking in the optical fiber. As shown and described below with respect to FIG. 30, a change in the optical insertion loss can lead to an artificial shift in the tracking wavelength, and thus an offset error in the pressure reading, if the optical locking level or threshold is not adjusted accordingly.

Figure 30:
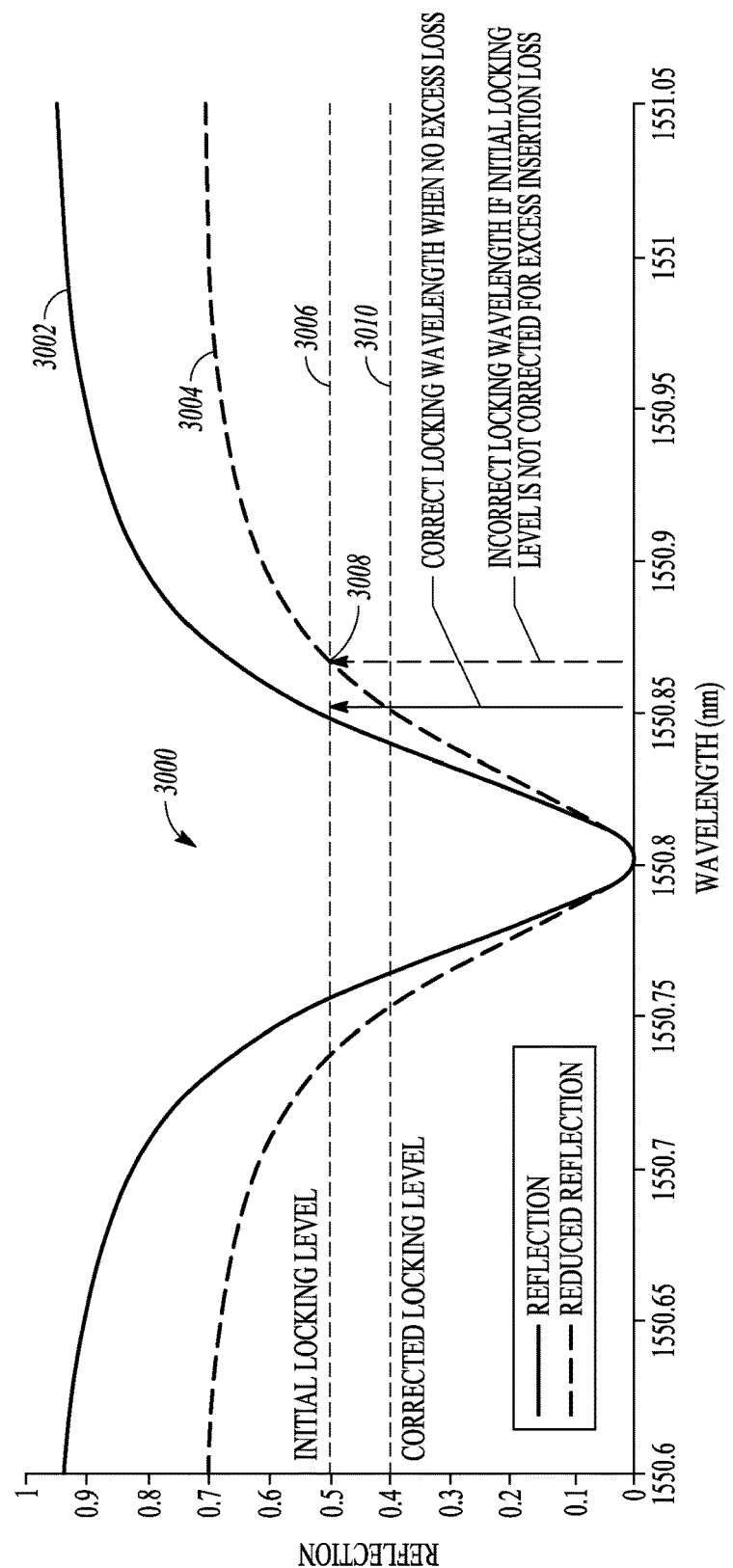
FIG. 30 depicts a conceptual response diagram illustrating the effect of an uncorrected locking level on a locking wavelength.

FIG. 30 depicts a conceptual response diagram illustrating the effect of an uncorrected locking level on a locking wavelength. In FIG. 30, where the x-axis represents wavelength and the y-axis represents the intensity of the reflected light, a transmission notch 3000 is shown within a reflection band 3002, and a reduced reflection band 3004, which is caused by insertion loss. An initial locking level, or optical threshold, 3006 is depicted, which corresponds to a wavelength of about 1550.85 nm and a reflection intensity of 50%.

If insertion loss is introduced, which results in the reduced reflection band 3004, then the locking level may move up or down the slope of the reduced reflection band 3004 in order to maintain its locking level, e.g., 50%, despite the fact that the transmission notch 3004 has not moved. If the insertion loss increases (optical power decreases), then the shift can be to a higher, incorrect locking wavelength because the locking circuit climbs the slope of the reduced reflection band 3004 to maintain the set optical level, as shown at 3008. If the insertion loss decreases (optical power increases)(not depicted in FIG. 30), then the shift can be to a lower, incorrect locking wavelength because the locking circuit moves down the slope of the reduced reflection band 3004 to maintain the set optical power level. Either of these conditions can lead to a significant drift in the apparent pressure level even if there has been no phase-shift change in the FBG filter.

As described in more detail below, using various techniques of this disclosure, the locking level 3006 can be corrected for insertion loss, resulting in a corrected locking level 3010. In accordance with this disclosure, a small dither signal can be added to the wavelength of the laser at, for example, a frequency outside those associated with the pressure sensing. Then, the AC component, which is the change in the optical signal reflected from the pressure sensor back to the optical detector, e.g., optical detector 608 of FIG. 6A, can be extracted from the optical signal via an electronic circuit associated with the optical detector. The magnitude of the AC component can then be used to make any adjustments to the locking level to null out any offset errors.

Figure 31:
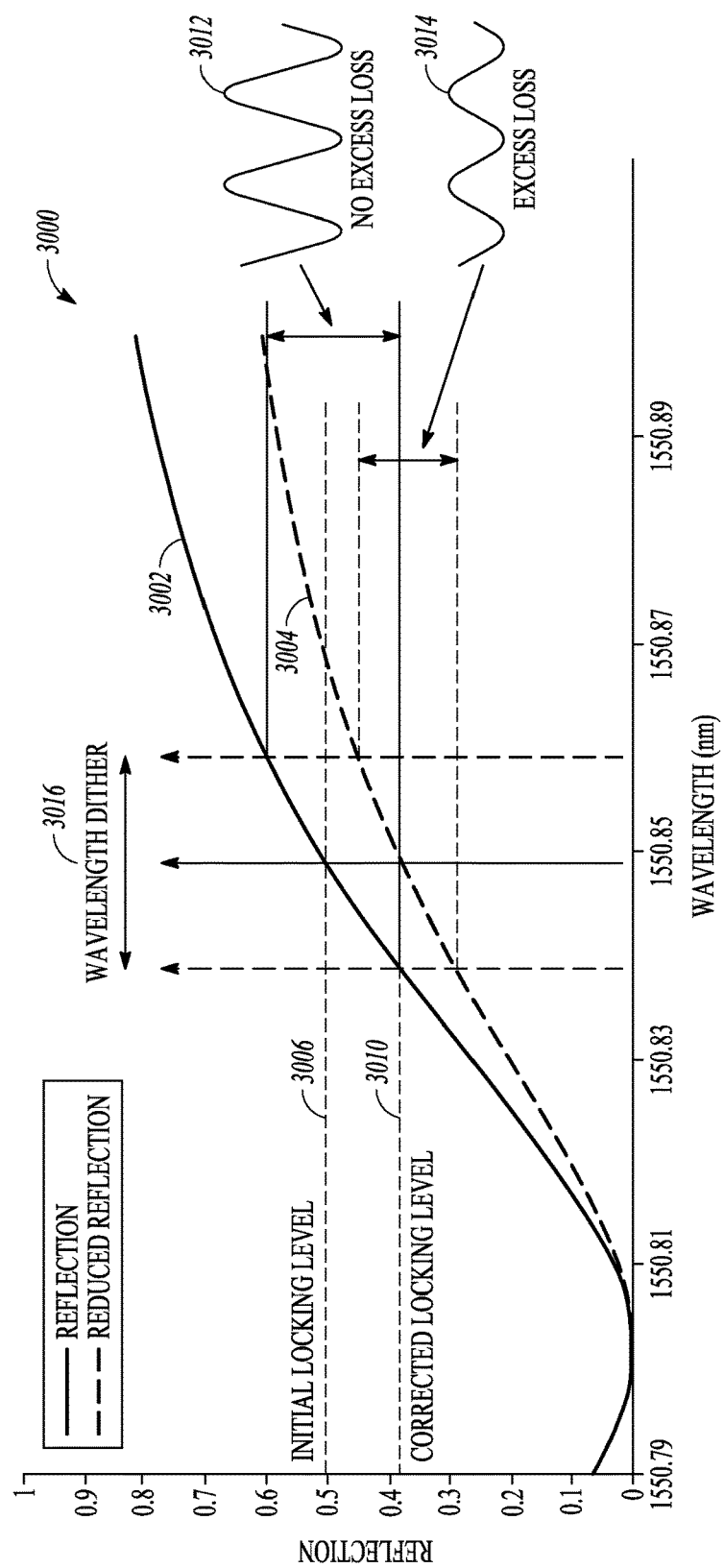
FIG. 31 depicts the conceptual response diagram of FIG. 30 compensated for optical insertion loss in an optical pressure sensor using various techniques of this disclosure.

FIG. 31 depicts the conceptual response diagram of FIG. 30 compensated for optical insertion loss in an optical pressure sensor using various techniques of this disclosure. In FIG. 31, where the x-axis represents wavelength and the y-axis represents the intensity of the reflected light, a transmission notch 3000 is shown within a reflection band 3002, and a reduced reflection band 3004, which is caused by insertion loss.

Two AC components 3012, 3014 are depicted in FIG. 31, where the AC component 3012 depicts a magnitude of the AC component with no excess loss and where the AC component 3014 depicts a magnitude of the AC component with excess loss. Thus, the magnitude of the AC component can change with insertion loss.

As indicated above, a small dither signal 3016 can be added to the wavelength of the laser. Then, an AC component can be extracted from the optical signal via an electronic circuit associated with the optical detector. As can be seen in FIG. 31, the amplitude of the AC components 3012, 3014 can vary in proportion to the overall signal level as long as the amount of wavelength dither is held constant. That is, if the wavelength range of the dither 3016 is held constant, the magnitude of the AC component can scale directly with the optical insertion loss.

By comparing a current value of the AC component, e.g., AC component 3014, to an initial value of the AC component, e.g., AC component 3012, the controller 602 (FIG. 6A) can determine whether the optical insertion loss has increased or decreased. The current value of the AC component can be fed back to the optical locking circuit of FIG. 6A, a portion of which is described below with respect to FIG. 33. Then, because the AC component is reduced in proportion to the change in insertion loss, the controller 602 of FIG. 6A can adjust the optical locking level accordingly to maintain the correct locking wavelength.

In some examples, a frequency and amplitude of the wavelength dither 3016 can be selected so as to be compatible with the pressure measurements. For example, for the dither frequency, a value can be selected that is higher than the necessary bandwidth for pressure sensing. Assuming, for example, that the pressure bandwidth is between 0-25 Hz, then it might be desirable to select a frequency for the wavelength dither at least five times higher than the pressure bandwidth.

Figure 32:
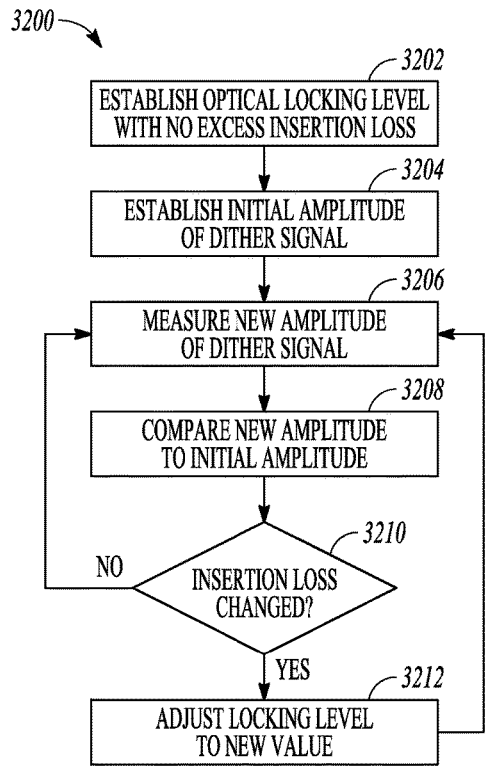
FIG. 32 is a flow diagram illustrating an example of a method for compensating for optical insertion loss in an optical pressure sensor using various techniques of this disclosure.

FIG. 32 is a flow diagram illustrating an example of a method 3200 for compensating for optical insertion loss in an optical pressure sensor using various techniques of this disclosure. The controller 602 of FIG. 6A can establish, or determine, an optical locking level with no excess insertion loss (3202), e.g., initial locking level 3006 of FIG. 31, and establish, or determine, an initial amplitude of a dither signal (3204), e.g., the AC component 3012 of FIG. 31, by extracting the dither signal from the optical signal reflected from the pressure sensor and measuring its amplitude. The controller 602 can measure a new amplitude of the dither signal (3206), e.g., the AC component 3014 and compare the new amplitude to the initial amplitude (3208). If the insertion loss has changed ("YES" branch of 3210), as determined by the comparison at 3208, then the controller 602 can control the laser drive current control 614 of FIG. 6A or the locking set point value 612 of FIG. 6A to adjust the locking level to a new value (3212), e.g., if the AC component decreases then the locking level is reduced by the appropriate amount. If the insertion loss has not changed ("NO" branch of 3210), as determined by the comparison at 3208, then the controller 602 can continue to measure the new amplitude of the dither signal at 3206.

Figure 33:
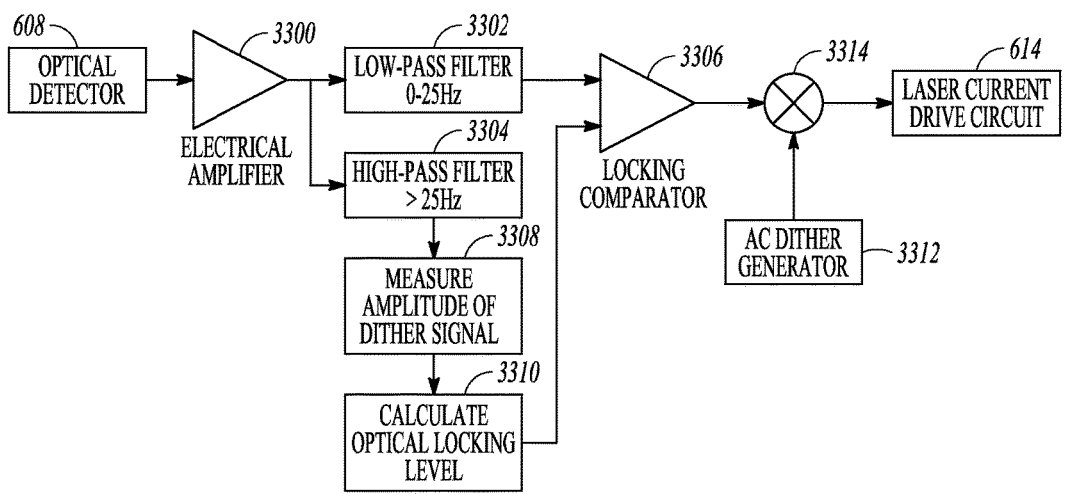
FIG. 33 is a block diagram of an example of a portion of the laser tracking system of FIG. 6A for compensating for optical insertion loss in an optical pressure sensor using various techniques of this disclosure, in accordance with this disclosure.

FIG. 33 is a block diagram of an example of a portion of the laser tracking system of FIG. 6A for compensating for optical insertion loss in an optical pressure sensor using various techniques of this disclosure, in accordance with this disclosure. An AC dither generator 3312 generates a dither signal that is summed together with the laser control current via summer 3314 and passed to the laser current drive circuit 614. The laser current drive circuit 614 generates a drive current for laser 604 of FIG. 6A.

An optical signal reflected back from the pressure sensor, e.g., pressure sensor 300 of FIG. 3, is detected by the optical detector 608, amplified by electrical amplifier 3300, and filtered by a low pass filter 3302, e.g., frequencies of about 0-25 Hz, and a high pass filter 3304, e.g., frequencies greater than 25 Hz. The low pass filter 3302 passes the DC level to a locking comparator 3306 and the high pass filter 3304 passes the high pass filtered signal, or AC component, to the controller 602, which measures the amplitude of the dither signal (3308), or AC component, and calculates the optical locking level (3310), e.g., if the AC component decreases then the locking level is reduced to the appropriate value. The controller 602 passes the calculated optical locking level to the locking comparator 3306, which compares the DC level and the calculated optical locking level. The laser current drive circuit 614 or the locking set point 612 can be adjusted based on the comparison. In this manner, a constant center wavelength is maintained. The same result can also be achieved by accounting for the wavelength shift in the form of a software correction.

In one example implementation, the frequency of the dither 3016 of FIG. 31 can be selected in order to design a low-pass filter 3302 that can reduce the residual AC dither component in the electrical path to the locking circuit controlled by the laser current drive circuit 614. This may be desirable in order to prevent the locking circuit from chasing the locking level at the frequency of the dither. It may be desirable for the locking circuit to see the average or DC level of the optical locking level.

There are many ways to filter the optical signal and only one example is presented in this disclosure. Other filtering techniques or techniques for suppressing the AC component could be employed and are considered within the scope of this disclosure.

In order to ensure that the laser is able to respond to the dither frequency chosen without any reduction in the actual wavelength shift desired, there may be factors to consider in selecting a dither frequency. For example, it has been found that the design of the laser submount has an effect on the frequency at which the laser can dither the laser.

Typical dither frequencies can range from around 100 Hz to 1000 Hz before the response starts to diminish. In one example implementation, it may be desirable to select a dither frequency between about 300 Hz and about 1000 Hz.

The dither magnitude can be selected to have an appropriate scale to give a detectable AC component, e.g., around ±10% of the overall DC signal level. In this example, if the maximum optical power level is assumed to be about 1000 µW and the slope is assumed to be about 50 µW/pm, then it may be desirable to shift the wavelength of the laser by the equivalent of about ±2 pm (±1000 µV). If the laser is assumed to have a wavelength coefficient of about 5 pm/mA, then this would equate to a bias current dither of about ±0.4 mA. These numbers are given for purposes of illustration only and could be adjusted within sensible limits.

The numbers given above for the dither parameters are appropriate for lasers that have a standard design. It may be possible to greatly increase the dither frequencies without any diminishing of the frequency shift by using a laser of a specific design suited to this application. For instance, there are laser designs that utilize a tunable section in the center of the laser chip that can be modulated at a much higher frequency. Using such a laser, the dither frequency can be increased to 10 kHz or higher, which would be beneficial as it can place the dither frequency further from the frequencies of the pressure signal thus allowing better separation.

To summarize, with respect to FIGS. 31-33, this disclosure describes, among other things, the following techniques: compensating for changes in optical insertion loss of the pressure sensor that would otherwise be seen as large drifts in the apparent measured pressure; calculating and adjusting an optical locking level to achieve compensation of changes in optical insertion loss by wavelength dithering of the tracking laser; applying wavelength dither to a tracking laser to generate a signal with amplitude proportional to optical insertion loss; and applying feedback to an optical locking level to compensate optical insertion loss.

It should be noted that the dither techniques described above can be used in a similar manner to track the insertion loss of an intravascular ultrasound (IVUS) imaging device and to make adjustments to the optical locking levels. It may also be desirable to make dynamic adjustments to a sensitivity correction matrix for the imaging elements in a receive mode. The quality of imaging can be improved when the sensitivity of the elements are balanced in the reconstruction matrix to reduce side-lobe levels.

A first order calibration of the receive sensitivity of the elements can be made by measuring the AC component from the wavelength dither as this indicates the slope of the sensing element. The expected receive ultrasound signal is proportional to the ultrasound energy imparted on the element (this is converted to a change in the optical cavity length or phase-shift) multiplied by the slope of the cavity. Therefore, by knowing the slope from the dither, an expected signal sensitivity from the element can be calculated.

In the case of IVUS, the relationship of the frequencies is reversed, where the dither frequency is well below the ultrasound frequencies and is filtered out by the ultrasound electrical circuits.

To summarize, with respect to IVUS imaging devices, this disclosure describes, among other things, the following techniques: dynamically adjusting optical locking levels; dynamically adjusting an element calibration matrix to improve image reconstruction; and calibrating receive sensitivity of elements based on dither slope measurements. Many of the techniques described in this disclosure are applicable to intravascular imaging devices, such as those described in Bates & Vardi U.S. Pat. No. 7,245,789, U.S. Pat. No. 7,447,388, U.S. Pat. No. 7,660,492, U.S. Pat. No. 8,059,923, U.S. Pat. Pub. No. US-2012-0108943-A1, and U.S. Provisional Patent Application No. 61/783,716, titled "Optical Fiber Ribbon Imaging Guidewire and Methods" to Tasker et al. and filed on Mar. 14, 2013, each of which is hereby incorporated by reference herein in its entirety.

Turning to another aspect, in any optical system with highly coherent light sources, e.g., a narrow linewidth laser, there is a possibility that any unintended reflections, even very weak ones, can form a resonant optical cavity within the device. The cavity can exhibit a strong frequency component that depends on the optical path length of the cavity (in this case the length of optical fiber between reflection points). The frequency of the cavity is given by:

$$\Delta v = \frac{c}{2L}$$

where $\Delta v$=frequency separation of maxima (Hz), C=speed of light, and L=optical path length (Length×refractive index). The longer the cavity, the more closely spaced the ripples in the frequency and wavelength domains.

A large amount of optical energy can be circulated within the pressure sensing device and, under certain conditions, can form undesirable optical resonances with other elements of the system. The undesirable resonances can be formed between any two points of optical reflection. For instance, the undesirable resonances can be formed between the FBGs and a system connector, or the FBGs and a pressure wire connector. In accordance with this disclosure and as described in more detail below with respect to FIGS. 34-37, these undesirable resonances can be averaged out using dither techniques, thereby reducing their overall effect on the pressure measurements.

Figure 34:
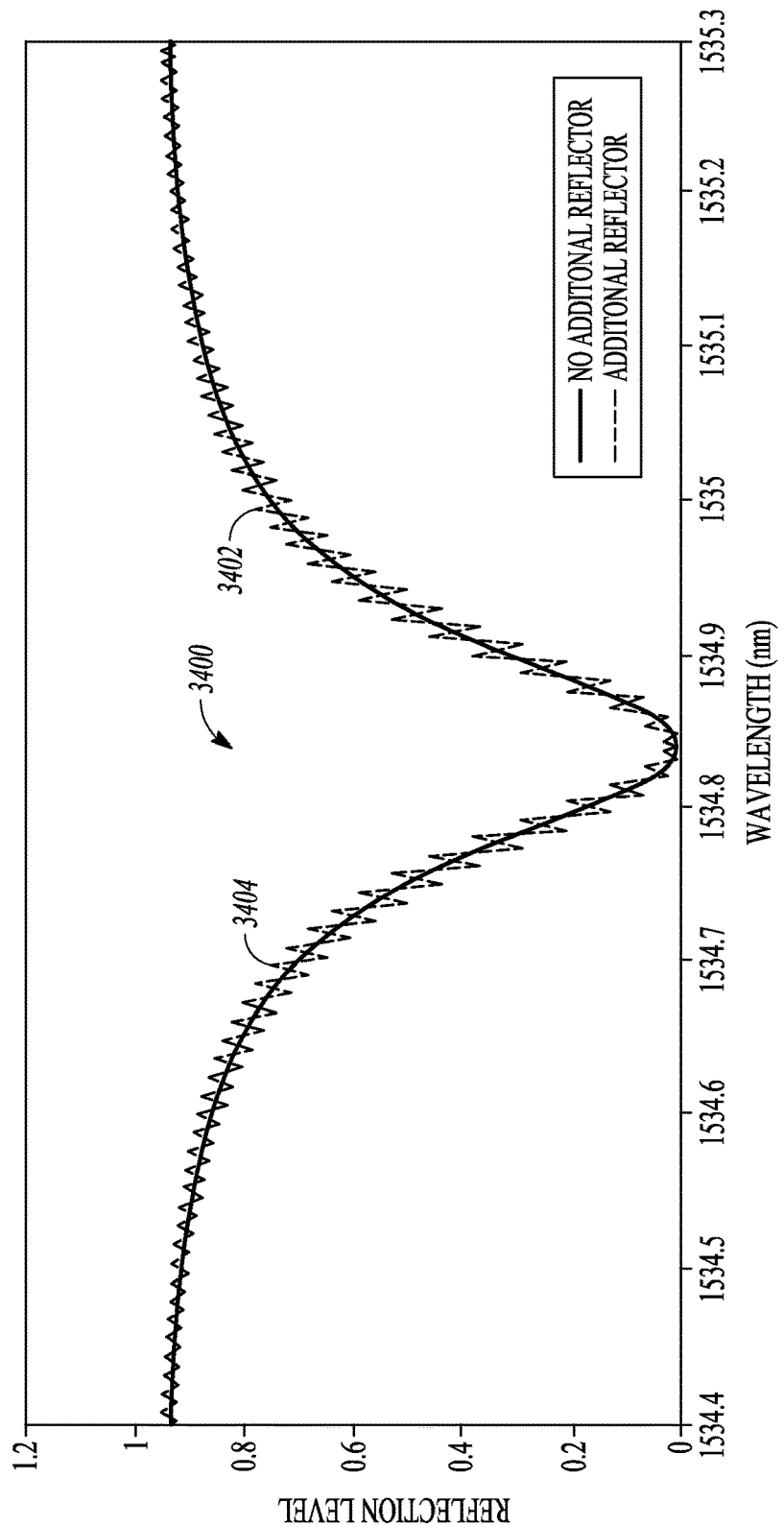
FIG. 34 depicts a conceptual response diagram illustrating undesirable optical resonances caused by additional reflection in an optical system.

FIG. 34 depicts a conceptual response diagram illustrating undesirable optical resonances caused by additional reflection in an optical system. In FIG. 34, where the x-axis represents wavelength and the y-axis represents the intensity of the reflected light, a transmission notch 3400 is shown within a reflection band 3402. The undesirable optical resonances are shown as ripples 3404 overlaid on the fundamental response. In this example the undesirable reflection point is at a distance of about 70 mm from the FBGs.

In an example of a pressure sensing device, there may be an optical connector to the system about two meters from the FBG filters that is a possible source of reflections. The calculated expected wavelength of the ripple caused by a reflection at two meters is approximately 0.4 pm (at 1550 nm). There is a possibility that the locking system can become confused by these ripples 3404 and hop between them, which appears as a sudden jump in the apparent pressure reading, e.g., 10 mm/Hg, shown and described below with respect to FIG. 35. In the context of pressure sensing, such a jump is unwanted and likely unacceptable due to the need for accurate pressure measurements.

Figure 35:
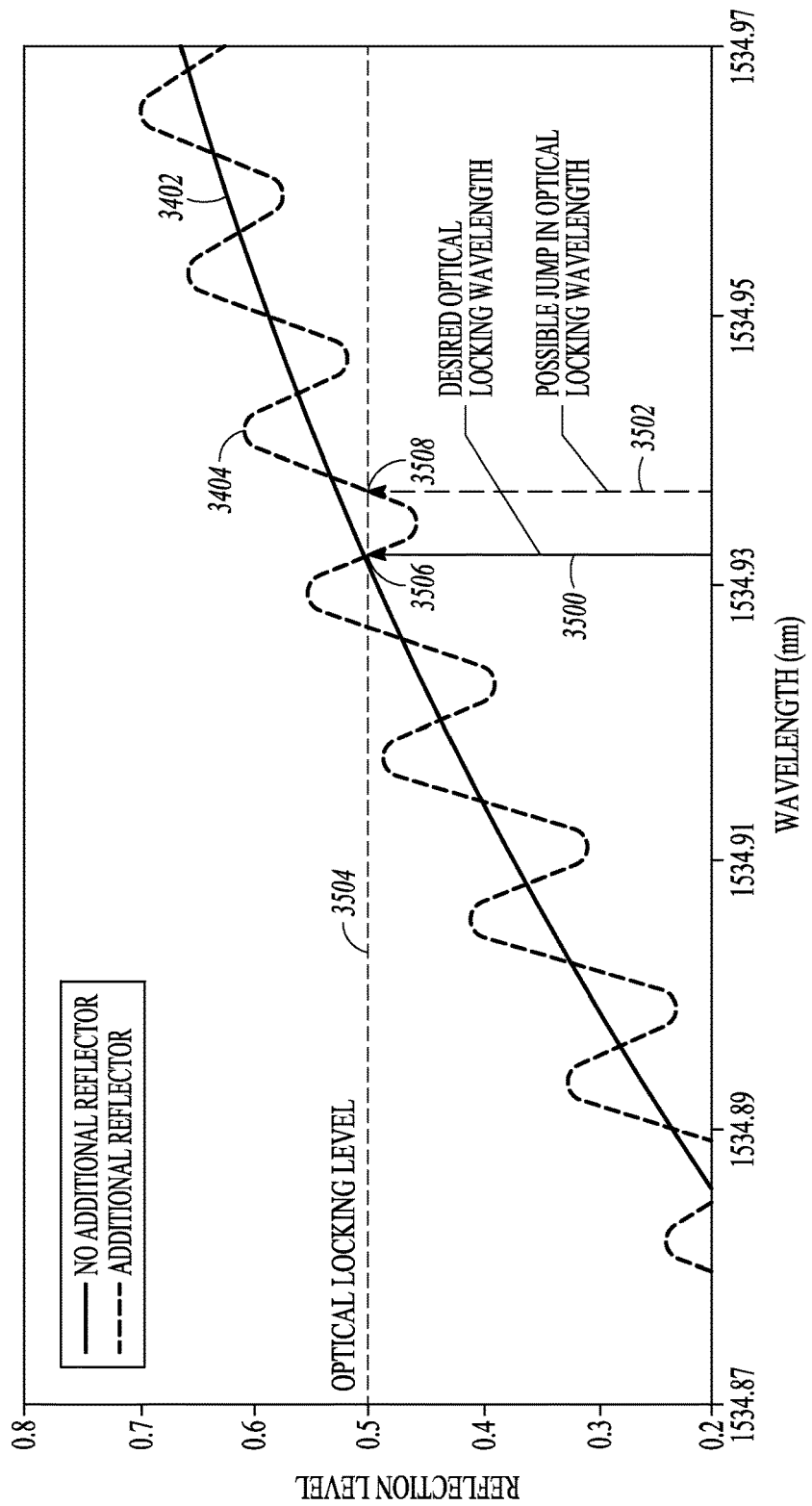
FIG. 35 depicts the conceptual response diagram of FIG. 34 further illustrating undesirable locking circuit wavelength hopping.

FIG. 35 depicts the conceptual response diagram of FIG. 34 further illustrating undesirable locking circuit wavelength hopping. FIG. 35 shows a calculated response for a weak reflection at 70 mm (a non-limiting example for purposes of illustration only) and how the locking circuit can become confused and shift to a different wavelength. More particularly, the locking circuit can become confused because the optical locking level 3504 can intersect both the fundamental response 3402 (at point 3506) and a ripple 3404 (at point 3508), resulting in two possible optical locking wavelengths. As a result of the ripple 3404, the desired optical locking wavelength at 3500 can jump to a higher optical locking wavelength 3502. Assuming that the sensor has a pressure-to-wavelength coefficient of around 1 pm for 25 mm/Hg and that the 2 m cavity has a ripple period of 0.4 pm, then the apparent shift is approximately 10 mm/Hg, which is highly undesirable.

In accordance with this disclosure and as described in more detail below with respect to FIG. 36, the optical dither techniques described above can be used to average through these ripples 3404 and to reduce or eliminate their effects on determining an optical locking wavelength.

Figure 36:
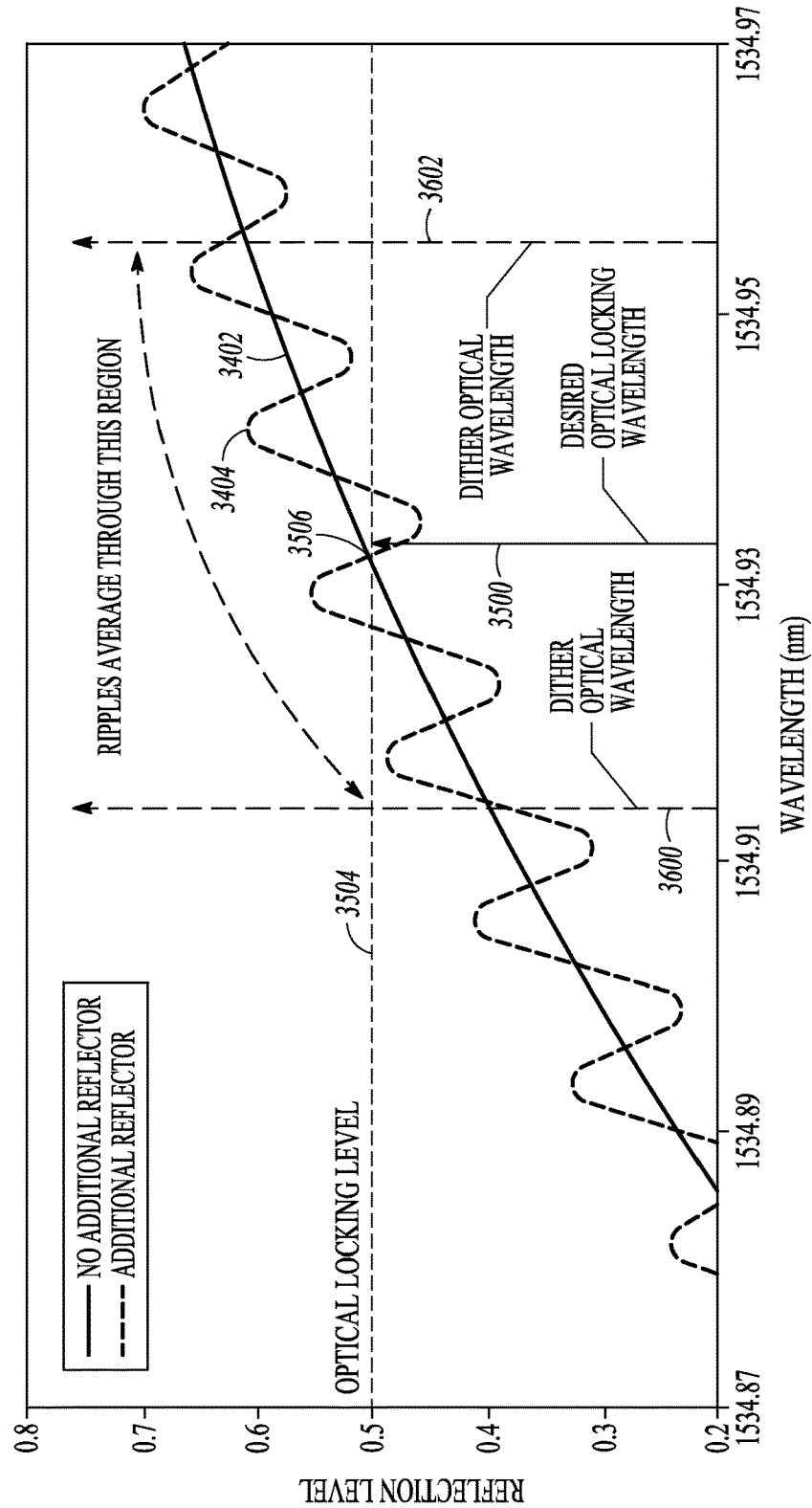
FIG. 36 depicts the conceptual response diagram of FIG. 35 compensated for optical cavity noise using various techniques of this disclosure.

FIG. 36 depicts the conceptual response diagram of FIG. 35 compensated for optical cavity noise using various techniques of this disclosure. In accordance with this disclosure, optical wavelength dither (described above) can be used to sweep or average through a number of the ripple periods. Examples of lower and upper bounds of the dither optical wavelength are depicted at 3600, 3602, respectively. In the example shown in FIG. 36, within the lower and upper wavelength bounds 3600, 3602 are four ripples 3404 that can be averaged. Less or more ripples can be averaged.

When the laser wavelength is dithered, e.g., at a frequency at least five times the bandwidth of the pressure signal, the high frequency AC component can be extracted from the optical signal by filtering, similar to what was described above with respect to the insertion loss compensation techniques and as depicted in FIG. 33. If the pressure signal has a bandwidth of about 0-25 Hz, then the dither frequency is at least 125 Hz, for example. In other examples, the dither frequency is about 300-400 Hz.

Once the high frequency AC component is extracted, then the controller 602 of FIG. 6 can average the AC component over the region of interest, e.g., over four ripples 3404 as in FIG. 36. The dithering occurs at a faster rate than the rate at which the ripples 3404 move side to side during the measurement. As a result, the controller 602 can average through the ripples 3404, thereby removing the optical cavity noise. The controller 602 can then determine an optical locking level and wavelength without becoming confused and jumping to an incorrect optical locking wavelength.

The amplitude and frequency requirements of the dither wavelength can be made to complement the insertion loss compensation (described above), e.g., a frequency of about 300-400 Hz. The amplitude of the wavelength dither can be calculated based on the wavelength separation of the undesirable ripples. In one example, it may be desirable to dither by a wavelength amount that would encompass a sufficient number of ripples to give satisfactory averaging. If the ripples are more closely spaced, then the controller 602 can control generation of a relatively smaller amount of dither than if the ripples were more widely spaced to achieve the same amount of averaging. Take, for example, a two meter long distance between the reflection points, the calculated wavelength of the ripple caused by a reflection at two meters is approximately 0.4 pm (at 1550 nm), then it may be desirable to dither the wavelength of the laser by 5 ripple periods to give satisfactory averaging. The wavelength of the laser can be dithered by a total of 2 pm (0.4 pm×5 ripples). This corresponds to a dither in the laser current of around 0.4 mA, where a typical laser is 5 pm/mA.

In one example implementation, the same dither frequency and electrical filtering used for the insertion loss compensation techniques described above can be used to compensate for the optical cavity noise to allow the usual detection of the pressure readings in the 0-25 Hz bandwidth. In some example implementations, the low frequencies, e.g., 0-25 Hz, that correspond to the pressure signals can be used to control the locking circuit in order to reduce the confusion presented by individual ripples. In one example, the electrical filter circuits can be used to present the average optical detector value to the locking circuits, thus reducing the discrete step nature of the individual ripples.

Figure 37:
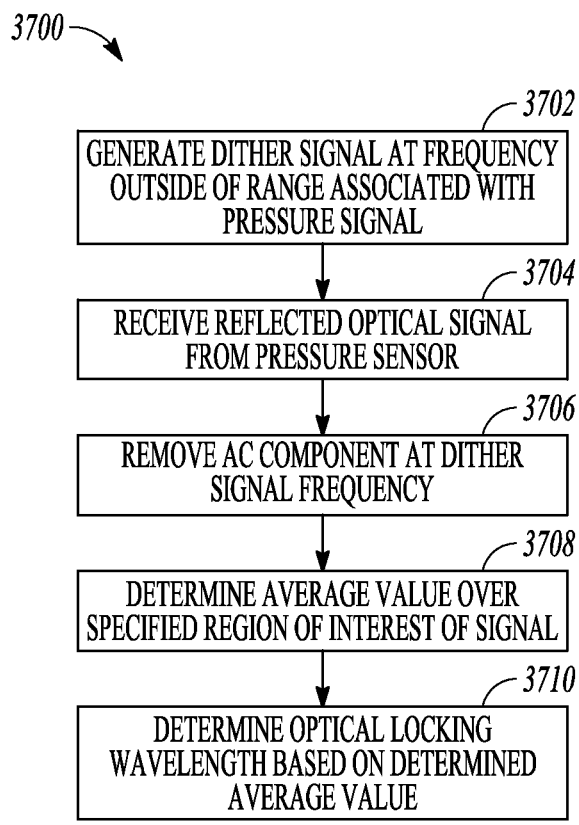
FIG. 37 depicts a flow diagram illustrating an example of a method for compensating for optical cavity noise in an optical pressure sensor using various techniques of this disclosure.

FIG. 37 depicts a flow diagram illustrating an example of a method 3700 for compensating for optical cavity noise in an optical pressure sensor using various techniques of this disclosure. In FIG. 37, the controller 602 of FIG. 6 can control the laser 604 to generate a dither signal at a frequency outside of the range associated with a pressure signal (3702). For example, for a pressure signal having a bandwidth of about 0-25 Hz, the dither frequency can be at least 125 Hz. In one specific example, the dither frequency can be about 300-400 Hz. Next, the optical detector 608 of FIG. 6A can receive the reflected optical signal from the pressure sensor (3704). A low pass filter, e.g., filter 3302 of FIG. 33, can remove or suppress the AC component at the dither signal frequency (3706). Then, the controller 602 can determine a low frequency value, e.g., the average locking level in the low frequency band (0-25 Hz), over the specified region of interest of the signal, e.g., over four ripples (3708). Finally, the controller 602 can determine a noise compensated optical locking wavelength based on the determined average low frequency value (3710).

Figure 38:
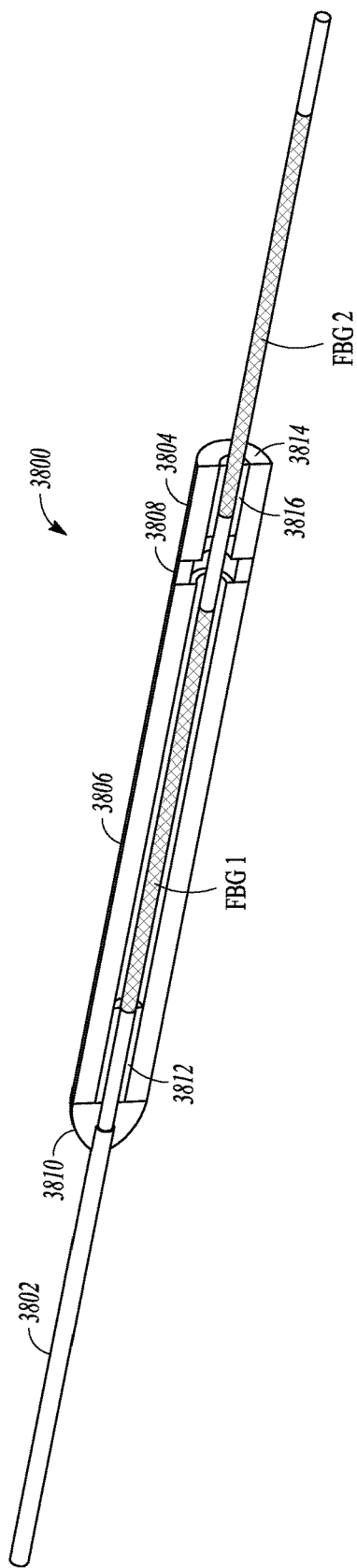
FIG. 38 depicts another example of a portion of a pressure sensor assembly.

FIG. 38 depicts another example of a portion of a pressure sensor assembly 3800. The pressure sensor assembly 3800 is similar in some respects to the concentric pressure sensor assembly 2400 depicted in FIG. 24. The pressure sensor assembly 3800 can include or be coupled to an optical fiber 3802, such as a reduced-diameter longitudinally extending central optical fiber 3802. The pressure sensor assembly 3800 can be located at or near a distal region of the optical fiber 3802.

The pressure sensor assembly 3800 can include a housing that includes a proximal housing portion 3806 and a distal housing portion 3804 separated by a window portion 3808. As described above with respect to FIG. 24, the proximal portion 3806 and the distal portion 3804 can be made from a hard, solid, or inelastic (e.g., fused silica) tubular or other housing. The window portion 3808 can be a soft, flexible, elastic, or compliant gasket located between the distal and proximal portions 3804, 3806 (e.g., silicone or polyurethane elastomer materials, pressure sensitive adhesive materials, or hot melt adhesive materials).

The optical fiber 3802 enters a proximal end 3810 of the proximal housing portion 3806 and can be securely captured, anchored, or affixed to the proximal housing portion 3806 via a tubular or other attachment (e.g., hardened epoxy or other adhesive) region 3812. Similarly, the optical fiber exits a distal end 3814 of the distal housing portion 3804 and can be securely captured, anchored, or affixed to the distal housing portion 3804 via a tubular or other attachment (e.g., hardened epoxy or other adhesive) region 3816.

The pressure sensor assembly 3800 of FIG. 38 can further include a sensing region that can include two FBGs, namely FBG 1 and FBG 2. As seen in FIG. 38, and in contrast to the concentric pressure sensor assembly 2400 of FIG. 24, an FBG, namely FBG 2, can extend distally beyond the distal end of the pressure sensor assembly 3800. By extending beyond the distal end of the pressure sensor assembly, the FBG 2 can be in direct contact with a bodily fluid, for example. In such an example configuration, any effect that securing materials, e.g., epoxies, may have on the FBG 2 can be eliminated. In addition, by extending the FBG 2 beyond the distal end of the pressure sensor assembly 3800 instead of containing the FBG 2 within the housing, the length of the housing of the pressure sensor assembly 3800 can be reduced. In some example configurations, FBG 1 can be used to measure both pressure and temperature while FBG 2 can be configured to measure ambient temperature, e.g., of the bodily fluid, thereby providing an example of a temperature compensated pressure sensor. In one example configuration, it may be desirable to include a non-reflective termination as close to the distal end of the FBG 2 as possible. Without such a termination, a reflection can modulate the optical signal returning from the pressure sensor, which can affect the accuracy of the measurements.

FIGS. 39-41 depict examples of portions of various pressure sensor assemblies. Each of the various pressure sensor assemblies depicted in FIGS. 39-41 include an FBG that extends distally beyond the distal end of each respective pressure sensor assemblies.

The example of a pressure sensor assembly depicted in FIG. 39 is similar to the pressure sensor assembly 3800 described above with respect to FIG. 38 and, as such, will not be described in detail again for purposes of conciseness. In some example configurations, each of FBG 1 and FBG 2 can include a phase shift, e.g., 180 degrees, in the center of the FBG. The phase shift can create a notch in the response, which can be tracked using a tracking circuit as described above.

FIG. 40 depicts an example of a pressure sensor assembly 4000 that can include four FBGs, namely FBGs 1-4. The pressure sensor assembly 4000 can include or be coupled to an optical fiber 4002, such as a reduced-diameter longitudinally extending central optical fiber 4002. The pressure sensor assembly 4000 can be located at or near a distal region of the optical fiber 4002.

The pressure sensor assembly 4000 can include a housing that includes a distal housing portion 4004 and a proximal housing portion 4006 separated by a window portion 4008. As described above with respect to FIG. 24, the distal portion 4004 and the proximal portion 4006 can be made from a hard, solid, or inelastic (e.g., fused silica) tubular or other housing. The window portion 4008 can be a soft, flexible, elastic, or compliant gasket located between the distal and proximal housing portions 4004, 4006.

The optical fiber 4002 enters a proximal end 4010 of the proximal housing portion 4006 and can be securely captured, anchored, or affixed to the proximal housing portion 4006 via a tubular or other attachment (e.g., hardened epoxy or other adhesive) region 4012. Similarly, the optical fiber 4002 exits a distal end 4014 of the distal housing portion 4004 and can be securely captured, anchored, or affixed to the distal housing portion 4004 via a tubular or other attachment (e.g., hardened epoxy or other adhesive) region 4016.

The pressure sensor assembly 4000 of FIG. 40 further includes a sensing region that can include four FBGs, namely FBGs 1-4. As seen in FIG. 40, an FBG, namely FBG 3, extends distally beyond the distal end of the pressure sensor assembly 4000. By extending beyond the distal end of the pressure sensor assembly, the FBG 3 can be in direct contact with a bodily fluid, for example. In such an example configuration, any effect that securing materials, e.g., epoxies, may have on the FBG 3 can be eliminated. In addition, by extending the FBG 3 beyond the distal end of the pressure sensor assembly 4000 instead of containing the FBG 3 within the housing, the length of the housing of the pressure sensor assembly 4000 can be reduced.

In some example configurations, from left to right, FBG 4 can be used to measure pressure, FBG 1 can be used to measure temperature, FBG 2 can be used to measure pressure, and FBG 3 can be configured to measure ambient temperature, e.g., of the bodily fluid, thereby providing an example of a temperature compensated FBG interferometer in optical communication with the optical fiber 4002. Increasing the distance between the two temperature gratings, namely FBG 1 and FBG 3, increases the finesse, which can increase the sensitivity of the sensor, e.g., a steeper slope in the reflection band, and improve the quality factor.

FIG. 41 depicts an example of a pressure sensor assembly 4100 that can include three FBGs, namely FBGs 1-3. The pressure sensor assembly 4100 can include or be coupled to an optical fiber 4102, such as a reduced-diameter longitudinally extending central optical fiber 4102. The pressure sensor assembly 4000 can be located at or near a distal region of the optical fiber 4102.

The pressure sensor assembly 4100 can include a housing that includes a distal housing portion 4104 and a proximal housing portion 4106 separated by a window portion 4108. As described above with respect to FIG. 24, the distal housing portion 4104 and the proximal housing portion 4106 can be made from a hard, solid, or inelastic (e.g., fused silica) tubular or other housing. The window portion 4108 can be a soft, flexible, elastic, or compliant gasket located between the distal and proximal housing portions 4104, 4106.

The optical fiber 4102 enters a proximal end 4110 of the second housing portion 4106 and can be securely captured, anchored, or affixed to the second housing portion 4106 via a tubular or other attachment (e.g., hardened epoxy or other adhesive) region 4112. Similarly, the optical fiber exits a distal end 4114 of the first housing portion 4104 and can be securely captured, anchored, or affixed to the first housing portion 4104 via a tubular or other attachment (e.g., hardened epoxy or other adhesive) region 4116.

The pressure sensor assembly 4100 of FIG. 41 further includes a sensing region that can include three FBGs, namely FBGs 1-3. As seen in FIG. 41, an FBG, namely FBG 3, extends distally beyond the distal end of the pressure sensor assembly 4100. By extending beyond the distal end of the pressure sensor assembly, the FBG 3 can be in direct contact with a bodily fluid, for example. In such an example configuration, any effect that materials, e.g., epoxies, may have on the FBG 3 can be eliminated. In addition, by extending the FBG 3 beyond the distal end of the pressure sensor assembly 4100 instead of containing the FBG 3 within the housing, the length of the housing of the pressure sensor assembly 4100 can be reduced.

In some example configurations, one of the three FBGs can have a response that is larger than the response of the other two FBGs. For example, one of the FBGs, e.g., FBG 2, can have a response with about twice the bandwidth as either FBG 1 or FBG 3. FBG 1 and FBG 3 can each have a narrowband response that resonates with a different portion of the grating of FBG 2.

In one example, FBG 1 can be used to measure pressure, e.g., narrowband response, FBG 3 can be used to measure temperature, e.g., narrowband response, and FBG 2 can be used to measure pressure, e.g., broadband response. As described above, in order to generate a pressure signal that is ambient temperature compensated, the signal generated by FBG 3 can be used as a reference to null a shift in temperature. A controller circuit can be configured to control subtraction of the temperature reference signal (from FBG 3) from the pressure signals (from FBGs 1 and 2), such as to generate a temperature compensated pressure signal. An example of a temperature compensation technique was described above with respect to FIG. 5.

Figure 42:
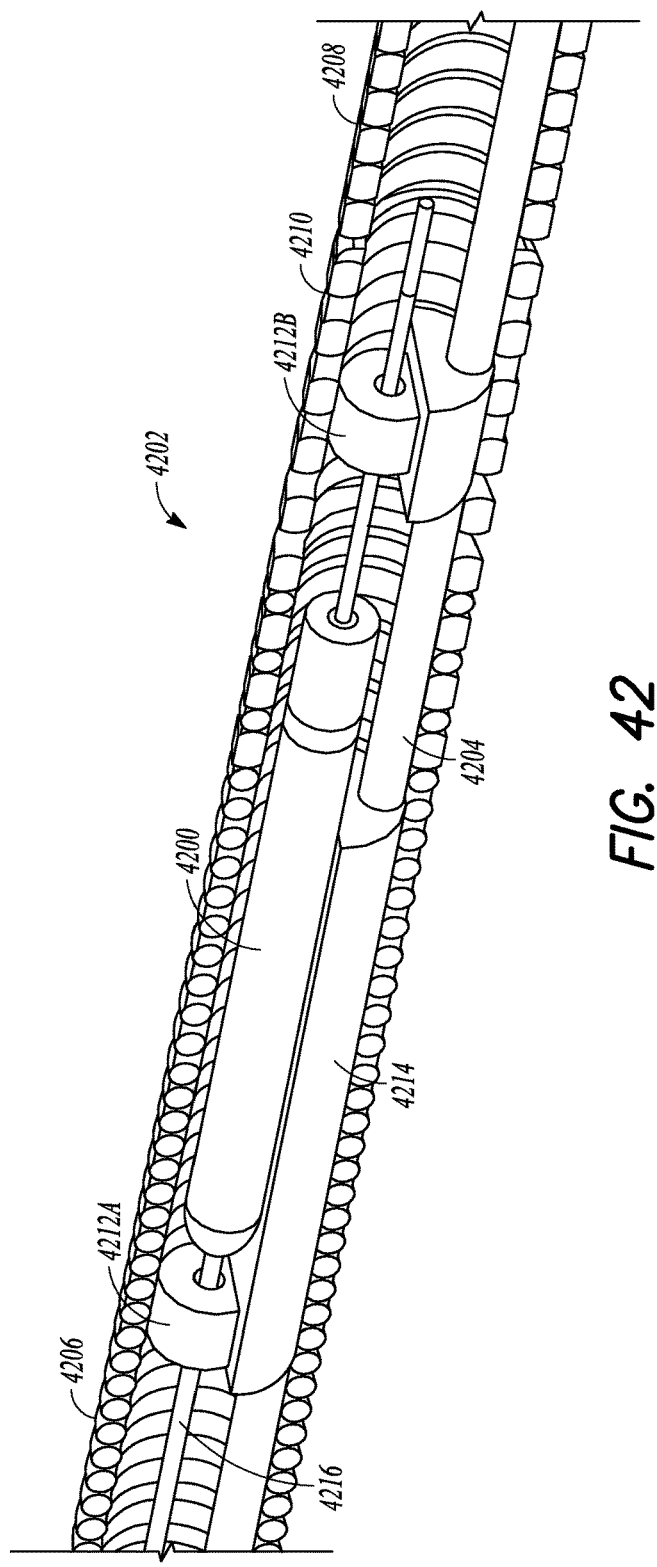
FIG. 42 depicts another example of a guidewire in combination with an optical fiber pressure sensor.

FIG. 42 depicts another example of a guidewire in combination with an optical fiber pressure sensor assembly. In FIG. 42, an optical pressure sensor assembly 4200, e.g., assemblies 3900, 4000, and 4100 of FIGS. 39-41, can be delivered to a desired site using a guidewire, shown generally at 4202. The guidewire 4202 can include a core wire 4204, a proximal coil 4206, and a distal coil 4208. The proximal coil 4206 and the distal coil 4208 can be joined together via a mechanical joint 4210, e.g., solder or adhesive.

The optical pressure sensor assembly 4200 can be mounted to the core wire 4204 via a mounting unit 4214. In turn, the mounting unit 4214 can then be attached to a coil, e.g., proximal coil 4206.

The guidewire 4202 can further include one or more disk spacers 4212A, 4212B (referred to collectively in this disclosure as disk spacers 4212). The disk spacers 4212 can define a hole through which the optical fiber 4216 can extend. The disk spacers 4212 can be included to prevent the optical fiber 4216 from contacting other components of the guidewire 4202, e.g., coils 4206, 4208.

FIGS. 43A-43C depict another example of a guidewire in combination with an optical fiber pressure sensor. In FIG. 43A, an optical pressure sensor assembly 4300, e.g., assemblies 3900, 4000, and 4100 of FIGS. 39-41, can be delivered to a desired site using a guidewire, shown generally at 4302. The guidewire 4302 can include a core wire 4304, a proximal coil 4306, and a distal coil 4308. The proximal coil 4306 and the distal coil 4308 can be joined together via a mechanical joint 4310, e.g., solder or adhesive.

The guidewire 4302 can further include a cradle 4312 to provide stiffness around the sensor assembly 4300. The cradle 4312, e.g., U-shaped, is shown in more detail in FIG. 43B. As seen in FIG. 43A, the optical pressure sensor assembly 4300 can fit within the cradle 4312. The optical fiber 4314 can extend into and out of the cradle 4312, and the cradle 4312 can fit inside the coils 4306, 4308. The pressure sensor assembly 4300 can be mounted to the core wire 4304 via a mounting material 4316, e.g., an epoxy, which can extend through the cradle 4312.

FIG. 43C depicts a cross-sectional view of the guidewire assembly shown in FIG. 43A. As seen in FIG. 43C, a portion of the diameter of the core wire 4304 can be reduced over a length of the cradle 4312 to provide sufficient room for mounting the pressure sensor assembly 4300.

FIGS. 44A-44C depict another example of a guidewire in combination with an optical fiber pressure sensor. In FIG. 44A, an optical pressure sensor assembly 4400, e.g., assemblies 3900, 4000, and 4100 of FIGS. 39-41, can be delivered to a desired site using a guidewire, shown generally at 4402. The guidewire 4402 can include a core wire 4404, a proximal coil 4406, and a distal coil 4408.

The guidewire 4402 can further include a tube assembly 4412 to provide stiffness around the sensor assembly 4400. The tube assembly 4412 is shown in more detail in FIG. 44B. The tube assembly includes a proximal end portion 4414 and a distal end portion 4416 that extend from the proximal and distal ends 4418, 4420, respectively, of a main body 4422 of the tube assembly 4412. A portion of the circumference of the main body 4422 of the main body 4422 can be removed to allow pressure signals to reach the pressure sensor assembly 4400.

As seen in FIG. 44A, the optical pressure sensor assembly 4400 can fit within the tube assembly 4412. The optical fiber 4424 can extend into and out of the tube assembly 4412. In contrast to the guidewire design in FIGS. 43A-43C, the tube assembly 4412 does not fit within the coils 4406, 4408. Instead, the coils 4406, 4408 can be affixed, respectively, to the proximal end portion 4414 and the distal end portion 4416 that extend from the proximal and distal ends 4418, 4420 respectively, of the tube assembly 4412. The pressure sensor assembly 4400 can be mounted to the core wire 4404 via a mounting material 4426, e.g., an epoxy, which can extend through the tube assembly 4412.

FIG. 44C depicts a cross-sectional view of the guidewire assembly shown in FIG. 44A. As seen in FIG. 44C, a portion of the diameter of the core wire 4404 can be reduced over a length of the tube assembly 4412 to provide sufficient room for mounting the pressure sensor assembly 4400.

FIGS. 45A-45B depict an example of a core wire, shown generally at 4500, that can be used in combination with an optical fiber pressure sensor. During manufacture, the diameter of the core wire 4500 can be varied over specified lengths in order to form a desired shape. For example, as seen in FIG. 45A, the core wire 4500 can be manufactured to include a portion 4502 with a diameter that is larger than the remaining proximal or distal portions 4504, 4506, respectively, of the core wire 4500. The core wire 4500 can be manufactured to include one or more tapered portions 4508A-4508C that taper the portion 4502 from its larger diameter to the smaller diameter of the proximal and distal portions 4504, 4506.

Figure 46A:
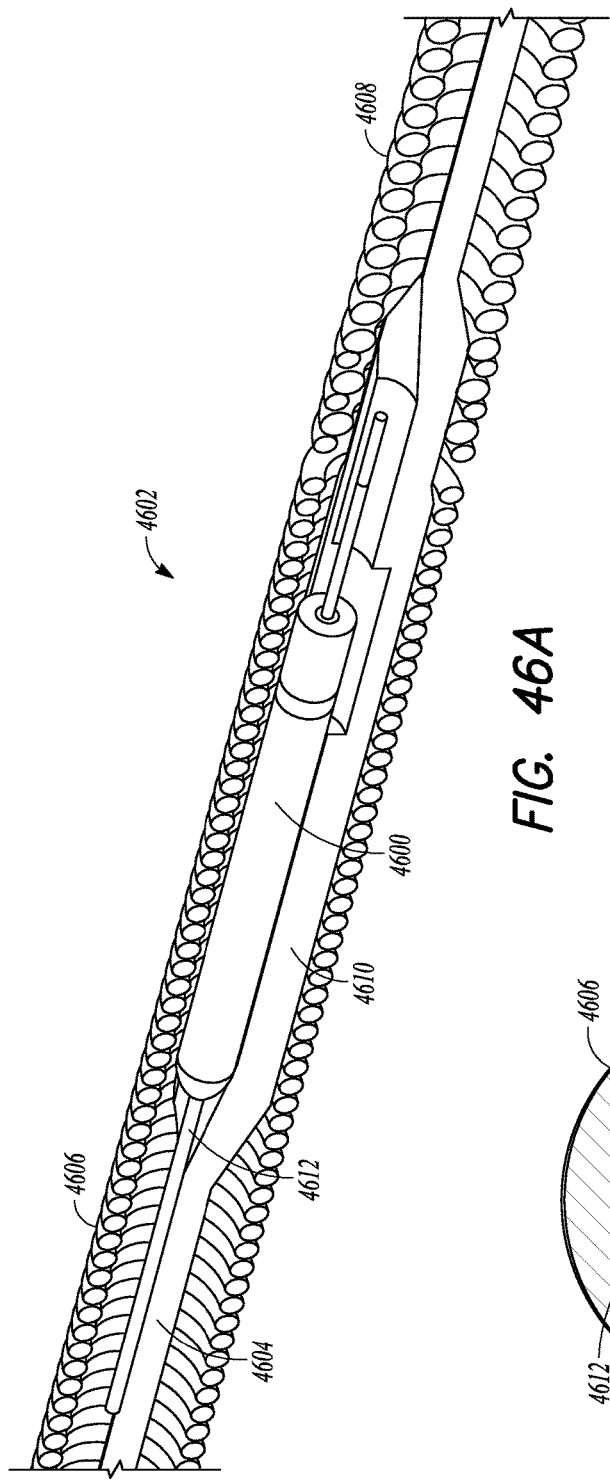
FIG. 46A depicts an example of a guidewire in combination with an optical fiber pressure sensor and the core wire of FIG. 45B.
Figure 46B:
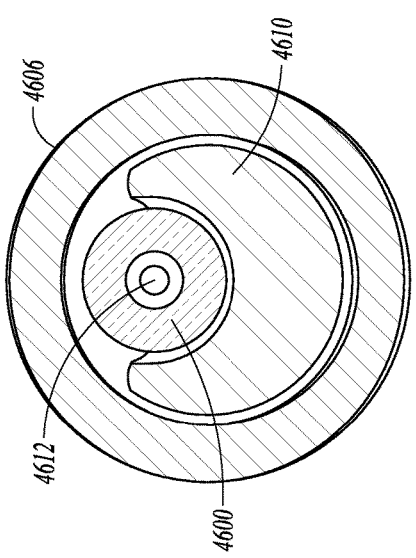
FIG. 46B depicts a cross-sectional view of the configuration shown in FIG. 46A.

After the core wire 4500 has been manufactured to the desired dimensions, a cradle can be formed, for example, in enlarged portion 4502, e.g., using a coining process, precision machining, micromachining micro EDM, or other processes, in the portion(s) with a larger diameter, as shown generally at 4510 in FIG. 45B. The cradle 4510 formed in the core wire 4500 can be used to provide a housing for a pressure sensor assembly, e.g., assemblies 3900, 4000, and 4100 of FIGS. 39-41, as shown in FIG. 46A-B.

The cradle 4510 can have varying inside dimensions to provide the ability to secure the sensor in varying ways. For example, in some embodiments, it may be advantageous to mount the sensor at its proximal portion only and to allow the rest of the sensor to be cantilevered in the cavity such that it cannot be touched during normal use of the guidewire. This arrangement can minimize the likelihood of guidewire bending producing erroneous or artificial pressure readings. In other embodiments, the cradle 4510 can have a shape that is rectangular or non-rectangular.

By way of example, the cradle 4510 as shown can have a shape that enables the mounting of a cylindrical shaped sensor without removing more material than necessary, which helps maintain the relative stiffness of the core in the region of the sensor. The cradle 4510, for example, may have a complex shape or it may have a semi-cylindrical shape. By way of example, the cradle of FIG. 45B has a size and shape that by itself does not protect the sensor. The sensor placed therein, as shown in FIG. 46, can be mounted such that the upper extremity of the cylindrical surface is higher than the side walls of the cradle 4510.

Such a cradle and core design can be advantageous because a single structure can function both as the core wire 4500 and as the housing of a pressure sensor assembly, which can improve its strength. In addition, the design of FIG. 45B can be advantageous because the core wire 4500 is coaxial with the guidewire, as shown in FIG. 46A, which can enhance the performance of the guidewire. For example, the guidewire can improve the steering of the guidewire and allow the guidewire to perform more predictably, e.g., without whip or latency, which can be important while assessing a lesion.

FIG. 46A depicts an example of a guidewire in combination with an optical fiber pressure sensor and the core wire of FIG. 45B. In FIG. 46A, an optical pressure sensor assembly 4600, e.g., assemblies 3900, 4000, and 4100 of FIGS. 39-41, can be delivered to a desired site using a guidewire, shown generally at 4602. The guidewire 4602 can include a core wire 4604, e.g., the core wire 4500 of FIG. 45B, a proximal coil 4606, and a distal coil 4608. As described above, the core wire 4604 can be formed to include a cradle 4610, e.g., the cradle 4510 of FIG. 45B, which can hold the pressure sensor assembly 4600. An optical fiber 4612 can extend along the core wire 4604. As seen in FIG. 46A, the core wire 4604 is coaxial with the guidewire 4602, which can enhance the performance of the guidewire.

Optical pressure sensor assembly 4600 can be seen mounted on the cradle 4610 in a cantilevered way. The degree of cantilever can be varied by varying the length of the mount which attaches to the proximal body of 4600. The rest of the cavity can be formed such that there is a gap around the distal body and the sensitive distal end of 4600. The core wire 4604, in the section defining the sensor mount, can be varied in size and shape. For example, the outside diameter of the cradle 4610 can have a constant diameter section and one or more tapered sections. The coil 4606 can, for example, be attached to the cradle 4610 at the constant diameter section and not at the tapered section such that the effect is to minimize the relatively stiff length of the construction in this area. This can be helpful in providing enhancements to the mechanical performance of the guidewire.

In another example, as mentioned in regard to FIG. 45B, the cradle can be sized and shaped such that sensor 4600 is not fully protected by the cradle. Such a configuration is shown in the cross-sectional view of FIG. 46B. In this example, coil 4606 can form an integral part of the protection means for the sensor 4600. The cradle 4610, in combination with the coil 4606, can form a housing that surrounds the sensor 4600 and completes the protection mechanism. The coil 4606 and the cradled enlarged portion of the core wire can be joined together to form a solid protection means. The joining process could be a suitable adhesive, solder or braze.

The smaller distal coil diameter (which can result from the larger diameter distal coil wire), shown in the example of a guidewire in combination with an optical fiber pressure sensor of FIG. 46A-B can be accommodated by reducing the diameter of the ground feature at its distal end. Alternatively, the distal coil inside diameter can be increased by forming the distal coil with a smaller diameter wire or a flattened wire thereby allowing both the proximal and distal coils to fit over the sensor protecting feature on the wire. It may also be advantageous to both reduce the distal diameter of the wire ground feature only slightly and increase the distal coil ID only slightly to fit the distal coil over the sensor protective feature.

It can also be advantageous to include a small through feature or channel in the distal end of the sensor housing, e.g., sensor housing 5014, to facilitate equalizing pressure within the pressure sensor housing cavity and the environment in which the distal end of the wire is positioned. In addition, a slight spreading of the coil loops over the location of the pressure communication channel can be included. The channel can be a straight through hole, but a wide variety of channels as well as starting and ending locations of the channel from the outside of the core wire through to the inside of the pressure sensor housing cavity can be utilized. It can be advantageous to have more than one channel for a variety of reasons, such as, for instance that each individual channel could be smaller, or placing them in the most favorable locations, etc.

Despite being exceptionally low-loss signal carriers, optical fibers can still attenuate optical signals, especially if the optical fiber is deformed in certain undesirable manners. Optical signals can be attenuated by, for example, macrobends and microbends in the optical fiber. Macrobending attenuation can occur when there are relatively large bends in the optical fiber significantly exceeding the diameter of the optical fiber. As the bend radius decreases, increasing amounts of light can leak out of the fiber due to lessening optical confinement. Microbending attenuation can occur when there are very small, e.g., microscopic, deformations of the optical fiber. These deformations can be caused, for example, by external forces applied to the optical fiber. For example, imperfections of the optical fiber coating or imperfections of a surface in contact with the optical fiber can impart forces on the optical fiber, which can create microbend induced variability in the optical losses.

The present inventors have determined that microbending losses can contribute to variability of the optical signal level as the guidewire is flexed, which can reduce the accuracy and stability of a measured pressure wave. The significance of a flow reducing lesion in a coronary artery can be determined by accurately measuring the Fractional Flow Reserve (FFR) under hyperemic conditions. Since the FFR index can be used to determine the significance of a flow reducing lesion in an artery, with a typical go/no go value of 0.8, for example, small inaccuracies in pressure readings can lead to incorrect decisions about treatment. It is desirable that a pressure sensing guidewire be able to accurately measure blood pressure. Minimization, or elimination, of the variable losses can improve signal quality and thus the accuracy of the device.

The present inventors have determined that microbending losses can be reduced, for example, by utilizing a wavelength of light which, given the size constraints of the guidewire and therefore the size constraints of the cladding and coating of the optical fiber, has more robust optical confinement. For example, a wavelength of 1310 nanometers can be used instead of 1550 nanometers. For a given optical fiber, if a lower wavelength of light is used, typically the diameter of the optical mode field can be reduced. In a standard size optical fiber this might not be of significant consequence but with the ultra reduced diameter of the fiber in this application it significantly reduces the amount of optical energy that interacts with the outer circumference of the fiber where there is an interface between the optical fiber and the fiber coating. With a reduction in energy at the outer circumference, the optical fiber will have a lower optical insertion loss.

A standard optical coating applied to optical fibers often has a refractive index that is higher than the refractive of the fiber cladding, which can strip any stray light from the cladding so that it cannot interfere with the light in the core of the fiber. This can be undesirable if the mode field of the light in the core is too close to the interface of the cladding and the optical coating due to the very small size of the fiber used in this application. If the insertion loss is too great then it is possible to reduce this by using an optical coating that has a refractive index lower than the refractive index of the cladding, which can help confine the optical mode field and reduce the insertion loss. It is also possible to achieve a similar desired effect by having a doped outer ring in the fiber cladding. This can be achieved by doping a small portion of the outer diameter of the fiber preform with an additive such as Fluorine. This is inherently embedded in the fiber as it is drawn from the preform unlike the coating which as applied to the fiber after it is drawn from the preform.

It can also be desirable to choose the mechanical properties of the optical coating such that it does not communicate surface imperfections to the optical fiber. This can mean choosing an optical coating whose mechanical modulus is soft enough that imperfections in the surrounding materials are dissipated through the volume of the coating rather than being transferred to the fiber.

Figure 63A:
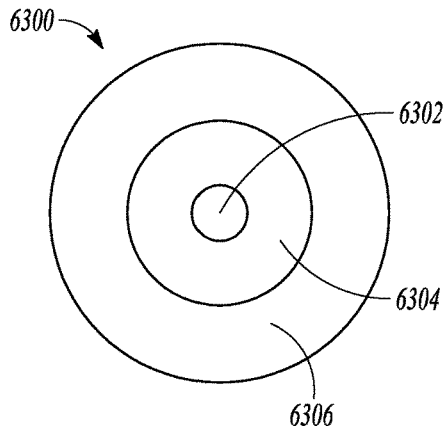
FIG. 63A is a cross-sectional view depicting an example of an optical fiber having a single coating, in accordance with this disclosure.

FIG. 63A is a cross-sectional view depicting an example of an optical fiber having a single coating, in accordance with this disclosure. FIG. 63A depicts an optical fiber 6300 having a fiber core 6302 surrounded by a fiber cladding 6304. The optical fiber 6300 can include a low modulus (soft), single fiber coating 6306 to dissipate any surface irregularities volume of the coating rather than being transferred to the optical fiber core 6302.

However, a very soft fiber coating can be accidently removed from the fiber by mechanical abrasion thereby leaving the fiber unprotected. To reduce the likelihood of this happening, it can be desirable to add an outer coating that is more resistant to mechanical abrasion.

Figure 63B:
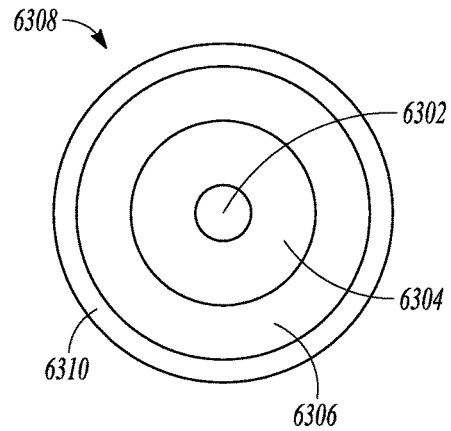
FIG. 63B is a cross-sectional view depicting an example of an optical fiber having a dual coating, in accordance with this disclosure.

FIG. 63B is a cross-sectional view depicting an example of an optical fiber having a dual coating, in accordance with this disclosure. FIG. 63B depicts an optical fiber 6308 having a fiber core 6302 surrounded by a fiber cladding 6304. Like in FIG. 63A, the optical fiber 6308 can include a low modulus (soft), soft fiber coating 6306 to dissipate any surface irregularities volume of the coating rather than being transferred to the optical fiber core 6302. In addition, the optical fiber 6308 can include a second coating 6310 surrounding the soft fiber coating 6306. The second coating 6310 can be a hard, durable coating that is more resistant than the soft fiber coating 6306 to mechanical abrasion.

For a given fiber design, the lower wavelength will usually be less susceptible to microbends and the resulting attenuation lower due to more robust optical confinement of the optical mode as long as the wavelength stays above the cutoff wavelength of the fiber, which is the wavelength below which the fiber ceases to be single mode.

There are other ways to lessen the undesirable outcoupling of light by advanced designs in the fiber. These can include carefully tailored waveguide designs referred to in this disclosure as depressed cladding designs, which is where an area around the core of the fiber is deliberately lowered in refractive index by adding a dopant such as fluorine.

Figure 64A:
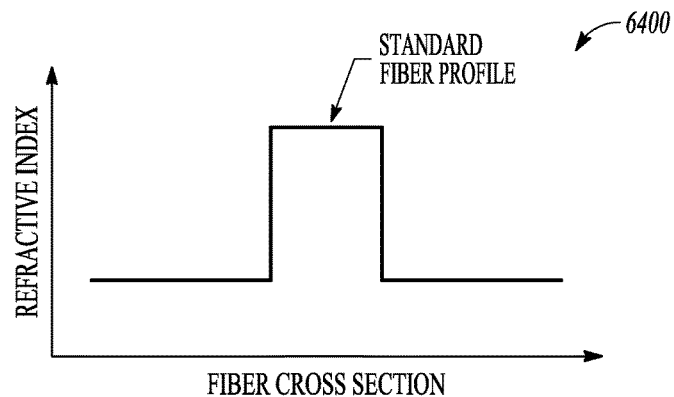
FIGS. 64A and 64B are conceptual illustrations of fiber profiles.
Figure 64B:
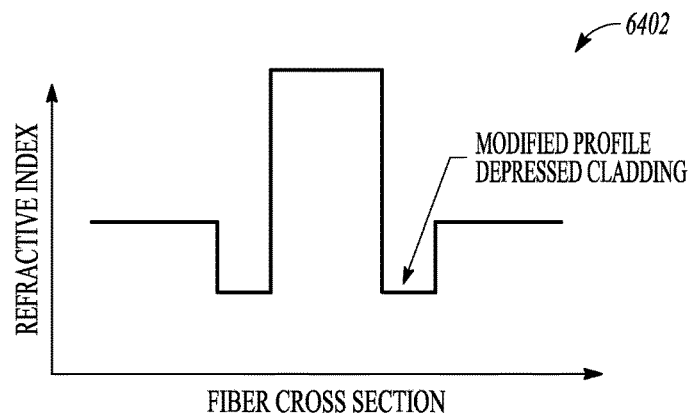

FIGS. 64A and 64B are conceptual illustrations of fiber profiles. FIG. 64A depicts a standard fiber profile 6400 and FIG. 64B depicts a modified profile 6402 utilizing a depressed cladding. In FIGS. 64A and 64B, the x-axis represents the fiber cross-section and the y-axis represents the refractive index. In contrast to the generally uniform refractive index adjacent the core in the standard fiber profile 6400 of FIG. 64A, the refractive index area around the core of the fiber can be deliberately lowered, as shown in FIG. 64B, by adding a dopant, e.g., fluorine. The lowering of the refractive index ring around the core can make the effective index difference appear to be relatively larger and thus is it more difficult for the light to be coupled out of the core by bending.

Additionally or alternatively, it can be desirable to eliminate any variable optical losses as the guidewire is twisted and bent in normal use within a tortuous body lumen, e.g., coronary artery. Typically, the distal end of a guidewire is designed with certain flexibility and torque transmission characteristics that enhance the ability to steer the guidewire into various branches of the coronary artery tree, for example, including the ability to cross stenoses of variable severity. When incorporating the optical fiber into typical guidewire constructions, it can be desirable to ensure that the optical fiber is not subjected to varying external pressures or pinch points along its length, particularly along the length that is incorporated in the distal, most flexible, region of the guidewire. Typically, this involves placing this length of optical fiber in between the core wire and the outer coil of the guidewire.

The present inventors have determined that the accuracy and stability of the optical pressure sensing guidewire can be improved by adding design elements that help reduce or eliminate the variability in optical losses along the length of the optical fiber caused by microbends, as shown and described below with respect to FIGS. 47 and 48. For example, the present inventors have found that it is preferable to create "channels" within this region that protect the optical fiber with a design objective of eliminating forces on the optical fiber that may create microbends.

Figure 47:
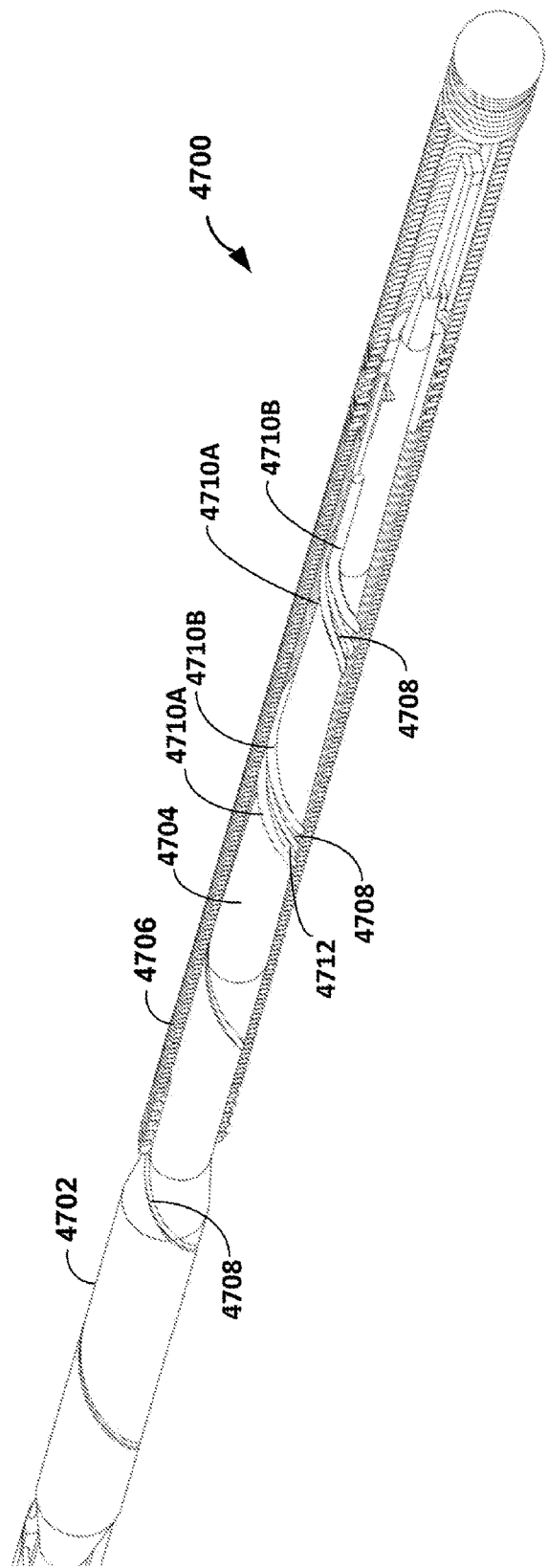
FIG. 47 depicts an example of a guidewire in combination with an optical fiber pressure sensor assembly that can be used to reduce the effects of microbending, using various techniques of this disclosure.

FIG. 47 depicts an example of a guidewire in combination with an optical fiber pressure sensor assembly that can be used to reduce the effects of microbending, using various techniques of this disclosure. FIG. 47 depicts a fiber pressure sensor assembly 4700, such as described above in numerous example configurations. As described in detail above, the fiber pressure sensor assembly 4700 can include a guidewire 4702 having a core wire 4704 and a coil 4706 disposed about a distal portion of the core wire 4704.

An optical fiber 4708 can be wound about the guidewire 4702 and the core wire 4704 underneath the coil 4706. The optical fiber 4708 can be wound around the core wire 4704 with or without any adhesive to attach the two together. As the two components flex in normal use, the relatively smooth surface of the core wire 4704 does not impart microbends into the optical fiber 4708. However, with the coil 4706 in place around the two components, the coil 4706 can contact the optical fiber 4708 in normal use, which can create pinch points or impart microbends into the optical fiber 4708.

In accordance with this disclosure, the fiber pressure sensor 4700 can include stand-offs or channels that can protect the optical fiber 4708 from being touched by the coil 4706, and thus prevent microbends. For example, one or more filament members 4710A, 4710B (collectively referred to in this disclosure as "filament members 4710") can be helically wound around the core wire 4704 between the windings of the optical fiber 4708. The filament members 4710 may be constructed of flexible materials, e.g., metallic or polymeric, that can prevent the coil 4706 from physically contacting the optical fiber 4708 without substantially changing the mechanical performance characteristics of the guidewire 4702.

As seen in FIG. 47, the paired filament members 4710A, 4710B can define a channel 4712 within which the optical fiber 4708 can be positioned. By using filament members 4710 that have a dimension, e.g., an outer diameter, greater than the outer diameter of the optical fiber 4708, the filament members 4710 can prevent the coil 4706 from contacting the optical fiber 4708.

Figure 48:
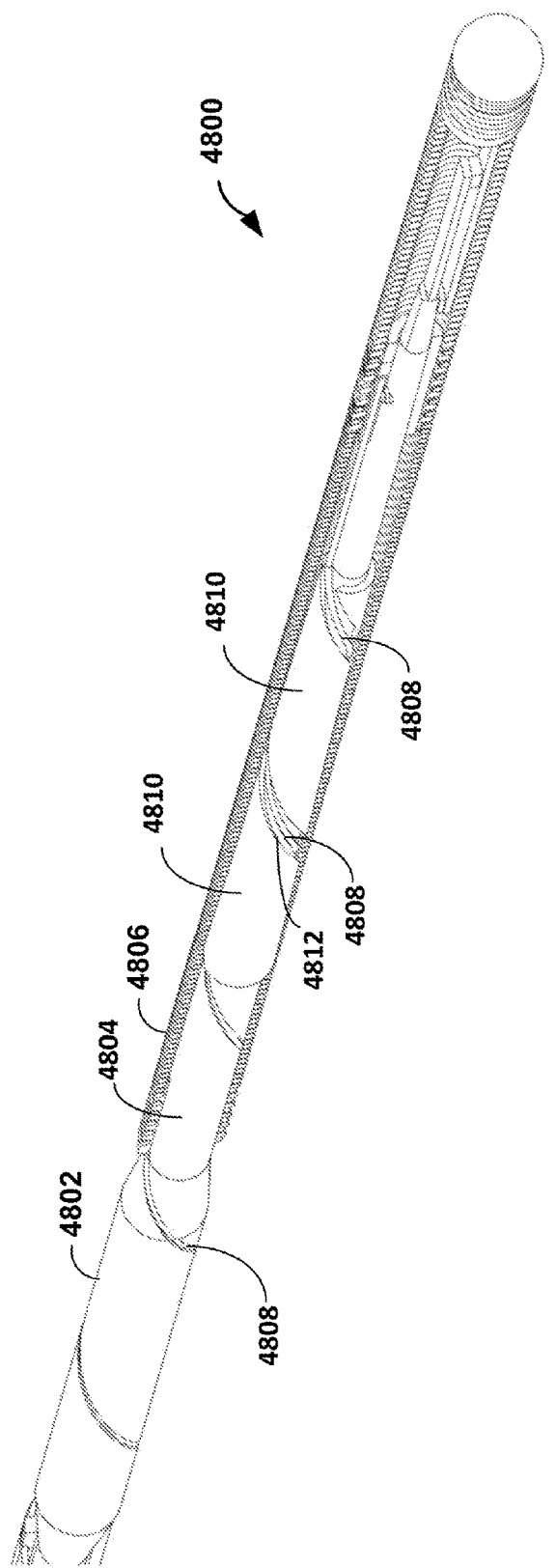
FIG. 48 depicts another example of a guidewire in combination with an optical fiber pressure sensor assembly that can be used to reduce the effects of microbending, using various techniques of this disclosure.

FIG. 48 depicts another example of a guidewire in combination with an optical fiber pressure sensor assembly that can be used to reduce the effects of microbending, using various techniques of this disclosure. FIG. 48 depicts a fiber pressure sensor assembly 4800, such as described above in numerous example configurations. As described in detail above, the fiber pressure sensor assembly 4800 can include a guidewire 4802 having a core wire 4804 and a coil 4806 disposed about a distal portion of the core wire 4804.

Instead of the filament members described above and depicted in FIG. 47, the fiber pressure sensor assembly 4800 of FIG. 48 can include a ribbon member 4810, e.g., tape-like member, that can be wrapped around the core wire 4804, and define a channel 4812 within which the optical fiber 4808 can be positioned. The ribbon member 4810 can have a dimension, e.g., thickness, that is greater than the outer diameter of the optical fiber 4808, thereby preventing the coil 4806 from contacting the optical fiber 4808. In some example configurations, the ribbon member 4810 can be of uniform thickness. In other example configurations, the ribbon member 4810 can be of varying thickness, which can accommodate tapers in the core wire 4804. In some examples, the ribbon member 4810 can be substantially flat.

The ribbon member 4810 can create stand-offs or channels that can protect the optical fiber 4808 from being touched by the coil 4806, and thus prevent microbends. The ribbon member 4810 may be of flexible materials, e.g., metallic or polymeric, that can prevent the coil 4806 from physically contacting the optical fiber 4808 without substantially changing the mechanical performance characteristics of the guidewire 4802. By using a ribbon member 4810 that has a thickness greater than the outer diameter of the optical fiber 4808, the ribbon member 4810 can prevent the coil 4806 from contacting the optical fiber 4808. Alternatively, the ribbon member design can be accomplished by casting in place a suitable layer of, for example, flexible polymer material. Once the layer of polymer material is in place, the channels for the optical fiber can be created by selective removal of the polymer material using scribing techniques or laser ablation. The polymer material may be of uniform thickness, or may be of variable thickness, or may be of uniform or variable outer diameter.

The filament members 4710 and the ribbon member 4810 can be referred to collectively as stand-off members. As described above and seen in FIGS. 47 and 48, these stand-off members are configured to prevent the coil from contacting the optical fiber positioned therebetween.

In some example configurations, the stand-offs need not be created by a separate structure, e.g., the filament members 4710 and the ribbon member 4810 of FIGS. 47 and 48. Instead, the stand-offs can be formed as a feature of the core wire 4804 during its fabrication (not depicted), e.g., integral to the core wire. For example, during fabrication of the core wire 4804, protrusions can be created that extend outwardly from an outer surface of the core wire 4804. These protrusions can serve as stand-offs to create channels within which an optical fiber can be positioned.

Alternatively or additionally, in one example configuration, a groove (not depicted) can be created in the core wire 4804 within which the optical fiber 4808 can be positioned. The optical fiber 4808 can positioned within the groove such that it is below the outer surface of the core wire, thereby preventing the coil from contacting the optical fiber.

It should be noted that in any of the above construction examples the optical fiber may be loosely coiled around the core wire, or it may be adhesively bonded to the core wire. In this latter case, the present inventors have determined that variability in the thickness of an adhesive so used can adversely affect the optical signal as microbends can be created at variances or discontinuities of the adhesive.

The present inventors have determined that a uniformly applied adhesive, such as a coating on the core wire, or a jacket on the optical fiber, performs much more favorably. In some examples, the optical fiber can be disposed within a groove and an adhesive can be uniformly applied over the top of the optical fiber.

In other examples, the optical fiber can be pre-coated with an adhesive, e.g., a hot melt adhesive, with a uniform thickness. Then the coated optical fiber can be positioned within a groove of the core wire and heated such that the adhesive flows. It should be noted that the stand-off techniques described above with respect to FIGS. 47 and 48 are not limited to sensing guidewires such as those described throughout this disclosure. Rather, it may be desirable to incorporate these stand-off techniques with non-sensing guidewires to keep the core wire and coil concentric and improve the torque to the distal tip of the guidewire.

Figure 49:
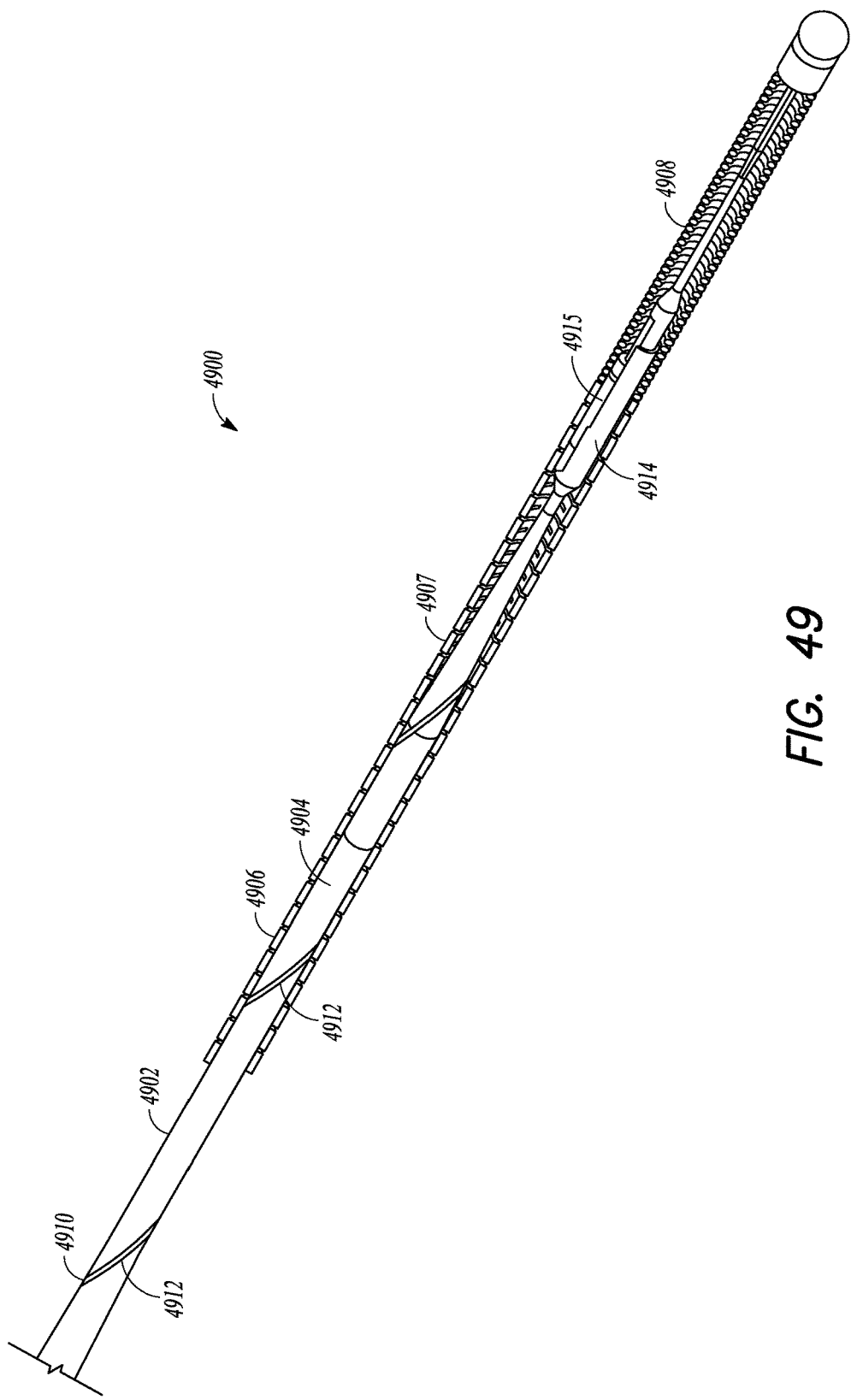
FIG. 49 depicts another example of a guidewire in combination with an optical fiber pressure sensor assembly that can be used to implement various techniques of this disclosure.

FIG. 49 depicts another example of a guidewire in combination with an optical fiber pressure sensor assembly that can be used to implement various techniques of this disclosure. FIG. 49 depicts a fiber pressure sensor assembly 4900, such as described above in numerous example configurations. As described in detail above, the fiber pressure sensor assembly 4900 can include a guidewire 4902 having a core wire 4904.

In contrast to the designs above that include a proximal coil, the fiber pressure sensor assembly 4900 can include a flexible slotted tube 4906 having one or more slots 4907 along its length. In some examples, the slots 4907 can be generally perpendicular to a longitudinal axis of the slotted tube 4906. As in other designs described above, the fiber pressure sensor assembly 4900 can include a distal coil 4908. Proximally, the slotted tube 4906 can be attached to the core wire 4904 incorporating the groove 4910 for the optical fiber 4912, as shown, utilizing adhesive, solder, welding, or other suitable techniques. Distally, the slotted tube 4906 may be attached to the sensor housing 4914 containing sensor 4915 using similar techniques. Alternatively, the slotted tube 4906 can be substituted by a spiral cut tube that imparts flexibility and strength. The spiral cut tube or the slotted tube, in some configurations, can also include a metallic polymer inner tube or liner tube.

Figure 50:
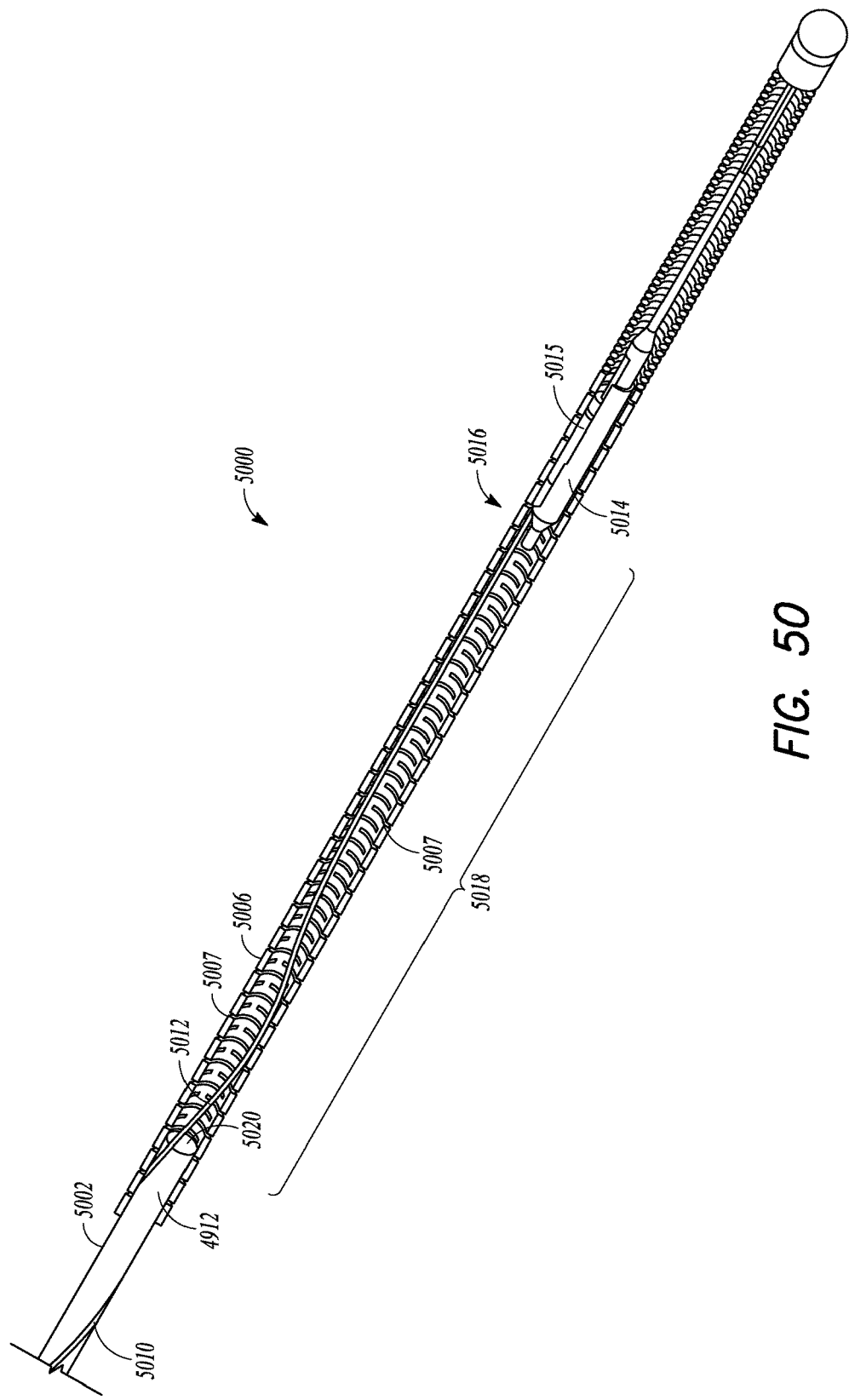
FIG. 50 depicts another example of a guidewire in combination with an optical fiber pressure sensor assembly that can be used to implement various techniques of this disclosure.

FIG. 50 depicts another example of a guidewire in combination with an optical fiber pressure sensor assembly that can be used to implement various techniques of this disclosure. FIG. 50 depicts a fiber pressure sensor assembly 5000, such as described above in numerous example configurations. As described in detail above, the fiber pressure sensor assembly 5000 can include a guidewire 5002 having a core wire 5004.

Like the example configuration depicted in FIG. 49, the fiber pressure sensor assembly 5000 of FIG. 50 includes a proximal slotted tube 5006 having a plurality of slots 5007 along its length. Proximally, the slotted tube 5006 can be attached to the core wire 5004 incorporating the groove 5010 for the optical fiber 5012, as shown, utilizing adhesive, solder, welding, or other suitable techniques. Distally, the slotted tube 5006 may be attached to the sensor housing 5014 containing sensor 5015 using similar techniques.

In the example configuration shown in FIG. 50, the spacing of the slots 5007 may be varied along a length of the slotted tube 5006. As seen in FIG. 50, the slots 5007 can be placed closer to one another at one end, e.g., the distal end 5016 of the slotted tube 5006, then the other end.

In addition, the core wire 5004 disposed within the slotted tube 5006 can be discontinuous along a length of the slotted tube 5006. That is, a gap 5018 can exist between a distal portion 5020 of the core wire 5004 and the sensor housing 5014 such that a portion of the optical fiber 5012 in the gap 5018 is not affixed or otherwise in contact with the core wire 5004. The variation in flexibility provided by the grooved, continuous profile of the core wire 4904 of FIG. 49 can instead be achieved by varying the pattern and frequency of the slots 5007 in the slotted tube 5006, for example, as shown in FIG. 50. The optical fiber 5012 can extend from the distal end 5020 of the grooved, solid core guidewire 5002 through the slotted tube 5006 to the separate distal sensor housing 5014.

Figure 51:
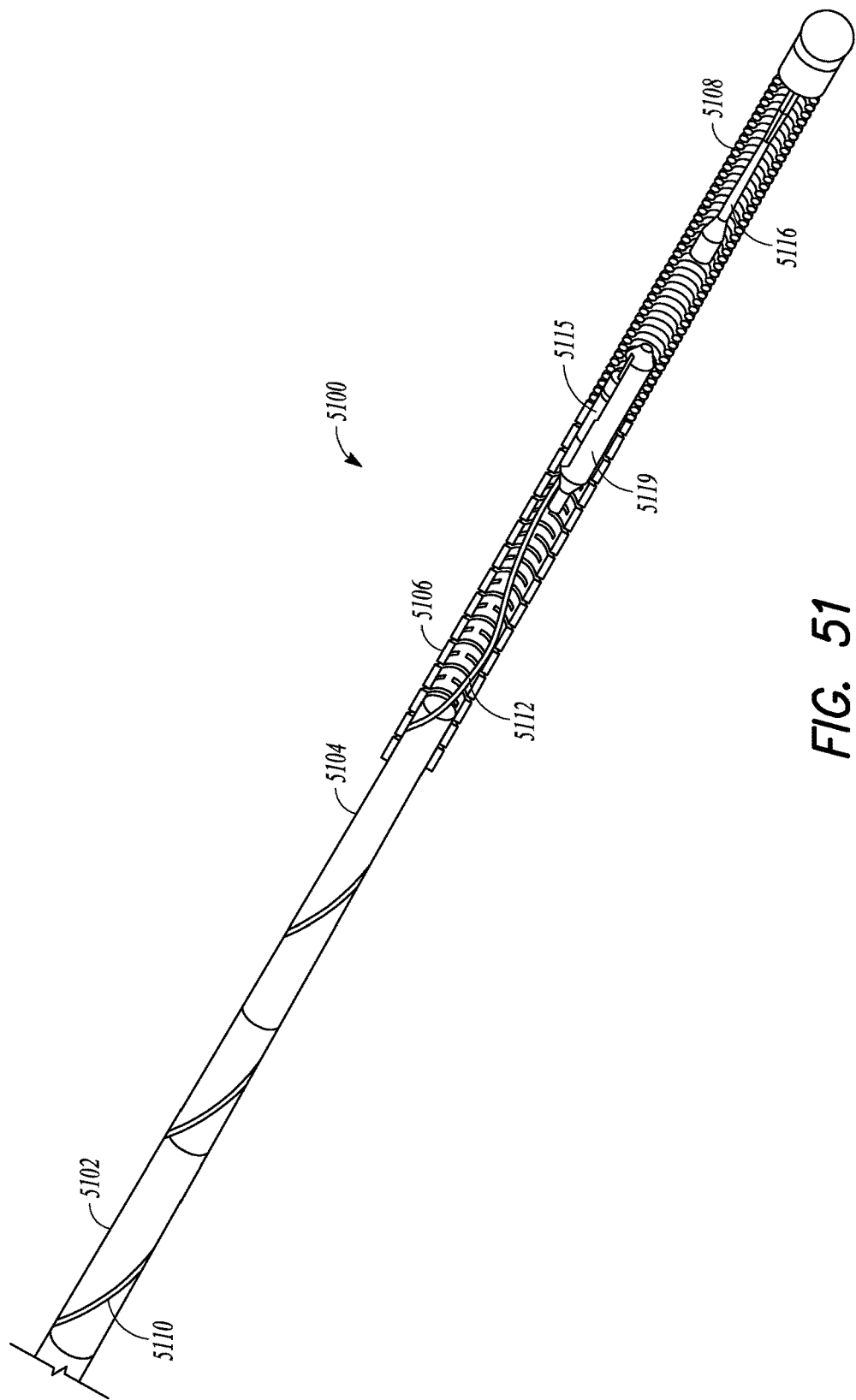
FIG. 51 depicts another example of a guidewire in combination with an optical fiber pressure sensor assembly that can be used to implement various techniques of this disclosure.

FIG. 51 depicts another example of a guidewire in combination with an optical fiber pressure sensor assembly that can be used to implement various techniques of this disclosure. FIG. 51 depicts a fiber pressure sensor assembly 5100, such as described above in numerous example configurations. As described in detail above, the fiber pressure sensor assembly 5100 can include a guidewire 5102 having a core wire 5104 with a groove 5110 for the optical fiber 5112.

Like the fiber pressure sensor assembly 5000 of FIG. 50, the core wire 5104 disposed within the slotted tube 5106 in FIG. 51 can be discontinuous along a length of the slotted tube 5106. The optical fiber 5112 between the proximal grooved solid core wire 5104 and the sensor housing 5114 can be allowed to freely locate within the slotted tube 5106, can be attached to the slotted tube 5106, can be protected further with a thicker coating or a suitable tubular member, can be wound around a thin core wire (not depicted), or can be provided with other suitable construction means. Additionally, as seen in the example configuration in FIG. 51, the distal core wire 5116 (and/or shaping ribbon) can be decoupled from the sensor housing 5114 containing sensor 5115, and securely and separately attached to the slotted tube 5106 and distal coil 5108.

Figure 52:
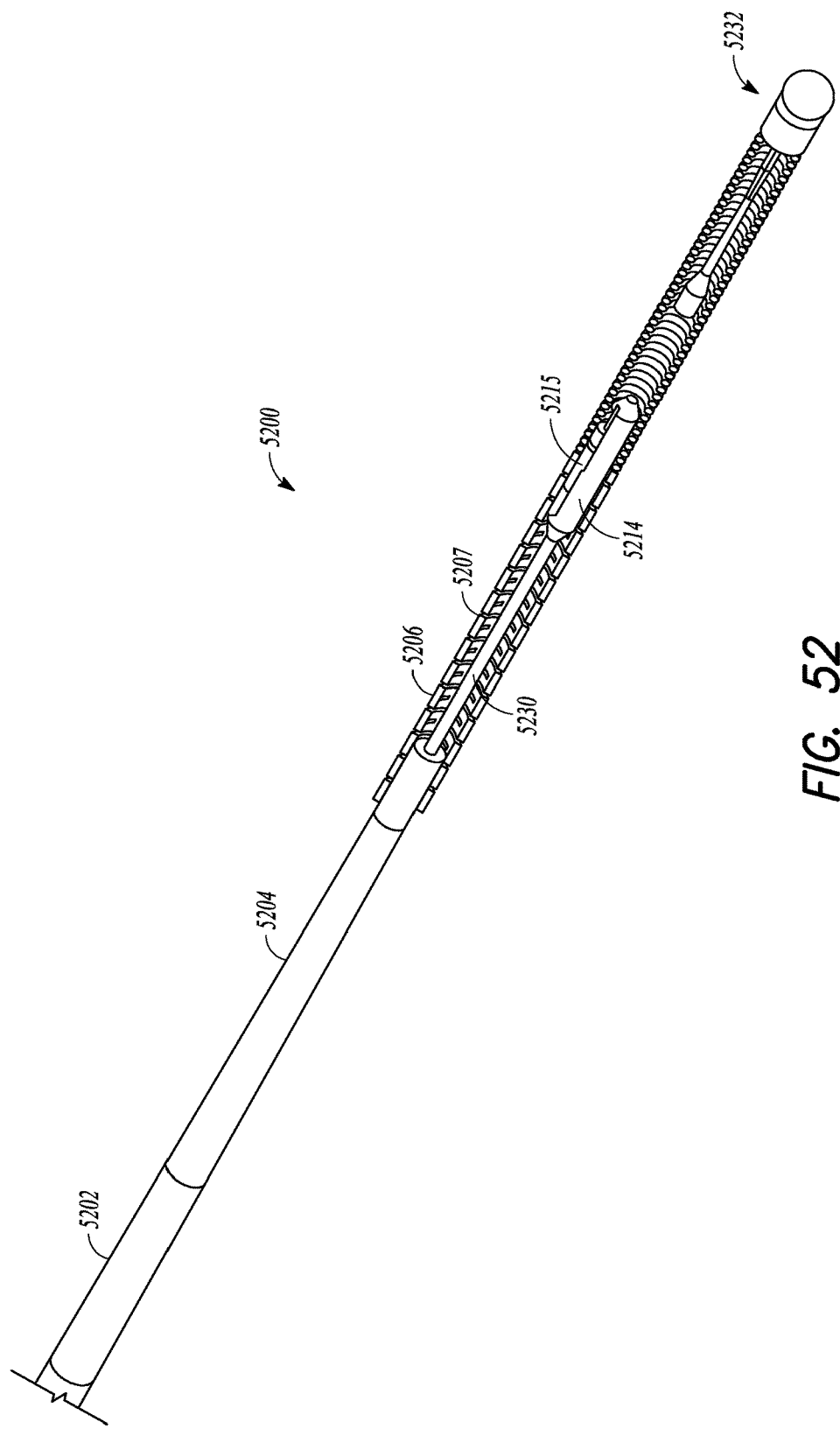
FIG. 52 depicts another example of a guidewire in combination with an optical fiber pressure sensor assembly that can be used to implement various techniques of this disclosure.

FIG. 52 depicts another example of a guidewire in combination with an optical fiber pressure sensor assembly that can be used to implement various techniques of this disclosure. FIG. 52 depicts a fiber pressure sensor assembly 5200, such as described above in numerous example configurations. As described in detail above, the fiber pressure sensor assembly 5200 can include a guidewire 5202 having a core wire 5204.

Like the example configuration depicted in FIG. 49, the fiber pressure sensor assembly 5200 of FIG. 52 includes a proximal slotted tube 5206 having a plurality of slots 5207 along its length. Proximally, the slotted tube 5206 can be attached to the core wire utilizing adhesive, solder, welding, or other suitable techniques.

In contrast to the fiber pressure sensor assembly designs shown and described in FIGS. 49-51, the sensor housing 5214, and thus the sensor 5215, can be moved along a length of the slotted tube 5206. In the example configuration shown in FIG. 52, the assembly 5200 can include a tube 5230, e.g., coaxially positioned, extending along a length of a hollow core wire 5204. The tube 5230 can be attached to the sensor housing 5214 and can contain the optical fiber (not depicted in FIG. 52). The tube 5230 can be constructed of metal or plastic, for example. Although not depicted, in some example configurations, the tube 5230 can include a slot extending along at least a portion of its length, e.g., straight or spirally formed, to accommodate the facile side loading of the optical fiber along its length.

One advantage of the assembly 5200 is that the guidewire 5202 can be positioned initially with its distal tip 5232 in a distal vessel and the sensor 5215 distal to a lesion. Without moving the guidewire 5202, a user, e.g., a clinician, can move the sensor 5215 from a position that is distal of the lesion to a position that is proximal of the lesion to determine if there has been any drift of the sensor 5215 and thereby verify that an FFR calibration is accurate. With current devices, the position of the sensor 5215 is fixed and, as such, a clinician needs to move the entire guidewire 5202 so that the sensor is proximal to the lesion to verify that an FFR calibration is accurate.

Figure 53:
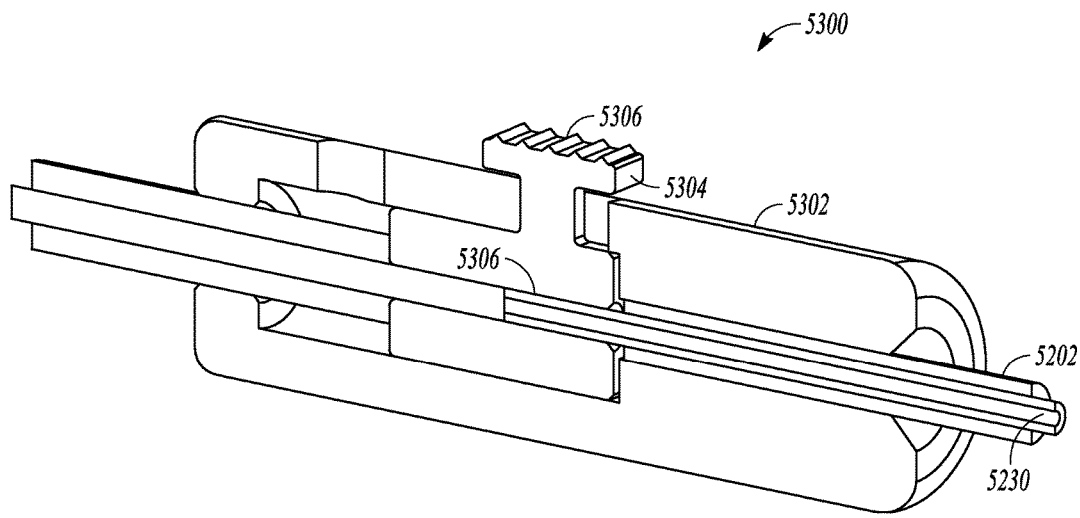
FIG. 53 depicts an example of an optical connector that can be used to implement various techniques of this disclosure.

FIG. 53 depicts an example of an optical connector that can be used to implement various techniques of this disclosure. More particularly, FIG. 53 depicts an optical connector 5300 that can be positioned at a proximal end of the assembly 5200 of FIG. 52, for example. The optical connector 5300 of FIG. 53 can include a housing 5302 and a control mechanism 5304 coupled to the housing 5302 and to a portion of a proximal end region 5306 of the tube 5230 of FIG. 52 that is positioned within the hollow guidewire 5202 of FIG. 52. When advanced distally or retracted proximally, e.g., using a thumb tab 5308, along a length of the optical connector 5300, for example, the control mechanism 5304 can slideably adjust a longitudinal position of the tube 5230 of FIG. 52, an optical fiber (not depicted), and the sensor housing 5214 of FIG. 52 attached to the tube 5230. In this manner, the sensor 5215 of the assembly 5200 can be moved along a length of the fiber pressure sensor assembly 5200.

In addition to the alignment improvement techniques described above with respect to FIGS. 29A and 29B, the present inventors have recognized that it can be desirable to utilize fusion splicing techniques in order to achieve a high precision alignment of optical fibers. An example technique is described below with respect to FIGS. 55A and 55B.

Figure 54:
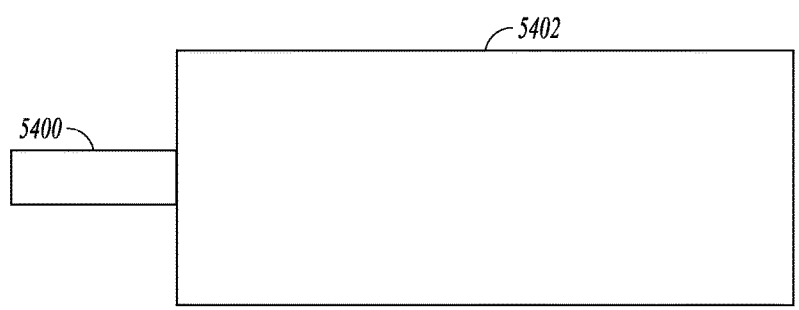
FIG. 54 depicts an example fusion splice between two optical fibers.

FIG. 54 depicts an example of a fusion splice between two optical fibers. In FIG. 54, a 25 micrometer outer diameter single mode optical fiber 5400 is spliced to a 125 micrometer outer diameter single mode optical fiber 5402. Generally speaking, an end of the 25 micrometer optical fiber 5400 and an end of the 125 micrometer optical fiber 5402 may be heated and softened through one or more heating cycles generated by a fusion splicing system. Once the ends of the two optical fibers 5400, 5402 are sufficiently viscous, the two ends may be pushed together whereby their surface tensions of the two materials join together. A solid joint between the two fibers is created after the fibers are cooled.

Additionally, mode field diameters may or may not be matched. The outer diameters listed above are for example purposes only. Other outer diameter combinations may also be useful. The fusion splicing technique can also be applied to multimode optical fibers. Fusion splicing may be accomplished using a laser based fusion splicing system, such as the LZM-100 splicing system available from AFL Corporation.

Figure 55A:
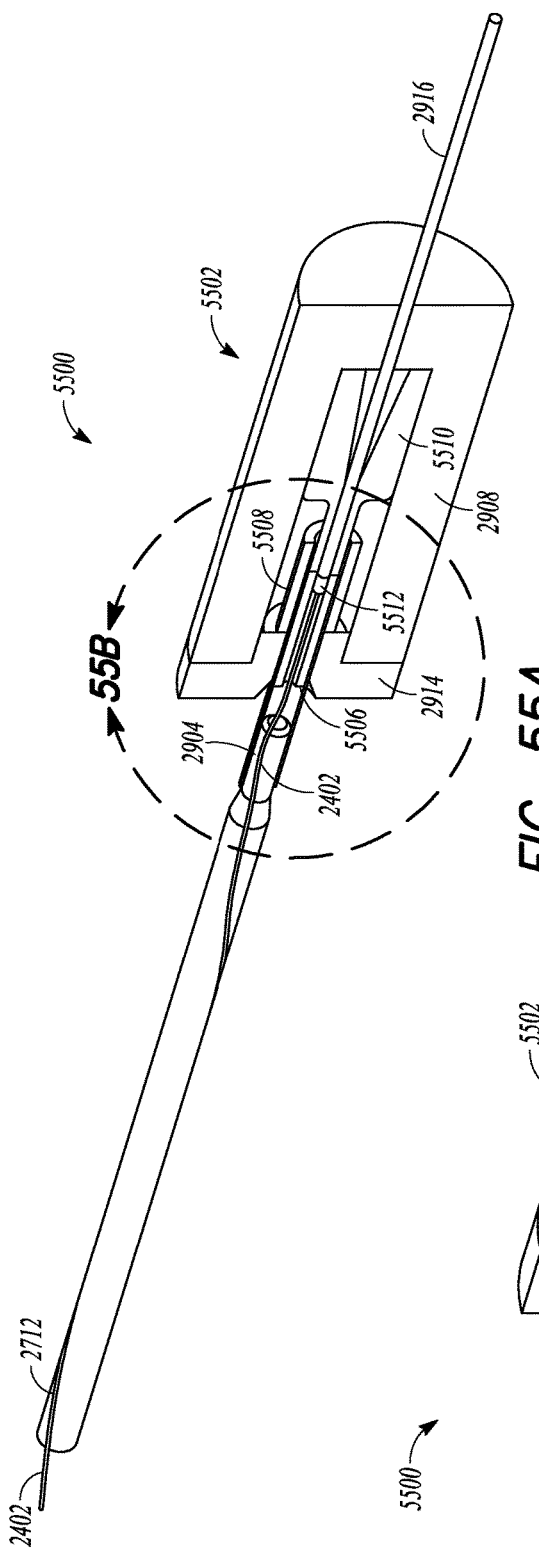
FIGS. 55A and 55B show an example of a proximal region of a guidewire assembly, such as one of the various guidewire assemblies described herein, terminating at a proximal end connector.
Figure 55B:
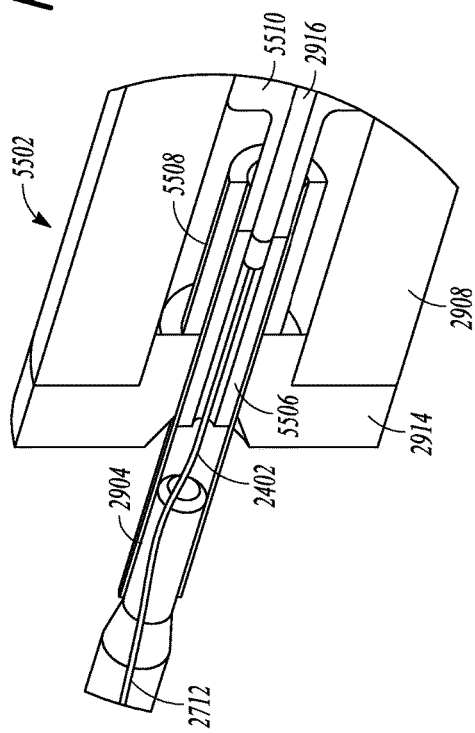

FIGS. 55A and 55B show an example of a proximal region of a guidewire assembly 5500, such as one of the various guidewire assemblies described herein, terminating at a proximal end connector 5502. FIG. 55B shows an enlarged region of FIG. 55A. FIGS. 55A and 55B will be described together for purposes of conciseness.

Like in FIG. 29A, the guidewire assembly 5500 can include a helically wound optical fiber 2402 that can be located in a helical groove 2712 along the guidewire body.

The proximal end connector 5502 can include separable portions: (1) a distal portion that can include a metal or other tube 2904 (also referred to as a tubular coupler) having an interior lumen diameter that can be attached to both the outer diameter of the body of the proximal region of the guidewire assembly 5500 and the outer diameter of a ceramic or other distal ferrule 5506 such that the optical fiber 2402 can extend from a periphery of the guidewire body to and through a center axis lumen of the distal ferrule 5506; and (2) a proximal portion that can include a connector housing 2908 carrying a ceramic or other proximal ferrule 5510, a split sleeve ferrule guide 5508, and a distal receptacle guide 2914 that can provide a tapered portion into which a portion of the distal ferrule 5506 and the metal tube 2904 can be received. In some example configurations, the distal receptacle guide 2914 can extend distally to encompass a proximal portion of the core wire of the guidewire assembly 5500.

In contrast to the technique depicted in FIG. 29A in which the proximal end of the distal ferrule 2906 defined a narrow channel that allowed the optical fiber 2402 to align with and butt against the optical fiber 2916 in the proximal ferrule 2910, FIGS. 55A and 55B depict the optical fiber 2402 fusion spliced to a short length of optical fiber 5512, e.g., 125 micrometers outer diameter, which is aligned with and butts against the optical fiber 2916. The short length of optical fiber 5512 (or "optical fiber stub 5512") can have a larger outer diameter than optical fiber 2402, with minimal optical losses. The spliced short segment optical fiber 5512 can have a diameter suitable to allow precision alignment with a proximal ferrule 5510.

Terminating the smaller diameter optical fiber 2402 into a larger diameter short length of optical fiber 5512 by fusion splicing may overcome the difficulty in terminating the smaller optical fiber 2402, e.g., 25 micrometers outer diameter, with high accuracy, e.g., with 1 micrometer accuracy, with optical fiber 2916. By fusion splicing the optical fiber 2402 to the short length of optical fiber 5512, the combination of the optical fiber 2402 and the short length of optical fiber 5512 can be positioned into the ferrule 5506 at the proximal end of the guide wire, polished, and mated to optical fiber 2916 on the other side of the connector 5502.

FIGS. 56A and 56B show an example of a proximal region of a guidewire assembly 5600, such as one of the various guidewire assemblies described herein, terminating at a proximal end connector 5602. FIG. 56B shows an enlarged region of FIG. 56A. FIGS. 56A and 56B will be described together for purposes of conciseness.

In contrast to the alignment techniques described above with respect to FIGS. 55A and 55B that used fusion splicing, the present inventors have also recognized that capillary tubes, e.g., high precision silica or other suitable material, may be disposed about the reduced outer diameter optical fiber 2402, e.g., 25 micrometer outer diameter, to increase the outer diameter such that a standard size ferrule or lower cost alignment device may be utilized. The capillary tube can be sized and shaped to be securely disposed about a proximal portion of the optical fiber.

In the example configuration shown FIGS. 56A and 56B, a reduced diameter optical fiber 2402, e.g., 25 micrometer outer diameter, can be placed inside a capillary tube 5605 (or "tubular member" 5605), e.g., silica or borosilicate tubing, with dimensions of 125 micrometer outer diameter and about 25.5 um inner diameter. The reduced diameter optical fiber 2402 and capillary tube 5605 may be bonded, as necessary, e.g., epoxy bonded or fusion bonded. The combined assembly may then be bonded to a ferrule 5606, e.g., alumina or other suitable material, with a relatively large inner diameter, e.g., an inner diameter of 125 micrometer. The ferrule can be sized and shaped to be securely disposed about the tubular member 5605. This approach can allow standard connection techniques to be achieved with lower cost ferrules.

Figure 56C:
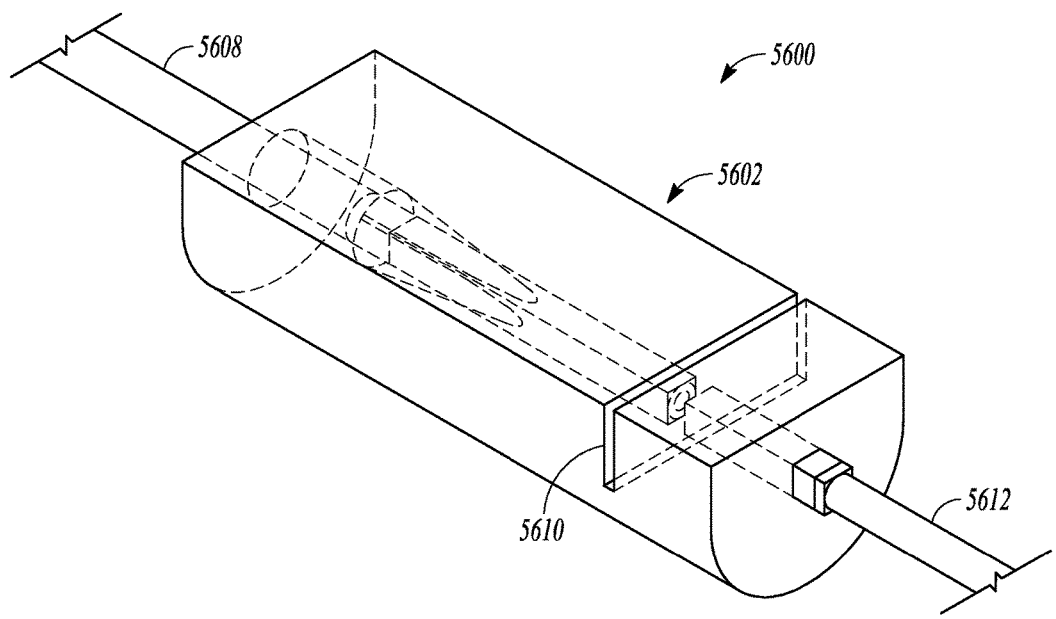
FIG. 56C shows another example of a proximal region of a guidewire assembly, such as one of the various guidewire assemblies described herein, terminating at a proximal end connector.

FIG. 56C show another example of a proximal region of a guidewire assembly 5600, such as one of the various guidewire assemblies described herein, terminating at a proximal end connector 5602. FIG. 56C shows an alternative connector for use with any of the guidewires or sensors described in this disclosure. Similar connection techniques can be found in U.S. Pat. No. 8,583,218 to Michael J. Eberle, which is incorporated herein by reference in its entirety. The connection surfaces can be formed by cutting through a guidewire assembly 5608 with a thin dicing blade at a slot 5610, thereby creating mirror image interfaces. Using this technique, the positioning of the optical fiber or fibers is not critical.

Figure 56D:
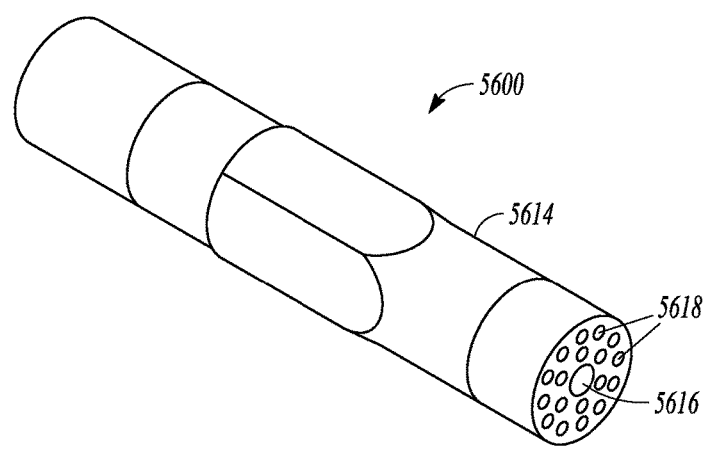
FIG. 56D shows an example of an optical imaging guidewire assembly.

A reduced size optical fiber can extend through a tubing or thin walled deformable metal tube 5614, as seen in FIG. 56D, and into the connector 5612, e.g., lead, of FIG. 56C. Within the metal tube 5614, the reduced size optical fiber 5616 can be encapsulated in a suitable material that can also contain filler materials 5618, such as glass bead, glass fibers or other fillers that can modify the physical properties of the encapsulant so that optimized dicing, polishing and connection can be achieved.

The reduced size optical fiber can alternatively be spliced to a larger fiber proximal to the dicing cut or alternatively within the lead section. The reduced size optical fiber can alternatively be fusion spliced to a larger optical fiber distal to the deformable metal tube or within the deformable metal tube and the dicing cut can be made through the section of the larger fiber 5616 for improved connection reliability.

Alternatively, the reduced size optical fiber may be spliced to a larger optical fiber within the deformable metal tube and the dicing cut can be made at the splice between the reduced size optical fiber and the larger fiber, yielding a small fiber to large fiber interface that is properly aligned. In the preceding examples, the dicing cut may be made orthogonal to the axis of the reduced size or larger optical fibers or alternatively at an angle to the axis to optimize connection reliability or to minimize optical reflections as appropriate.

Many of the assemblies described above can include a groove formed along the length of the guidewire core, e.g., groove 2712 of FIG. 56A, into which an optical fiber may be positioned. In some example configurations, e.g., FIG. 27, the groove extends along a tapered section of the core wire. The present inventors have recognized that the groove along the tapered section of the core wire can be advantageously created while the core wire material is at its original, constant diameter (pre-tapering). A specialized fixture to accommodate a reduced diameter core wire may not be needed if the core wire has a constant diameter. As described below with respect to FIGS. 57A and 57B, the present inventors have recognized that the groove may be formed in the core wire material before it is further processed by, for example, centerless grinding. In this manner, a lower cost component may be achieved with a high quality groove.

Figure 57A:
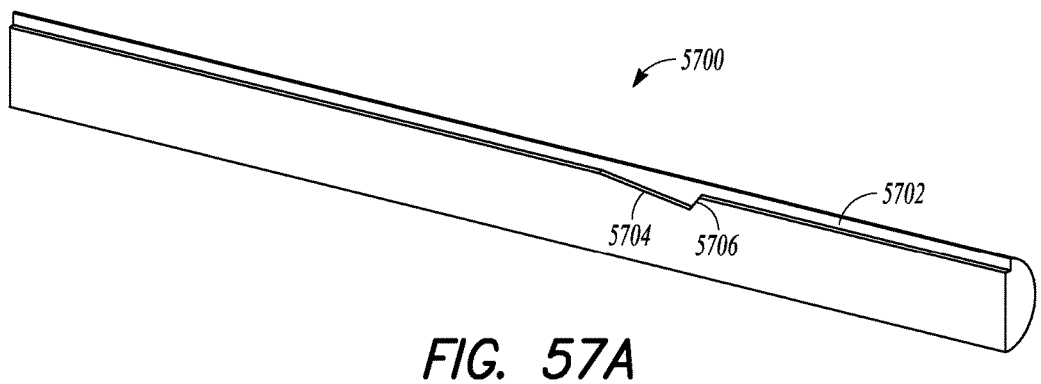
FIGS. 57A and 57B depict an example of a technique for forming a groove into the raw material of the core wire as part of the drawing process for the core wire.
Figure 57B:
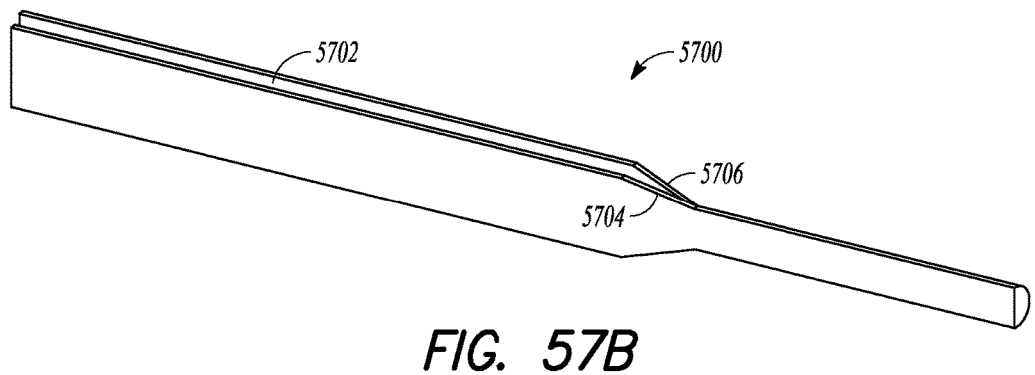

FIGS. 57A and 57B depict an example of a technique for forming a groove into the raw material of the core wire as part of the drawing process for the core wire. FIG. 57A depicts a portion of core wire 5700 defining a groove 5702 extending along a length of the core wire 5700. The groove 5702 can be made by removing material of the core wire 5700 to a first depth along a length of the core wire. The groove 5702 can be suitable for use along the majority of the length of the guidewire without further processing. The groove 5702 may also be formed with or without a spiral component. In accordance with this disclosure, a section of the core wire length for tapering can be identified, e.g., section 5704 in FIG. 57A. Next, using techniques including, but not limited to, micromachining, laser, electric discharge machining (EDM), dicing techniques, etc., the manufactured groove 5702 in the section 5704 can be made deeper, as shown at 5706 in FIG. 57A. The deeper groove 5706 can have one or more depths, e.g., a second depth deeper than the first depth of the groove 5702, or may have a tapered depth along its length. In some example configurations, the deeper groove may be straight and/or spiral cut.

Once the deeper groove 5706 is accomplished, the core wire 5700 may then be centerless ground or otherwise processed to remove material and reduce its diameter while preserving some or all of the deeper groove 5704 as required, as seen in FIG. 57B. The tapered section may allow the optical fiber to fit under a coil, e.g., proximal spring coil region 2504 of FIG. 27, without being pinched or other restricted by the coil.

In some example implementations, the core wire 5700 of FIG. 57B can be manufactured using precision 3D printing techniques.

The present inventors have also recognized that it may be desirable to achieve a robust proximal optical connector on the guidewire that can be mated to the lead assembly reliably and often. To that end, the present inventors have recognized that it may be desirable to accommodate significant linear force to the optical fiber and ferrule such that the optical fiber of the guidewire is maintained in close contact with the optical fiber of the lead. Additionally, the present inventors have recognized that a relatively simple assembly process is desirable, as well as low cost and, if desired, no requirement for a groove to be formed in the tapered section of the proximal core wire. The present inventors have determined that these features can be achieved by implementing the assembly shown and described below with respect to FIGS. 58A-58B.

FIGS. 58A-58B depict an example of a proximal region of a guidewire assembly, terminating at a proximal end connector. FIG. 58B is a cross-sectional side view of the assembly of FIG. 58A. FIGS. 58A-58B will be described together for purposes of conciseness.

In FIG. 58A, a tubular member 5800 can form a support between the proximal core wire 5802 and the ferrule 5510 such that significant linear force is accommodated without disturbance of the adhesives or optical fiber 2402. The tubular member 5800 defines a slot 5805 that can accommodate the optical fiber 2402 over the transition from the groove 2712 along the outer diameter of the core wire 5802 to the central lumen of the ferrule 5510 without the addition of a groove along the tapered section of the proximal core wire 5802 (as in FIG. 29A, for example). The slot 5805 of the tubular member 5800 and the tapered core wire 5802 can allow the optical fiber 2402 to be routed from the groove 2712 that extends along the outside diameter of the core wire 5802 and brought to a coaxial position such that the optical fiber 2402 is coaxial with the assembly proximally and can enter the connector 5802 coaxially. As seen in FIG. 58B, a metal or other tube 2904 (also referred to as a tubular coupler) can then be placed around the tubular member 5800 to secure the assembly together.

In some example implementations, the tubular member 5800, ferrule 5510, and the core wire 5802 contact one another such that a push on the ferrule 5510 pushes the tubular member 5800, but a push on the core wire 5802 does not displace the ferrule 5510. In this manner, the configuration in FIGS. 58A-58B can result in a solid, robust design without the need for an adhesive as a primary strength member (although an adhesive may still be used in the assembly process generally). In summary, instead of creating a groove in the proximal region of the core wire 5802, the design in FIGS. 58A-58B utilizes a slot 5805 in the tubular member 5800 so that the optical fiber 2402 can be located within the slot 5805 until the core wire 5802 has a diameter small enough that no slot is needed.

The present inventors have also recognized that optical sensor assemblies of the type described throughout this disclosure may exhibit variations in characteristics due to variations in the raw components, assembly techniques, manufacturing processes or tolerances, etc. These types of variations can be corrected for during use of the devices by providing characteristic data to an external instrument, e.g., controller 602 of FIG. 6A, that controls the device laser light sources, optical components, and measurement and control circuitry.

For example, imaging and physiologic measurement devices have previously been marketed since the mid-1990s where the characteristic data was supplied in the form of trim resistors, digital data stored in EPROMS, and, more recently, RFID chips or other forms of memory, with each set of data being unique to the device in use. The data set can be stored in device characteristic module that is attached to or separate from the device, and may include information relating to characteristics such as sensitivity, calibration, operating wavelength or may include device identifying serial number or equivalent. Alternatively or additionally, characteristic data may be stored on a connected or accessible local server or in the cloud.

As described in detail above with respect to FIGS. 6A-6B, one or more techniques of this disclosure can remove and/or compensate for the effects of temperature drifts and other deleterious effects that might compromise the accuracy of the pressure reading. For example, polarization scrambling techniques, ambient temperature nulling techniques, laser tracking techniques, and laser temperature monitoring techniques can be used in combination to correct for temperature drifts that can affect the accuracy of the pressure readings. As described above and shown in FIG. 6B, the present inventors have recognized that it may be desirable in some example implementations to include two lasers in the laser tracking system in order to provide the ambient temperature nulling techniques, laser tracking techniques, and laser temperature monitoring techniques, for example. As such, in the example configuration shown and described below with respect to FIG. 59, for each laser, a controller, optical detector, and optical locking set point, zero pressure DC offset value, and gain value can be provided.

In addition and as described in more detail below with respect to FIG. 59, the present inventors have recognized that sensors and systems formed using various techniques described in this disclosure may include laser diodes with varying operating characteristics. By way of example, the described method of detecting pressure may include a modulation of a laser diode current to track an operating wavelength. Laser diodes from various manufacturers, or within lots from the same manufacturer, may exhibit different characteristics. In response to the modulation of the laser diode current, the laser may, to varying degrees, also exhibit corresponding or related variation in the laser optical output power. This variation in power may contribute to noise or uncertainty about the pressure measurement and, therefore, it may be desirable to reduce or eliminate it.

The present inventors have recognized that the output power variation can be regulated by variable optical attenuators (VOAs), e.g., an optical power regulator, with feedback loops, which can stabilize the output power of a laser. It may be further desirable to implement the VOAs in each of the optical pathways for every laser, e.g. for the temperature sensing laser and the temperature/pressure sensing laser.

Figure 59:
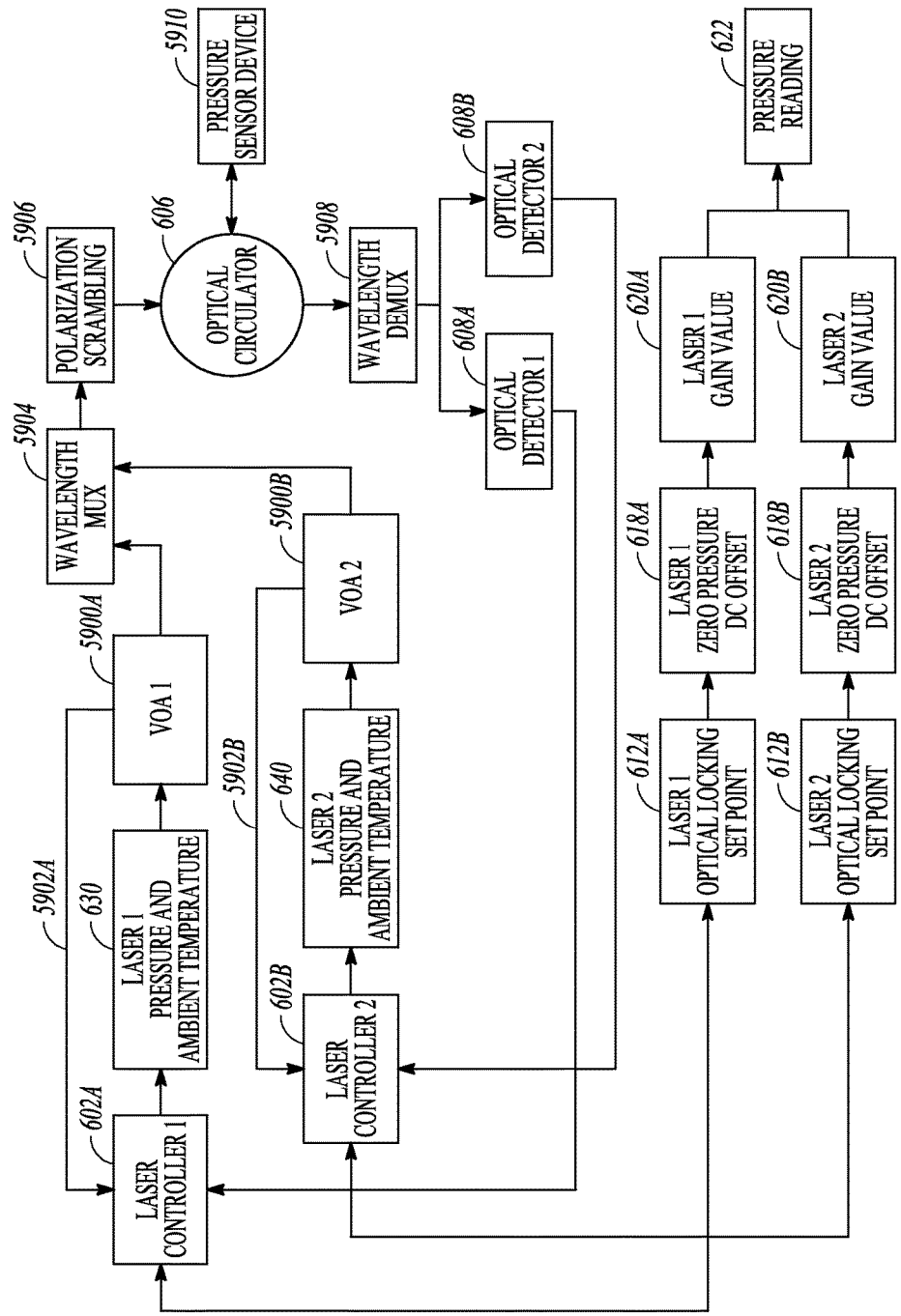
FIG. 59 is a block diagram of another example of a laser tracking system, in accordance with this disclosure.

FIG. 59 is a block diagram of another example of a laser tracking system, in accordance with this disclosure. In FIG. 59, for each laser, a controller, optical detector, and optical locking set point, zero pressure DC offset value, and gain value can be provided. Many of the components in FIG. 59 were described above with respect to FIGS. 6A and 6B and, for purposes of conciseness, will not be described again. Like numerals having different letter suffixes in FIG. 59 may represent different instances of similar components in FIGS. 6A and 6B. For example, laser controllers 602A, 602B of FIG. 59 represent different instances of controller 602 of FIG. 6A, optical detectors 608A, 608B of FIG. 59 represent different instances of optical detector 608 of FIG. 6A, etc.

As mentioned above and in accordance with this disclosure, FIG. 59 also includes two VOAs, namely VOA 1 5900A and VOA 2 5900B (referred to collectively in this disclosure as VOAs 5900). VOA 1 5900A and VOA 2 5900B receive an output from the laser 1 630 and the laser 2 640, respectively. The VOAs 5900 can help stabilize the optical power injected into the system from each of the lasers 630, 640 via feedback paths 5902A, 5902B. The VOAs 5900 can help maintain a constant level of optical power output by each of the lasers 630, 640, despite any changes in conditions, e.g., changes in pressure, changes in insertion loss, optical tracking.

The addition of the VOAs 5900A, 5900B can have the added benefit that they remove changes in the optical output power caused by changes to the drive current of the lasers 630, 640 to facilitate optical insertion loss monitoring. When the lasers are dithered to generate the tone for insertion loss monitoring (FIG. 33), there can also be an associated optical power variation that may need to be subtracted from the insertion loss signal before an accurate value can be calculated. This can be eliminated, however, if the VOAs are chosen to respond with sufficient bandwidth.

Described above with respect to FIGS. 30-33 are techniques that can dynamically adjust a locking level to account for any changes in optical insertion loss. There are other techniques that may be applied to achieve a similar result. For example, another technique to account for insertion loss can utilize passive correction, as described in FIG. 65.

Figure 65:
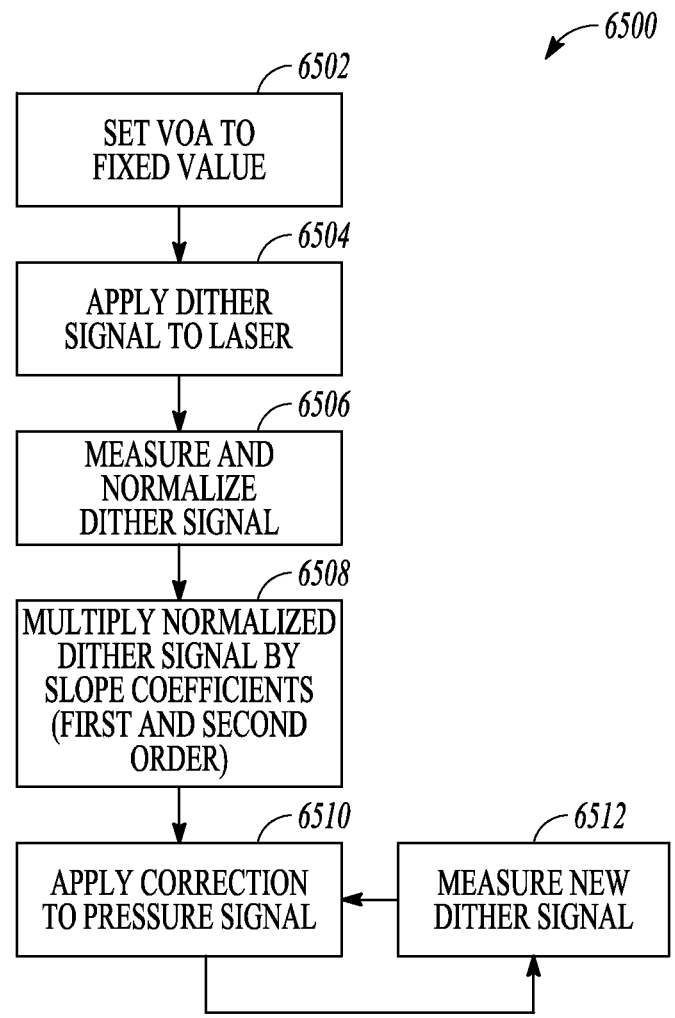
FIG. 65 is a flow diagram illustrating another example of a method for compensating for optical insertion loss in an optical pressure sensor using various techniques of this disclosure.

FIG. 65 is a flow diagram illustrating another example of a method 6500 for compensating for optical insertion loss in an optical pressure sensor using various techniques of this disclosure. The compensation technique of FIG. 65 is a passive correction technique in that there is no dynamic correction of the locking level, but instead a scaling of the dither tone by at least one first order coefficient and possibly higher order polynomial correction factor. The result of this scaling can be added or subtracted from the apparent pressure reading to give the correct value. As seen in FIG. 65, the VOAs, e.g., VOAs 5900A, 5900B of FIG. 59, can be set to a fixed value (block 6502) and a dither generator, e.g., AC dither generator 3312 of FIG. 33, can apply a dither signal to the laser controllers, e.g., laser controllers 602A, 602B of FIG. 59 (block 6504). The laser controllers can measure and normalize the dither signal (block 6506) and multiply the normalized dither signal by the slope coefficient(s), e.g., first and second order coefficients (block 6508). The resulting correction value can then be applied to, e.g., added to or subtracted from, the pressure signal (block 6510). Finally, the laser controllers can continue to measure the dither signal (block 6512) and apply the determined correction, as needed, to the pressure signal (block 6510).

The technique of FIG. 65 can be suitable for small changes in the insertion loss but may not be sufficiently accurate for large changes. It can also be desirable to ensure that the scaling coefficients are very accurate. The scaling factor can be dependent on the slope of the optical filter Fabry-Perot. An accurate scaling factor can be achieved by using a dynamic normalization at the start of the measurement. This can involve normalizing the signal generated by the dither tone and scaling by a known slope factor that was factory determined for that particular pressure sensing device. Alternatively, a direct measure of the optical slope can be determined if the laser is dithered by a known amount.

Figure 66:
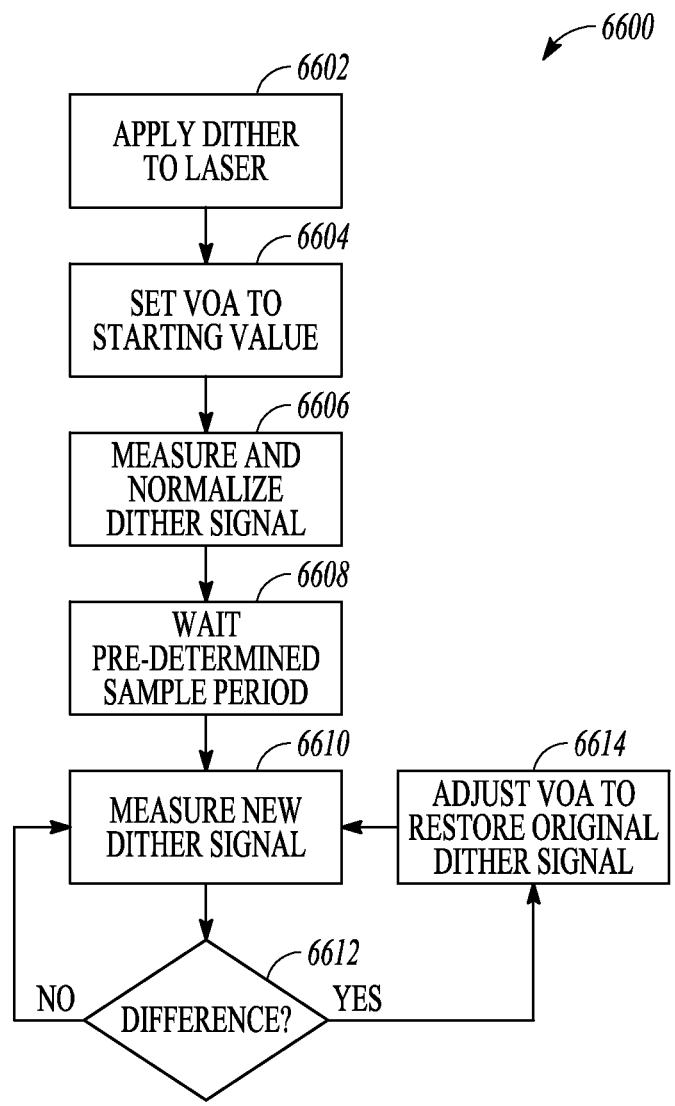
FIG. 66 is a flow diagram illustrating another example of a method for compensating for optical insertion loss in an optical pressure sensor using various techniques of this disclosure.

FIG. 66 is a flow diagram illustrating another example of a method 6600 for compensating for optical insertion loss in an optical pressure sensor using various techniques of this disclosure. The technique shown in FIG. 66 does not depend on having very accurate slope coefficients and can offer extended dynamic range to account for insertion loss changes. This technique can use the VOAs 5900A, 5900B in a feedback loop. For example, a dither generator, e.g., AC dither generator 3312 of FIG. 33, can apply a dither signal to the laser controllers, e.g., laser controllers 602A, 602B of FIG. 59 (block 6602). The VOAs, e.g., VOAs 5900A, 5900B of FIG. 59, can be set to a starting value (block 6604). The laser controllers 602A, 602B can monitor the insertion loss dither tone and use electronic feedback to the VOAs 5900A, 5900B to maintain the tone at a fixed level. The laser controllers 602A, 602B can measure and normalize the dither signal (block 6606), wait a predetermined sample period (block 6608), and measure a new dither signal (6610). If there is a difference between the new dither signal and the normalized dither signal ("YES" branch of block 6612), then the laser controllers 602A, 602B can adjust the VOAs 5900A, 5900B to restore the original dither signal (block 6614). If there is no difference between the new dither signal and the normalized dither signal ("NO" branch of block 6612), then the laser controllers 602A, 602B can again measure the dither signal (block 6610).

Under normal insertion loss conditions, the VOAs can be operated in a manner such that there is a reserve of optical power, e.g., the VOAs are operating in a lossy state. As the insertion loss of the system changes, the dither tone will likely also change. The VOAs can be adjusted to bring the dither tone back to the original value. For instance, if the insertion loss of the optical system increased, then the VOA scan be adjusted to allow more light into the system, thereby preserving the magnitude of the dither tone.

The opposite is also true. If the insertion loss of the optical system decreased, the VOAs can be adjusted to allow less light into the system, thereby preserving the magnitude of the dither tone. The advantage of this method is that accurate scaling coefficients are not needed as in the passive correction technique described above, and there is no need to dynamically adjust the locking level because the relative optical shape of the filter is not changed. It also has the advantage of much better dynamic range as compared to the other techniques, only limited by the dynamic range of the VOAs. Another benefit is that the optical power at the sensor is kept constant thereby avoiding any changes in the optical self heating effects within the sensor.

In addition, the system of FIG. 59 can include a wavelength multiplexer 5904, which can couple a first wavelength from the laser 630 and a second wavelength from the laser 640 to the same optical fiber. The coupled wavelengths can be output to a polarization scrambler 5906, e.g., a series of "optical waveplates" physically located between where the laser beams exit lasers 602A, 602B and the FBGs of the optical fiber pressure sensor device. As described in detail above, the polarization scrambler 5906 can be used to scramble or average a range of polarization states so the final result is not biased to any given combination of birefringent axis of the FBG and incident polarization state. In this manner, the polarization scrambler 5906 can overcome the effects of birefringence and determine a true pressure reading. The system of FIG. 59 can also include a wavelength demultiplexer 5908 that can separate a light beam reflected from the pressures sensor device 5910 into its constituent wavelengths, which can then be detected by optical detectors 608A, 608B and be used to generate a pressure reading.

This disclosure describes various methods of forming optical pressure sensors. In some example implementations, these methods include assembling sensors utilizing epoxy bonds of the fiber to the surrounding apparatus. For example, as described above with respect to FIG. 38, the optical fiber 3802 can be securely affixed to the proximal housing portion 3806 via an epoxy 3812, and the optical fiber 3802 can be securely affixed to the distal housing portion 3804 via an epoxy 3816. The present inventors have recognized, however, that the use of the epoxy bonds can cause variations in sensors and, to some extent, unpredictable behavior of the sensors. Thus, in some example configurations, it can be desirable to eliminate epoxy as the method of attaching the optical fiber to the sensor apparatus.

As described below with respect to FIG. 60, the present inventors have recognized that it can be desirable in some implementations to construct a sensor assembly, e.g., pressure sensor assembly 3800, without the epoxy bond by creating fusion bonds of the optical fiber glass directly to the glass of the sensor housing. Such bonds can be accomplished by way of laser fusion bonding utilizing, for example, a laser based fusion splicing system, such as the LZM-100 splicing system available from AFL Corporation.

Figure 60:
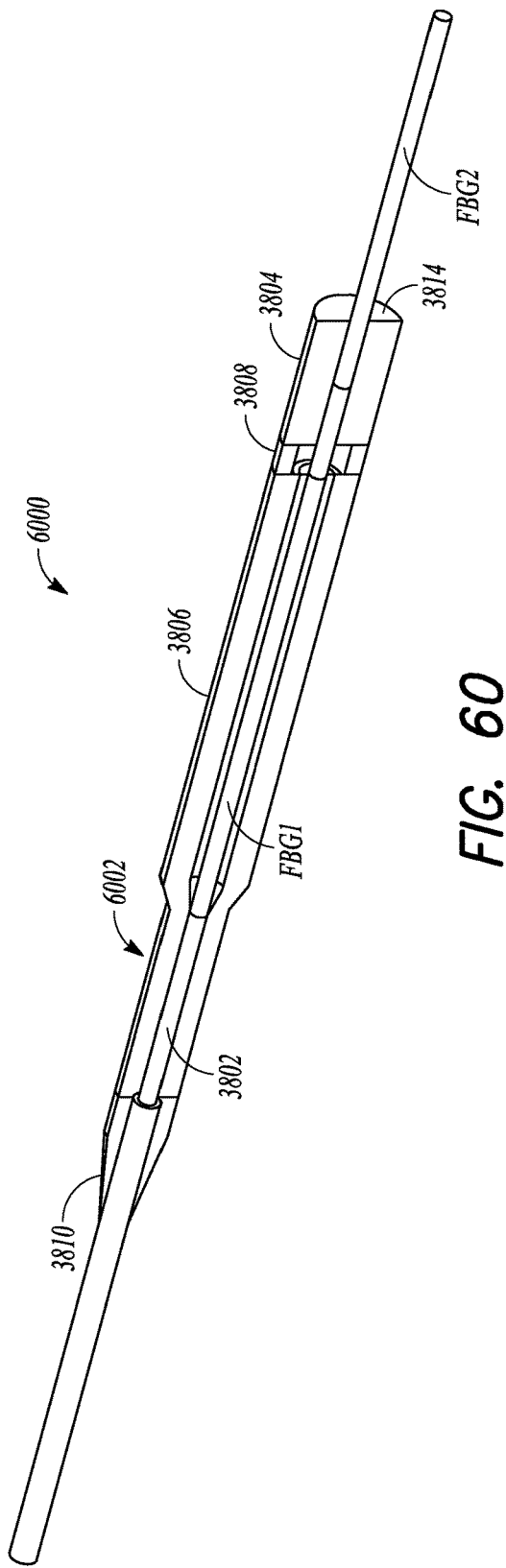
FIG. 60 depicts another example of a portion of a pressure sensor assembly.

FIG. 60 depicts another example of a portion of a pressure sensor assembly 6000. Many of the components shown in FIG. 60 are similar to those described above with respect to FIG. 38 and, for purposes of conciseness, will not be described again. As mentioned above, however, the assembly 6000 can be fusion bonded together without the use of the epoxy, e.g., epoxy 3812, 3816, utilized in the example of an assembly shown in FIG. 38.

For example, the proximal end 3810 of the housing 3806 can be necked down around the optical fiber 3802, thereby reducing or eliminating the need for epoxy, e.g., epoxy 3812 of FIG. 38. In one example, a small section 6002 of the proximal end 3810 can be heated and, when pulled, the section 6002 necks down around the optical fiber 3802. In another example, a small section 6002 of the proximal end 3810 can be heated and a vacuum can be applied to pull it down around the optical fiber 3802. As the section 6002 of the proximal end 3810 of the housing 3806 is heated, the heat can transfer through the section of the housing 3806 and heat an adjacent section of the optical fiber 3802, which has an outer diameter that closely matches the inner diameter of the housing 3806. Once the optical fiber 3802 is sufficiently heated, the optical fiber 3802 (glass) and the housing 3806 (glass) in the heated region will be fusion bonded together.

FIGS. 61A and 61B depict another example of a portion of a pressure sensor assembly 6100. FIG. 61B depicts an enlarged region of FIG. 61A. FIGS. 61A and 61B will be described together. Many of the components shown in FIGS. 61A and 61B are similar to those described above with respect to FIGS. 38 and 60 and, for purposes of conciseness, will not be described again.

As described above with respect to FIG. 38, the sensor membrane of the window 3808 located between the distal and proximal portions 3804, 3806 can be formed of silicone in some example configurations. Silicone, however, may not be sufficiently linear for some sensor applications. The present inventors have recognized that it may be desirable for the sensor membrane of the window to behave as linearly as possible.

In the example depicted in FIGS. 61A and 61B, the window 6108 can include a thin-walled bellows-shaped sensor membrane 6110. In one example implementation, the bellows-shaped sensor membrane 6110 can be made of silicon, which exhibits linear elasticity (like a spring), in contrast to silicone. In another example implantation, the bellows-shaped sensor membrane 6110 can be made of a metal that exhibits linear elasticity. In another example implantation, the bellows-shaped sensor membrane 6110 can be made of fused silica, which also exhibits linear elasticity. Other materials exhibiting linear elasticity are possible and are considered within the scope of this disclosure.

In some example implementations, one or more components of the optical pressure sensor assembly 6100 of FIGS. 61A and 61B can be manufactured using precision 3D printing techniques. For example, fused silica, or other transparent materials, can be exposed using high power laser light, e.g., highly focused high power pulsed laser light. In certain materials, substrates exposed can be etched using hydrofluoric acid (HF acid), which reacts more quickly with the exposed regions than with the unexposed regions. Using this technique, the sensor housing and sensor membrane can be manufactured from a single substrate, or multiple components can be manufactured separately and then assembled. A system and method for achieving this technique is available from Femtoprint (www.femtoprint.eu/).

The present inventors have also recognized that the pressure sensors described in this disclosure can be enhanced by reducing the diameter of the optical fiber in select regions, for example, FBG 1 of FIGS. 38, 60, and 61A, or a portion thereof, to increase the overall pressure sensitivity of the device. The diameter reduction can be achieved by, for example, selectively exposing the region to HF acid. In other examples, the pressure sensors described in this disclosure can be enhanced by reducing the diameter of the optical fiber in, for example, FBG 2 of FIGS. 38, 60, and 61A, or a portion thereof. In another example, the pressure sensors described in this disclosure can be enhanced by reducing the diameter of the optical fiber in, for example, both FBG 1 and FBG 2 of FIGS. 38, 60, and 61A, or a portion thereof.

The present inventors have also recognized that the pressure sensors described throughout this disclosure can be coated with one or more therapeutic agents, e.g., an antithrombotic agent. Additionally or alternatively, the present inventors have also recognized that the pressure sensors described throughout this disclosure can be coated with one or more lubricious coatings, e.g., hydrophilic and/or hydrophobic coating materials. In some examples, the sensor cavity of the pressure sensor, e.g., the space surrounding the sensor housing and the distal FBG, can be filled with a gel or oil, e.g., a biocompatible gel or oil, which can protect the pressure sensor and help prevent the trapping of bubbles.

In computing an FFR value, the proximal aortic pressure (proximal to a stenosis) is normally measured by a dedicated fluid coupled transducer attached in fluid communication with the guide catheter, which can then measure a proximal aortic pressure when attached to an installed patient monitoring system. This pressure measurement can then be provided electronically to the dedicated FFR instrument. The present inventors have recognized that an advantageous pressure sensing instrument can be achieved by providing a dedicated fluid coupled pressure sensor in series with the pressure sensor utilized by the patient monitoring system of the catheterization laboratory, as described below with respect to FIG. 62.

Figure 62:
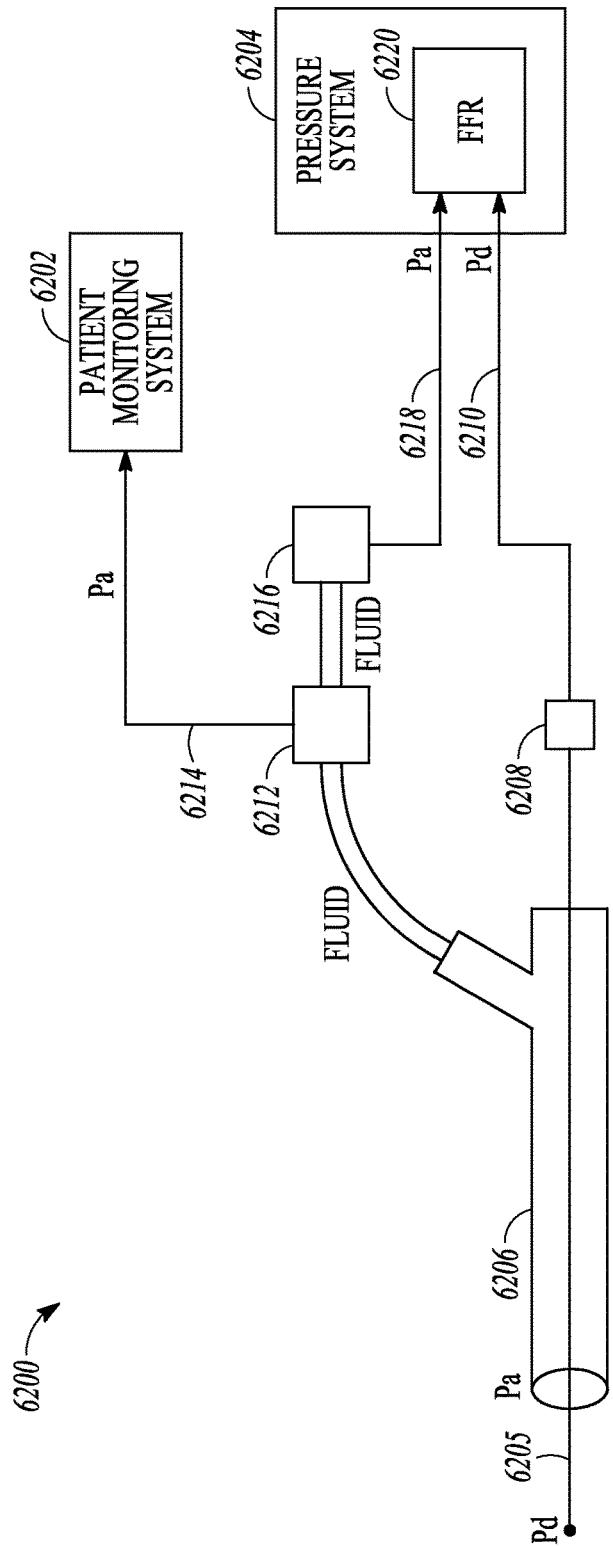
FIG. 62 is a block diagram of an example pressure sensing system, in accordance with this disclosure.

FIG. 62 is a block diagram of an example pressure sensing system 6200, in accordance with this disclosure. One FFR computation approach can utilize electronic communication between a patient monitoring system 6202 of the catheterization laboratory and a dedicated pressure system 6204. For example, one FFR computation approach can utilize electronic communication of either a Pd pressure measurement (the pressure distal to the stenosis) from the dedicated pressure system to the patient monitoring system, or a Pa pressure measurement (the pressure proximal to the stenosis) from the patient monitoring system to the dedicated pressure system, where FFR=Pd/Pa. In contrast to these approaches, the pressure sensing system 6200 of FIG. 62 can allow the pressure system 6204 to compute an FFR value without electronically communicating either a value of Pd or a value of Pa between the patient monitoring system 6202 and the pressure system 6204, e.g., a standalone computation.

As seen in FIG. 62, a guidewire system including a pressure sensing guidewire 6205 (e.g., the optical pressure sensor assembly 3800 of FIG. 38, any of the numerous other optical pressure sensor assemblies described in this disclosure, or any existing pressure sensing guidewires) can sense the Pd pressure. The guidewire 6205 can transmit a signal representing the Pd pressure via a connector 6208 and an optical fiber or wire 6210 to the pressure system 6204.

A guide catheter system including a guide catheter 6206 can be in fluid communication with a pressure sensor 6212 utilized by the patient monitoring system 6202. The pressure sensor 6212 can determine a first Pa pressure measurement and transmit the determined first Pa pressure measurement via wire 6214 to the patient monitoring system 6202.

In accordance with this disclosure, a dedicated second external pressure sensor or ("external transducer") 6216 can be fluid coupled in series with the pressure sensor 6212 utilized by the patient monitoring system 6202. Sensors 6216 and 6212 can be arranged to be closely coupled and placed at the same height in relation to the patient. The dedicated pressure sensor 6216 can determine a second identical Pa pressure measurement and transmit the determined second Pa pressure measurement via a wire 6218 to the pressure system 6204. Then, the pressure system 6204 can compute an FFR based on the received Pa and Pd measurements using an FFR circuitry or module 6220. In this manner, communication of Pa (or Pd) pressure measurements between the patient monitoring system 6202 and the patient system 6204 can be eliminated. As such, this approach can simplify the design of the instrument and minimize the necessity to supply any dedicated electronic connections. Further, this approach can provide greater electrical isolation and patient safety.

Pressure system 6204 can take different forms. For example, pressure system 6204 can be a stand-alone battery powered or mains powered console with connections solely to the external transducer 6216 by the wire (or other connector) 6218 along with optical fiber or wire 6210 connecting console 6204 to the guidewire (or "sensing device") 6205. For some sensors, applications or configurations, the wire 6218 may be unnecessary. Alternatively, pressure system 6204 (also referred to in this disclosure as "console 6204") can be a module in a larger console designed to accommodate other instrumentation, sensing mechanisms, imaging mechanisms, treatment mechanisms or other suitable functions. Alternatively, console 6204 can be a sensing system other than a pressure sensing system similarly achieved by a stand-alone console or an integrated module as described above.

Console 6204 can be capable of stand-alone measurement and diagnostic functionality through various outputs or display of data for the end user, such as through screen displays, numeric displays, portable memory transportation, printer outputs and the like. Alternatively or inclusively, console 6204 can provide signals that communicate relevant data to other instruments. Signals can include analog or digital signals, which can conform to various standards or can be unique to the instrument, for passage to other instruments via suitable means. Suitable means can include, RF, Bluetooth or Wi-Fi signals or similar, as well as custom cables, Ethernet cables, electrical cables or fiber optic cables or similar.

Console 6204 can provide data or signals that can be provided to multiple function instruments via connection or integration therein. The data can be displayed separately or in combination with other measurements or 2D or 3D images in real-time or through memory means for subsequent display, analysis or processing. By way of further example, pressure measurement data can be provided to imaging systems such that the pressure readings can be coregistered to the images of, for example, coronary or other blood vessels in such a way as the physician can see the variation in pressure along the image of the blood vessel. The images can be provided by fluoroscopy, x-rays, IVUS or OCT or similar. The pressure guidewire 6205 can also incorporate sensors, transponders, visual characteristics, x-ray opacity or other means that can assist in the coregistration of the pressure data on the images. Coregistration can be accomplished by detection or processing of the coregistration information through electronic or software means. Coregistration can be applied to other sensor forms or multiple sensors in parallel or serially. Data provided or displayed can be stored as part of the patient record through printout, electronic, or other means.

The console 6204 can provide data that is used to guide treatment, such as FFR. Data can be provided in multiple formats either raw or in processed or calibrated form. Data can be used for decision making about treatment strategies, cost control strategies, or short or long term outcome strategies. Data can be generated at one point in a treatment procedure or at multiple times throughout a procedure. Multiple measurements can be placed in the patient record. Data can be generated in various clinical settings or patient physiologic conditions. Data can be generated in combination with the administration of a drug, during a diagnostic procedure or during a treatment procedure.

The console 6204 can provide data that is used to guide or directly control other treatment instruments or devices. Data or signals derived from sensors can be used, for example, to control blood infusion pumps, balloon pumps or other life support instruments or devices. Data or signals can be used to guide or control tissue or blood modification or removal instruments. Data or signals can be used to turn on or turn off treatment devices and instruments, synchronize their functionality or increase or decrease their functionality. Instruments or devices can include atherectomy or aspiration devices, laser ablation devices, electrical devices or any other suitable device.

The console 6204 can be located close to the patient or remotely. The console 6204 can incorporate control functions, user interfaces, dedicated or touch controls, software control algorithms and similar. The console 6204 can be controlled directly or remotely through an electrical or optical control, infra-red or wireless control. The console 6204 can support multiple displays of data, for example, multiple pressure signal screens at various locations.

In another example of the invention described herein, the guidewire 6205 can be provided with the incorporated sensor functionality which can be activated if the procedure requires the sensing measurement to be made. For example, the guidewire 6205 is a high performance guidewire with integrated highly miniaturized pressure sensing capability. In one example, the cost of integration of the pressure sensing capability is minimal compared with the cost of providing the guidewire. The guidewire 6205 can be provided to the physician with the option of activating the sensor at any time through the procedure. The optical fiber or wire (or other connection) 6210 can be provided as a separate device, which enables a separate charge to be made for the sensing measurement only if the measurement is deemed necessary. In this manner, the physician does not have to commit to the cost of the sensing measurement in advance of the procedure. In this example, the connector 6208 is universal for the operation of any sensing guidewire 6205 with the optical fiber or wire 6210. In an alternative example, the sensing guidewire 6205 is provided with a unique characteristic module. The characteristic module can be a low cost disposable storage data device that can be necessary to operate or calibrate the sensing guidewire 6205 and can be used if the physician decided to activate the measurement functionality of guidewire 6205. The characteristic module can be any suitable form of device, such as a memory stick, RFID device or similar. In operation, the characteristic module can be in communication with the console 6204, and the console 6204 can adjust the operation or calibration of the guidewire 6205 in order to provide an accurate sensing measurement.

By way of another example, the characteristic module can contain a unique identifier, such as a serial number or similar, that is communicated to the console 6204. The console 6204 can incorporate memory such that the serial number is recorded upon first use, or it may be connected to a data base through wireless, Ethernet, internet or other means, to verify the device has not been used previously, and is prohibited from being used at a later time or for another patient. Alternatively, the optical fiber or wire (or other connection) 6210 can incorporate the same or a different unique identifier such that it can be prevented from being used a second time.

As can be appreciated from this arrangement, a low cost, high performance guidewire can be provided with on board sensor ready configuration that can be activated at the command of the physician by purchasing and using a separate optical fiber or wire (or other connection) 6210. This arrangement can help minimize concern over the choice of an expensive sensing guidewire in advance of the knowledge of the merits of the sensing measurement. In addition, by way of a further example, second fluid pressure sensor 6216 and wire 6218 can be provided together with the optical fiber or wire (or other connection) 6210. Second pressure sensor 6216 can be a single use pressure sensor.

Alternatively, guidewire 6205 and connection means 6210 can be provided together as matching sets together with or separately from external sensor 6216. Connection means 6210 may also incorporate the characteristic module described herein, or it may be provided separately.

Using one or more techniques such as disclosed herein, the present applicant has described an optical pressure sensing guidewire suitable for delivery within a body lumen of a patient, e.g., for diagnostic assessment of coronary obstructions. The present applicant has determined that the highly miniaturized pressure sensors and optical fibers disclosed herein can be incorporated into devices and constructions other than guidewires.

By way of example, the highly miniaturized pressure sensors and optical fibers can be incorporated into medical catheters. The medical catheters can take various forms and can be utilized for various applications. By way of example, the medical catheter can be a rapid exchange catheter that can track over a guidewire, as shown by way of example in FIGS. 70A, 70B. A rapid exchange catheter can be advantageous as it allows for a guidewire to remain in place throughout a procedure and would allow pressure sensing to be achieved in conjunction with the guidewire that a physician may choose for a specific application. In addition, the rapid exchange catheter incorporating the highly miniaturized sensors and optical fibers described herein can be made small enough such that its introduction into a vessel or lesion would not cause reduced flow or significant changes in pressure. This would be an important advance over the state of the art of rapid exchange pressure sensing catheters as the clinical utility of, for example, FFR has been established over many years with low profile guidewires.

By way of example, any of the pressure sensing guidewires disclosed herein can be adapted to track along a guidewire already in place. This is accomplished by attaching, for example, a polymer tube to the guidewire which can accommodate the guidewire already in place. The polymer tube is of sufficient length to track the guidewire smoothly without dislodging its position. The polymer tube length may range from a millimeter to several centimeters. The polymer tube can be constructed with relatively thin walls such that the obstruction to blood flow is minimized. The rapid exchange catheter can be inserted over the already in place guidewire as needed throughout the procedure. Because the rapid exchange catheter can be removed, it would not be necessary to include a proximal connection and separable connection means. The optical fiber of the sensor can be continuous from the distal sensor to the console connection. This can greatly simplify construction and cost, and can improve reliability of the connection. The console connection can be achieved by utilizing, for example, the connection method of FIG. 55B can be applied to industry standard optical connectors, such as the LC connector.

Alternatively, the rapid exchange catheter design can have simplified construction as it is not required to deliver therapy. Therefore, the design can be adjusted to optimize tracking over a guidewire, which, for example, can be accomplished with a single material core construction such as stainless steel. Alternatively or additionally, the guidewire profile can be reduced in the regions distal and proximal to the pressure sensor. For example, the distal coil can be eliminated and the proximal coil can be removed, reduced in size, or replaced by a thin walled tube. This enables the construction of a device that is very low profile. These changes can help ensure that the rapid exchange catheter creates minimal obstruction in the artery and in any present lesion(s). Furthermore, the rapid exchange catheter can have a built in feature, such as a handle, which enables the physician to easily maneuver the device in the patient. This feature can be permanently attached as needed.

Figure 67A:
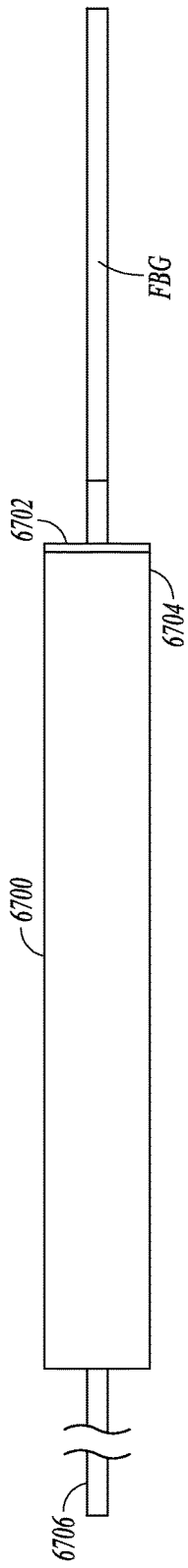
FIG. 67A is side view of another example of a pressure sensor housing, in accordance with this disclosure.

FIG. 67A is side view of another example of a pressure sensor housing, in accordance with this disclosure. FIG. 67A depicts a main housing 6700 having a diaphragm 6702 at an end 6704, an optical fiber 6706 entering the main housing 6700, and an FBG extending from the end 6704.

Figure 67B:
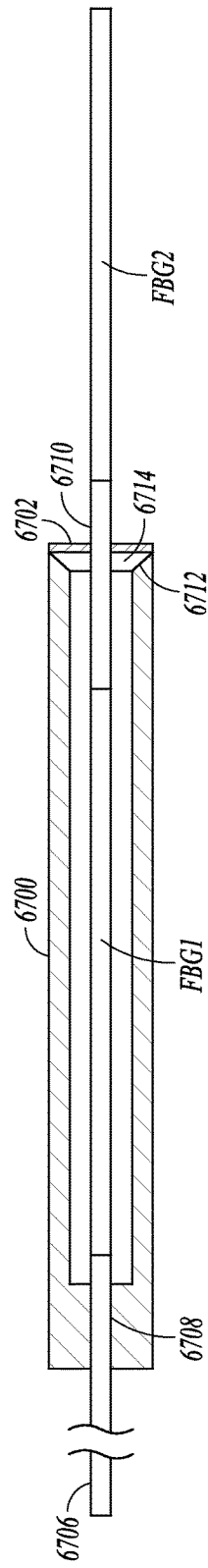
FIG. 67B is cross-sectional view of the pressure sensor housing of FIG. 67A, in accordance with this disclosure.

FIG. 67B is cross-sectional view of the pressure sensor housing of FIG. 67A, in accordance with this disclosure. In the example shown in FIG. 67B, a single diaphragm 6702 can be used, in contrast to a distal disc and gasket design, e.g., FIG. 38 at 3804 and 3808. The diaphragm 6702 can act as a flexible plate that deflects inwards as the pressure on the surface increases. The fiber 6706 that includes FBG1 can be held under a slight tension between the bonds 6708 and 6710 similar to previous implementations. As the pressure increases, the diaphragm 6702 can deflect inwards, thereby releasing some of the tension on the fiber 6706 and shifting the wavelength of FBG1 slightly downwards.

The downwards shift in wavelength can be detected by techniques previously described and converted to a pressure reading. The thickness of the diaphragm 6702 can be on the order of several microns to several tens of microns depending on the material of the diaphragm. Example diaphragm materials can include a type of glass or polyimide. It can be desirable for the diaphragm material to behave in the manner of a perfect spring over small deflections. Alternatively, the diaphragm can behave in a predictable non-linear manner.

One advantage of the diaphragm 6702 is that is shortens the overall length of the pressure sensor housing and it is also less susceptible to vibrational forces in lateral and longitudinal directions. The disc in the designs described above can be susceptible to vibration or even gravitational forces as it is a relatively large mass placed in contact with a gasket with a very small spring constant. This mass can impart unwanted influence on the section of fiber contained within the housing.

For improved performance, the pressure sensor housing 6700 can be stiff to prevent an unwanted bending or other distortions. In some example configuration, this can mean sizing the inner diameter closely, but without interference to the optical fiber 6706. However, this configuration may not be ideal for the diaphragm design as the smaller the inner diameter, the less deflection is expected for a diaphragm of given material and thickness, which can have a detrimental effect on the device sensitivity.

To solve this problem, the pressure sensor housing of FIGS. 67A, 67B can include a section, shown at 6712, where the diaphragm 6702 is attached to the sensor housing 6700 in which the inner diameter is expanded for a distance relatively short compared to the overall length of the housing 6700. The shape of the housing 6700 can allow the diaphragm 6702 to have a larger unsupported diameter, which can increase the deflection for a given applied pressure and thus increase the sensitivity to an acceptable level. The shape of the housing 6712 in FIG. 67B is shown as a tapered flute 6714 but could be other shapes, including, for example, a step to achieve the same desired affect as the deflection of the diaphragm is very small.

One of the advantages achieved by the thinness of the diaphragm 6702 presents a challenge with the bonding of the fiber 6706 to the diaphragm 6702. In previous designs, e.g., FIG. 38, the bond has been achieved by using a section of epoxy, shown at 3816. The diaphragm 6702, however, may not present enough length with which to achieve a satisfactory epoxy bond. As such, a stopper can be attached to the fiber 6706.

Figure 67C:
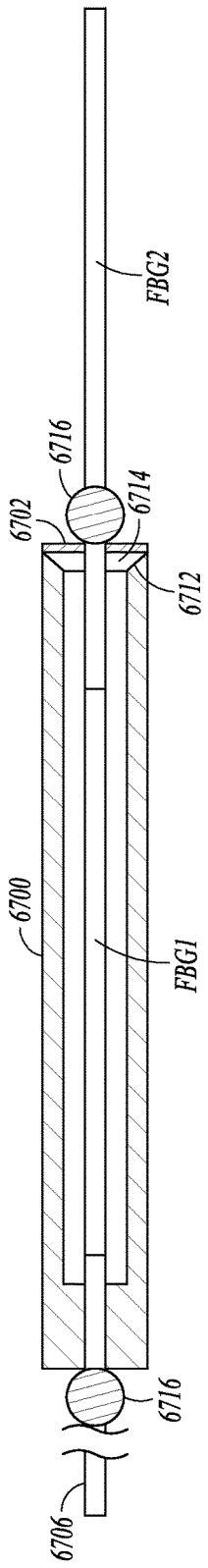
FIG. 67C is cross-sectional view of the pressure sensor housing of FIG. 67A, including a fused fiber bond, in accordance with this disclosure.

FIG. 67C is cross-sectional view of the pressure sensor housing of FIG. 67A, including a fused fiber bond, in accordance with this disclosure. As seen in FIG. 67C, fused fiber bonds 6716, or "stoppers", can act to stop the fiber 6706 from being pulled through the hole in the diaphragm 6706. The stoppers 6716 can be attached to the fiber 6706 in the gap between the FBG inside the housing and the FBG outside the housing. The stoppers can be shaped such that there is only a small area of contact between the stopper 6716 and the diaphragm 6702. This is intentional as any significant area of contact can increase the apparent stiffness of the diaphragm 6702 and thus reduce the deflection and, by extension, the sensitivity of the pressure sensing function.

Although the shape of the stopper 6716 is depicted as being circular, in other examples, the shape can be a step or taper. There can be a small amount of sealing material applied between the stopper 6716 and the diaphragm to ensure the interface is airtight. The stopper 6716 can be attached by various methods such as epoxy, glass solder, metal solder or glass fusion.

Epoxy bonds may not be the most suitable technique for ensuring very stable operation of the pressure sensing device. For example, epoxy bonds can suffer from mechanical creep, ingress of moisture and other generally unstable characteristics. The small nature of the optical fiber used in the pressure sensing devices of this disclosure means there is a very small surface area available on which to realize a stable bond. Thus, it can be desirable to use a material or materials that are both harder and more stable than epoxy.

One technique to achieve the bond is a glass fusion technique. Instead of using the same material as is present in the fiber, which can damage the function of the fiber as it is heated to the temperature necessary to achieve a glass to glass fusion, a borosilicate glass can be used to attach the stopper. A borosilicate glass has a melt temperature significantly lower than the fused silica glass used in the optical fiber so it possible to melt and fuse the borosilicate stopper without distorting the optical fiber. A bead or short section of borosilicate capillary can be threaded over the optical fiber and positioned in the correct position. A method of heating can be used that is just sufficient to melt the borosilicate glass without melting the optical fiber. By controlling the process, the shape of the stopper can be controlled to leave it more like a flat disc, or by using the natural surface tension achieve a more ball like shape. Suitable heating methods can include, but are not limited to, resistive heating elements, plasma heating between electrodes, CO2 laser heating, and hot air. It may be desirable to eliminate all epoxy bonds that are critical to the stability of the device. As such, the borosilicate glass technique can used for the bond 6716 of the optical fiber at the proximal end of the pressure housing as well as the distal bond. As has been mentioned above, each pressure sensing device may have a unique characteristics. When the device is connected to the pressure system, the parameters that constitute the characteristics of the device may need to be transferred to the system so that the correct operation is achieved. The characteristics can also be described as the calibration of the device relative to a known reference. The techniques used to transfer the characteristics to the pressure sensing system have been described above and can include, but are not limited to, manual data entry, RFID chip, barcode scan, disposable chip or read only memory device.

The complete calibration can consist of at least two parts. The first part can be a calibration of the lasers within the system or console and the second part can be the calibration of the disposable device. The lasers within the system may need to be fully characterized relative to known standards. These calibrations can include wavelength under standard operating conditions (e.g. fixed temperature and operating current), and power output, for example.

There can also be a matrix of calibrations that will fully characterize the lasers so the output conditions are known for any combination of operating parameters, e.g., output wavelength and power for a range of operating temperatures and operating currents. From this matrix, any rate of change to output power or wavelength can be determined that will allow calculation of the shift of the laser caused by external stimulus, e.g., change of wavelength relative to operating current when tracking the optical filter.

The second part of the calibration is the pressure sensing device. During the manufacturing process, the device can be calibrated against known standards to determine, amongst other things, the exact wavelength, optical insertion loss and slope of the wavelength response for the optical filter. These parameters can be programmed into the characteristics for the device so they can be read into any system and the system can configure itself to work accurately with that device.

It is common when performing medical procedures with this type of device to cross calibrate with an external pressure sensor during the initial phase of the procedure. This also serves an important function with verification of procedure efficacy after the procedure is complete as the reading from the pressure sensing device can be compared to the external pressure sensor to make sure the readings are in agreement. A cross calibration procedure that includes two main parts, as described below with respect to FIG. 68, can be used for calibration.

Figure 68:
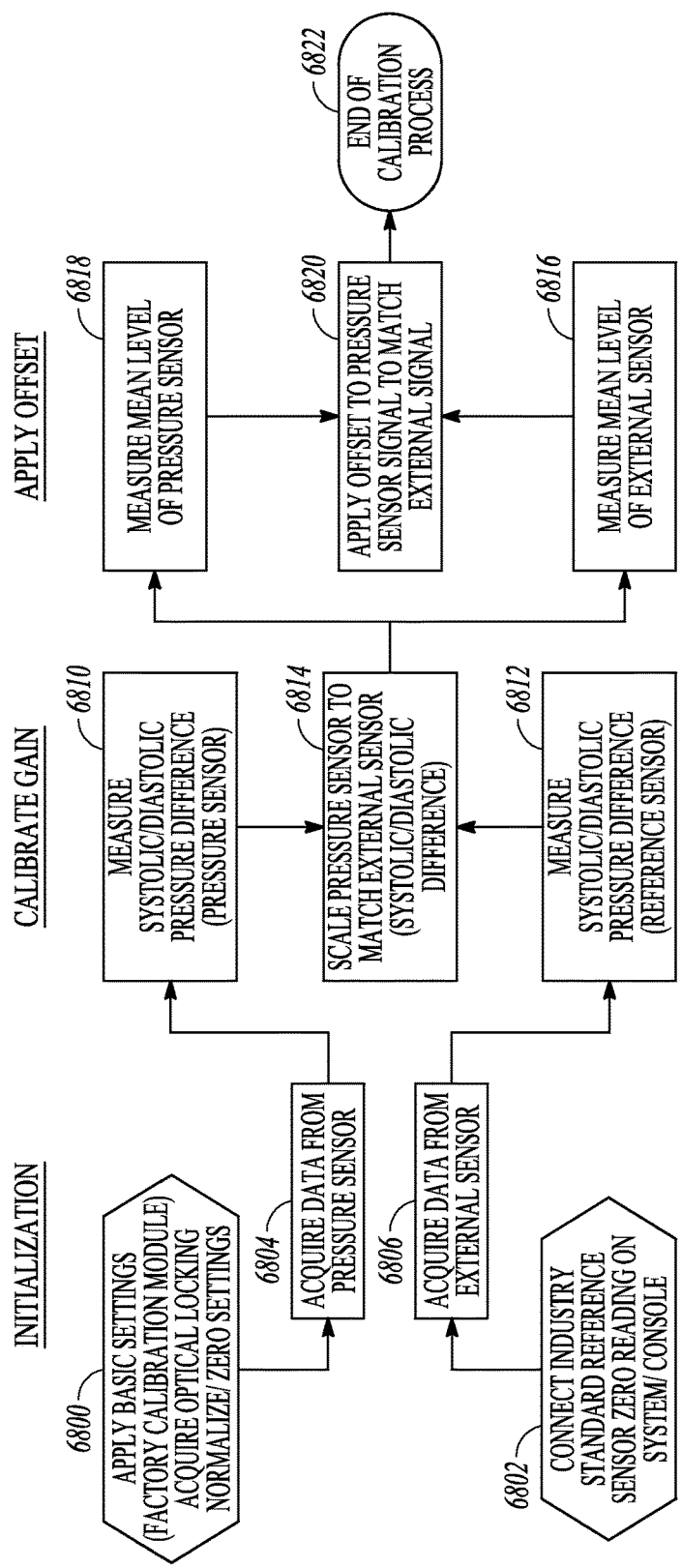
FIG. 68 is a flow diagram illustrating an example of a calibration technique, in accordance with this disclosure.

FIG. 68 is a flow diagram illustrating an example of a calibration technique, in accordance with this disclosure. First, an initialization occurs. The initialization can include, for example, applying basic settings (e.g., factory calibration module), acquiring optical locking, and normalizing/zero settings (block 6800). In addition, the initialization can include connecting an industry standard reference sensor and obtaining a zero reading on the system/console (block 6802). Next, the pressure sensing device acquires data (block 6804) and the external sensor acquires data (block 6806). The initialization uses the parameters of the device characteristics to set the lasers to the correct operating conditions and achieve a satisfactory lock on the slope of the optical filter. There may be some small optimization of the laser operating conditions to ensure best dynamic range.

The first main part ("Calibrate GAIN" in FIG. 68) of the cross calibration procedure can include matching the difference between systolic (maximum) pressure and diastolic (minimum) pressures and the second main part ("Apply OFFSET") can include matching the average or mean pressure. In this example technique, it is assumed that the pressure signal from the external pressure sensor can be compared with the FFR pressure sensor. The external pressure sensor can be one that is compliant with the requirements of the published specification ANSI/AAMI BP22: 1994/(R) 2011, which relates to a standard bridge type sensor that typically has a sensitivity of 5 µV/V/mmHg. Depending on the configuration of the system there can be a provision for this type of input built directly into the FFR console or it will be supplied from another piece of equipment.

The first part of the cross calibration can include measuring the difference between systolic and diastolic pressure over a number of cycles for the pressure sensing device (block 6810) and the reference sensor (block 6812). Once an accurate number has been established for the external sensor, this can be used to calibrate the difference for the FFR sensor. That is, the FFR sensor can be scaled to match the external sensor using the systolic/diastolic different (block 6814). This can also be thought of as a gain figure.

The second main part of the cross calibration can include measuring the mean of the external sensor over a number of cycles (block 6816), measuring the mean of the FFR pressure sensing device over a number of cycles (block 6818), and then using this number to set the mean for the FFR pressure sensing device by applying an offset to the pressure sensing device to match the external signal (block 6820). This can be thought of as an offset number. Once these actions have been completed, the FFR sensor is accurately calibrated (block 6822).

There are situations where large changes in the operating conditions of the device are possible. These occur mostly when the FFR device is being inserted into the patient after being calibrated outside the body. One reason for this is the difference between room temperature (typically around 25° C.) and body temperature (typically around 37° C.). The FBG devices are sensitive to temperature changes and a change of 12° C. will change the operating wavelength by approximately 120 pm (10 pm/° C.). This wavelength shift may be too much to correct with a change of operating current. The coefficient for the lasers is around 5 pm/mA, which can mean a change of approximately 24 mA, which may not be possible. One solution is to use the operating temperature of the lasers to account for large changes. A typical laser can have a wavelength coefficient of approximately 100 pm/° C. so the operating temperature can be adjusted by approximately 1.2° C. to account for the body temperature difference and keep the operating current the same.

In one example implementation, the operating current of the laser required to keep a lock on the optical filter can be continually monitored and then the operating temperature of the laser can be dynamically adjusted to keep the operating current at an optimum value. Another technique that may be advantageous is to have predictive settings, as shown and described below with respect to FIG. 69.

Figure 69:
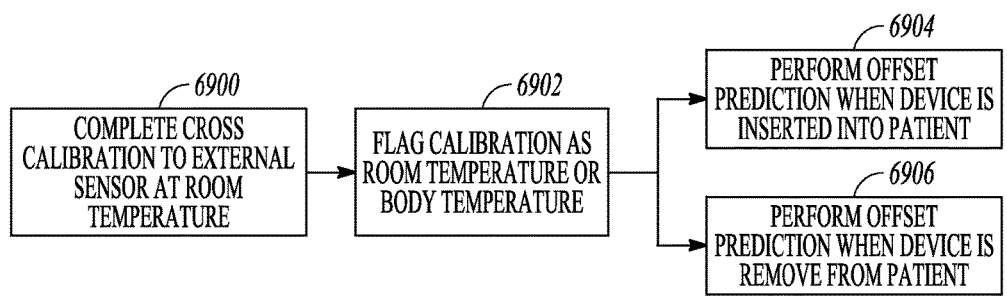
FIG. 69 is a flow diagram illustrating an example of an offset prediction technique, in accordance with this disclosure.

FIG. 69 is a flow diagram illustrating an example of an offset prediction technique, in accordance with this disclosure. A cross calibration to the external sensor at room temperature can be performed (block 6900). If the device is calibrated outside the body (or inside the body), the system can denote this calibration as a room temperature calibration (or body temperature calibration) (block 6902). The system can then automatically predict what the appropriate laser parameters will be once the FFR device is inserted into the body (block 6904) or when the FFR device is removed from the body (6906). This can be useful in achieving rapid locking under certain circumstances. Once the FFR device is inserted into the patient the temperature fluctuations are generally small, which can coincide with events such as injection of contrast agents.

Figure 70A:
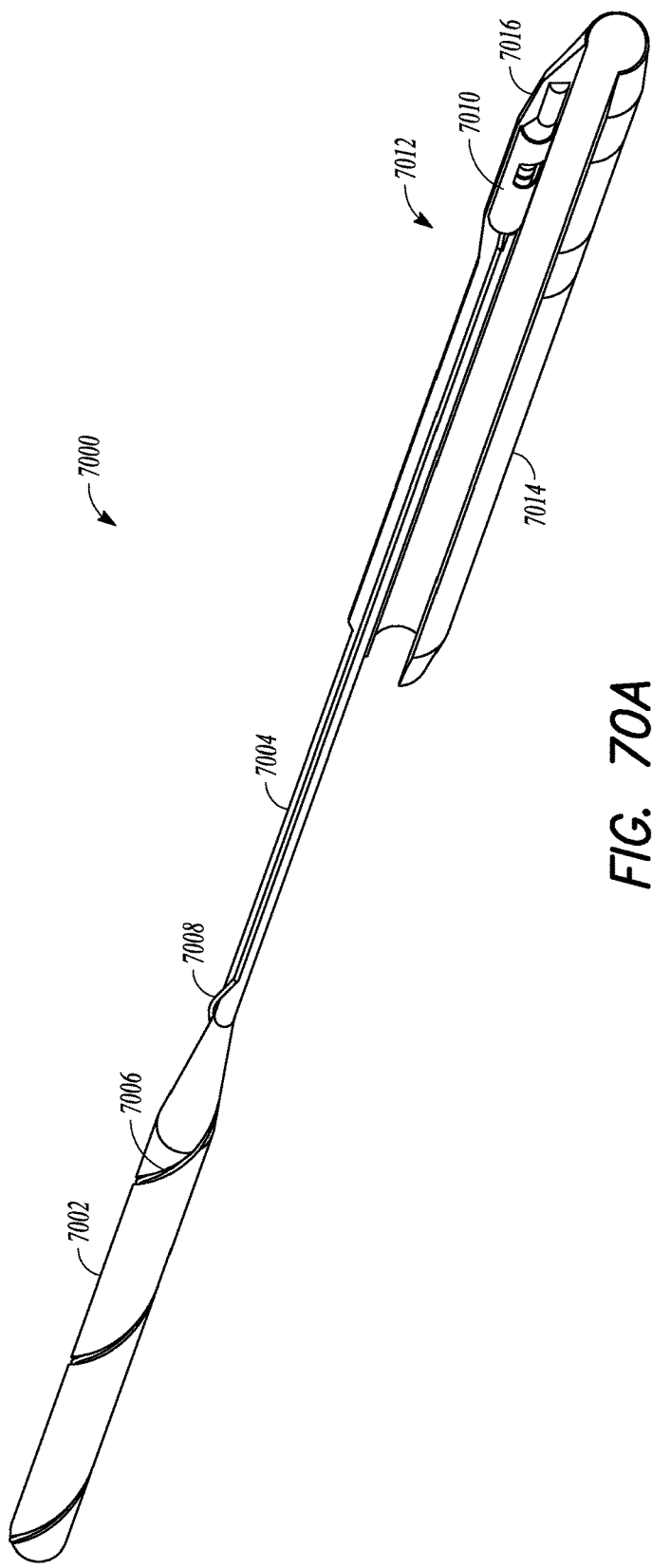
FIG. 70A depicts a cut away view of an optical fiber pressure sensor configured into a rapid exchange sensor assembly for measuring pressure in a cardiovasculature, in accordance with this disclosure.

FIG. 70A depicts an optical fiber pressure sensor configured into a rapid exchange sensor assembly for measuring pressure in a cardiovasculature, in accordance with this disclosure. More particularly, FIG. 70A depicts an optical fiber pressure sensor assembly 7000 including a guidewire 7002 having a core wire 7004 and defining channel or groove 7006 into which an optical fiber 7008 can be positioned, and a pressure sensor housing 7010 containing a pressure sensor as described in this disclosure, in combination with a rapid exchange sensor assembly 7012. The rapid exchange sensor assembly 7012 can include a guiding tube 7014 encapsulating the pressure sensor housing 7010 located in a cavity 7016 at the distal end of the guidewire. In some examples, the cavity 7016 can be formed within a bulge in the guidewire itself. For clarity, FIG. 70A is depicted in a cut away view configuration to illustrate the inner construction.

In the illustrated configuration, the distal end of the wire including the cavity containing the optical fiber pressure sensor housing has been incorporated into a short, e.g., 1 to 2 cm, single lumen polymer member (made from suitable stiffness PEBAX, PTFE, PTFE lined PEBAX, or other similar materials) with a soft, tapered, atraumatic tip. Optimizing the length and the stiffness of the guiding tube portion for flexibility can provide better tracking of the rapid exchange sensor assembly 7012 over the guidewire 7002. One or more pressure communication channels through the polymer layer covering the sensor cavity can be provided to allow the sensor access to the blood pressure. In this example, the guiding tube lumen is sized to accommodate a 0.014″ guidewire and the outside diameter dimension is less than 500 microns except in the region of the sensor where it is less than 700 microns.

In this configuration, the optical fiber 7008 is shown both in a groove in the wire over the proximal shaft as well as routed along the wire surface where it can be captured in the polymer coating or polymer guiding tube member. Alternatively, the guidewire core could be grooved all the way to the sensor cavity 7016. In another configuration, the guidewire core cross section could be noncircular for some length proximal of the sensor cavity in the blivet to minimize the polymer guiding tube member major dimension.

The rapid exchange sensor can be advanced over the guidewire already in place into the ascending aorta and positioned near the distal end of the guide catheter to measure the aortic pressure. The measured aortic pressure can be normalized to the external pressure sensor and then the rapid exchange sensor can be advanced further, guided by the guidewire already in place, to cross the stenosis and measure the pressure distal of the lesion.

Figure 70B:
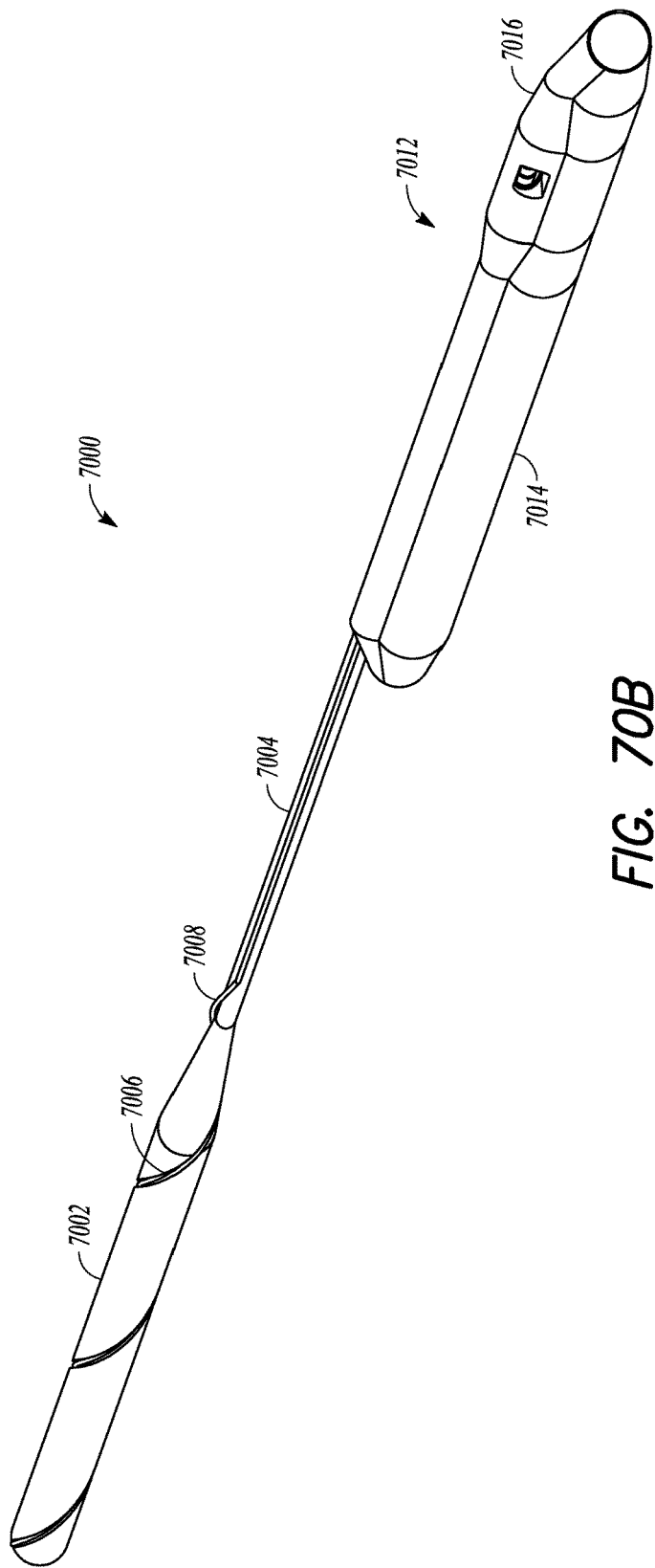
FIG. 70B depicts the optical fiber pressure sensor configured into a rapid exchange sensor assembly of FIG. 70A, with the guiding tube in a closed configuration.

FIG. 70B depicts the optical fiber pressure sensor configured into a rapid exchange sensor assembly of FIG. 70A, without the cut away view.

Using the one or more techniques such as disclosed herein, the present applicant has described an optical pressure sensing guidewire suitable for delivery within a body lumen of a patient, e.g., for diagnostic assessment of coronary obstructions. This can advantageously optionally provide temperature compensation for sensing pressure within a body lumen. In addition, the present subject matter can advantageously mechanically enhance the sensitivity of the fiber to pressure, such as with an extrinsic arrangement. Further, the present subject matter can utilize Fiber Bragg Gratings in the miniaturized optical fiber thereby resulting in a cost effective and manufacturable design.

This application is related to (1) PCT Application No. PCT/US2013/042769 titled, "OPTICAL FIBER PRESSURE SENSOR" to Eberle et al. and filed on May 24, 2013, and to (2) U.S. patent application Ser. No. 13/902,334 titled, "OPTICAL FIBER PRESSURE SENSOR GUIDEWIRE" to Eberle et al. and filed on May 24, 2013, and to (3) U.S.

Provisional Application No. 61/791,486 titled, "OPTICAL FIBER PRESSURE SENSOR GUIDEWIRE" to Eberle et al. and filed on Mar. 15, 2013, and to (4) U.S. Provisional Application No. 61/753,221, titled, "OPTICAL FIBER PRESSURE SENSOR GUIDEWIRE" to Eberle et al. and filed on Jan. 16, 2013, and to (5) U.S. Provisional Application No. 61/709,781, titled, "OPTICAL FIBER PRESSURE SENSOR GUIDEWIRE" to Eberle et al. and filed on Oct. 4, 2012, and to (6) U.S. Provisional Application No. 61/659,596, titled, "OPTICAL FIBER PRESSURE SENSOR GUIDEWIRE" to Eberle et al. and filed on Jun. 14, 2012, and to (7) U.S. Provisional Application No. 61/651,832, titled, "OPTICAL FIBER PRESSURE SENSOR GUIDEWIRE" to Eberle et al. and filed on May 25, 2012, the entire content of each being incorporated herein by reference in its entirety.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

In an example, the circuits described herein, including its various elements discussed in this document, can include a combination of hardware and software. For example, one or more portions, elements, or circuits included can be implemented, such as using an application-specific circuit constructed to perform one or more particular functions or a general-purpose circuit programmed to perform such function(s). Such a general-purpose circuit (e.g., a processor circuit) can include, but is not limited to, a microprocessor or a portion thereof, a microcontroller or portions thereof, and a programmable logic circuit or a portion thereof, such as configured to execute or otherwise perform instructions stored within or on a medium readable by a machine or device, such as a memory circuit.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed is:
1. An apparatus comprising:
  an elongated assembly, at least a portion of which is sized, shaped, or otherwise configured to be inserted into a human body to measure a physiological parameter at an internal location within the body, wherein the elongated assembly includes:
  an elongated member having a length, wherein the elongated member defines a longitudinal optical fiber carrier that extends longitudinally along at least a first portion of the length of the elongated member, wherein the optical fiber carrier includes at least one of a groove or a flat;
  an optical fiber, helically extending longitudinally along the optical fiber carrier, the optical fiber configured to communicate light between a location outside of the human body and a portion of the optical fiber that is to be located at or near the internal location within the human body at which the physiological parameter is to be measured, wherein the optical fiber carrier is sized for and carries only one optical fiber, and wherein the only one optical fiber has a diameter of between 25 micrometers and 30 micrometers, inclusive;
  an optical fiber pressure sensor, located at a distal portion of the elongated member, the optical fiber pressure sensor including:

a first optical fiber anchor, to which a first portion of the optical fiber is secured;

a second optical fiber anchor, to which a second portion of the optical fiber is secured;

a gasket longitudinally arranged between the first and second anchors and including a passage through which a third portion of the optical fiber passes, the gasket being more elastic or compliant than the first and second anchors; and wherein the first and second anchors and the gasket are arranged to use the elastic or compliant nature of the gasket to allow at least one of longitudinal stretching or compression of the optical fiber between the first and second anchors to sense pressure at the internal location within the body;

a housing disposed about the optical fiber pressure sensor; and a guidewire tube, coupled to the housing, the guidewire tube defining a receptacle sized and shaped to accept a guidewire to permit the distal portion of the elongated member to slide along the guidewire during insertion of the elongated assembly into the human body.

2. The apparatus of claim 1, wherein the optical fiber includes a Fiber Bragg Grating (FBG) located at the optical fiber pressure sensor.

3. The apparatus of claim 2, wherein the optical fiber pressure sensor includes an FBG interferometer, included in the optical fiber, wherein the FBG interferometer comprises at least two Fiber Bragg Gratings, wherein the at least two Fiber Bragg Gratings are arranged or otherwise configured to permit optically discriminating, at or near the internal location within the body at which pressure is to be measured, between a change in pressure and a change in temperature.

4. The apparatus of claim 1, wherein the optical fiber carrier includes a first guidewire, and further including a second guidewire, sized and shaped to pass through the guidewire tube, wherein the guidewire tube is attached to the first guidewire.

5. The apparatus of claim 1, wherein the optical fiber is a first optical fiber, the apparatus comprising a proximal end connector configured to be coupled to a proximal end of the elongated member, the proximal end connector comprising:

a distal portion including:

a tube defining an interior first passage that is sized and shaped to receive the proximal end of the elongated member;

a distal guide ferrule, at least a portion of which defines a transitional interior second passage that is sized and shaped to allow the optical fiber to be transitionally routed from an outer circumferential periphery of the proximal end of the elongated member to a more longitudinally central location toward a proximal end of the distal guide ferrule; and a proximal portion including:

a proximal guide ferrule including a lumen sized and shaped for passing a second optical fiber having a larger diameter than the first optical fiber; and wherein the distal and proximal portions are user-attachable to bring the first and second optical fibers into concentric longitudinal alignment with each other.

6. A method comprising:

inserting a first guidewire into a human body toward an internal location within the body at which it is desired to measure a physiological parameter;

inserting into the human body an elongated assembly, at least a portion of which is sized, shaped, or otherwise configured to be inserted into a human body to measure a physiological parameter at an internal location within the body, wherein the elongated assembly includes:

an elongated member having a length, wherein the elongated member defines a longitudinal optical fiber carrier that extends longitudinally along at least a first portion of the length of the elongated member, wherein the optical fiber carrier includes at least one of a groove or a flat;

an optical fiber, helically extending longitudinally along the optical fiber carrier, the optical fiber configured to communicate light between a location outside of the human body and a portion of the optical fiber that is to be located at or near the internal location within the human body at which the physiological parameter is to be measured, wherein the optical fiber carrier is sized for and carries only one optical fiber, and wherein the only one optical fiber has a diameter of between 25 micrometers and 30 micrometers, inclusive;

an optical fiber pressure sensor, located at a distal portion of the elongated member, the optical fiber pressure sensor including:

a first optical fiber anchor, to which a first portion of the optical fiber is secured;

a second optical fiber anchor, to which a second portion of the optical fiber is secured;

a gasket longitudinally arranged between the first and second anchors and including a passage through which a third portion of the optical fiber passes, the gasket being more elastic or compliant than the first and second anchors; and wherein the first and second anchors and the gasket are arranged to use the elastic or compliant nature of the gasket to allow at least one of longitudinal stretching or compression of the optical fiber between the first and second anchors to sense pressure at the internal location within the body;

a housing disposed about the optical fiber pressure sensor; and a guidewire tube, coupled to the housing, the guidewire tube defining a receptacle sized and shaped to accept a guidewire to permit the distal portion of the elongated member to slide along the guidewire during insertion of the elongated assembly into the human body; and wherein the inserting into the human body the elongated assembly includes guiding the elongated assembly using the first guidewire passing through the guidewire tube.

7. An apparatus comprising:

an elongated assembly, at least a portion of which is sized, shaped, or otherwise configured to be inserted into a human body to measure a physiological parameter at an internal location within the body, wherein the elongated assembly includes:

an elongated member having a length, wherein the elongated member defines a longitudinal optical fiber carrier that extends longitudinally along at least a first portion of the length of the elongated member, wherein the optical fiber carrier includes at least one of a groove or a flat;

a first optical fiber, helically extending longitudinally along the optical fiber carrier, the optical fiber configured to communicate light between a location outside of the human body and a portion of the optical fiber that is to be located at or near the internal location within the human body at which the physiological parameter is to be measured, wherein the optical fiber carrier is sized for and carries only one optical fiber, and wherein the only one optical fiber has a diameter of between 25 micrometers and 30 micrometers, inclusive;

an optical fiber pressure sensor, located at a distal portion of the elongated member;

a housing disposed about the optical fiber pressure sensor;

a guidewire tube, coupled to the housing, the guidewire tube defining a receptacle sized and shaped to accept a guidewire to permit the distal portion of the elongated member to slide along the guidewire during insertion of the elongated assembly into the human body; and a proximal end connector configured to be coupled to a proximal end of the elongated member, the proximal end connector comprising:

a distal portion including:

a tube defining an interior first passage that is sized and shaped to receive the proximal end of the elongated member;

a distal guide ferrule, at least a portion of which defines a transitional interior second passage that is sized and shaped to allow the optical fiber to be transitionally routed from an outer circumferential periphery of the proximal end of the elongated member to a more longitudinally central location toward a proximal end of the distal guide ferrule; and a proximal portion including:

a proximal guide ferrule including a lumen sized and shaped for passing a second optical fiber having a larger diameter than the first optical fiber;

wherein the distal and proximal portions are user-attachable to bring the first and second optical fibers into concentric longitudinal alignment with each other.

* * * * *

UNITED STATES PATENT AND TRADEMARK OFFICE
CERTIFICATE OF CORRECTION

Page 1 of 2

PATENT NO. : 10,258,240 B1
APPLICATION NO. : 14/949605
DATED : April 16, 2019
INVENTOR(S) : Eberle et al.

It is certified that error appears in the above-identified patent and that said Letters Patent is hereby corrected as shown below:

In the Specification

In Column 4, Line 53, delete "FIG." and insert --FIGS.-- therefor

In Column 4, Line 55, delete "FIG." and insert --FIGS.-- therefor

In Column 13, Line 14, delete "308." and insert --304.-- therefor

In Column 15, Line 49, delete "X1" and insert --$\lambda$1-- therefor

In Column 15, Line 55, delete "X2" and insert --$\lambda$2-- therefor

In Column 22, Line 4, delete "706." and insert --716.-- therefor

In Column 23, Line 3, delete "804." and insert --800.-- therefor

In Column 24, Line 24, delete "904." and insert --900.-- therefor

In Column 24, Line 33, delete "904." and insert --900.-- therefor

In Column 25, Line 50, delete "1004." and insert --1000.-- therefor

In Column 25, Line 55, delete "member" and insert --membrane-- therefor

In Column 26, Line 51, delete "1106" and insert --1102-- therefor

In Column 27, Line 24, delete "1204" and insert --1200-- therefor

In Column 29, Line 17, delete "1306" and insert --1304-- therefor

Signed and Sealed this
Fifth Day of May, 2020

Andrei Iancu
*Director of the United States Patent and Trademark Office*

CERTIFICATE OF CORRECTION (continued)
U.S. Pat. No. 10,258,240 B1

In Column 29, Line 27, delete "1402" and insert --1404-- therefor

In Column 34, Line 25, delete "1912" and insert --1910-- therefor

In Column 38, Line 18, delete "Fe2Ti" and insert --$Fe_2Ti$-- therefor

In Column 38, Line 65, delete "keton-based" and insert --ketone-based-- therefor In Column 44, Line 33, delete "202" and insert --2302-- therefor In Column 48, Line 53, delete "2500" and insert --2400-- therefor In Column 53, Line 58, delete "3004" and insert --3000-- therefor In Column 56, Line 11, delete "(±1000 μV)." and insert --(±100 μW).-- therefor In Column 63, Line 39, delete "FIG." and insert --FIGS.-- therefor In Column 64, Line 51, delete "FIG." and insert --FIGS.-- therefor In Column 72, Line 63, delete "um" and insert --μm-- therefor In Column 74, Line 18, delete "5704" and insert --5706-- therefor In Column 77, Lines 52-53, delete "VOA scan" and insert --VOAs can-- therefor In Column 80, Line 63, delete "patient" and insert --pressure-- therefor In Column 85, Line 12, delete "6706." and insert --6702.-- therefor In Column 85, Line 54, delete "CO2" and insert --$CO_2$-- therefor